United States Patent
Ryan et al.

(10) Patent No.: US 10,900,034 B2
(45) Date of Patent: *Jan. 26, 2021

(54) GUIDE RNA WITH CHEMICAL MODIFICATIONS

(71) Applicant: Agilent Technologies, Inc., Santa Clara, CA (US)

(72) Inventors: Daniel E. Ryan, San Francisco, CA (US); Douglas J. Dellinger, Boulder, CO (US); Jeffrey R. Sampson, San Jose, CA (US); Robert Kaiser, Santa Clara, CA (US); Joel Myerson, Berkeley, CA (US)

(73) Assignee: AGILENT TECHNOLOGIES, INC., Santa Clara, CA (US)

(*) Notice: Subject to any disclaimer, the term of this patent is extended or adjusted under 35 U.S.C. 154(b) by 708 days.

This patent is subject to a terminal disclaimer.

(21) Appl. No.: 14/757,204

(22) Filed: Dec. 3, 2015

(65) Prior Publication Data

US 2016/0289675 A1 Oct. 6, 2016

Related U.S. Application Data

(60) Provisional application No. 62/256,095, filed on Nov. 16, 2015, provisional application No. 62/146,189, filed on Apr. 10, 2015, provisional application No. 62/087,211, filed on Dec. 3, 2014.

(51) Int. Cl.
| | |
|---|---|
| *C12N 15/113* | (2010.01) |
| *C12N 9/22* | (2006.01) |
| *C12N 15/11* | (2006.01) |
| *C07H 21/02* | (2006.01) |
| *C12N 15/90* | (2006.01) |
| *C12Q 1/6876* | (2018.01) |

(52) U.S. Cl.
CPC ............ *C12N 15/111* (2013.01); *C07H 21/02* (2013.01); *C12N 9/22* (2013.01); *C12N 15/113* (2013.01); *C12N 15/907* (2013.01); *C12Q 1/6876* (2013.01); *C12N 2310/10* (2013.01); *C12N 2310/20* (2017.05); *C12N 2310/312* (2013.01); *C12N 2310/315* (2013.01); *C12N 2310/321* (2013.01); *C12N 2310/322* (2013.01); *C12N 2310/323* (2013.01); *C12N 2310/3231* (2013.01); *C12N 2310/333* (2013.01); *C12N 2310/335* (2013.01); *C12N 2310/346* (2013.01); *C12N 2310/3517* (2013.01); *C12N 2310/531* (2013.01); *C12N 2320/51* (2013.01); *C12N 2320/53* (2013.01); *C12N 2330/31* (2013.01)

(58) Field of Classification Search
None
See application file for complete search history.

(56) References Cited

U.S. PATENT DOCUMENTS

| | | | |
|---|---|---|---|
| 5,032,401 | A | 7/1991 | Jamas et al. |
| 5,607,677 | A | 3/1997 | Jamas et al. |
| 7,371,580 | B2 | 5/2008 | Yakhini et al. |
| 8,202,983 | B2 | 6/2012 | Dellinger et al. |
| 8,906,616 | B2 | 12/2014 | Zhang et al. |
| 9,822,407 | B2 | 11/2017 | Joung et al. |
| 2005/0281781 | A1 | 12/2005 | Ostroff |
| 2010/0076183 | A1 | 3/2010 | Dellinger et al. |
| 2014/0090113 | A1 | 3/2014 | Cogan et al. |
| 2014/0090116 | A1 | 3/2014 | Ainley et al. |
| 2014/0170753 | A1 | 6/2014 | Zhang |
| 2014/0242664 | A1* | 8/2014 | Zhang ................... C12N 15/902 435/188 |
| 2014/0273037 | A1 | 9/2014 | Wu |
| 2014/0273226 | A1 | 9/2014 | Wu |
| 2014/0273233 | A1 | 9/2014 | Chen et al. |
| 2014/0273235 | A1 | 9/2014 | Voytas et al. |
| 2014/0294773 | A1 | 10/2014 | Brouns et al. |
| 2014/0295555 | A1 | 10/2014 | Mishra |
| 2014/0295557 | A1 | 10/2014 | Joung et al. |
| 2014/0309487 | A1 | 10/2014 | Lee et al. |
| 2014/0310828 | A1 | 10/2014 | Lee et al. |
| 2014/0349400 | A1 | 11/2014 | Jakimo et al. |
| 2014/0357523 | A1 | 12/2014 | Zeiner et al. |
| 2014/0364333 | A1 | 12/2014 | Wu et al. |
| 2015/0044191 | A1 | 2/2015 | Liu et al. |
| 2015/0044192 | A1 | 2/2015 | Liu et al. |
| 2015/0044772 | A1 | 2/2015 | Zhao |
| 2015/0064149 | A1 | 3/2015 | West et al. |
| 2015/0064708 | A1 | 3/2015 | Sastry-Dent et al. |
| 2015/0067921 | A1 | 3/2015 | Cogan et al. |
| 2015/0071906 | A1 | 3/2015 | Liu et al. |

(Continued)

FOREIGN PATENT DOCUMENTS

| | | |
|---|---|---|
| CN | 104854241 A | 8/2015 |
| EP | 2800811 A1 | 11/2014 |

(Continued)

OTHER PUBLICATIONS

Larson et al., Real-Time Observation of Transcription Initiation and Elongation on an Endogenous Yeast Gene, Science. Apr. 22, 2011; 332(6028): 475-478.*

Bisaria et al., "Lessons from enzyme kinetics reveal specificity principles for RNA-guided nucleases in RNA interference and CRISPR-based genome editing," Cell Syst., 4:21-29, (2017).

Cho et al., "Analysis of off-target effects of CRISPR/Cas-derived RNA-guided endonucleases and nickases," Genome Res., vol. 24, pp. 0132-0141, (2014).

Doyon et al., "Enhancing Zinc-Finger_Nuclease Activity with Improved Obligate Heterodimeric Architectures", nat. Methods, vol. 8, pp. 74-81, (2011).

(Continued)

*Primary Examiner* — Channing S Mahatan
(74) *Attorney, Agent, or Firm* — Faegre Drinker Biddle & Reath LLP

(57) ABSTRACT

The present invention relates to modified guide RNAs and their use in clustered, regularly interspaced, short palindromic repeats (CRISPR)/CRISPR-associated (Cas) systems.

33 Claims, 18 Drawing Sheets

Specification includes a Sequence Listing.

(56) References Cited

U.S. PATENT DOCUMENTS

| | | | |
|---|---|---|---|
| 2015/0071946 A1 | 3/2015 | Solyom et al. |
| 2015/0079680 A1 | 3/2015 | Bradley et al. |
| 2015/0098954 A1 | 4/2015 | Hyde et al. |
| 2015/0118216 A1 | 4/2015 | Liu et al. |
| 2015/0128307 A1 | 5/2015 | Sastry-Dent et al. |
| 2015/0128308 A1 | 5/2015 | Sastry-Dent et al. |
| 2015/0128309 A1 | 5/2015 | Sastry-Dent et al. |
| 2015/0133315 A1 | 5/2015 | Jacobson et al. |
| 2015/0140664 A1 | 5/2015 | Byrne et al. |
| 2015/0156996 A1 | 6/2015 | Fahrenkrug et al. |
| 2015/0315252 A1 | 11/2015 | Haugwitz et al. |
| 2015/0315576 A1 | 11/2015 | Caliando et al. |
| 2015/0322432 A1 | 11/2015 | Anderson et al. |
| 2015/0344836 A1 | 12/2015 | Finer et al. |
| 2016/0030477 A1 | 2/2016 | Conway et al. |
| 2016/0046959 A1 | 2/2016 | Landel et al. |
| 2016/0090622 A1 | 3/2016 | Liu et al. |
| 2016/0138027 A1 | 5/2016 | Gan et al. |
| 2016/0168592 A1 | 6/2016 | Church et al. |
| 2016/0206566 A1 | 7/2016 | Lu et al. |
| 2016/0257974 A1 | 9/2016 | Bradley et al. |
| 2016/0298097 A1 | 10/2016 | Chavez et al. |
| 2016/0339064 A1 | 11/2016 | Kovarik et al. |
| 2017/0051296 A1 | 2/2017 | Beetham et al. |
| 2017/0166893 A1* | 6/2017 | Doudna ............... C12N 15/113 |
| 2017/0298383 A1 | 10/2017 | Albertsen et al. |

FOREIGN PATENT DOCUMENTS

| | | |
|---|---|---|
| EP | 2892321 A2 | 7/2015 |
| EP | 2893006 A1 | 7/2015 |
| EP | 3241902 B1 | 2/2018 |
| WO | 2013126794 A1 | 8/2013 |
| WO | 2013141680 A1 | 9/2013 |
| WO | 2013142578 A1 | 9/2013 |
| WO | 2013176772 | 11/2013 |
| WO | WO2013176772 A1 | 11/2013 |
| WO | WO2013176844 A1 | 11/2013 |
| WO | 2014039684 | 3/2014 |
| WO | 2014039702 | 3/2014 |
| WO | 2014065596 A1 | 5/2014 |
| WO | 2014071219 A1 | 5/2014 |
| WO | 2014089290 A1 | 6/2014 |
| WO | 2014089513 A1 | 6/2014 |
| WO | 2014089533 A2 | 6/2014 |
| WO | 2014093595 A1 | 6/2014 |
| WO | 2014093622 A2 | 6/2014 |
| WO | 2014093635 A1 | 6/2014 |
| WO | 2014093655 A2 | 6/2014 |
| WO | 2014093661 A2 | 6/2014 |
| WO | 2014093688 A1 | 6/2014 |
| WO | 2014093694 A1 | 6/2014 |
| WO | 2014093701 A1 | 6/2014 |
| WO | 2014093709 A1 | 6/2014 |
| WO | 2014093712 A1 | 6/2014 |
| WO | 2014093718 A1 | 6/2014 |
| WO | 2014099744 A1 | 6/2014 |
| WO | 2014099750 A2 | 6/2014 |
| WO | 2014144288 A1 | 9/2014 |
| WO | 2014145599 A2 | 9/2014 |
| WO | 2014150624 A1 | 9/2014 |
| WO | 2014152432 A2 | 9/2014 |
| WO | 2014153118 A1 | 9/2014 |
| WO | WO2014144592 A2 | 9/2014 |
| WO | WO2014144761 A2 | 9/2014 |
| WO | 2014039970 A9 | 10/2014 |
| WO | 2014159719 A1 | 10/2014 |
| WO | 2014165349 A1 | 10/2014 |
| WO | 2014165825 A2 | 10/2014 |
| WO | 2014172458 A1 | 10/2014 |
| WO | 2014172470 A2 | 10/2014 |
| WO | 2014186585 A2 | 11/2014 |
| WO | 2014191128 A1 | 12/2014 |
| WO | 2014191518 A1 | 12/2014 |
| WO | 2014191521 A2 | 12/2014 |
| WO | 2014197568 A2 | 12/2014 |
| WO | 2014201015 A2 | 12/2014 |
| WO | 2014204725 A1 | 12/2014 |
| WO | 2014204726 A1 | 12/2014 |
| WO | 2015006294 A2 | 1/2015 |
| WO | 2015006437 A1 | 1/2015 |
| WO | 2015006498 A2 | 1/2015 |
| WO | 2015013583 A2 | 1/2015 |
| WO | 2015026883 A1 | 2/2015 |
| WO | 2015026885 A1 | 2/2015 |
| WO | 2015026886 A1 | 2/2015 |
| WO | 2015030881 A1 | 3/2015 |
| WO | 2015033293 A1 | 3/2015 |
| WO | 2015035136 A2 | 3/2015 |
| WO | 2015035139 A2 | 3/2015 |
| WO | 2015035162 A2 | 3/2015 |
| WO | 2015040075 A1 | 3/2015 |
| WO | 2015052133 A1 | 4/2015 |
| WO | 2015052231 A2 | 4/2015 |
| WO | 2015053995 A1 | 4/2015 |
| WO | 2015054253 A1 | 4/2015 |
| WO | 2015054375 A2 | 4/2015 |
| WO | 2015066636 A2 | 5/2015 |
| WO | 2015066637 A1 | 5/2015 |
| WO | 2015070083 A1 | 5/2015 |
| WO | 2015075056 A1 | 5/2015 |
| WO | 2015089277 A1 | 6/2015 |
| WO | 2015089351 A1 | 6/2015 |
| WO | 2015089354 A1 | 6/2015 |
| WO | 2015089406 A1 | 6/2015 |
| WO | 2015089419 A2 | 6/2015 |
| WO | 2015089427 A1 | 6/2015 |
| WO | 2015089462 A1 | 6/2015 |
| WO | 2015089465 A1 | 6/2015 |
| WO | 2015089473 A1 | 6/2015 |
| WO | 2015089486 A2 | 6/2015 |
| WO | 2014204728 A8 | 7/2015 |
| WO | 2015184259 A1 | 12/2015 |
| WO | 2015184262 A1 | 12/2015 |
| WO | 2015184268 A1 | 12/2015 |
| WO | 2015200334 A1 | 12/2015 |
| WO | 2015200378 A1 | 12/2015 |
| WO | 2015200555 A2 | 12/2015 |
| WO | 2015200725 A1 | 12/2015 |
| WO | 2014204723 A9 | 2/2016 |
| WO | 2016022363 A2 | 2/2016 |
| WO | 2014204724 A9 | 3/2016 |
| WO | 2016033246 A1 | 3/2016 |
| WO | 2016033315 A2 | 3/2016 |
| WO | 2016046288 A1 | 3/2016 |
| WO | 2016049024 A2 | 3/2016 |
| WO | 2016049163 A2 | 3/2016 |
| WO | 2016049251 A1 | 3/2016 |
| WO | 2016049657 A1 | 3/2016 |
| WO | 2016057755 A1 | 4/2016 |
| WO | 2016057800 A1 | 4/2016 |
| WO | 2016057821 A2 | 4/2016 |
| WO | 2016057835 A2 | 4/2016 |
| WO | 2016057951 A2 | 4/2016 |
| WO | 2016069282 A1 | 5/2016 |
| WO | 2016069283 A1 | 5/2016 |
| WO | 2016070037 A2 | 5/2016 |
| WO | 2016073079 A2 | 5/2016 |
| WO | 2017104404 A1 | 6/2017 |
| WO | 2017105991 A1 | 6/2017 |
| WO | 2017106414 A1 | 6/2017 |
| WO | 2017106569 A1 | 6/2017 |
| WO | 2017106657 A1 | 6/2017 |
| WO | 2017106767 A1 | 6/2017 |

OTHER PUBLICATIONS

Frock et al., "Genome-wide detection of DNA double-stranded breaks induced by engineered nucleases," Nat. Biotechnol., vol. 33, pp. 179-186, (2015).

Gao et al., "Single Cas9 nickase induced generation of NRAMP1 knockin cattle with reduced off-target effects," Genome Biol., vol. 18, p. 13, (2017).

(56) References Cited

OTHER PUBLICATIONS http://crispr.mit.edu, Accessed Apr. 18, 2017.
http://www.rgenome.net/Cas-OFF-Finder, Accessed Apr. 18, 2017.
https://cm.jefferson.edu/Off-Spotter, Accessed Apr. 18, 2017.
Piccirilli, J.A., et al., "Enzymatic Incorporation of a New Base pair into DNA and RNA Extends the Genetic Alphabet." Nature, vol. 343, 33, (1990).
Schneider et al., "Information Content of Binding Sites on Nucleotide Sequences" J. Mol. Biol., 188, 415-431 (1986).
Kuznetsova, S.A., "Synthesis and properties of DNA duplexes containing hydrocarbon bridges instead of a nucleoside residue", Bioorganicheskala khimiia/Akademiia nauk SSSR, vol. 14:12, pp. 1656-1662, (1988).
Miller et al., "An improved zinc-finger nuclease architecture for highly specific genome editing", nat. Biotechnol. vol. 25, pp. 778-785, (2007).
New England Biolabs Catalog, 1996.
Ran, et al., "In vivo genome editing using *Staphylococcus aureus* Cas9", Nature, vol. 520, pp. 186-191, (2015).
Rappaport, H.P., "Replication of the Base Pair 6-Thioguanine/S-Methyl-2-pyrimidinonwe ith the Large Klenow Fragment of *Escherichia coli* DNA Polymerase I", Biochemistry, vol. 32, p. 3047, (1993).
Shabarova, "Synthesis and properties of DNA duplexes containing hydrocarbon bridges instead of a nucleoside residue", Bioorg. Khim., vol. 14:12, pp. 1656-1662 (1988).
Gori et al., "Delivery and specificity of CRISPR/Cas9 genome editing technologies for human gene therapy," Hum. Gene Ther., vol. 26, pp. 443-451, (2015).
Szczpek et al., "Structure-based redesign of the dimerization interface reduces the toxicity of zinc-finger nucleases", Nat. Biotechnol., vol. 25, pp. 786-793, (2007).
Tietze et al., "Squaric Acid Diethyl Ester: A New Coupling Reagent for the formation of Drug Biopolymer conjugates. Synthesis of Squaric Acid Ester Amides and Diamides", Chem Ber., vol. 124, pp. 1215-1221, (1991).
Fu et al., "Distinct patterns of Cas9 mismatch tolerance in vitro and in vivo," Nucleic Acids Res., vol. 44, pp. 5365-5377, (2016).
Cradick et al., "CRISPR/Cas9 systems targeting R-globin and CCR5 genes have substantial off-target activity," Nucleic Acids Res., vol. 41, pp. 9584-9592, (2013).
Davis et al., "Small molecule-triggered Cas9 protein with improved genome-editing specificity," Nat. Chem. Biol., vol. 11, pp. 316-318, (2013).
Doench et al., "Optimized sgRNA design to maximize activity and minimize off-target effects of CRISPR-Cas9," Nat. Biotechnol., vol. 34, pp. 184-191 (2016).
Guilinger et al., "Fusion of catalytically inactive Cas9 to FokI nuclease improves the specificity of genome modification," Nat. Biotechnol. 32, 577-582 (2014).
Haeussler et al., "Evaluation of off-target and on-target scoring algorithms and integration into the guide RNA selection tool CRISPOR," Genome Biol. 17, 148 (2016).
Havlicek et al., "Re-engineered RNA-guided FokI-nucleases for improved genome editing in human cells," Mol. Ther. 25, 342-355 (2017).
Hendel et al., "Quantifying genome-editing outcomes at endogenous loci with SMRT sequencing," Cell Rep. 7, 293-305 (2014).
Hruscha et al., "Efficient CRISPR/Cas9 genome editing with low off-target effects in zebrafish," Development 140, 4982-4987 (2013).
Hsu et al., "DNA targeting specificity of RNA-guided Cas9 nucleases," Nat. Biotechnol. 31, 827-832 (2013).
Hu et al., "Detecting DNA double-stranded breaks in mammalian genomes by linear amplification-mediated high-throughput genome-wide translocation sequencing," Nat Protoc. 11, 853-871 (2016).
Iyer et al. "Off-target mutations are rare in Cas9-modified mice," Nat. Methods 12, 479 (2015).
Kim et al., "Highly Efficient RNA-guided genome editing in human cells via delivery of purified Cas9 ribonucleoproteins," Genome Res. 24, 1012-1019 (2014).

Kim et al., "Digenome-seq: genome-wide profiling of CRISPR-Cas9 off-target effects in human cells," Nat. Methods 12, 237-243 (2015).
Kim et al., "Genome-wide target specificities of CRISPR-Cas9 nucleases revealed by multiplex Digenome-seq," Genome Res. 26, 406-415 (2016).
Kim et al., "Genome-wide analysis reveals specificities of Cpf1 endonucleases in human cells," Nat. Biotechnol. 34, 863-868 (2016).
Kleinstiver et al., "High-fidelity CRISPR-Cas9 nucleases with no detectable genome-wide off-target effects," Nature 529, 490-495 (2016).
Kleinstiver et al., "Genome-wide specificities of CRISPR-Cas Cpf1 nucleases in human cells," Nat. Biotechnol. 34, 869-874 (2016).
Knight et al. "Dynamics of CRISPR-Cas9 genome interrogation in living cells," Science 350, 823-826 (2015).
Komor et al., "Programmable editing of a target base in genomic DNA without double-stranded DNA cleavage," Nature 533, 420-424 (2016).
Koo et al., "Measuring and reducing off-target activities of programmable nucleases including CRISPR-Cas9," Mol. Cells 38, 475-481 (2015).
Kuscu et al., "Genome-wide analysis reveals characteristics of off-target sites bound by Cas9 endonuclease," Nat. Biotechnol. 32, 677-683 (2014).
Lee et al., "Nuclease target site selection for maximizing on-target activity and minimizing off-target effects in genome editing," Mol. Ther. 24, 475-487 (2016).
Ledford, "CRISPR, the Disruptor," Nature 522, 20-24 (2015).
Lim et al., "Structural roles of guide RNAs in the nuclease activity of Cas9 endonuclease," Nat. Commun. 7, 13350 (2016).
Lin et al., "CRISPR/Cas9 systems have off-target activity with insertions or deletions between target DNA and guide RNA sequences," Nucleic Acids Res. 42, 7473-7485 (2014).
Ma et al., "CRISPR-Cas9 nuclear dynamics and target recognition in living cells," J. Cell Biol. 214, 529-537 (2016).
Pattanayak et al., "High-throughput profiling of off-target DNA cleavage reveals RNA-programmed Cas9 nuclease specificity," Nat Biotechnol. 31, 839-843 (2013).
Peterson et al., "Genome-wide assessment of efficiency and specificity in CRISPR/Cas9 mediated multiple site targeting in *Arabidopsis*," PLoS One 11, e0162169 (2016).
Polstein et al., "Genome-wide specificity of DNA binding, gene regulation, and chromatin remodeling by TALE- and CRISPR/Cas9-based transcriptional activators," Genome Res. 25, 1158-1169 (2015).
Qiu et al., "Mutation detection using Surveyor™ nuclease," Biotechniques 36, 702-707 (2004).
Dellinger et al., "Solid-Phase Chemical Synthesis of Phosphonoacetate and Thiophosphonoacetate Oligodeoxynucleotides," J. Am. Chem. Soc. (2003), 125, 940-50.
Dellinger et al., "Streamlined Process for the Chemical Synthesis of RNA Using 2-O-Thionocarbamate-Protected Nucleoside Phosphoramidites in the Solid Phase," J. Am. Chem. Soc. (2011), 133, 11540-56.
Kumar et al., "Template-Directed Oligonucleotide Strand Ligation, Covalent Intramolecular DNA Circularization and Catenation Using Click Chemistry," J. Am. Chem. Soc. (2007), 129, 6859-64.
Mojibul et al., "DNA-associated click chemistry," Sci. China Chem. (2014), 57:2, 215-31.
Threlfall et al., "Synthesis and biological activity of phosphonoacetate- and thiophosphonoacetate-modified 2-O-methyl oligoribonucleotides," Org. Biomol. Chem. (2012), 10, 746-54.
Yamada et al., "Synthesis and Biochemical Evaluation of Phosphonoformate Oligodeoxyribonucleotides" J. Am. Chem. Soc. (2006), 128:15, 5251-61.
Zhang et al., "Evolution of Functional Six-Nucleotide DNA", J. Am. Chem. Soc., 2015, 137 (21), 6734-6737.
Karvelis, et al., "crRNA and tracrRNA guide Cas9-mediated DNA interference in *Streptococcus thermophilus*", RNA Biology, vol. 10, No. 5, May 2013, 841-851.
PCT, "International Search Report and Written Opinion dated Apr. 19, 2016", Application No. PCT/US2015/000143.
Zheng et al. "Profiling single-guide RNA specificity reveals a mismatch sensitive core sequence," Sci. Rep. 7, 40638 (2017).

(56) References Cited

OTHER PUBLICATIONS

Ren et al., "Enhanced specificity and efficiency of the CRISPR/Cas9 system with optimized sgRNA parameters in *Drosophila*," Cell Rep. 9, 1151-1162 (2014).
Semenova et al., "Interference by clustered regularly interspaced short palindromic repeat (CRISPR) RNA is governed by a seed sequence," Proc. Natl. Acad. Sci. USA 108, 10098-10103 (2011).
Shen et al., "Efficient genome modification by CRISPR-Cas9 nickase with minimal off-target effects," Nat. Methods 11, 399-402 (2014).
Singh et al., "Cas9-chromatin binding information enables more accurate CRISPR off-target prediction," Nucleic Acids Res. 43, e118 (2015).
Singh et al., "Real-time observation of DNA recognition and rejection by the RNA-guided endonuclease Cas9," Nat. Commun. 7, 12778 (2016).
Slaymaker et al., "Rationally engineered Cas9 nucleases with improved specificity", Science 351, 84-88 (2016).
Smith et al., "Whole-genome sequencing analysis reveals high specificity of CRISPR/Cas9 and TALEN-based genome editing in human iPSCs," Cell Stem Cell. 15, 12-13 (2014).
Zischewski et al. "Detection of on-target and off-target mutations generated by CRISPR/Cas9 and other sequence-specific nucleases," Biotech. Adv. 35, 95-104 (2017).
Tsai et al., "GUIDE-seq enables genome-wide profiling of off-target cleavage by CRISPR-Cas nucleases," Nat. Biotechnol. 33, 187-197 (2015).
Tsai & Joung, "Defining and improving the genome-wide specificities of CRISPR-Cas9 nucleases," Nat. Rev. Genet. 17, 300-312 (2016).
Tycko et al., "Methods for optimizing CRISPR-Cas9 genome editing specificity," Mol. Cell 63, 355-370 (2016).
Wang et al., "Unbiased detection of off-target cleavage by CRISPR-Cas9 and TALENs using integrase-defective lentiviral vectors," Nat. Biotechnol. 33, 175-178 (2015).
Wu et al., "Genome-wide binding of the CRISPR endonuclease Cas9 in mammalian cells," Nat. Biotechnol. 32, 670-676 (2014).
Wu et al., "Target specificity of the CRISPR-Cas9 system," Quant. Biol. 2, 59-70 (2014).
Wyvekens et al., "Dimeric CRISPR RNA-guided FokI-dCas9 nucleases directed by truncated gRNAs for highly specific genome editing," Hum. Gene Ther. 26, 425-431 (2015).
Yang et al., "Targeted and genome-wide sequencing reveal single nucleotide variations impacting specificity of Cas9 in human stem cells," Nat. Commun. 5, 5507 (2014).
Zetsche et al., "Cpf1 is a single RNA-guided endonuclease of a Class 2 CRISPR-Cas system," Cell, 163, 759-771 (2015).
Belfort, et al., "Homing Endonucleases: Keeping the House in Order", Nucleic Acids Research, vol. 25, 1997, 3379-3388.
Briner, et al., "Guide RNA Functional Modules Direct Cas9 Activity and Orthogonality", Mol. Cell, vol. 56, 2014, 333-339.
Chen, et al., "Dynamic Imaging of Genomic Loci in Living Human Cells by an Optimized CRISPR/Cas System", Cell, vol. 155, 2013, 1479-1491.
Cho, et al., "Targeted Genome Engineering in Human Cells with the Cas9 RNA-guided Endonuclease", Nat. Biotechnol, vol. 33, No. 3, Mar. 2013, 230-232.
Cong, et al., "Multiplex Genome Engineering Using Crispr / Cas Systems", Science 339, vol. 6121, Feb. 15, 2013, 819-823.
El-Sagheer, "Click Chemistry with DNA", Chem. Soc. Rev., vol. 39, 2010, 1388-1405.
Fu, et al., "High-frequency Off-target Mutagenesis Induced by CRISPR-Cas Nucleases in Human Cells", Nature Biotechnology, vol. 31, No. 9, Sep. 2013, 822-826.
Fu, et al., "Improving CRISPR-Cas Nuclease Specificity Using Truncated Guide RNAs", Nature Biotechnology, vol. 32, No. 3, Mar. 2014, 279-284.
Gasiunas, et al., "Cas9—crRNA Ribonucleoprotein Complex Mediates Specific DNA Cleavage for Adaptive Immunity in Bacteria", Proc. Natl. Acad. Sci., vol. 109, No. 39, 2012, E2579-E2586.
Hendel, et al., "Chemically Modified Guide RNAs Enhance CRISPR-Cas Genome Editing in Human Primary Cells", Nature Biotechnology, vol. 33, No. 9, Sep. 2015, 985-989.
Hwang, et al., "Efficient in Vivo Genome Editing Using RNA-Guided Nucleases", Nat Biotechnol., vol. 31, No. 3, Mar. 2013, 227-229.
Jiang, et al., "A Cas9-guide RNA Complex Preorganized for Target DNA Recognition", Science, vol. 348, Issue 6242, Jun. 26, 2015, 1477-1481.
Jinek, et al., "RNA-programmed Genome Editing in Human Cells", eLife, 2013, 1-9.
Jinek, et al., "Supplementary Materials for A Programmable Dual-RNA-Guided DNA Endonuclease in Adaptive Bacterial Immunity", Science, vol. 337, 2012, 37 Pages.
Krueger, et al., "Synthesis and Properties of Size-expanded DNAs: Toward Designed, Functional Genetic Systems", Acc. Chem. Res., vol. 40, No. 2, Feb. 2007, 141-150.
Lahoud, et al., "Enzymatic Synthesis of Structure-free DNA with Pseudo-complementary Properties", Nucl. Acids Res., vol. 36, No. 10, 2008, 3409-3419.
Lange, et al., "Classical Nuclear Localization Signals: Definition, Function, and Interaction with Importin a*", J. Biol. Chem., vol. 282, 2007, 5101-5105.
Lujambio, et al., "Genetic Unmasking of an Epigenetically Silenced Micro RNA in Human Cancer Cells", Spanish National Cancer Centre, Cancer Res., vol. 67, Feb. 2007, 1424-1429.
Mali, et al., "CAS9 transcriptional activators for target specificity screening and paired nickases for cooperative genome engineering", Nature Biotechnology, vol. 31, 2013, 833-838.
Mali, et al., "RNA-Guided Human Genome Engineering via CAS9", Science, vol. 339, No. 6121, Feb. 15, 2013, 823-826.
Niishimasu, et al., "Crystal Structure of Cas9 in Complex with Guide RNA and Target DNA", Cell, vol. 156(5), Feb. 27, 2014, 935-49.
Ran, et al., "Double Nicking by RNA-Guided CRISPR Cas9 For Enhanced Genome Editing Specificity", Cell, vol. 154, No. 6, Sep. 12, 2013, 1380-1389.
Shechner, et al., "CRISPR Display: A Modular Method for Locus-specific Targeting of Long Noncoding RNAs and Synthetic RNA Devices in Vivo", Nat. Methods, vol. 12, No. 7, 2015, 664-670.
Tsai, et al., "Dimeric CRISPR RNA-Guided FokI Nucleases for Highly Specific Genome Editing", Nat. Biotechnol, vol. 32, No. 6, Jun. 2014, 569-576.
Zhang, et al., "Evolution of Functional Six-Nucleotide DNA", J. Am. Chem. Soc., vol. 137, No. 21, 2015, 6734-6737.
Nishimasu et al., "Crystal Structure of Cas9 in Complex with Guide RNA and Target DNA," Cell (2014) 156, 1-15.
Jiang et al., "A Cas9-guide RNA complex preorganized for target DNA recognition," Science (2015) 348:6242, 1477-81.
Hendel et al., "Chemically modified guide RNAs enhance CRISPR-Cas genome editing in human primary cells," Nat. Biotechnol. (2015) 33:9, 985-9.
Yang et al., "Artificially expanded genetic information system: a new base pair with an alternative hydrogen bonding pattern," Nucleic Acids Res. (2006), 34, 6095-101.
Krueger et al., "Synthesis and Properties of Size-Expanded DNAs: Toward Designed, Functional Genetic Systems"; Acc. Chem. Res. (2007), 40, 141-50.
Lahoud et al., "Enzymatic synthesis of structure-free DNA with pseudo-complementary properties," Nucl. Acids Res. (1991), 36:10, 3409-19.
Gasiunas et al., "Cas9-crRNA ribonucleoprotein complex mediates specific DNA cleavage for adaptive immunity in bacteria," Proc. Natl. Acad. Sci. USA (2012), 109:39, E2579-E2586.
El-Sagheer et al.,"Click chemistry with DNA", Chem. Soc. Rev. (2010), 39, 1388-1405.
Briner et al., "Guide RNA Functional Modules Direct Cas9 Activity and Orthogonality," Mol. Cell (2014), 56, 333-9.
Schechner et al., "CRISPR Display: A modular method for locus-specific targeting of long noncoding RNAs and synthetic RNA devices in vivo," Nat. Methods (2015), 12(7): 664-670.

(56) References Cited

OTHER PUBLICATIONS

Chen et al., "Dynamic Imaging of Genomic Loci in Living Human Cells by an Optimized CRISPR/Cas System," Cell (2013), 155, 1479-1491.
Jinek et al., "A Programmable Dual-RNA-Guided DNA Endonuclease In Adaptive Bacterial Immunity," Science (2012), 337, 816-21.
Mali et al., "RNA-Guided Human Genome Engineering via Cas9," Science (2013), 339:6121, 823-6.
Cong et al., "Multiplex Gemone Engineering Using CRISPR/Cas Systems," Science (2013), 339:6121, 819-23.
Hwang et al., "Efficient in Vivo Genome Editing Using RNA-Guided Nucleases," Nat. Biotechnol. (2013) 31:3, 227-9.
Jinek et al., "RNA-programmed genome editing in human cells," eLife (2013), 2, e00471.
Belfort et al., "Homing endonucleases: keeping the house in order," Nucleic Acids Res. (1997), 25, 3379-88.
Lange et al., "Classical Nuclear Localization Signals: Definition, Function, and Interaction with Importin," J. Biol. Chem. (2007), 282, 5101-5.
Lujambo et al., "Genetic Unmasking of an Epigenetically Silenced microRNA in Human Cancel Cells," (Spanish National Cancer Centre) Cancer Res. Feb. 2007.
Cho et al., "Targeted genome engineering in human cells with the Cas9 RNA-guided endonuclease," (Seoul National Univ.) Nat. Biotechnol. Mar. 2013.
Ran et al., "Double nicking by RNA-guided CRISPT Cas9 for enhanced genome editing specificity," Cell (2013), 154, 1380-9.
Tsai et al., "Dimeric CRISPR RNA-guided FokI nucleases for highly specific genome editing," Nat. Biotechnol. (2014), 32, 569-76.
Fu et al., "Improving CRISPR-Cas nuclease specificity using truncated guide RNAs," Nat. Biotechnol. (2014), 32, 279-84.
Mali et al., "CAS9 transcriptional activators for target specificity screening and paired nickases for cooperative genome engineering," Nat. Biotechnol. (2013), 31, 833-8.
Deng, Wulan et al., CASFISH: CRISPR/Cas9-Mediated In Situ Labeling Of Genomic Loci In Fixed Cells, Proceedings of The National Academy of Sciences, vol. 112, No. 38, Sep. 22, 2015, 11870-11875.
Extended European Search Report dated Jun. 13, 2018, Application No. 15866342.7, 14 pages.
Hendel, Ayal et al., Chemically Modified Guide RNAs Enhance Crispr-cas Genome Editing in Human Primary Cells, Nature Biotechnology, vol. 33, No. 9, Sep. 2015, 985-989.
Rahdar, Meghdad et al., Synthetic CRISPR RNA-Cas9-Guided Genome Editing Human Cells, Proceedings of The National Academy Of Sciences., Nov. 16, 2015, 8 pages.

* cited by examiner

Standard cleavage conditions:

| stock | volume (uL) | conc. | stoich. |
|---|---|---|---|
| 10x buffer | 2.0 | 1x | |
| 125 ng/uL Cas9 wt protein | 1.0 | 40 nM | 16 — if every ng of Cas9 in our protein prep were active |
| 1 uM guide RNA | 1.0 | 50 nM | 20 |
| 25 ng/uL linearized CLTA target | 4.0 | 2.5 nM | 1 |
| ddH2O (DEPC-treated) | 12.0 | | |
| | 20.0 | | |

In a pre-warmed SureCycler:

(i) incubate at 37 °C for 30 min (ii) + RNase cocktail, incubate at 37 °C for 5 min, then at 70 °C for 15 min (iii) + Proteinase K, incubate at 37 °C for 15 min Analyze crude products on Bioanalyzer.

FIG. 3

TABLE 1

| Name of synthetic guide RNA | SEQ ID NO | Length (nt) | % Cleaved target in vitro | Sequence (5' → 3') |
|---|---|---|---|---|
| Chemical modifications tolerated by Cas9 | | | | |
| CLTA1 (unmodified control) | 42 | 113 | 95% | AGUCCUCAUCUCCCUCAAGCGUUUAAGAGCUAUGCUGGUAACAGCA UAGCAAGUUUAAAUAAGGCUAGUCCGUUAUCAACUUGAAAAAGUGG CACCGAGUCGGUGCUUUUUU |
| 2xOMePACE_CLTA1 | 91 | 113 | 95% | A*G*UCCUCAUCUCCCUCAAGCGUUUAAGAGCUAUGCUGGUAACAG CAUAGCAAGUUUAAAUAAGGCUAGUCCGUUAUCAACUUGAAAAAAGU GGCACCGAGUCGGUGCUUUUUU |
| 4xOMePACE_CLTA1 | 93 | 113 | 88% | A*G*U*C*CUCAUCUCCCUCAAGCGUUUAAGAGCUAUGCUGGUAAC AGCAUAGCAAGUUUAAAUAAGGCUAGUCCGUUAUCAACUUGAAAAA GUGGCACCGAGUCGGUGCUUUUUU |
| CLTA1_4xOMePACE | 95 | 113 | 91% | AGUCCUCAUCUCCCUCAAGCGUUUAAGAGCUAUGCUGGUAACAGCA UAGCAAGUUUAAAUAAGGCUAGUCCGUUAUCAACUUGAAAAAGUGG CACCGAGUCGGUGCUUU*U*U*U |
| CLTA1_5xOMePACE | 96 | 113 | 91% | AGUCCUCAUCUCCCUCAAGCGUUUAAGAGCUAUGCUGGUAACAGCA UAGCAAGUUUAAAUAAGGCUAGUCCGUUAUCAACUUGAAAAAGUGG CACCGAGUCGGUGCUU*U*U*U*U |
| CLTA1_2'OMe+20 | 67 | 113 | 93% | AGUCCUCAUCUCCCUCAAGCGUUUAAGAGCUAUGCUGGUAACAGCA UAGCAAGUUUAAAUAAGGCUAGUCCGUUAUCAACUUGAAAAAGUGG CACCGAGUCGGUGCUUUUUU |
| CLTA1_2'OMe+19 | 68 | 113 | 93% | AGUCCUCAUCUCCCUCAAGCGUUUAAGAGCUAUGCUGGUAACAGCA UAGCAAGUUUAAAUAAGGCUAGUCCGUUAUCAACUUGAAAAAGUGG CACCGAGUCGGUGCUUUUUU |
| CLTA1_2'OMe+18 | 69 | 113 | 91% | AGUCCUCAUCUCCCUCAAGCGUUUAAGAGCUAUGCUGGUAACAGCA UAGCAAGUUUAAAUAAGGCUAGUCCGUUAUCAACUUGAAAAAGUGG CACCGAGUCGGUGCUUUUUU |
| CLTA1_2'OMe+17 | 70 | 113 | 93% | AGUCCUCAUCUCCCUCAAGCGUUUAAGAGCUAUGCUGGUAACAGCA UAGCAAGUUUAAAUAAGGCUAGUCCGUUAUCAACUUGAAAAAGUGG CACCGAGUCGGUGCUUUUUU |

FIG. 4

| Name | | | Sequence |
|---|---|---|---|
| CLTA1_2'OMe+17,18 | 71 | 113 | 90% | AGUCCUCAUCUCCCUCAAGCGUUUAAGAGCUAUGCUGGUAACAGCA UAGCAAGUUUAAAUAAGGCUAGUCCGUUAUCAACUUGAAAAAGUGG CACCGAGUCGGUGCUUUUUUU |
| CLTA1_20_Deoxy | 131 | 113 | 7% | AGUCCUCAUCUCCCUCAAGCGUUUAAGAGCUAUGCUGGUAACAGCA UAGCAAGUUUAAAUAAGCUAGUCCGUUAUCAACUUGAAAAAGUGG CACCGAGUCGGUGCUUUUUUU |
| CLTA1_20_2'OMe | 74 | 113 | 89% | AGUCCUCAUCUCCCUCAAGCGUUUAAGAGCUAUGCUGGUAACAGCA UAGCAAGUUUAAAUAAGGCUAGUCCGUUAUCAACUUGAAAAAGUGG CACCGAGUCGGUGCUUUUUUU |
| CLTA1_37_2'OMe | 76 | 113 | 88% | AGUCCUCAUCUCCCUCAAGCGUUUAAGAGCUAUGCUGGUAACAGCA UAGCAAGUUUAAAUAAGGCUAGUCCGUUAUCAACUUGAAAAAGUGG CACCGAGUCGGUGCUUUUUUU |
| CTLA1_5'SS | 63 | 113 | 96% | AsGsUCCUCAUCUCCCUCAAGCGUUUAAGAGCUAUGCUGGAAACAG CAUAGCAAGUUUAAAUAAGGCUAGUCCGUUAUCAACUUGAAAAAGU GGCACCGAGUCGGUGCUUUUUUU |
| CTLA1_5'SSS | 64 | 113 | 94% | AsGsUsCCCUCAUCUCCCUCAAGCGUUUAAGAGCUAGUCCGUUAUGCUGGAAACA GCAUAGCAAGUUUAAAUAAGGCUAGUCCGUUAUCAACUUGAAAAAG UGGCACCGAGUCGGUGCUUUUUUU |
| CTLA1_5'SSSS | 65 | 113 | 100% | AsGsUsCsCUCAUCUCCCUCAAGCGUUUAAGAGCUAUGCUGGAAAC AGCAUAGCAAGUUUAAAUAAGGCUAGUCCGUUAUCAACUUGAAAAA GUGGCACCGAGUCGGUGCUUUUUU |
| CTLA1_3'SSSS | 66 | 113 | 94% | AGUCCUCAUCUCCCUCAAGCGUUUAAGAGCUAUGCUGGUAACAGCA UAGCAAGUUUAAAUAAGGCUAGUCCGUUAUCAACUUGAAAAAGUGG CACCGAGUCGGUGCUUUsUsUsU |
| 3xOMe_CLTA1_3xOMe | 72 | 113 | 89% | AGUCCUCAUCUCCCUCAAGCGUUUAAGAGCUAUGCUGGUAACAGCA UAGCAAGUUUAAAUAAGGCUAGUCCGUUAUCAACUUGAAAAAGUGG CACCGAGUCGGUGCUUUUUUU |
| 3xOMeThio_CLTA1_3xOMeThio | 107 | 113 | 92% | AsGsUsCCCUCAUCUCCCUCAAGCGUUUAAGAGCUAUGCUGGUAACA GCAUAGCAAGUUUAAAUAAGGCUAGUCCGUUAUCAACUUGAAAAAG UGGCACCGAGUCGGUGCUUUsUsUsU |
| 3xOMeThioPACE_CLTA1_3x2'OMeThioPACE | 110 | 113 | 89% | A*sG*sU*sCCUCAUCUCCCAAGCGUUUAAAUAAGAGCUAUGCUGGUA ACAGCAUAGCAAGUUUAAAUAAGCUAGUCCGUUAUCAACUUGAAA AAGUGGCACCGAGUCGGUGCUUUU*sU*sU*sU |

FIG. 4 (cont.)

| | | | |
|---|---|---|---|
| CLTA1_ZZ_70,71 | 122 | 113 | AGUCCUCAUCUCCCUCAAGCGUUUAAGAGCUAUGCUGGUAACAGCA UAGCAAGUUUAAAUAAGGCUAGUZZGUUAUCAACUUGAAAAAGUGG CACCGAGUCGGUGCUUUUUU |
| CLTA1_ZZ_95,96 | 132 | 113 | AGUCCUCAUCUCCCUCAAGCGUUUAAGAGCUAUGCUGGUAACAGCA UAGCAAGUUUAAAUAAGGCUAGUCCGUUAUCAACUUGAAAAAGUGG CANNGAGUCGGUGCUUUUUU |
| CLTA1_QB3+GNRA_DMT-ON | 55 | 113 | (dmt) AGUCCUCAUCUCCCUCAAGCGUUUAAGAGCUAUGCUGGUAA CAGCAUAGCAAGUUUAAAUAAGGCUAGUCCGUUAUCAACUUGAAAA AGUGGCACCGAGUCGGUGCUUUUUU |
| Chemical modifications NOT tolerated by Cas9 | | | |
| CLTA1_37_Deoxy | 133 | 113 | AGUCCUCAUCUCCCUCAAGCGUUUAAGAGCUAUGCUGGUAACAGCA UAGCAAGUUUAAAUAAGGCUAGUCCGUUAUCAACUUGAAAAAGUGG CACCGAGUCGGUGCUUUUUU |

LEGEND

N* = 2'OMe,3'PACE modification of nucleotide N

N*s = 2'OMe,3'thioPACE modification of nucleotide N

N = 2'OMe modification of nucleotide N

N = 2'deoxyribonucleotide N

NsN = phosphorothioate linkage noted by s

Z = Z nucleotide dmt = dimethoxytrityl

FIG. 4 (cont.)

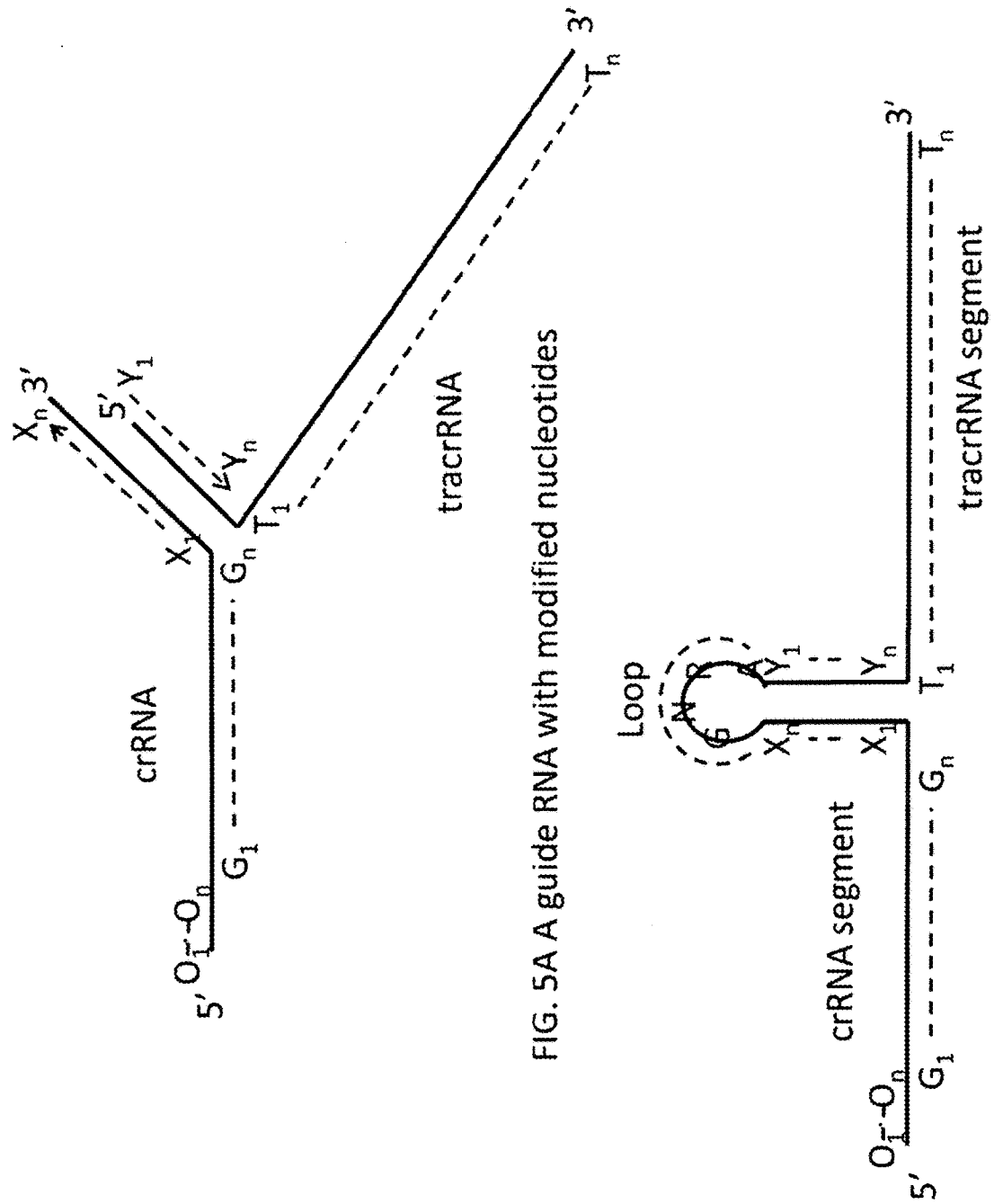

FIG. 6

1. 2'-OMe
2. 2'-H
3. 2'-MOE analog
4. 2'-fluoro analog
5. 2'-amino analog
6. 2'-arabino analog
7. 2'-F-arabino analog
8. 2'-LNA analog
9. 2'-ULNA analog
10. 4'-thioribosyl moiety
11. O-P(S) linkage
12. PACE linkage
13. thioPACE linkage
14. MethylPhosphonate
15. Boranophosphonate
16. Phosphorodithioate
17. 2'-thio(U/C)
18. 4-thiouracil
19. 6-thioguanine
20. 2-aminoadenine
21. 2-aminopurine
22. pseudouracil
23. Hypoxanthine
24. 7-deaza(A/G)
25. 7-deaza-8-aza(A/G)
26. 5-methyl (U/C)
27. 5-hydroxymethyl (U/C)
28. 5,6-dehydrouracil
29. 5-propynyl (U/C)
30. 5-ethynyl (U/C)
31. 5-allyl (U/C)
32. 5-aminoallyl (U/C)
33. 5-methyl-2-pyrimidine
34. Z / P bases
35. UNA
36. x (A/G/C/T)
37. y (A/G/C/T)
38. Iso(C/G)
39. Abasic nucleotide
40. PEG
41. Hydrocarbon spacer
42. Linker-dye
43. Spermine-modification

| Single mod / Double mod | Sugar | Phosphorus Linkage | Base modification* | Other |
|---|---|---|---|---|
| Sugar/Sugar | X | | X | X |
| Sugar/P link | X | X | | X |
| Sugar/Base | X | | X | X |
| Sugar/other | X | | X | X |
| P link/P link | X | X | | X |
| P link/base | | X | X | X |
| P link/other | | X | | X |
| Base/Base | | | X | X |
| Base/other | | | X | X |
| other/other | | | | X |

*Base modifications includes Base Pair Modifications

Sugar modifications ("Sugar"): 2'-O-Methyl (=2'-OMe) (2'-OC$_1$-C$_4$ alkyl), 2'-H, 2'-MOE (2'- OC$_1$-C$_3$ alkyl-OC$_1$-C$_3$ alkyl), 2'-F, 2'-amino, 2'-arabino, 2'-F-arabino, 2'-LNA, 2'-UNLA, 4'-thioribosyl nucleotide.
Internucleotide linkage and 3' and/or 5' terminal nucleotide modifications ("Phosphorus Linkage" or "P link"): -P(S) (phosphorothioate), -PACE (phosphonoacetate, phosphonocarboxylate), -thioPACE (thiophosphonoacetate, thiophosphonocarboxylate), -P(CH$_3$) (methylphosphonate, alkylphosphonate), -P(BH$_3$) (boranophosphonate), -P(S)$_2$ (phosphorodithioate)
Base modifications: 2-thiouracil, 2-thiocytosine, 4-thiouracil, 6-thioguanine, 2-aminoadenine, 2-aminopurine, pseudouracil, hypoxanthine, 7-deazaguanine, 7-deaza-8-azaguanine, 7-deazaadenine, 7-deaza-8-azaadenine, 5-methylcytosine, 5-methyluracil, 5-hydroxymethylcytosine,5-hydroxymethyluracil, 5,6-dehydrouracil, 5-propynylcytosine, 5-propynyluracil, 5-ethynylcytosine, 5-ethynyluracil,5-allylcytosine, 5-allyluracil, 5-aminoallyl-uracil, 5-aminoallyl-cytosine and abasic nucleotides.
Base Pair modifications: Z/P nucleotides, UNA, isoC/isoG, 6-thioG/5-methyl-pyrimidine, x(A,G,C,T) and y(A,G,C,T).
Other: End modifications and/or spacer/linker (ends or internal) modifications: PEG, hydrocarbon spacer, (including: heteroatom (O,S,N)-substituted hydrocarbon spacers, halo-substituted-hydrocarbon spacers, (keto,carboxy,amido,thionyl,carbamoyl,thionocarbamaoyl)-containing hydrocarbon spacers), spermine, dyes linkers including: 6-Fluorescein-phosphoramidite and the like, squarate conjugation, Diels-Alder conjugation, or "Click" chemistry conjugation.

FIG. 7

Using chemical modifications to improve specificity

| Target Name | CLTA1 On- or Off-Target Site | Genomic Coordinates | COSMID Score | MIT Design Score |
|---|---|---|---|---|
| CLTA1 ON1 | AGTCCTCATCTCCCTCAAGCAGG TCAGGAGTAGAGGAGTTCGTCC | Chr9:36211735-36211757 | 0 | 100.0 |
| CLTA1 OFF1 | AGTCCTCAACTCCCTCAAGCAGG TCAGGAGTTGAGGGAGTTCGTCC | Chr8:15688928-15688950 | 0.35 | 61.1 |
| CLTA1 OFF2 | AGCCCTCATTTCCCTCAAGCAGG TCGGGAGTAAAGGGAGTTCGTCC | Chr3:54189084-54189106 | 0.65 | 6.4 |
| CLTA1 OFF3 | ACTCCTCATCCCCTCAAGCCGG TGAGGAGTAGGGGGAGTTCGGCC | Chr15:88845439-88845461 | 0.83 | 4.5 |

Example:
- CLTA1_2thioU+11 crRNA: 5′ AGUCCUCAUC(2sU)CCCUCAAGCGUUUAAGAGCUAUGCUGUUUGA AUGGUCCCAAAAC 3′
- CLTA1_2thioU+9
- CLTA1_2thioU+3

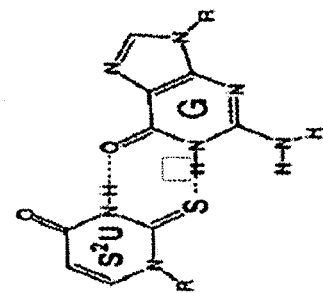

Sulfur in 2-thioU cannot H-bond with G to form a wobble pair that lowers specificity.

FIG. 9A

GUIDE RNA WITH CHEMICAL MODIFICATIONS

CROSS REFERENCE TO RELATED APPLICATIONS

This application claims the benefit of U.S. Provisional Application No. 62/256,095, filed Nov. 16, 2015, U.S. Provisional Application No. 62/146,189, filed Apr. 10, 2015, and U.S. Provisional Application No. 62/087,211, filed Dec. 3, 2014, the contents of each of which is incorporated by reference in its entirety.

SEQUENCE LISTING

The instant application contains a Sequence Listing which has been submitted electronically in ASCII format and is hereby incorporated by reference in its entirety. Said ASCII copy, created on Aug. 5, 2020, is named 20160013_ 04_ SL.txt and is 114,989 bytes in size

FIELD OF THE INVENTION

The present invention relates to the field of molecular biology. In particular, the present invention relates to the clusters of regularly interspaced short palindromic repeats (CRISPR) technology.

BACKGROUND OF THE INVENTION

The native prokaryotic CRISPR-Cas system comprises an array of short repeats with intervening variable sequences of constant length (i.e., clusters of regularly interspaced short palindromic repeats, or "CRISPR"), and CRISPR-associated ("Cas") proteins. The RNA of the transcribed CRISPR array is processed by a subset of the Cas proteins into small guide RNAs, which generally have two components as discussed below. There are at least three different systems: Type I, Type II and Type III. The enzymes involved in the processing of the RNA into mature crRNA are different in the 3 systems. In the native prokaryotic system, the guide RNA ("gRNA") comprises two short, non-coding RNA species referred to as CRISPR RNA ("crRNA") and trans-acting RNA ("tracrRNA"). In an exemplary system, the gRNA forms a complex with a Cas nuclease. The gRNA:Cas nuclease complex binds a target polynucleotide sequence having a protospacer adjacent motif ("PAM") and a protospacer, which is a sequence complementary to a portion of the gRNA. The recognition and binding of the target polynucleotide by the gRNA:Cas nuclease complex induces cleavage of the target polynucleotide. The native CRISPR-Cas system functions as an immune system in prokaryotes, where gRNA:Cas nuclease complexes recognize and silence exogenous genetic elements in a manner analogous to RNAi in eukaryotic organisms, thereby conferring resistance to exogenous genetic elements such as plasmids and phages.

It has been demonstrated that a single-guide RNA ("sgRNA") can replace the complex formed between the naturally-existing crRNA and tracrRNA.

Considerations relevant to developing a gRNA, including a sgRNA, include specificity, stability, and functionality. Specificity refers to the ability of a particular gRNA:Cas nuclease complex to bind to and/or cleave a desired target sequence, whereas little or no binding and/or cleavage of polynucleotides different in sequence and/or location from the desired target occurs. Thus, specificity refers to minimizing off-target effects of the gRNA:Cas nuclease complex. Stability refers to the ability of the gRNA to resist degradation by enzymes, such as nucleases, and other substances that exist in intra-cellular and extra-cellular environments. Thus, there is a need for providing gRNA, including sgRNA, having increased resistance to nucleolytic degradation, increased binding affinity for the target polynucleotide, and/or reduced off-target effects while, nonetheless, having gRNA functionality. Further considerations relevant to developing a gRNA include transfectability and immunostimulatory properties. Thus, there is a need for providing gRNA, including sgRNA, having efficient and titratable transfectability into cells, especially into the nuclei of eukaryotic cells, and having minimal or no immunostimulatory properties in the transfected cells. Another important consideration for gRNA is to provide an effective means for delivering it into and maintaining it in the intended cell, tissue, bodily fluid or organism for a duration sufficient to allow the desired gRNA functionality.

BRIEF DESCRIPTION OF THE DRAWINGS

FIG. 3 shows exemplary conditions and procedures for the biochemical cleavage assay which uses purified components in vitro.

FIG. 4 is a table showing the data obtained using exemplary modified guide RNAs in the cleavage assay.

FIG. 5A shows an exemplary guide RNA disclosed in the application.

FIG. 5B shows an exemplary single guide RNA (sgRNA) disclosed in the application.

FIG. 6 is a table showing exemplary guide RNAs having at least two chemical modifications (e.g., a first modification and a second modification). Each number represents a modification as indicated and each "x" indicates the combination of modifications in a guide RNA. In certain embodiments, the first and second modifications are present on a single nucleotide. In certain embodiments, the first and second modifications are present on separate nucleotides.

FIG. 7 shows exemplary types of guide RNAs having at least three chemical modifications. The lower part of FIG. 7 lists several types of modifications. The table in the upper part of FIG. 7 indicates how a double modification ("double mod," a combination of two types of modifications) can be combined with a single modification ("single mod," one type of modification). An "x" indicates the presence of the corresponding double mod and single mod in a guide RNA.

In FIG. 8A, the RNA sequence (SEQ ID NO: 135) of a sgRNA for CLTA1 is shown, including a position where a fluorescent dye or a label could be attached to the sgRNA. Target DNA is SEQ ID NO: 134. FIG. 8B shows a structure determined by Xray crystallography of a Cas9:sgRNA complex, as reported in Nishimasu et al., *Cell* 2014, 156, 1-15.

FIG. 9A shows CLTA1 sgRNAs modified with 2-thiouridine at certain locations (positions 3, 9 and 11) in an effort to improve specificity for the target CTLA1. Top strand and bottom strand sequences (respectively) of the CTLA1 targets are: ON1 (SEQ ID NOs: 136 and 137); OFF1 (SEQ ID NOs: 138 and 139); OFF2 (SEQ ID NOs: 140 and 141); and OFF3 (SEQ ID NOs: 142 and 143).

DETAILED DESCRIPTION OF THE INVENTION

Figure 1:
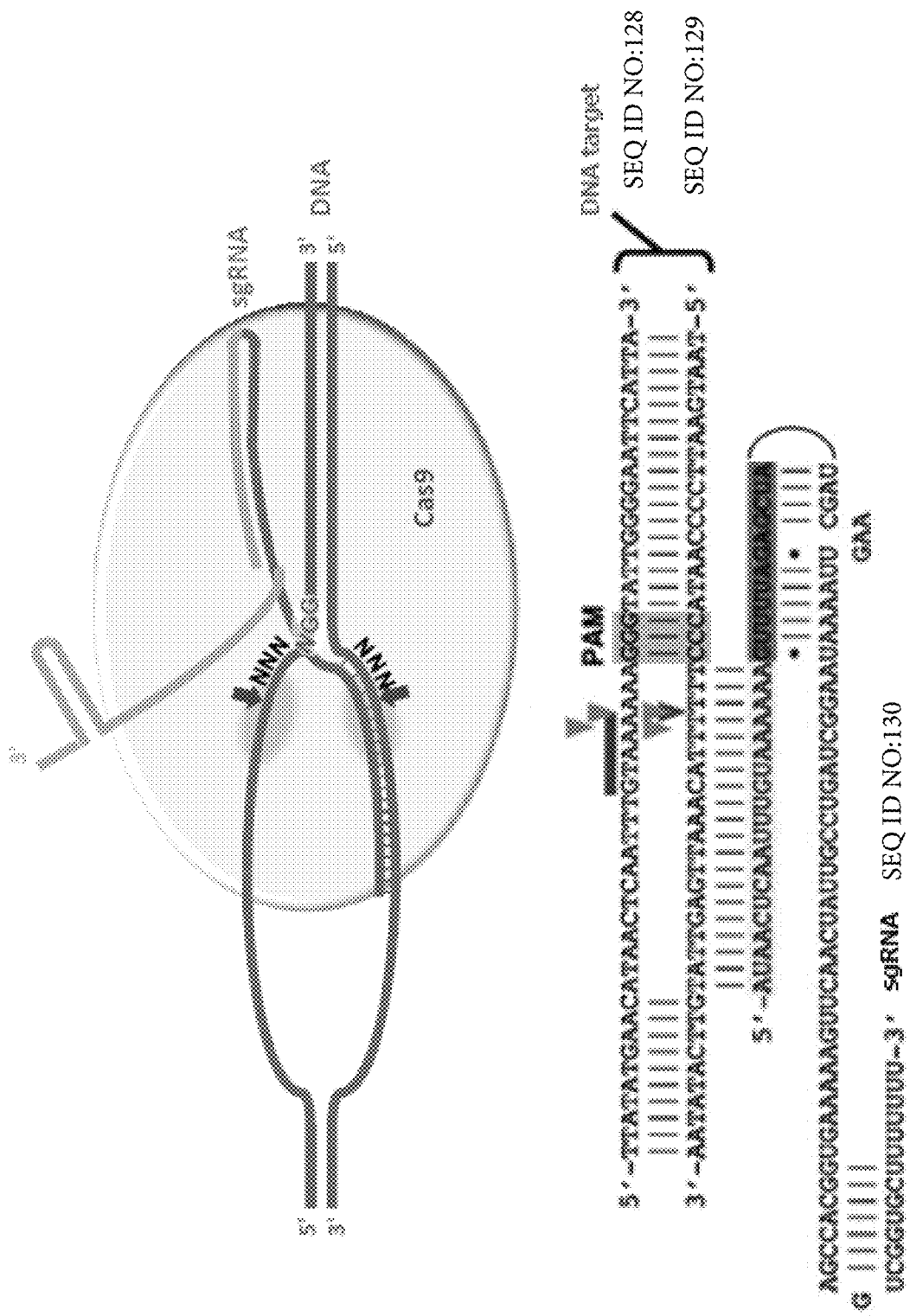
FIG. 1 is a set of diagrams showing a schematic model of an exemplary CRISPR-Cas system. The exemplary system shown here is a Type II system having a Cas nuclease. In this particular example, the Cas nuclease is the Cas9 nuclease. The Cas9 nuclease recognizes a PAM sequence (here, the PAM sequence is a 3-nt sequence of NGG, where N is A, G, C or T, but other PAM sequences are known to exist). The sgRNA includes a guide sequence, a crRNA sequence or segment, and tracrRNA sequence or segment. The guide sequence of the sgRNA hybridizes with the DNA target directly upstream of the PAM sequence. In the example shown here, Cas9 mediates a double-stranded break upstream of the PAM sequence (arrows).
Figures 2A, 2B:
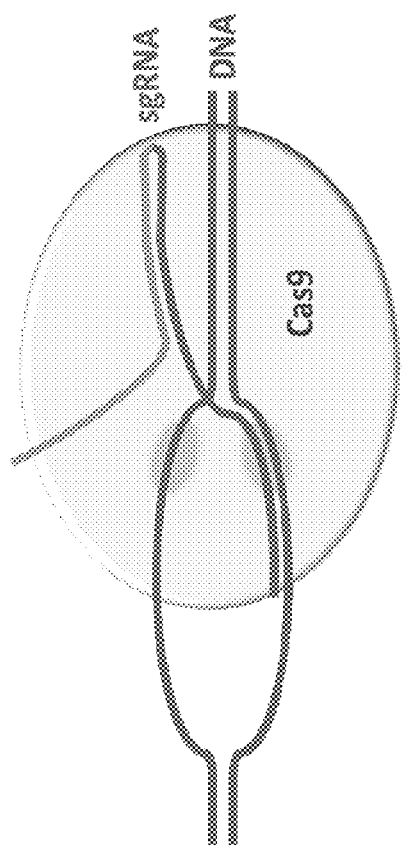
FIG. 2A is a diagram showing an exemplary CRISPR-Cas9-mediated cleavage assay.
FIG. 2B is a table showing components and their concentrations for a biochemical cleavage assay used to generate the data in FIG. 4.
Figures 2C, 2D:
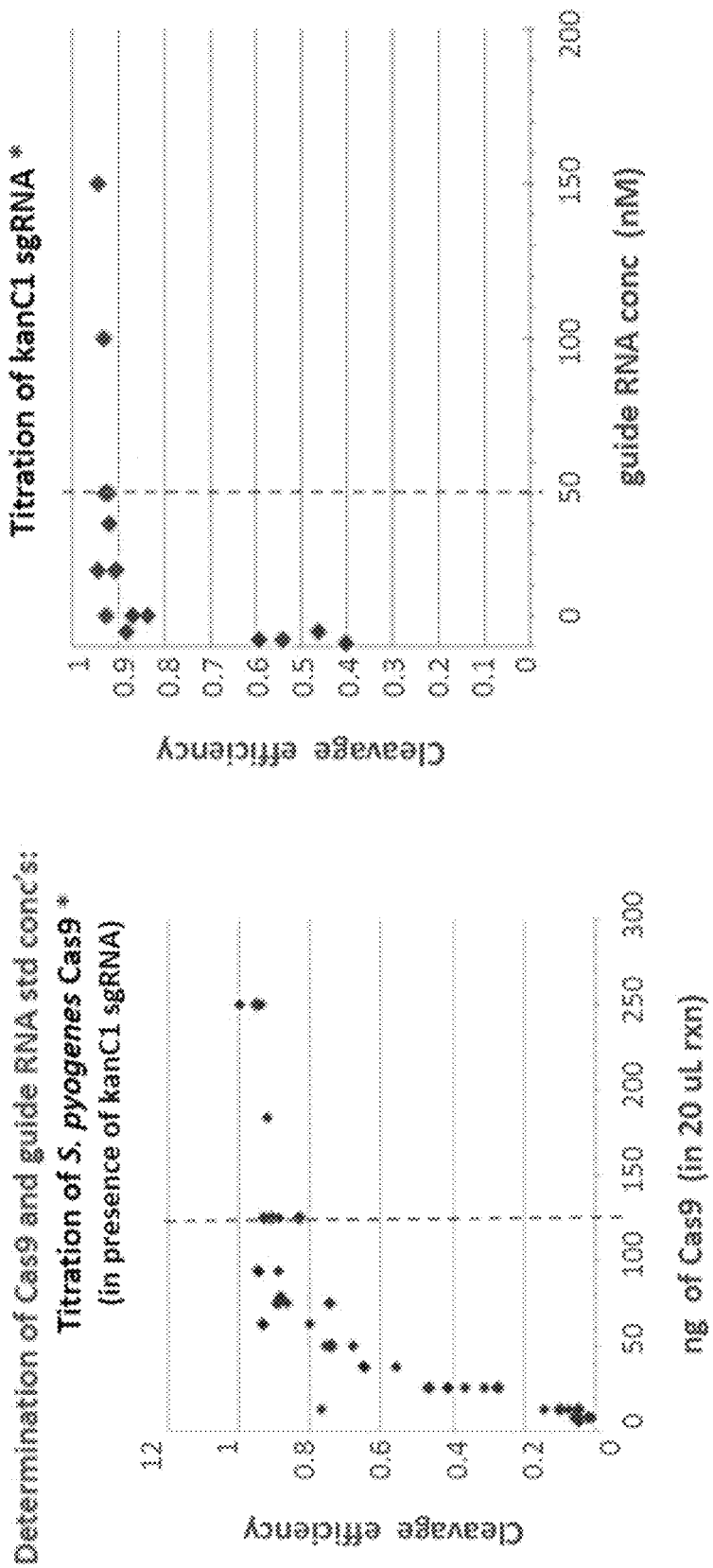
FIG. 2C is a diagram showing titration of *Streptococcus pyogenes* Cas9 nuclease for the biochemical cleavage assay.
FIG. 2D is a diagram showing titration of an exemplary sgRNA for the biochemical cleavage assay. In this example a sgRNA named kanC1 is targeted to a complementary sequence in the kanamycin resistance gene.
Figure 8A:
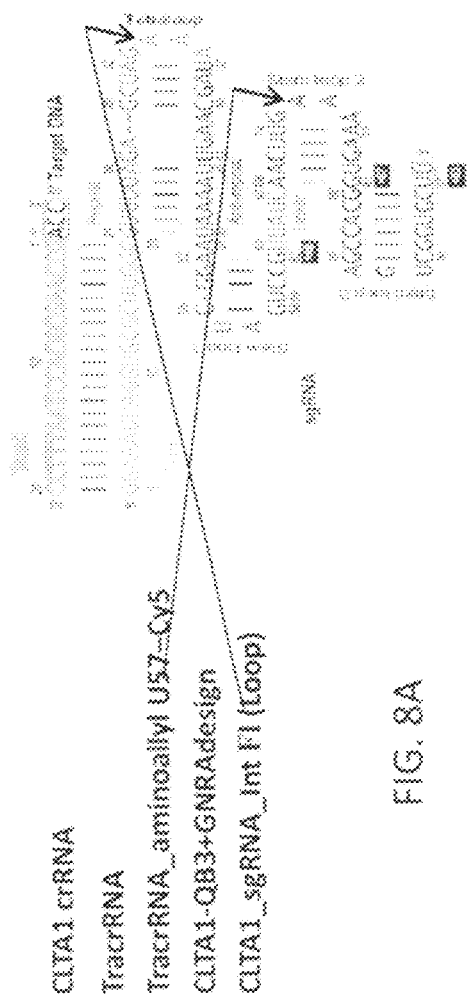
FIGS. 8A and 8B show fluorophore-modified CLTA1 sgRNAs for in vitro testing.
Figure 8B:
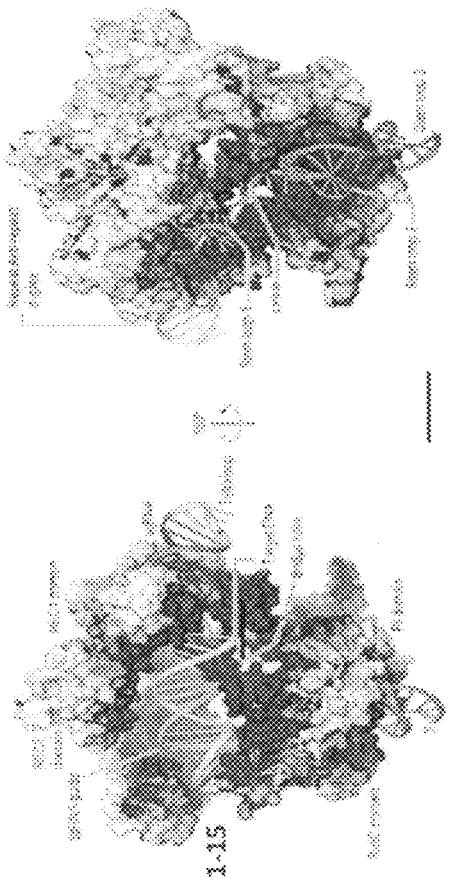
Figure 9B:
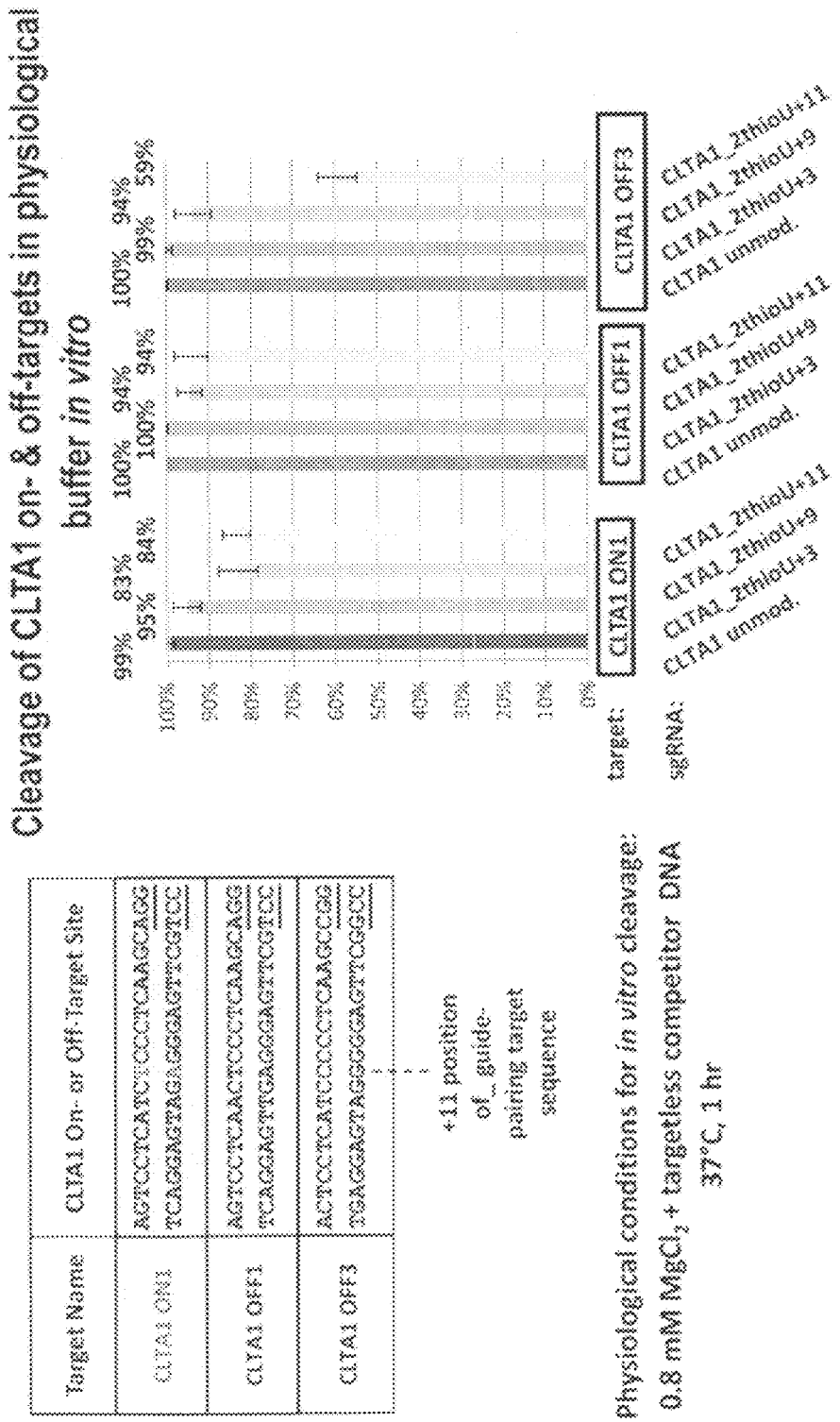
FIG. 9B shows that gRNA modified with 2-thioU (SEQ ID NO: ###) can increase target specificity of the gRNAs when off-target sites involve U-G wobble pairing. In particular, the CTLA1_2thioU+11 had much lower cleavage of the off-target sequence CLTA1 OFF3, which has a T to C mutation at the 11 position in the 5' strand. Top strand and bottom strand sequences (respectively) of the CTLA1 targets are: ON1 (SEQ ID NOs: 136 and 137); OFF1 (SEQ ID NOs: 138 and 139); and OFF3 (SEQ ID NOs: 142 and 143).

This invention is based, at least in part, on an unexpected discovery that certain chemical modifications to gRNA are tolerated by the CRISPR-Cas system. In particular, certain chemical modifications believed to increase the stability of the gRNA, to alter the thermostability of a gRNA hybridization interaction, and/or to decrease the off-target effects of Cas:gRNA complexation do not substantially compromise the efficacy of Cas:gRNA binding to, nicking of, and/or cleavage of the target polynucleotide. Furthermore, certain chemical modifications are believed to provide gRNA, including sgRNA, having efficient and titratable transfectability into cells, especially into the nuclei of eukaryotic cells, and/or having minimal or no immunostimulatory properties in the transfected cells. Certain chemical modifications are believed to provide gRNA, including sgRNA, which can be effectively delivered into and maintained in the intended cell, tissue, bodily fluid or organism for a duration sufficient to allow the desired gRNA functionality.

I. Definitions

As used herein, the term "guide RNA" generally refers to an RNA molecule (or a group of RNA molecules collectively) that can bind to a Cas protein and aid in targeting the Cas protein to a specific location within a target polynucleotide (e.g., a DNA). A guide RNA can comprise a crRNA segment and a tracrRNA segment. As used herein, the term "crRNA" or "crRNA segment" refers to an RNA molecule or portion thereof that includes a polynucleotide-targeting guide sequence, a stem sequence, and, optionally, a 5'-overhang sequence. As used herein, the term "tracrRNA" or "tracrRNA segment" refers to an RNA molecule or portion thereof that includes a protein-binding segment (e.g., the protein-binding segment is capable of interacting with a CRISPR-associated protein, such as a Cas9). The term "guide RNA" encompasses a single guide RNA (sgRNA), where the crRNA segment and the tracrRNA segment are located in the same RNA molecule. The term "guide RNA" also encompasses, collectively, a group of two or more RNA molecules, where the crRNA segment and the tracrRNA segment are located in separate RNA molecules.

The term "scaffold" refers to the portions of guide RNA molecules comprising sequences which are substantially identical or are highly conserved across natural biological species. Scaffolds include the tracrRNA segment and the portion of the crRNA segment other than the polynucleotide-targeting guide sequence at or near the 5' end of the crRNA segment, excluding any unnatural portions comprising sequences not conserved in native crRNAs and tracrRNAs.

The term "nucleic acid", "polynucleotide" or "oligonucleotide" refers to a DNA molecule, an RNA molecule, or analogs thereof. As used herein, the terms "nucleic acid", "polynucleotide" and "oligonucleotide" include, but are not limited to DNA molecules such as cDNA, genomic DNA or synthetic DNA and RNA molecules such as a guide RNA, messenger RNA or synthetic RNA. Moreover, as used herein, the terms "nucleic acid" and "polynucleotide" include single-stranded and double-stranded forms.

The term "modification" in the context of an oligonucleotide or polynucleotide includes but is not limited to (a) end modifications, e.g., 5' end modifications or 3' end modifications, (b) nucleobase (or "base") modifications, including replacement or removal of bases, (c) sugar modifications, including modifications at the 2', 3', and/or 4' positions, and (d) backbone modifications, including modification or replacement of the phosphodiester linkages. The term "modified nucleotide" generally refers to a nucleotide having a modification to the chemical structure of one or more of the base, the sugar, and the phosphodiester linkage or backbone portions, including nucleotide phosphates.

The terms "Z" and "P" refer to the nucleotides, nucleobases, or nucleobase analogs developed by Steven Benner and colleagues as described for example in "Artificially expanded genetic information system: a new base pair with an alternative hydrogen bonding pattern" Yang, Z., Hutter, D., Sheng, P., Sismour, A. M. and Benner, S. A. (2006) *Nucleic Acids Res.*, 34, 6095-101, the contents of which is hereby incorporated by reference in its entirety.

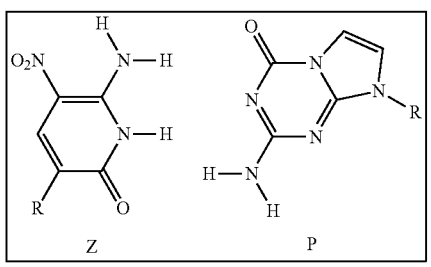

The terms "xA", "xG", "xC", "xT", or "x(A,G,C,T)" and "yA", "yG", "yC", "yT", or "y(A,G,C,T)" refer to nucleotides, nucleobases, or nucleobase analogs as described by Krueger et al in "Synthesis and Properties of Size-Expanded DNAs: Toward Designed, Functional Genetic Systems"; Andrew T. Krueger, Haige Lu, Alex H. F. Lee, and Eric T. Kool (2007) *Acc. Chem. Res.,* 40, 141-50, the contents of which is hereby incorporated by reference in its entirety.

The term "Unstructured Nucleic Acid" or "UNA" refers to nucleotides, nucleobases, or nucleobase analogs as described in U.S. Pat. No. 7,371,580, the contents of which is hereby incorporated by reference in its entirety. An unstructured nucleic acid, or UNA, modification is also referred to as a "pseudo-complementary" nucleotide, nucleobase or nucleobase analog (see e.g., Lahoud et al. (1991) *Nucl. Acids Res.,* 36:10, 3409-19).

The terms "PACE" and "thioPACE" refer to internucleotide phosphodiester linkage analogs containing phosphonoacetate or thiophosphonoacetate groups, respectively. These modifications belong to a broad class of compounds comprising phosphonocarboxylate moiety, phosphonocarboxylate ester moiety, thiophosphonocarboxylate moiety and thiophosphonocarboxylate ester moiety. These linkages can be described respectively by the general formulae $P(CR_1R_2)_n COOR$ and $(S)-P(CR_1R_2)_n COOR$ wherein n is an integer from 0 to 6 and each of $R_1$ and $R_2$ is independently selected from the group consisting of H, an alkyl and substituted alkyl. Some of these modifications are described by Yamada et al. in "Synthesis and Biochemical Evaluation of Phosphonoformate Oligodeoxyribonucleotides" Christina M. Yamada, Douglas J. Dellinger and Marvin H. Caruthers (2006) *J. Am. Chem. Soc.* 128:15, 5251-61, the contents of which is hereby incorporated by reference in its entirety.

As used herein, "modification" refers to a chemical moiety, or portion of a chemical structure, which differs from that found in unmodified ribonucleotides, namely adenosine, guanosine, cytidine, and uridine ribonucleotides. The term "modification" may refer to type of modification. For example, "same modification" means same type of modification, and "the modified nucleotides are the same" means the modified nucleotides have the same type(s) of modification while the base (A, G, C, U, etc.) may be different. Similarly, a guide RNA with "two modifications" is a guide RNA with two types of modifications, which may or may not be in the same nucleotide, and each type may appear in multiple nucleotides in the guide RNA. Similarly, a guide RNA with "three modifications" is a guide RNA with three types of modifications, which may or may not be in the same nucleotide, and each type may appear in multiple nucleotides.

As used herein, the term "target polynucleotide" or "target" refers to a polynucleotide containing a target nucleic acid sequence. A target polynucleotide may be single-stranded or double-stranded, and, in certain embodiments, is double-stranded DNA. In certain embodiments, the target polynucleotide is single-stranded RNA. A "target nucleic acid sequence" or "target sequence," as used herein, means a specific sequence or the complement thereof that one wishes to bind to, nick, or cleave using a CRISPR system.

The term "hybridization" or "hybridizing" refers to a process where completely or partially complementary polynucleotide strands come together under suitable hybridization conditions to form a double-stranded structure or region in which the two constituent strands are joined by hydrogen bonds. As used herein, the term "partial hybridization" includes where the double-stranded structure or region contains one or more bulges or mismatches. Although hydrogen bonds typically form between adenine and thymine or adenine and uracil (A and T or A and U) or cytosine and guanine (C and G), other noncanonical base pairs may form (See e.g., Adams et al., "The Biochemistry of the Nucleic Acids," 11th ed., 1992). It is contemplated that modified nucleotides may form hydrogen bonds that allow or promote hybridization.

The term "cleavage" or "cleaving" refers to breaking of the covalent phosphodiester linkage in the ribosylphosphodiester backbone of a polynucleotide. The terms "cleavage" or "cleaving" encompass both single-stranded breaks and double-stranded breaks. Double-stranded cleavage can occur as a result of two distinct single-stranded cleavage events. Cleavage can result in the production of either blunt ends or staggered ends.

The term "CRISPR-associated protein" or "Cas protein" refers to a wild type Cas protein, a fragment thereof, or a mutant or variant thereof. The term "Cas mutant" or "Cas variant" refers to a protein or polypeptide derivative of a wild type Cas protein, e.g., a protein having one or more point mutations, insertions, deletions, truncations, a fusion protein, or a combination thereof. In certain embodiments, the "Cas mutant" or "Cas variant" substantially retains the nuclease activity of the Cas protein. In certain embodiments, the "Cas mutant" or "Cas variant" is mutated such that one or both nuclease domains are inactive. In certain embodiments, the "Cas mutant" or "Cas variant" has nuclease activity. In certain embodiments, the "Cas mutant" or "Cas variant" lacks some or all of the nuclease activity of its wild-type counterpart.

The term "nuclease domain" of a Cas protein refers to the polypeptide sequence or domain within the protein which possesses the catalytic activity for DNA cleavage. A nuclease domain can be contained in a single polypeptide chain, or cleavage activity can result from the association of two (or more) polypeptides. A single nuclease domain may consist of more than one isolated stretch of amino acids within a given polypeptide. Examples of these domains include RuvC-like motifs (amino acids 7-22, 759-766 and 982-989 in SEQ ID NO: 1) and HNH motif (aa 837-863). See Gasiunas et al. (2012) *Proc. Natl. Acad. Sci. USA,* 109:39, E2579-E2586 and WO2013176772.

A synthetic guide RNA that has "gRNA functionality" is one that has one or more of the functions of naturally occurring guide RNA, such as associating with a Cas protein, or a function performed by the guide RNA in association with a Cas protein. In certain embodiments, the functionality includes binding a target polynucleotide. In certain embodiments, the functionality includes targeting a Cas protein or a gRNA:Cas protein complex to a target polynucleotide. In certain embodiments, the functionality includes nicking a target polynucleotide. In certain embodiments, the functionality includes cleaving a target polynucleotide. In certain embodiments, the functionality includes associating with or binding to a Cas protein. In certain embodiments, the functionality is any other known function of a guide RNA in a CRISPR-Cas system with a Cas protein, including an artificial CRISPR-Cas system with an engineered Cas protein. In certain embodiments, the functionality is any other function of natural guide RNA. The synthetic guide RNA may have gRNA functionality to a greater or lesser extent than a naturally occurring guide RNA. In certain embodiments, a synthetic guide RNA may have greater functionality as to one property and lesser functionality as to another property in comparison to a similar naturally occurring guide RNA.

A "Cas protein having a single-strand nicking activity" refers to a Cas protein, including a Cas mutant or Cas variant, that has reduced ability to cleave one of two strands of a dsDNA as compared to a wild type Cas protein. For example, in certain embodiments, a Cas protein having a single-strand nicking activity has a mutation (e.g., amino acid substitution) that reduces the function of the RuvC domain (or the HNH domain) and as a result reduces the ability to cleave one strand of the target DNA. Examples of such variants include the D10A, H839A/H840A, and/or N863A substitutions in *S. pyogenes* Cas9, and also include the same or similar substitutions at equivalent sites in Cas9 enzymes of other species.

As used herein, the term "portion" or "fragment" of a sequence refers to any portion of the sequence (e.g., a nucleotide subsequence or an amino acid subsequence) that is smaller than the complete sequence. Portions of polynucleotides can be any length, for example, at least 5, 10, 15, 20, 25, 30, 40, 50, 75, 100, 150, 200, 300 or 500 or more nucleotides in length. A portion of a guide sequence can be about 50%, 40%, 30%, 20%, 10% of the guide sequence, e.g., one-third of the guide sequence or shorter, e.g., 7, 6, 5, 4, 3, or 2 nucleotides in length.

The term "derived from" in the context of a molecule refers to a molecule isolated or made using a parent molecule or information from that parent molecule. For example, a Cas9 single mutant nickase and a Cas9 double mutant null-nuclease are derived from a wild-type Cas9 protein.

The term "substantially identical" in the context of two or more polynucleotides (or two or more polypeptides) refers to sequences or subsequences that have at least about 60%, at least about 70%, at least about 80%, at least about 90%, about 90-95%, at least about 95%, at least about 98%, at least about 99% or more nucleotide (or amino acid) sequence identity, when compared and aligned for maximum correspondence using a sequence comparison algorithm or by visual inspection. Preferably, the "substantial identity" between polynucleotides exists over a region of the polynucleotide at least about 50 nucleotides in length, at least about 100 nucleotides in length, at least about 200 nucleotides in length, at least about 300 nucleotides in length, at least about 500 nucleotides in length, or over the entire length of the polynucleotide. Preferably, the "substantial identity" between polypeptides exists over a region of the polypeptide at least about 50 amino acid residues in length, at least about 100 amino acid residues in length, or over the entire length of the polypeptide.

As disclosed herein, a number of ranges of values are provided. It is understood that each intervening value, to the tenth of the unit of the lower limit, between the upper and lower limits of that range is also specifically contemplated. Each smaller range or intervening value encompassed by a stated range is also specifically contemplated. The term "about" generally refers to plus or minus 10% of the indicated number. For example, "about 10%" may indicate a range of 9% to 11%, and "about 20" may mean from 18-22. Other meanings of "about" may be apparent from the context, such as rounding off, so, for example "about 1" may also mean from 0.5 to 1.4.

II. CRISPR-Mediated Sequence-Specific Binding and/or Cleavage

Shown in FIG. 1 is a diagram of CRISPR-Cas9-mediated sequence-specific cleavage of DNA. The guide RNA is depicted as sgRNA with an exemplary 20-nucleotide (20-nt) guide sequence (other guide sequences may be, for example, from about 15 to about 30 nts in length) within the 5' domain, an internally positioned base-paired stem, and a 3' domain. The guide sequence is complementary to an exemplary 20-nt target sequence in a DNA target. The stem corresponds to a repeat sequence in crRNA and is complementary to a sequence in the tracrRNA. The 3' domain of the guide RNA corresponds to the 3' domain of the tracrRNA that binds a Cas9 nuclease. The Cas9:guide RNA complex binds and cleaves a target DNA sequence or protospacer directly upstream of a PAM sequence recognized by Cas9. In FIG. 1, a 3-nt PAM sequence is exemplified; however other PAM sequences, including 4-nt and 5-nt PAM sequences are known. In the system exemplified in FIG. 1, both strands of the target sequence in DNA are cleaved by Cas9 at the sites indicated by arrows.

III. Guide RNAs

In at least one aspect, the present invention comprises a chemically modified guide RNA that has guide RNA functionality. A guide RNA that comprises any nucleotide other than the four canonical ribonucleotides, namely A, C, G, and U, whether unnatural or natural (e.g., a pseudouridine, inosine or a deoxynucleotide), is a chemically modified guide RNA. Likewise a guide RNA that comprises any backbone or internucleotide linkage other than a natural phosphodiester internucleotide linkage possesses a chemical modification and therefore is a chemically modified guide RNA. In certain embodiments, the retained functionality includes binding a Cas protein. In certain embodiments, the retained functionality includes binding a target polynucleotide. In certain embodiments, the retained functionality includes targeting a Cas protein or a gRNA:Cas protein complex to a target polynucleotide. In certain embodiments, the retained functionality includes nicking a target polynucleotide by a gRNA:Cas protein complex. In certain embodiments, the retained functionality includes cleaving a target polynucleotide by a gRNA:Cas protein complex. In certain embodiments, the retained functionality is any other known function of a guide RNA in a CRISPR-Cas system with a Cas protein, including an artificial CRISPR-Cas system with an engineered Cas protein. In certain embodiments, the retained functionality is any other function of a natural guide RNA.

A. Exemplary Modifications

In certain embodiments, a nucleotide sugar modification incorporated into the guide RNA is selected from the group consisting of 2'-O—$C_{1-4}$alkyl such as 2'-O-methyl ("2'-OMe"), 2'-deoxy ("2'-H"), 2'-O—$C_{1-3}$alkyl-O—$C_{1-3}$alkyl such as 2'-methoxyethyl ("2'-MOE"), 2'-fluoro ("2'-F"), 2'-amino ("2'-NH$_2$"), 2'-arabinosyl ("2'-arabino") nucleotide, 2'-F-arabinosyl ("2'-F-arabino") nucleotide, 2'-locked nucleic acid ("LNA") nucleotide, 2'-unlocked nucleic acid ("ULNA") nucleotide, a sugar in L form ("L-sugar"), and 4'-thioribosyl nucleotide. In certain embodiments, an internucleotide linkage modification incorporated into the guide RNA is selected from the group consisting of: phosphorothioate "P(S)" (P(S)), phosphonocarboxylate (P(CH$_2$)$_n$COOR) such as phosphonoacetate "PACE" (P(CH$_2$COO$^-$)), thiophosphonocarboxylate ((S)P(CH$_2$)$_n$COOR) such as thiophosphonoacetate "thioPACE" ((S)P(CH$_2$COO$^-$)), alkylphosphonate (P(C$_{1-3}$alkyl) such as methylphosphonate —P(CH$_3$), boranophosphonate (P(BH$_3$)), and phosphorodithioate (P(S)$_2$).

In certain embodiments, a nucleobase ("base") modification incorporated into the guide RNA is selected from the group consisting of: 2-thiouracil ("2-thioU"), 2-thiocytosine ("2-thioC"), 4-thiouracil ("4-thioU"), 6-thioguanine ("6-thioG"), 2-aminoadenine ("2-aminoA"), 2-aminopurine, pseudouracil, hypoxanthine, 7-deazaguanine, 7-deaza-8-azaguanine, 7-deazaadenine, 7-deaza-8-azaadenine, 5-methylcytosine ("5-methylC"), 5-methyluracil ("5-methylU"), 5-hydroxymethylcytosine, 5-hydroxymethyluracil, 5,6-dehydrouracil, 5-propynylcytosine, 5-propynyluracil, 5-ethynylcytosine, 5-ethynyluracil, 5-allyluracil ("5-allylU"), 5-allylcytosine ("5-allylC"), 5-aminoallyluracil ("5-aminoallylU"), 5-aminoallyl-cytosine ("5-aminoallylC"), an abasic nucleotide, Z base, P base, Unstructured Nucleic Acid ("UNA"), isoguanine ("isoG"), isocytosine ("isoC") [as described in "Enzymatic Incorporation of a New Base pair into DNA and RNA Extends the Genetic Alphabet." Piccirilli, J. A.; Krauch, T.; Moroney, S. E.; Benner, S. A. (1990) *Nature*, 343, 33], 5-methyl-2-pyrimidine [as described in Rappaport, H. P. (1993) *Biochemistry*, 32, 3047], x(A,G,C,T) and y(A,G,C,T).

In certain embodiments, one or more isotopic modifications are introduced on the nucleotide sugar, the nucleobase, the phosphodiester linkage and/or the nucleotide phosphates. Such modifications include nucleotides comprising one or more $^{15}$N, $^{13}$C, $^{14}$C, Deuterium, $^{3}$H, $^{32}$P, $^{125}$I, $^{131}$I atoms or other atoms or elements used as tracers.

In certain embodiments, an "end" modification incorporated into the guide RNA is selected from the group consisting of: PEG (polyethyleneglycol), hydrocarbon linkers (including: heteroatom (O,S,N)-substituted hydrocarbon spacers; halo-substituted hydrocarbon spacers; keto-, carboxyl-, amido-, thionyl-, carbamoyl-, thionocarbamaoyl-containing hydrocarbon spacers), spermine linkers, dyes including fluorescent dyes (for example fluoresceins, rhodamines, cyanines) attached to linkers such as for example 6-fluorescein-hexyl, quenchers (for example dabcyl, BHQ) and other labels (for example biotin, digoxigenin, acridine, streptavidin, avidin, peptides and/or proteins). In certain embodiments, an "end" modification comprises a conjugation (or ligation) of the guide RNA to another molecule comprising an oligonucleotide (comprising deoxynucleotides and/or ribonucleotides), a peptide, a protein, a sugar, an oligosaccharide, a steroid, a lipid, a folic acid, a vitamin and/or other molecule. In certain embodiments, an "end" modification incorporated into the guide RNA is located internally in the guide RNA sequence via a linker such as for example 2-(4-butylamidofluorescein)propane-1,3-diol bis (phosphodiester) linker (depicted below), which is incorporated as a phosphodiester linkage and can be incorporated anywhere between two nucleotides in the guide RNA.

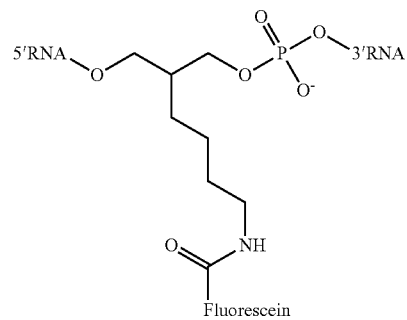

2-(4-butylamidofluorescein)propane-1,3-diol bis(phosphodiester) linker

Other linkers include for example by way of illustration, but are not limited to:

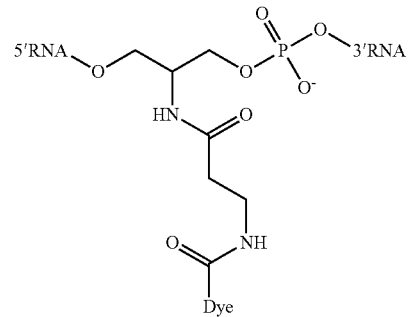

2-(3-(dye-amido)propanamido)propane-1,3-diol bis (phosphodiester) linker

In certain embodiments, the end modification comprises a terminal functional group such as an amine, a thiol (or sulfhydryl), a hydroxyl, a carboxyl, carbonyl, thionyl, thiocarbonyl, a carbamoyl, a thiocarbamoyl, a phoshoryl, an alkene, an alkyne, an halogen or a functional group-terminated linker, either of which can be subsequently conjugated to a desired moiety, for example a fluorescent dye or a non-fluorescent label or tag or any other molecule such as for example an oligonucleotide (comprising deoxynucleotides and/or ribonucleotides, including an aptamer), an amino acid, a peptide, a protein, a sugar, an oligosaccharide, a steroid, a lipid, a folic acid, a vitamin. The conjugation employs standard chemistry well-known in the art, including but not limited to coupling via N-hydroxysuccinimide, isothiocyanate, DCC (or DCI), and/or any other standart method as described in "Bioconjugate Techniques" by Greg T. Hermanson, Publisher Eslsevier Science, 3$^{rd}$ ed. (2013), the contents of which are incorporated herein by reference in their entireties.

In certain embodiments, the label or dye is attached or conjugated to a modified nucleotide in the gRNA. The conjugation of a fluorescent dye or other moiety such as a non-fluorescent label or tag (for example biotin, avidin, streptavidin, or moiety containing an isotopic label such as $^{15}$N, $^{13}$C, $^{14}$C, Deuterium, $^{3}$H, $^{32}$P, $^{125}$I and the like) or any other molecule such as for example an oligonucleotide (comprising deoxynucleotides and/or ribonucleotides including an aptamer), an amino acid, a peptide, a protein, a sugar, an oligosaccharide, a steroid, a lipid, a folic acid, a vitamin or other molecule can be effectuated using the so-called "click" chemistry or the so-called "squarate" conjugation chemistry. The "click" chemistry refers to the [3+2] cycloaddition of an alkyne moiety with an azide moiety, leading to a triazolo linkage between the two moieties as shown in the following scheme:

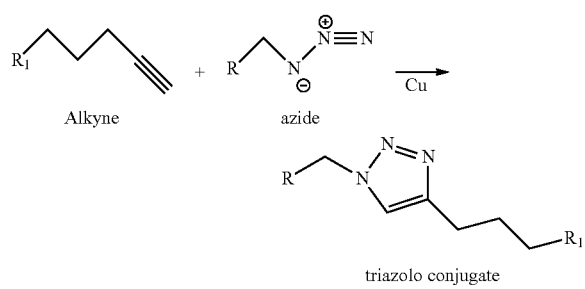

as described for example in El-Sagheer, A. H. and Brown, T. "Click chemistry with DNA", *Chem. Soc. Rev.*, 2010, 39, 1388-1405 and Mojibul, H. M. and XiaoHua, P., DNA-associated click chemistry, *Sci. China Chem.*, 2014, 57:2, 215-31, the contents of which are hereby incorporated by reference in their entirety.

In certain embodiments, the conjugation can be effectuated by alternative cycloaddition such as Diels-Alder [4+2] cycloaddition of a π-conjugated diene moiety with an alkene moiety.

The "squarate" conjugation chemistry links two moieties each having an amine via a squarate derivative to result in a squarate conjugate that contains a squarate moiety (see e.g., Tietze et al. (1991) *Chem. Ber.*, 124, 1215-21, the contents of which are hereby incorporated by reference in their entirety). For example, a fluorescein containing a linker amine is conjugated to an oligoribonucleotide containing an amine through a squarate linker as described in the scheme below. An example of the squarate linker is depicted in the following scheme:

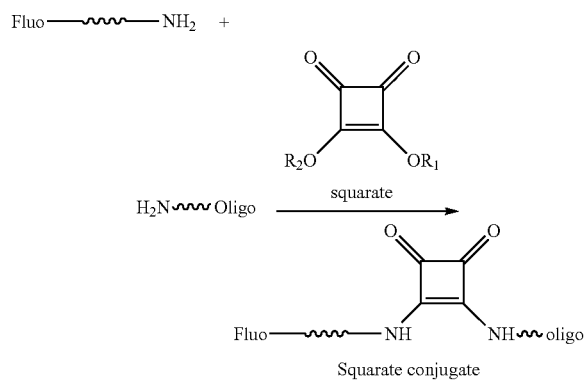

In certain embodiments, a chemical modification incorporated into the guide RNA is selected from the group consisting of 2'-O—C$_{1-4}$alkyl, 2'-H, 2'-O—C$_{1-3}$alkyl-O—C$_{1-3}$alkyl, 2'-F, 2'-NH$_2$, 2'-arabino, 2'-F-arabin, 4'-thioribosyl, 2-thioU, 2-thioC, 4-thioU, 6-thioG, 2-aminoA, 2-aminopurine, pseudouracil, hypoxanthine, 7-deazaguanine, 7-deaza-8-azaguanine, 7-deazaadenine, 7-deaza-8-azaadenine, 5-methylC, 5-methylU, 5-hydroxymethylcytosine, 5-hydroxymethyluracil, 5,6-dehydrouracil, 5-propynylcytosine, 5-propynyluracil, 5-ethynylcytosine, 5-ethynyluracil, 5-allylU, 5-allylC, 5-aminoallyl-uracil, 5-aminoallyl-cytosine, an abasic nucleotide ("abN"), Z, P, UNA, isoC, isoG, 5-methyl-pyrimidine, x(A,G,C,T) and y(A,G,C,T), a phosphorothioate internucleotide linkage, a phosphonoacetate internucleotide linkage, a thiophosphonoacetate internucleotide linkage, a methylphosphonate internucleotide linkage, a boranophosphonate internucleotide linkage, a phosphorodithioate internucleotide linkage, 4'-thioribosyl nucleotide, a locked nucleic acid ("LNA") nucleotide, an unlocked nucleic acid ("ULNA") nucleotide, an alkyl spacer, a heteroalkyl (N, O, S) spacer, a 5'- and/or 3'-alkyl terminated nucleotide, a Unicap, a 5'-terminal cap known from nature, an xRNA base (analogous to "xDNA" base), an yRNA base (analogous to "yDNA" base), a PEG substituent, or a conjugated linker to a dye or non-fluorescent label (or tag) or other moiety as described above. Exemplary modified nucleotides are also depicted in Table 2.

TABLE 2

Exemplary modified nucleotides contained in a synthetic guide sequence.

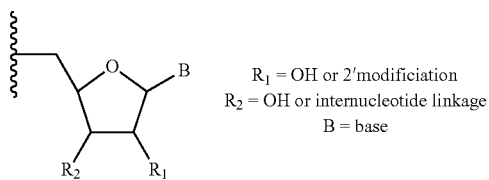

R$_1$ = OH or 2'modificiation
R$_2$ = OH or internucleotide linkage
B = base

| # | R$_1$ | R$_2$ | B |
|---|---|---|---|
| A1 | OH | OH | uridine |
| A2 | OMe | OH | uridine |
| A3 | F | OH | uridine |
| A4 | Cl | OH | uridine |
| A5 | Br | OH | uridine |
| A6 | I | OH | uridine |
| A7 | NH$_2$ | OH | uridine |
| A8 | H | OH | uridine |
| A9 | OH | phosphodiester | uridine |
| A10 | OMe | phosphodiester | uridine |
| A11 | F | phosphodiester | uridine |
| A12 | Cl | phosphodiester | uridine |
| A13 | Br | phosphodiester | uridine |
| A14 | I | phosphodiester | uridine |
| A15 | NH$_2$ | phosphodiester | uridine |
| A16 | H | phosphodiester | uridine |
| A17 | OH | phosphonoacetate | uridine |
| A18 | OMe | phosphonoacetate | uridine |
| A19 | F | phosphonoacetate | uridine |
| A20 | Cl | phosphonoacetate | uridine |
| A21 | Br | phosphonoacetate | uridine |
| A22 | I | phosphonoacetate | uridine |
| A23 | NH$_2$ | phosphonoacetate | uridine |
| A24 | H | phosphonoacetate | uridine |
| A25 | OH | thiophosphonoacetate | uridine |
| A26 | OMe | thiophosphonoacetate | uridine |
| A27 | F | thiophosphonoacetate | uridine |
| A28 | Cl | thiophosphonoacetate | uridine |
| A29 | Br | thiophosphonoacetate | uridine |
| A30 | I | thiophosphonoacetate | uridine |
| A31 | NH$_2$ | thiophosphonoacetate | uridine |
| A32 | H | thiophosphonoacetate | uridine |
| A33 | OH | phosphorothioate | uridine |
| A34 | OMe | phosphorothioate | uridine |
| A35 | F | phosphorothioate | uridine |
| A36 | Cl | phosphorothioate | uridine |
| A37 | Br | phosphorothioate | uridine |
| A38 | I | phosphorothioate | uridine |
| A39 | NH$_2$ | phosphorothioate | uridine |
| A40 | H | phosphorothioate | uridine |

TABLE 2-continued

Exemplary modified nucleotides contained in a synthetic guide sequence.

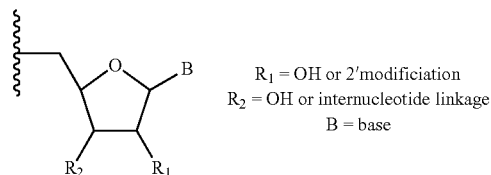

$R_1$ = OH or 2′modificiation
$R_2$ = OH or internucleotide linkage
B = base

TABLE 2-continued

Exemplary modified nucleotides contained in a synthetic guide sequence.

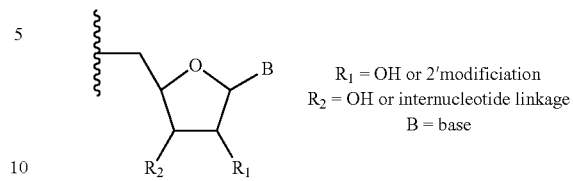

$R_1$ = OH or 2′modificiation
$R_2$ = OH or internucleotide linkage
B = base

| # | $R_1$ | $R_2$ | B | # | $R_1$ | $R_2$ | B |
|---|---|---|---|---|---|---|---|
| A41 | OH | phosphorodithioate | uridine | B43 | F | phosphorodithioate | adenosine |
| A42 | OMe | phosphorodithioate | uridine | B44 | Cl | phosphorodithioate | adenosine |
| A43 | F | phosphorodithioate | uridine | B45 | Br | phosphorodithioate | adenosine |
| A44 | Cl | phosphorodithioate | uridine | B46 | I | phosphorodithioate | adenosine |
| A45 | Br | phosphorodithioate | uridine | B47 | $NH_2$ | phosphorodithioate | adenosine |
| A46 | I | phosphorodithioate | uridine | B48 | H | phosphorodithioate | adenosine |
| A47 | $NH_2$ | phosphorodithioate | uridine | B49 | OH | methylphosphonate | adenosine |
| A48 | H | phosphorodithioate | uridine | B50 | OMe | methylphosphonate | adenosine |
| A49 | OH | methylphosphonate | uridine | B51 | F | methylphosphonate | adenosine |
| A50 | OMe | methylphosphonate | uridine | B52 | Cl | methylphosphonate | adenosine |
| A51 | F | methylphosphonate | uridine | B53 | Br | methylphosphonate | adenosine |
| A52 | Cl | methylphosphonate | uridine | B54 | I | methylphosphonate | adenosine |
| A53 | Br | methylphosphonate | uridine | B55 | $NH_2$ | methylphosphonate | adenosine |
| A54 | I | methylphosphonate | uridine | B56 | H | methylphosphonate | adenosine |
| A55 | $NH_2$ | methylphosphonate | uridine | B57 | OH | boranophosphonate | adenosine |
| A56 | H | methylphosphonate | uridine | B58 | OMe | boranophosphonate | adenosine |
| A57 | OH | boranophosphonate | uridine | B59 | F | boranophosphonate | adenosine |
| A58 | OMe | boranophosphonate | uridine | B60 | Cl | boranophosphonate | adenosine |
| A59 | F | boranophosphonate | uridine | B61 | Br | boranophosphonate | adenosine |
| A60 | Cl | boranophosphonate | uridine | B62 | I | boranophosphonate | adenosine |
| A61 | Br | boranophosphonate | uridine | B63 | $NH_2$ | boranophosphonate | adenosine |
| A62 | I | boranophosphonate | uridine | B64 | H | boranophosphonate | adenosine |
| A63 | $NH_2$ | boranophosphonate | uridine | C1 | OH | OH | cytidine |
| A64 | H | boranophosphonate | uridine | C2 | OMe | OH | cytidine |
| B1 | OH | OH | adenosine | C3 | F | OH | cytidine |
| B2 | OMe | OH | adenosine | C4 | Cl | OH | cytidine |
| B3 | F | OH | adenosine | C5 | Br | OH | cytidine |
| B4 | Cl | OH | adenosine | C6 | I | OH | cytidine |
| B5 | Br | OH | adenosine | C7 | $NH_2$ | OH | cytidine |
| B6 | I | OH | adenosine | C8 | H | OH | cytidine |
| B7 | $NH_2$ | OH | adenosine | C9 | OH | phosphodiester | cytidine |
| B8 | H | OH | adenosine | C10 | OMe | phosphodiester | cytidine |
| B9 | OH | phosphodiester | adenosine | C11 | F | phosphodiester | cytidine |
| B10 | OMe | phosphodiester | adenosine | C12 | Cl | phosphodiester | cytidine |
| B11 | F | phosphodiester | adenosine | C13 | Br | phosphodiester | cytidine |
| B12 | Cl | phosphodiester | adenosine | C14 | I | phosphodiester | cytidine |
| B13 | Br | phosphodiester | adenosine | C15 | $NH_2$ | phosphodiester | cytidine |
| B14 | I | phosphodiester | adenosine | C16 | H | phosphodiester | cytidine |
| B15 | $NH_2$ | phosphodiester | adenosine | C17 | OH | phosphonoacetate | cytidine |
| B16 | H | phosphodiester | adenosine | C18 | OMe | phosphonoacetate | cytidine |
| B17 | OH | phosphonoacetate | adenosine | C19 | F | phosphonoacetate | cytidine |
| B18 | OMe | phosphonoacetate | adenosine | C20 | Cl | phosphonoacetate | cytidine |
| B19 | F | phosphonoacetate | adenosine | C21 | Br | phosphonoacetate | cytidine |
| B20 | Cl | phosphonoacetate | adenosine | C22 | I | phosphonoacetate | cytidine |
| B21 | Br | phosphonoacetate | adenosine | C23 | $NH_2$ | phosphonoacetate | cytidine |
| B22 | I | phosphonoacetate | adenosine | C24 | H | phosphonoacetate | cytidine |
| B23 | $NH_2$ | phosphonoacetate | adenosine | C25 | OH | thiophosphonoacetate | cytidine |
| B24 | H | phosphonoacetate | adenosine | C26 | OMe | thiophosphonoacetate | cytidine |
| B25 | OH | thiophosphonoacetate | adenosine | C27 | F | thiophosphonoacetate | cytidine |
| B26 | OMe | thiophosphonoacetate | adenosine | C28 | Cl | thiophosphonoacetate | cytidine |
| B27 | F | thiophosphonoacetate | adenosine | C29 | Br | thiophosphonoacetate | cytidine |
| B28 | Cl | thiophosphonoacetate | adenosine | C30 | I | thiophosphonoacetate | cytidine |
| B29 | Br | thiophosphonoacetate | adenosine | C31 | $NH_2$ | thiophosphonoacetate | cytidine |
| B30 | I | thiophosphonoacetate | adenosine | C32 | H | thiophosphonoacetate | cytidine |
| B31 | $NH_2$ | thiophosphonoacetate | adenosine | C33 | OH | phosphorothioate | cytidine |
| B32 | H | thiophosphonoacetate | adenosine | C34 | OMe | phosphorothioate | cytidine |
| B33 | OH | phosphorothioate | adenosine | C35 | F | phosphorothioate | cytidine |
| B34 | OMe | phosphorothioate | adenosine | C36 | Cl | phosphorothioate | cytidine |
| B35 | F | phosphorothioate | adenosine | C37 | Br | phosphorothioate | cytidine |
| B36 | Cl | phosphorothioate | adenosine | C38 | I | phosphorothioate | cytidine |
| B37 | Br | phosphorothioate | adenosine | C39 | $NH_2$ | phosphorothioate | cytidine |
| B38 | I | phosphorothioate | adenosine | C40 | H | phosphorothioate | cytidine |
| B39 | $NH_2$ | phosphorothioate | adenosine | C41 | OH | phosphorodithioate | cytidine |
| B40 | H | phosphorothioate | adenosine | C42 | OMe | phosphorodithioate | cytidine |
| B41 | OH | phosphorodithioate | adenosine | C43 | F | phosphorodithioate | cytidine |
| B42 | OMe | phosphorodithioate | adenosine | C44 | Cl | phosphorodithioate | cytidine |

TABLE 2-continued

Exemplary modified nucleotides contained in a synthetic guide sequence.

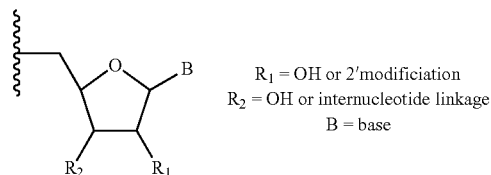

$R_1$ = OH or 2′modificiation
$R_2$ = OH or internucleotide linkage
B = base

| # | $R_1$ | $R_2$ | B |
|---|---|---|---|
| C45 | Br | phosphorodithioate | cytidine |
| C46 | I | phosphorodithioate | cytidine |
| C47 | $NH_2$ | phosphorodithioate | cytidine |
| C48 | H | phosphorodithioate | cytidine |
| C49 | OH | methylphosphonate | cytidine |
| C50 | OMe | methylphosphonate | cytidine |
| C51 | F | methylphosphonate | cytidine |
| C52 | Cl | methylphosphonate | cytidine |
| C53 | Br | methylphosphonate | cytidine |
| C54 | I | methylphosphonate | cytidine |
| C55 | $NH_2$ | methylphosphonate | cytidine |
| C56 | H | methylphosphonate | cytidine |
| C57 | OH | boranophosphonate | cytidine |
| C58 | OMe | boranophosphonate | cytidine |
| C59 | F | boranophosphonate | cytidine |
| C60 | Cl | boranophosphonate | cytidine |
| C61 | Br | boranophosphonate | cytidine |
| C62 | I | boranophosphonate | cytidine |
| C63 | $NH_2$ | boranophosphonate | cytidine |
| C64 | H | boranophosphonate | cytidine |
| D1 | OH | OH | guanosine |
| D2 | OMe | OH | guanosine |
| D3 | F | OH | guanosine |
| D4 | Cl | OH | guanosine |
| D5 | Br | OH | guanosine |
| D6 | I | OH | guanosine |
| D7 | $NH_2$ | OH | guanosine |
| D8 | H | OH | guanosine |
| D9 | OH | phosphodiester | guanosine |
| D10 | OMe | phosphodiester | guanosine |
| D11 | F | phosphodiester | guanosine |
| D12 | Cl | phosphodiester | guanosine |
| D13 | Br | phosphodiester | guanosine |
| D14 | I | phosphodiester | guanosine |
| D15 | $NH_2$ | phosphodiester | guanosine |
| D16 | H | phosphodiester | guanosine |
| D17 | OH | phosphonoacetate | guanosine |
| D18 | OMe | phosphonoacetate | guanosine |
| D19 | F | phosphonoacetate | guanosine |
| D20 | Cl | phosphonoacetate | guanosine |
| D21 | Br | phosphonoacetate | guanosine |
| D22 | I | phosphonoacetate | guanosine |
| D23 | $NH_2$ | phosphonoacetate | guanosine |
| D24 | H | phosphonoacetate | guanosine |
| D25 | OH | thiophosphonoacetate | guanosine |
| D26 | OMe | thiophosphonoacetate | guanosine |
| D27 | F | thiophosphonoacetate | guanosine |
| D28 | Cl | thiophosphonoacetate | guanosine |
| D29 | Br | thiophosphonoacetate | guanosine |
| D30 | I | thiophosphonoacetate | guanosine |
| D31 | $NH_2$ | thiophosphonoacetate | guanosine |
| D32 | H | thiophosphonoacetate | guanosine |
| D33 | OH | phosphorothioate | guanosine |
| D34 | OMe | phosphorothioate | guanosine |
| D35 | F | phosphorothioate | guanosine |
| D36 | Cl | phosphorothioate | guanosine |
| D37 | Br | phosphorothioate | guanosine |
| D38 | I | phosphorothioate | guanosine |
| D39 | $NH_2$ | phosphorothioate | guanosine |
| D40 | H | phosphorothioate | guanosine |
| D41 | OH | phosphorodithioate | guanosine |
| D42 | OMe | phosphorodithioate | guanosine |
| D43 | F | phosphorodithioate | guanosine |
| D44 | Cl | phosphorodithioate | guanosine |
| D45 | Br | phosphorodithioate | guanosine |
| D46 | I | phosphorodithioate | guanosine |

TABLE 2-continued

Exemplary modified nucleotides contained in a synthetic guide sequence.

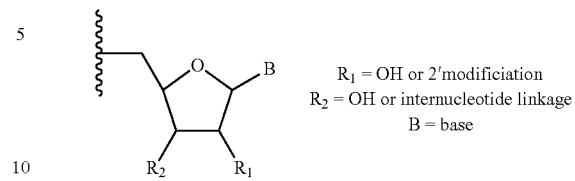

$R_1$ = OH or 2′modificiation
$R_2$ = OH or internucleotide linkage
B = base

| # | $R_1$ | $R_2$ | B |
|---|---|---|---|
| D47 | $NH_2$ | phosphorodithioate | guanosine |
| D48 | H | phosphorodithioate | guanosine |
| D49 | OH | methylphosphonate | guanosine |
| D50 | OMe | methylphosphonate | guanosine |
| D51 | F | methylphosphonate | guanosine |
| D52 | Cl | methylphosphonate | guanosine |
| D53 | Br | methylphosphonate | guanosine |
| D54 | I | methylphosphonate | guanosine |
| D55 | $NH_2$ | methylphosphonate | guanosine |
| D56 | H | methylphosphonate | guanosine |
| D57 | OH | boranophosphonate | guanosine |
| D58 | OMe | boranophosphonate | guanosine |
| D59 | F | boranophosphonate | guanosine |
| D60 | Cl | boranophosphonate | guanosine |
| D61 | Br | boranophosphonate | guanosine |
| D62 | I | boranophosphonate | guanosine |
| D63 | $NH_2$ | boranophosphonate | guanosine |
| D64 | H | boranophosphonate | guanosine |
| E1 | OH | OH | 2-thiouridine |
| E2 | OMe | OH | 2-thiouridine |
| E3 | F | OH | 2-thiouridine |
| E4 | Cl | OH | 2-thiouridine |
| E5 | Br | OH | 2-thiouridine |
| E6 | I | OH | 2-thiouridine |
| E7 | $NH_2$ | OH | 2-thiouridine |
| E8 | H | OH | 2-thiouridine |
| E9 | OH | phosphodiester | 2-thiouridine |
| E10 | OMe | phosphodiester | 2-thiouridine |
| E11 | F | phosphodiester | 2-thiouridine |
| E12 | Cl | phosphodiester | 2-thiouridine |
| E13 | Br | phosphodiester | 2-thiouridine |
| E14 | I | phosphodiester | 2-thiouridine |
| E15 | $NH_2$ | phosphodiester | 2-thiouridine |
| E16 | H | phosphodiester | 2-thiouridine |
| E17 | OH | phosphonoacetate | 2-thiouridine |
| E18 | OMe | phosphonoacetate | 2-thiouridine |
| E19 | F | phosphonoacetate | 2-thiouridine |
| E20 | Cl | phosphonoacetate | 2-thiouridine |
| E21 | Br | phosphonoacetate | 2-thiouridine |
| E22 | I | phosphonoacetate | 2-thiouridine |
| E23 | $NH_2$ | phosphonoacetate | 2-thiouridine |
| E24 | H | phosphonoacetate | 2-thiouridine |
| E25 | OH | thiophosphonoacetate | 2-thiouridine |
| E26 | OMe | thiophosphonoacetate | 2-thiouridine |
| E27 | F | thiophosphonoacetate | 2-thiouridine |
| E28 | Cl | thiophosphonoacetate | 2-thiouridine |
| E29 | Br | thiophosphonoacetate | 2-thiouridine |
| E30 | I | thiophosphonoacetate | 2-thiouridine |
| E31 | $NH_2$ | thiophosphonoacetate | 2-thiouridine |
| E32 | H | thiophosphonoacetate | 2-thiouridine |
| E33 | OH | phosphorothioate | 2-thiouridine |
| E34 | OMe | phosphorothioate | 2-thiouridine |
| E35 | F | phosphorothioate | 2-thiouridine |
| E36 | Cl | phosphorothioate | 2-thiouridine |
| E37 | Br | phosphorothioate | 2-thiouridine |
| E38 | I | phosphorothioate | 2-thiouridine |
| E39 | $NH_2$ | phosphorothioate | 2-thiouridine |
| E40 | H | phosphorothioate | 2-thiouridine |
| E41 | OH | phosphorodithioate | 2-thiouridine |
| E42 | OMe | phosphorodithioate | 2-thiouridine |
| E43 | F | phosphorodithioate | 2-thiouridine |
| E44 | Cl | phosphorodithioate | 2-thiouridine |
| E45 | Br | phosphorodithioate | 2-thiouridine |
| E46 | I | phosphorodithioate | 2-thiouridine |
| E47 | $NH_2$ | phosphorodithioate | 2-thiouridine |
| E48 | H | phosphorodithioate | 2-thiouridine |

TABLE 2-continued

Exemplary modified nucleotides contained in a synthetic guide sequence.

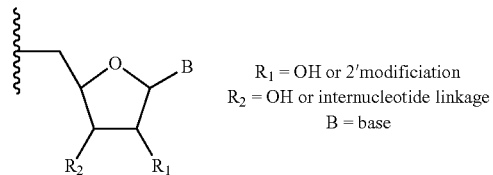

$R_1$ = OH or 2′modification
$R_2$ = OH or internucleotide linkage
B = base

| # | $R_1$ | $R_2$ | B |
|---|---|---|---|
| E49 | OH | methylphosphonate | 2-thiouridine |
| E50 | OMe | methylphosphonate | 2-thiouridine |
| E51 | F | methylphosphonate | 2-thiouridine |
| E52 | Cl | methylphosphonate | 2-thiouridine |
| E53 | Br | methylphosphonate | 2-thiouridine |
| E54 | I | methylphosphonate | 2-thiouridine |
| E55 | $NH_2$ | methylphosphonate | 2-thiouridine |
| E56 | H | methylphosphonate | 2-thiouridine |
| E57 | OH | boranophosphonate | 2-thiouridine |
| E58 | OMe | boranophosphonate | 2-thiouridine |
| E59 | F | boranophosphonate | 2-thiouridine |
| E60 | Cl | boranophosphonate | 2-thiouridine |
| E61 | Br | boranophosphonate | 2-thiouridine |
| E62 | I | boranophosphonate | 2-thiouridine |
| E63 | $NH_2$ | boranophosphonate | 2-thiouridine |
| E64 | H | boranophosphonate | 2-thiouridine |
| F1 | OH | OH | 4-thiouridine |
| F2 | OMe | OH | 4-thiouridine |
| F3 | F | OH | 4-thiouridine |
| F4 | Cl | OH | 4-thiouridine |
| F5 | Br | OH | 4-thiouridine |
| F6 | I | OH | 4-thiouridine |
| F7 | $NH_2$ | OH | 4-thiouridine |
| F8 | H | OH | 4-thiouridine |
| F9 | OH | phosphodiester | 4-thiouridine |
| F10 | OMe | phosphodiester | 4-thiouridine |
| F11 | F | phosphodiester | 4-thiouridine |
| F12 | Cl | phosphodiester | 4-thiouridine |
| F13 | Br | phosphodiester | 4-thiouridine |
| F14 | I | phosphodiester | 4-thiouridine |
| F15 | $NH_2$ | phosphodiester | 4-thiouridine |
| F16 | H | phosphodiester | 4-thiouridine |
| F17 | OH | phosphonoacetate | 4-thiouridine |
| F18 | OMe | phosphonoacetate | 4-thiouridine |
| F19 | F | phosphonoacetate | 4-thiouridine |
| F20 | Cl | phosphonoacetate | 4-thiouridine |
| F21 | Br | phosphonoacetate | 4-thiouridine |
| F22 | I | phosphonoacetate | 4-thiouridine |
| F23 | $NH_2$ | phosphonoacetate | 4-thiouridine |
| F24 | H | phosphonoacetate | 4-thiouridine |
| F25 | OH | thiophosphonoacetate | 4-thiouridine |
| F26 | OMe | thiophosphonoacetate | 4-thiouridine |
| F27 | F | thiophosphonoacetate | 4-thiouridine |
| F28 | Cl | thiophosphonoacetate | 4-thiouridine |
| F29 | Br | thiophosphonoacetate | 4-thiouridine |
| F30 | I | thiophosphonoacetate | 4-thiouridine |
| F31 | $NH_2$ | thiophosphonoacetate | 4-thiouridine |
| F32 | H | thiophosphonoacetate | 4-thiouridine |
| F33 | OH | phosphorothioate | 4-thiouridine |
| F34 | OMe | phosphorothioate | 4-thiouridine |
| F35 | F | phosphorothioate | 4-thiouridine |
| F36 | Cl | phosphorothioate | 4-thiouridine |
| F37 | Br | phosphorothioate | 4-thiouridine |
| F38 | I | phosphorothioate | 4-thiouridine |
| F39 | $NH_2$ | phosphorothioate | 4-thiouridine |
| F40 | H | phosphorothioate | 4-thiouridine |
| F41 | OH | phosphorodithioate | 4-thiouridine |
| F42 | OMe | phosphorodithioate | 4-thiouridine |
| F43 | F | phosphorodithioate | 4-thiouridine |
| F44 | Cl | phosphorodithioate | 4-thiouridine |
| F45 | Br | phosphorodithioate | 4-thiouridine |
| F46 | I | phosphorodithioate | 4-thiouridine |
| F47 | $NH_2$ | phosphorodithioate | 4-thiouridine |
| F48 | H | phosphorodithioate | 4-thiouridine |
| F49 | OH | methylphosphonate | 4-thiouridine |
| F50 | OMe | methylphosphonate | 4-thiouridine |

TABLE 2-continued

Exemplary modified nucleotides contained in a synthetic guide sequence.

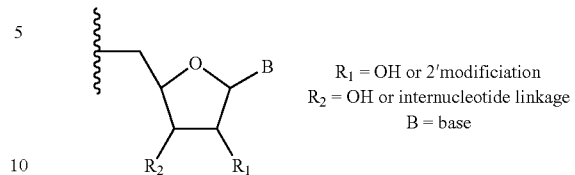

$R_1$ = OH or 2′modification
$R_2$ = OH or internucleotide linkage
B = base

| # | $R_1$ | $R_2$ | B |
|---|---|---|---|
| F51 | F | methylphosphonate | 4-thiouridine |
| F52 | Cl | methylphosphonate | 4-thiouridine |
| F53 | Br | methylphosphonate | 4-thiouridine |
| F54 | I | methylphosphonate | 4-thiouridine |
| F55 | $NH_2$ | methylphosphonate | 4-thiouridine |
| F56 | H | methylphosphonate | 4-thiouridine |
| F57 | OH | boranophosphonate | 4-thiouridine |
| F58 | OMe | boranophosphonate | 4-thiouridine |
| F59 | F | boranophosphonate | 4-thiouridine |
| F60 | Cl | boranophosphonate | 4-thiouridine |
| F61 | Br | boranophosphonate | 4-thiouridine |
| F62 | I | boranophosphonate | 4-thiouridine |
| F63 | $NH_2$ | boranophosphonate | 4-thiouridine |
| F64 | H | boranophosphonate | 4-thiouridine |
| G1 | OH | OH | 2-aminoadenosine |
| G2 | OMe | OH | 2-aminoadenosine |
| G3 | F | OH | 2-aminoadenosine |
| G4 | Cl | OH | 2-aminoadenosine |
| G5 | Br | OH | 2-aminoadenosine |
| G6 | I | OH | 2-aminoadenosine |
| G7 | $NH_2$ | OH | 2-aminoadenosine |
| G8 | H | OH | 2-aminoadenosine |
| G9 | OH | phosphodiester | 2-aminoadenosine |
| G10 | OMe | phosphodiester | 2-aminoadenosine |
| G11 | F | phosphodiester | 2-aminoadenosine |
| G12 | Cl | phosphodiester | 2-aminoadenosine |
| G13 | Br | phosphodiester | 2-aminoadenosine |
| G14 | I | phosphodiester | 2-aminoadenosine |
| G15 | $NH_2$ | phosphodiester | 2-aminoadenosine |
| G16 | H | phosphodiester | 2-aminoadenosine |
| G17 | OH | phosphonoacetate | 2-aminoadenosine |
| G18 | OMe | phosphonoacetate | 2-aminoadenosine |
| G19 | F | phosphonoacetate | 2-aminoadenosine |
| G20 | Cl | phosphonoacetate | 2-aminoadenosine |
| G21 | Br | phosphonoacetate | 2-aminoadenosine |
| G22 | I | phosphonoacetate | 2-aminoadenosine |
| G23 | $NH_2$ | phosphonoacetate | 2-aminoadenosine |
| G24 | H | phosphonoacetate | 2-aminoadenosine |
| G25 | OH | thiophosphonoacetate | 2-aminoadenosine |
| G26 | OMe | thiophosphonoacetate | 2-aminoadenosine |
| G27 | F | thiophosphonoacetate | 2-aminoadenosine |
| G28 | Cl | thiophosphonoacetate | 2-aminoadenosine |
| G29 | Br | thiophosphonoacetate | 2-aminoadenosine |
| G30 | I | thiophosphonoacetate | 2-aminoadenosine |
| G31 | $NH_2$ | thiophosphonoacetate | 2-aminoadenosine |
| G32 | H | thiophosphonoacetate | 2-aminoadenosine |
| G33 | OH | phosphorothioate | 2-aminoadenosine |
| G34 | OMe | phosphorothioate | 2-aminoadenosine |
| G35 | F | phosphorothioate | 2-aminoadenosine |
| G36 | Cl | phosphorothioate | 2-aminoadenosine |
| G37 | Br | phosphorothioate | 2-aminoadenosine |
| G38 | I | phosphorothioate | 2-aminoadenosine |
| G39 | $NH_2$ | phosphorothioate | 2-aminoadenosine |
| G40 | H | phosphorothioate | 2-aminoadenosine |
| G41 | OH | phosphorodithioate | 2-aminoadenosine |
| G42 | OMe | phosphorodithioate | 2-aminoadenosine |
| G43 | F | phosphorodithioate | 2-aminoadenosine |
| G44 | Cl | phosphorodithioate | 2-aminoadenosine |
| G45 | Br | phosphorodithioate | 2-aminoadenosine |
| G46 | I | phosphorodithioate | 2-aminoadenosine |
| G47 | $NH_2$ | phosphorodithioate | 2-aminoadenosine |
| G48 | H | phosphorodithioate | 2-aminoadenosine |
| G49 | OH | methylphosphonate | 2-aminoadenosine |
| G50 | OMe | methylphosphonate | 2-aminoadenosine |
| G51 | F | methylphosphonate | 2-aminoadenosine |
| G52 | Cl | methylphosphonate | 2-aminoadenosine |

TABLE 2-continued

Exemplary modified nucleotides contained in a synthetic guide sequence.

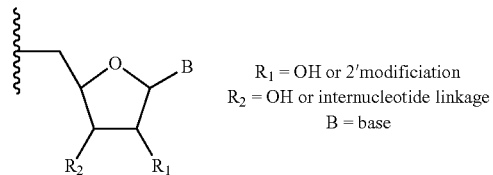

$R_1$ = OH or 2′modificiation
$R_2$ = OH or internucleotide linkage
B = base

| # | $R_1$ | $R_2$ | B |
|---|---|---|---|
| G53 | Br | methylphosphonate | 2-aminoadenosine |
| G54 | I | methylphosphonate | 2-aminoadenosine |
| G55 | $NH_2$ | methylphosphonate | 2-aminoadenosine |
| G56 | H | methylphosphonate | 2-aminoadenosine |
| G57 | OH | boranophosphonate | 2-aminoadenosine |
| G58 | OMe | boranophosphonate | 2-aminoadenosine |
| G59 | F | boranophosphonate | 2-aminoadenosine |
| G60 | Cl | boranophosphonate | 2-aminoadenosine |
| G61 | Br | boranophosphonate | 2-aminoadenosine |
| G62 | I | boranophosphonate | 2-aminoadenosine |
| G63 | $NH_2$ | boranophosphonate | 2-aminoadenosine |
| G64 | H | boranophosphonate | 2-aminoadenosine |
| H1 | OH | OH | 7-deazaguanosine |
| H2 | OMe | OH | 7-deazaguanosine |
| H3 | F | OH | 7-deazaguanosine |
| H4 | Cl | OH | 7-deazaguanosine |
| H5 | Br | OH | 7-deazaguanosine |
| H6 | I | OH | 7-deazaguanosine |
| H7 | $NH_2$ | OH | 7-deazaguanosine |
| H8 | H | OH | 7-deazaguanosine |
| H9 | OH | phosphodiester | 7-deazaguanosine |
| H10 | OMe | phosphodiester | 7-deazaguanosine |
| H11 | F | phosphodiester | 7-deazaguanosine |
| H12 | Cl | phosphodiester | 7-deazaguanosine |
| H13 | Br | phosphodiester | 7-deazaguanosine |
| H14 | I | phosphodiester | 7-deazaguanosine |
| H15 | $NH_2$ | phosphodiester | 7-deazaguanosine |
| H16 | H | phosphodiester | 7-deazaguanosine |
| H17 | OH | phosphonoacetate | 7-deazaguanosine |
| H18 | OMe | phosphonoacetate | 7-deazaguanosine |
| H19 | F | phosphonoacetate | 7-deazaguanosine |
| H20 | Cl | phosphonoacetate | 7-deazaguanosine |
| H21 | Br | phosphonoacetate | 7-deazaguanosine |
| H22 | I | phosphonoacetate | 7-deazaguanosine |
| H23 | $NH_2$ | phosphonoacetate | 7-deazaguanosine |
| H24 | H | phosphonoacetate | 7-deazaguanosine |
| H25 | OH | thiophosphonoacetate | 7-deazaguanosine |
| H26 | OMe | thiophosphonoacetate | 7-deazaguanosine |
| H27 | F | thiophosphonoacetate | 7-deazaguanosine |
| H28 | Cl | thiophosphonoacetate | 7-deazaguanosine |
| H29 | Br | thiophosphonoacetate | 7-deazaguanosine |
| H30 | I | thiophosphonoacetate | 7-deazaguanosine |
| H31 | $NH_2$ | thiophosphonoacetate | 7-deazaguanosine |
| H32 | H | thiophosphonoacetate | 7-deazaguanosine |
| H33 | OH | phosphorothioate | 7-deazaguanosine |
| H34 | OMe | phosphorothioate | 7-deazaguanosine |
| H35 | F | phosphorothioate | 7-deazaguanosine |
| H36 | Cl | phosphorothioate | 7-deazaguanosine |
| H37 | Br | phosphorothioate | 7-deazaguanosine |
| H38 | I | phosphorothioate | 7-deazaguanosine |
| H39 | $NH_2$ | phosphorothioate | 7-deazaguanosine |
| H40 | H | phosphorothioate | 7-deazaguanosine |
| H41 | OH | phosphorodithioate | 7-deazaguanosine |
| H42 | OMe | phosphorodithioate | 7-deazaguanosine |
| H43 | F | phosphorodithioate | 7-deazaguanosine |
| H44 | Cl | phosphorodithioate | 7-deazaguanosine |
| H45 | Br | phosphorodithioate | 7-deazaguanosine |
| H46 | I | phosphorodithioate | 7-deazaguanosine |
| H47 | $NH_2$ | phosphorodithioate | 7-deazaguanosine |
| H48 | H | phosphorodithioate | 7-deazaguanosine |
| H49 | OH | methylphosphonate | 7-deazaguanosine |
| H50 | OMe | methylphosphonate | 7-deazaguanosine |
| H51 | F | methylphosphonate | 7-deazaguanosine |
| H52 | Cl | methylphosphonate | 7-deazaguanosine |
| H53 | Br | methylphosphonate | 7-deazaguanosine |
| H54 | I | methylphosphonate | 7-deazaguanosine |

TABLE 2-continued

Exemplary modified nucleotides contained in a synthetic guide sequence.

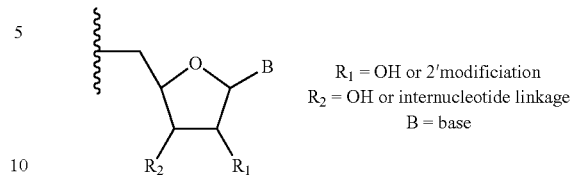

$R_1$ = OH or 2′modificiation
$R_2$ = OH or internucleotide linkage
B = base

| # | $R_1$ | $R_2$ | B |
|---|---|---|---|
| H55 | $NH_2$ | methylphosphonate | 7-deazaguanosine |
| H56 | H | methylphosphonate | 7-deazaguanosine |
| H57 | OH | boranophosphonate | 7-deazaguanosine |
| H58 | OMe | boranophosphonate | 7-deazaguanosine |
| H59 | F | boranophosphonate | 7-deazaguanosine |
| H60 | Cl | boranophosphonate | 7-deazaguanosine |
| H61 | Br | boranophosphonate | 7-deazaguanosine |
| H62 | I | boranophosphonate | 7-deazaguanosine |
| H63 | $NH_2$ | boranophosphonate | 7-deazaguanosine |
| H64 | H | boranophosphonate | 7-deazaguanosine |
| I1 | OH | OH | inosine |
| I2 | OMe | OH | inosine |
| I3 | F | OH | inosine |
| I4 | Cl | OH | inosine |
| I5 | Br | OH | inosine |
| I6 | I | OH | inosine |
| I7 | $NH_2$ | OH | inosine |
| I8 | H | OH | inosine |
| I9 | OH | phosphodiester | inosine |
| I10 | OMe | phosphodiester | inosine |
| I11 | F | phosphodiester | inosine |
| I12 | Cl | phosphodiester | inosine |
| I13 | Br | phosphodiester | inosine |
| I14 | I | phosphodiester | inosine |
| I15 | $NH_2$ | phosphodiester | inosine |
| I16 | H | phosphodiester | inosine |
| I17 | OH | phosphonoacetate | inosine |
| I18 | OMe | phosphonoacetate | inosine |
| I19 | F | phosphonoacetate | inosine |
| I20 | Cl | phosphonoacetate | inosine |
| I21 | Br | phosphonoacetate | inosine |
| I22 | I | phosphonoacetate | inosine |
| I23 | $NH_2$ | phosphonoacetate | inosine |
| I24 | H | phosphonoacetate | inosine |
| I25 | OH | thiophosphonoacetate | inosine |
| I26 | OMe | thiophosphonoacetate | inosine |
| I27 | F | thiophosphonoacetate | inosine |
| I28 | Cl | thiophosphonoacetate | inosine |
| I29 | Br | thiophosphonoacetate | inosine |
| I30 | I | thiophosphonoacetate | inosine |
| I31 | $NH_2$ | thiophosphonoacetate | inosine |
| I32 | H | thiophosphonoacetate | inosine |
| I33 | OH | phosphorothioate | inosine |
| I34 | OMe | phosphorothioate | inosine |
| I35 | F | phosphorothioate | inosine |
| I36 | Cl | phosphorothioate | inosine |
| I37 | Br | phosphorothioate | inosine |
| I38 | I | phosphorothioate | inosine |
| I39 | $NH_2$ | phosphorothioate | inosine |
| I40 | H | phosphorothioate | inosine |
| I41 | OH | phosphorodithioate | inosine |
| I42 | OMe | phosphorodithioate | inosine |
| I43 | F | phosphorodithioate | inosine |
| I44 | Cl | phosphorodithioate | inosine |
| I45 | Br | phosphorodithioate | inosine |
| I46 | I | phosphorodithioate | inosine |
| I47 | $NH_2$ | phosphorodithioate | inosine |
| I48 | H | phosphorodithioate | inosine |
| I49 | OH | methylphosphonate | inosine |
| I50 | OMe | methylphosphonate | inosine |
| I51 | F | methylphosphonate | inosine |
| I52 | Cl | methylphosphonate | inosine |
| I53 | Br | methylphosphonate | inosine |
| I54 | I | methylphosphonate | inosine |
| I55 | $NH_2$ | methylphosphonate | inosine |
| I56 | H | methylphosphonate | inosine |

TABLE 2-continued

Exemplary modified nucleotides contained in a synthetic guide sequence.

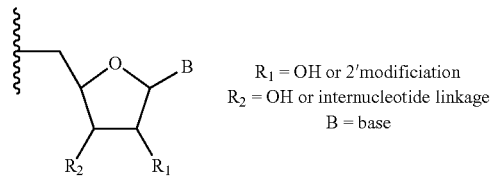

$R_1$ = OH or 2'modificiation
$R_2$ = OH or internucleotide linkage
B = base

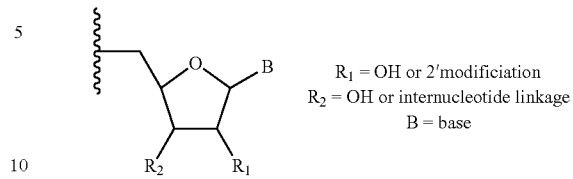

$R_1$ = OH or 2'modificiation
$R_2$ = OH or internucleotide linkage
B = base

| # | $R_1$ | $R_2$ | B |
|---|---|---|---|
| I57 | OH | boranophosphonate | inosine |
| I58 | OMe | boranophosphonate | inosine |
| I59 | F | boranophosphonate | inosine |
| I60 | Cl | boranophosphonate | inosine |
| I61 | Br | boranophosphonate | inosine |
| I62 | I | boranophosphonate | inosine |
| I63 | $NH_2$ | boranophosphonate | inosine |
| I64 | H | boranophosphonate | inosine |
| J1 | OH | OH | 5-methylcytidine |
| J2 | OMe | OH | 5-methylcytidine |
| J3 | F | OH | 5-methylcytidine |
| J4 | Cl | OH | 5-methylcytidine |
| J5 | Br | OH | 5-methylcytidine |
| J6 | I | OH | 5-methylcytidine |
| J7 | $NH_2$ | OH | 5-methylcytidine |
| J8 | H | OH | 5-methylcytidine |
| J9 | OH | phosphodiester | 5-methylcytidine |
| J10 | OMe | phosphodiester | 5-methylcytidine |
| J11 | F | phosphodiester | 5-methylcytidine |
| J12 | Cl | phosphodiester | 5-methylcytidine |
| J13 | Br | phosphodiester | 5-methylcytidine |
| J14 | I | phosphodiester | 5-methylcytidine |
| J15 | $NH_2$ | phosphodiester | 5-methylcytidine |
| J16 | H | phosphodiester | 5-methylcytidine |
| J17 | OH | phosphonoacetate | 5-methylcytidine |
| J18 | OMe | phosphonoacetate | 5-methylcytidine |
| J19 | F | phosphonoacetate | 5-methylcytidine |
| J20 | Cl | phosphonoacetate | 5-methylcytidine |
| J21 | Br | phosphonoacetate | 5-methylcytidine |
| J22 | I | phosphonoacetate | 5-methylcytidine |
| J23 | $NH_2$ | phosphonoacetate | 5-methylcytidine |
| J24 | H | phosphonoacetate | 5-methylcytidine |
| J25 | OH | thiophosphonoacetate | 5-methylcytidine |
| J26 | OMe | thiophosphonoacetate | 5-methylcytidine |
| J27 | F | thiophosphonoacetate | 5-methylcytidine |
| J28 | Cl | thiophosphonoacetate | 5-methylcytidine |
| J29 | Br | thiophosphonoacetate | 5-methylcytidine |
| J30 | I | thiophosphonoacetate | 5-methylcytidine |
| J31 | $NH_2$ | thiophosphonoacetate | 5-methylcytidine |
| J32 | H | thiophosphonoacetate | 5-methylcytidine |
| J33 | OH | phosphorothioate | 5-methylcytidine |
| J34 | OMe | phosphorothioate | 5-methylcytidine |
| J35 | F | phosphorothioate | 5-methylcytidine |
| J36 | Cl | phosphorothioate | 5-methylcytidine |
| J37 | Br | phosphorothioate | 5-methylcytidine |
| J38 | I | phosphorothioate | 5-methylcytidine |
| J39 | $NH_2$ | phosphorothioate | 5-methylcytidine |
| J40 | H | phosphorothioate | 5-methylcytidine |
| J41 | OH | phosphorodithioate | 5-methylcytidine |
| J42 | OMe | phosphorodithioate | 5-methylcytidine |
| J43 | F | phosphorodithioate | 5-methylcytidine |
| J44 | Cl | phosphorodithioate | 5-methylcytidine |
| J45 | Br | phosphorodithioate | 5-methylcytidine |
| J46 | I | phosphorodithioate | 5-methylcytidine |
| J47 | $NH_2$ | phosphorodithioate | 5-methylcytidine |
| J48 | H | phosphorodithioate | 5-methylcytidine |
| J49 | OH | methylphosphonate | 5-methylcytidine |
| J50 | OMe | methylphosphonate | 5-methylcytidine |
| J51 | F | methylphosphonate | 5-methylcytidine |
| J52 | Cl | methylphosphonate | 5-methylcytidine |
| J53 | Br | methylphosphonate | 5-methylcytidine |
| J54 | I | methylphosphonate | 5-methylcytidine |
| J55 | $NH_2$ | methylphosphonate | 5-methylcytidine |
| J56 | H | methylphosphonate | 5-methylcytidine |
| J57 | OH | boranophosphonate | 5-methylcytidine |
| J58 | OMe | boranophosphonate | 5-methylcytidine |
| J59 | F | boranophosphonate | 5-methylcytidine |
| J60 | Cl | boranophosphonate | 5-methylcytidine |
| J61 | Br | boranophosphonate | 5-methylcytidine |
| J62 | I | boranophosphonate | 5-methylcytidine |
| J63 | $NH_2$ | boranophosphonate | 5-methylcytidine |
| J64 | H | boranophosphonate | 5-methylcytidine |
| K1 | OH | OH | 5-aminoallyluridine |
| K2 | OMe | OH | 5-aminoallyluridine |
| K3 | F | OH | 5-aminoallyluridine |
| K4 | Cl | OH | 5-aminoallyluridine |
| K5 | Br | OH | 5-aminoallyluridine |
| K6 | I | OH | 5-aminoallyluridine |
| K7 | $NH_2$ | OH | 5-aminoallyluridine |
| K8 | H | OH | 5-aminoallyluridine |
| K9 | OH | phosphodiester | 5-aminoallyluridine |
| K10 | OMe | phosphodiester | 5-aminoallyluridine |
| K11 | F | phosphodiester | 5-aminoallyluridine |
| K12 | Cl | phosphodiester | 5-aminoallyluridine |
| K13 | Br | phosphodiester | 5-aminoallyluridine |
| K14 | I | phosphodiester | 5-aminoallyluridine |
| K15 | $NH_2$ | phosphodiester | 5-aminoallyluridine |
| K16 | H | phosphodiester | 5-aminoallyluridine |
| K17 | OH | phosphonoacetate | 5-aminoallyluridine |
| K18 | OMe | phosphonoacetate | 5-aminoallyluridine |
| K19 | F | phosphonoacetate | 5-aminoallyluridine |
| K20 | Cl | phosphonoacetate | 5-aminoallyluridine |
| K21 | Br | phosphonoacetate | 5-aminoallyluridine |
| K22 | I | phosphonoacetate | 5-aminoallyluridine |
| K23 | $NH_2$ | phosphonoacetate | 5-aminoallyluridine |
| K24 | H | phosphonoacetate | 5-aminoallyluridine |
| K25 | OH | thiophosphonoacetate | 5-aminoallyluridine |
| K26 | OMe | thiophosphonoacetate | 5-aminoallyluridine |
| K27 | F | thiophosphonoacetate | 5-aminoallyluridine |
| K28 | Cl | thiophosphonoacetate | 5-aminoallyluridine |
| K29 | Br | thiophosphonoacetate | 5-aminoallyluridine |
| K30 | I | thiophosphonoacetate | 5-aminoallyluridine |
| K31 | $NH_2$ | thiophosphonoacetate | 5-aminoallyluridine |
| K32 | H | thiophosphonoacetate | 5-aminoallyluridine |
| K33 | OH | phosphorothioate | 5-aminoallyluridine |
| K34 | OMe | phosphorothioate | 5-aminoallyluridine |
| K35 | F | phosphorothioate | 5-aminoallyluridine |
| K36 | Cl | phosphorothioate | 5-aminoallyluridine |
| K37 | Br | phosphorothioate | 5-aminoallyluridine |
| K38 | I | phosphorothioate | 5-aminoallyluridine |
| K39 | $NH_2$ | phosphorothioate | 5-aminoallyluridine |
| K40 | H | phosphorothioate | 5-aminoallyluridine |
| K41 | OH | phosphorodithioate | 5-aminoallyluridine |
| K42 | OMe | phosphorodithioate | 5-aminoallyluridine |
| K43 | F | phosphorodithioate | 5-aminoallyluridine |
| K44 | Cl | phosphorodithioate | 5-aminoallyluridine |
| K45 | Br | phosphorodithioate | 5-aminoallyluridine |
| K46 | I | phosphorodithioate | 5-aminoallyluridine |
| K47 | $NH_2$ | phosphorodithioate | 5-aminoallyluridine |
| K48 | H | phosphorodithioate | 5-aminoallyluridine |
| K49 | OH | methylphosphonate | 5-aminoallyluridine |
| K50 | OMe | methylphosphonate | 5-aminoallyluridine |
| K51 | F | methylphosphonate | 5-aminoallyluridine |
| K52 | Cl | methylphosphonate | 5-aminoallyluridine |
| K53 | Br | methylphosphonate | 5-aminoallyluridine |
| K54 | I | methylphosphonate | 5-aminoallyluridine |
| K55 | $NH_2$ | methylphosphonate | 5-aminoallyluridine |
| K56 | H | methylphosphonate | 5-aminoallyluridine |
| K57 | OH | boranophosphonate | 5-aminoallyluridine |
| K58 | OMe | boranophosphonate | 5-aminoallyluridine |
| K59 | F | boranophosphonate | 5-aminoallyluridine |
| K60 | Cl | boranophosphonate | 5-aminoallyluridine |

TABLE 2-continued

Exemplary modified nucleotides contained in a synthetic guide sequence.

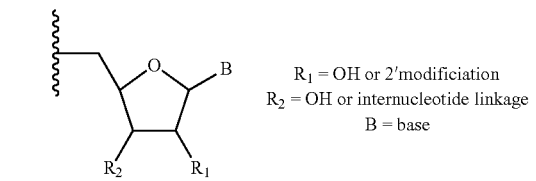

$R_1$ = OH or 2'modificiation
$R_2$ = OH or internucleotide linkage
B = base

| # | $R_1$ | $R_2$ | B |
|---|---|---|---|
| K61 | Br | boranophosphonate | 5-aminoallyluridine |
| K62 | I | boranophosphonate | 5-aminoallyluridine |
| K63 | $NH_2$ | boranophosphonate | 5-aminoallyluridine |
| K64 | H | boranophosphonate | 5-aminoallyluridine |
| L1 | OH | OH | 5-methyluridine |
| L2 | OMe | OH | 5-methyluridine |
| L3 | F | OH | 5-methyluridine |
| L4 | Cl | OH | 5-methyluridine |
| L5 | Br | OH | 5-methyluridine |
| L6 | I | OH | 5-methyluridine |
| L7 | $NH_2$ | OH | 5-methyluridine |
| L8 | H | OH | 5-methyluridine |
| L9 | OH | phosphodiester | 5-methyluridine |
| L10 | OMe | phosphodiester | 5-methyluridine |
| L11 | F | phosphodiester | 5-methyluridine |
| L12 | Cl | phosphodiester | 5-methyluridine |
| L13 | Br | phosphodiester | 5-methyluridine |
| L14 | I | phosphodiester | 5-methyluridine |
| L15 | $NH_2$ | phosphodiester | 5-methyluridine |
| L16 | H | phosphodiester | 5-methyluridine |
| L17 | OH | phosphonoacetate | 5-methyluridine |
| L18 | OMe | phosphonoacetate | 5-methyluridine |
| L19 | F | phosphonoacetate | 5-methyluridine |
| L20 | Cl | phosphonoacetate | 5-methyluridine |
| L21 | Br | phosphonoacetate | 5-methyluridine |
| L22 | I | phosphonoacetate | 5-methyluridine |
| L23 | $NH_2$ | phosphonoacetate | 5-methyluridine |
| L24 | H | phosphonoacetate | 5-methyluridine |
| L25 | OH | thiophosphonoacetate | 5-methyluridine |
| L26 | OMe | thiophosphonoacetate | 5-methyluridine |
| L27 | F | thiophosphonoacetate | 5-methyluridine |
| L28 | Cl | thiophosphonoacetate | 5-methyluridine |
| L29 | Br | thiophosphonoacetate | 5-methyluridine |
| L30 | I | thiophosphonoacetate | 5-methyluridine |
| L31 | $NH_2$ | thiophosphonoacetate | 5-methyluridine |
| L32 | H | thiophosphonoacetate | 5-methyluridine |
| L33 | OH | phosphorothioate | 5-methyluridine |
| L34 | OMe | phosphorothioate | 5-methyluridine |
| L35 | F | phosphorothioate | 5-methyluridine |
| L36 | Cl | phosphorothioate | 5-methyluridine |
| L37 | Br | phosphorothioate | 5-methyluridine |
| L38 | I | phosphorothioate | 5-methyluridine |
| L39 | $NH_2$ | phosphorothioate | 5-methyluridine |
| L40 | H | phosphorothioate | 5-methyluridine |
| L41 | OH | phosphorodithioate | 5-methyluridine |
| L42 | OMe | phosphorodithioate | 5-methyluridine |
| L43 | F | phosphorodithioate | 5-methyluridine |
| L44 | Cl | phosphorodithioate | 5-methyluridine |
| L45 | Br | phosphorodithioate | 5-methyluridine |
| L46 | I | phosphorodithioate | 5-methyluridine |
| L47 | $NH_2$ | phosphorodithioate | 5-methyluridine |
| L48 | H | phosphorodithioate | 5-methyluridine |
| L49 | OH | methylphosphonate | 5-methyluridine |
| L50 | OMe | methylphosphonate | 5-methyluridine |
| L51 | F | methylphosphonate | 5-methyluridine |
| L52 | Cl | methylphosphonate | 5-methyluridine |
| L53 | Br | methylphosphonate | 5-methyluridine |
| L54 | I | methylphosphonate | 5-methyluridine |
| L55 | $NH_2$ | methylphosphonate | 5-methyluridine |
| L56 | H | methylphosphonate | 5-methyluridine |
| L57 | OH | boranophosphonate | 5-methyluridine |
| L58 | OMe | boranophosphonate | 5-methyluridine |
| L59 | F | boranophosphonate | 5-methyluridine |
| L60 | Cl | boranophosphonate | 5-methyluridine |
| L61 | Br | boranophosphonate | 5-methyluridine |
| L62 | I | boranophosphonate | 5-methyluridine |

TABLE 2-continued

Exemplary modified nucleotides contained in a synthetic guide sequence.

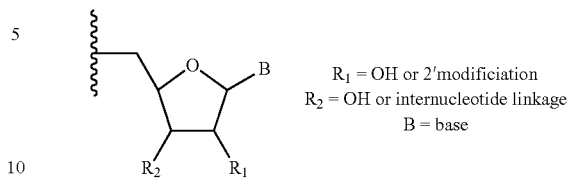

$R_1$ = OH or 2'modificiation
$R_2$ = OH or internucleotide linkage
B = base

| # | $R_1$ | $R_2$ | B |
|---|---|---|---|
| L63 | $NH_2$ | boranophosphonate | 5-methyluridine |
| L64 | H | boranophosphonate | 5-methyluridine |

As described herein, certain unnatural base pairs (e.g., isoG and isoC, Z base and P base; see Zhang et al. (2015) *J. Am. Chem. Soc.*) may be advantageous for affecting the thermostability of the guide RNA secondary structure. These modifications can be used to prevent misfolding of the guide RNA scaffold with other domains of a guide RNA sequence.

Figure 10:
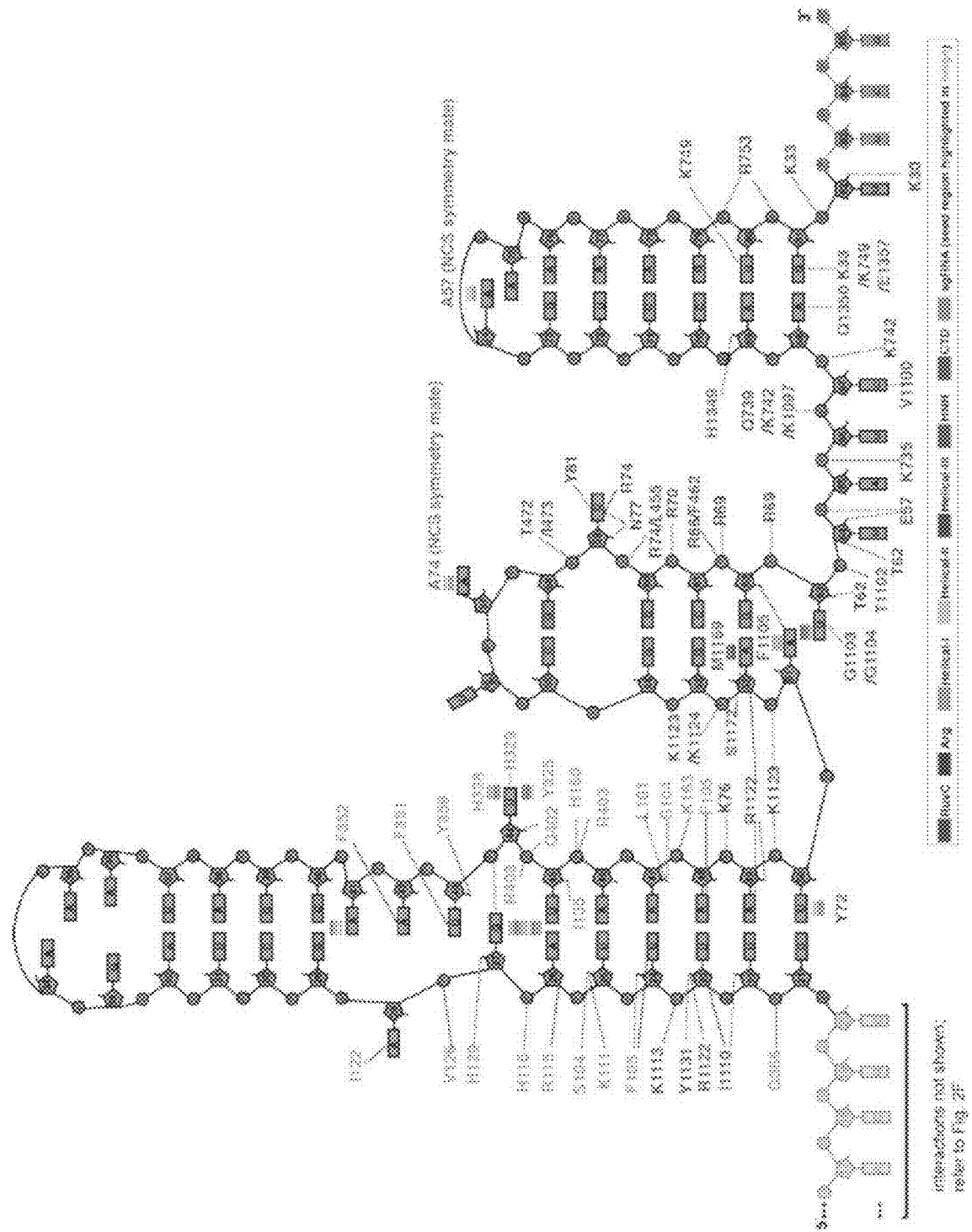
FIG. 10 shows the guide RNA scaffold secondary structure, displaying noncovalent binding interactions with amino acids of Cas9, as reported in Jiang et al., *Science* (2015) 348:6242, 1477-81.

Recent guide RNA:Cas9 protein structural information (FIG. 10, as reported in Jiang et al. 2015, *Science*) and in vivo/in vitro functional mutation studies (see, e.g., Briner et al. 2014, *Mol. Cell*, 56, 333-9) indicate that the guide RNA scaffold is predominantly structurally conserved. This reinforces the importance of correct folding of the conserved domain of guide RNAs for functionality with Cas9. FIG. 10 shows the guide RNA scaffold secondary structure, displaying interactions with amino acids of Cas9. Most of the guide RNA nitrogenous bases are not involved in binding interactions with Cas9 protein.

The flanking sequences of the sgRNA scaffold increase the likelihood of misfolding and hence misfunction. The 20 nt guide targeting sequence, 5' of the scaffold region, is user-specified for each target, thus the likelihood of misfolding is variable or target-specific. Also, many emerging CRISPR-Cas applications append functional sequences 3' of the scaffold, such as CRISPRdisplay (Schechner et al., *Nat. Methods* 2015) and CRISPR-i/-a (Chen et al., *Cell* 2013), which are riboswitches or aptamers that also need to correctly and independently fold to function properly. To ensure that each of the functional domains (i.e. targeting guide, scaffold, aptamer) of a given sgRNA folds in a modular, independent manner, the structurally conserved scaffold base pairs can be substituted with unnatural, orthogonal base pairs (e.g., isoG and isoC; Z base and P base), and in some embodiments, substituted exclusively with unnatural, orthogonal base pairs. This ensures that the sgRNA scaffold sequences will not stably interact in a secondary structure with elements of the target-pairing guide sequence or other non-native domains incorporated in the guide RNA such as any aptamer sequences or any non-native 5' or 3' overhangs on the guide RNA. Alternatively, the unnatural, orthogonal base pairs mentioned above could be incorporated in any non-native overhangs or aptamers that may be present, thus to prevent secondary structures involving misfolding of the scaffold sequence(s).

B. Guide RNA with at Least One Modification

In one aspect, the present technology provides a guide RNA having at least one modification, constituting a modified gRNA.

In certain embodiments, the modified gRNA comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 modified nucleotides. In other embodiments, the modified gRNA comprises at least 55, 60, 65, 70, 75, 80, 85, 90, 95, 100, 110, 120, 130 or 140 modified nucleotides. In certain embodiments, all nucleotides are modified. In certain embodiments, all the modifications are the same. In certain embodiments, all the modified nucleotides have the same type of modification. In certain embodiments, the modified gRNA comprises a combination of differently modified nucleotides. In certain embodiments, the modified gRNA comprises two or more modified nucleotides. In certain embodiments, the modified gRNA comprises three or more modified nucleotides. In certain embodiments, the modified nucleotides are arranged contiguously. In certain embodiments, the modified gRNA comprises at least one contiguous stretch of modified nucleotides. In certain embodiments, the modified gRNA comprises a contiguous stretch of at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 modified nucleotides. Each modified nucleotide may independently comprise one or more types of modifications. In certain embodiments, no modified nucleotides are contiguous, or some but not all are contiguous, in the sequence of the modified gRNA.

In certain embodiments, the modification is within the 5' portion of the guide RNA. In certain embodiments, the modification is within the first five (5) nucleotides of the 5' portion of the guide RNA. In certain embodiments, the modification is within the first three (3) nucleotides of the 5' portion of the guide RNA. In certain embodiments, the modification is within the 3' portion of the guide RNA. In certain embodiments, the modification is within the last five (5) nucleotides of the 3' portion of the guide RNA. In certain embodiments, the modification is within the last three (3) nucleotides of the 3' portion of the guide RNA. In certain embodiments, the modification is within the internal region (i.e., between the 5' end and the 3' end) of the guide RNA.

In certain embodiments, the modification is incorporated in the 5' portion or the 3' portion of the guide RNA, particularly within the first 5 or 10 nucleotides of the 5' portion or within the last 5 or 10 nucleotides of the 3' portion to, for example, protect the RNA from degradation by nucleases or for other purposes. In some other embodiments, the modification is in both the 5' portion and the 3' portion of the guide RNA, particularly within the first 5 or 10 nucleotides of the 5' portion and within the last 5 or 10 nucleotides of the 3' portion to, for example, protect the RNA from degradation by nucleases or for other purposes. In certain embodiments, more than one type of modification is present in both the 5' portion and the 3' portion of the guide RNA. In certain embodiments, the modifications are located at the 5' end, at the 3' end, and within the internal sequence of the guide RNA. In certain embodiments, a guide RNA comprises 40 or fewer, alternatively 20 or fewer, alternatively 15 or fewer, alternatively 10 or fewer, alternatively 5 or fewer, alternatively 3 or fewer deoxyribonucleotide residues in the 5' or 3' portion of the guide RNA.

In certain embodiments, the modification is within the crRNA segment of the guide RNA. In certain embodiments, the modification is within the guide sequence of the crRNA. In certain embodiments, the modification is within the first five (5) nucleotides of the crRNA segment. In certain embodiments, the modification is within the first three (3) nucleotides of the crRNA segment. In certain embodiments, the modification is within a 5'-overhang on the crRNA segment. In certain embodiments, the modification is within the tracrRNA segment of the guide RNA. In certain embodiments, the modification is within the last five (5) nucleotides of the tracrRNA segment of the guide RNA. In certain embodiments, the modification is within the last three (3) nucleotides of the tracrRNA segment of the guide RNA. In certain embodiments, when the guide RNA is a single guide RNA, the modification is located within the loop of the guide RNA. In certain embodiments, one or more modifications is within the loop L region. In certain embodiments, the modification comprises a dye, a non-fluorescent label, or a tag conjugated to a linker incorporated between two nucleotides as described above, for example by conjugation to a 2-(3-(dye/label/tag-amido)propanamido)propane-1,3-diol bis(phosphodiester) linker or to a modified base of a nucleotide in the loop or L region.

In certain embodiments, the modification comprises an end modification, such as a 5' end modification or a 3' end modification. Examples of end modifications include, but are not limited to phosphorylation (as natural phosphate or polyphosphate or as modified phosphonate groups such as for example, alkylphosphonate, phosphonocarboxylate, phosphonoacetate, boranophosphonate, phosphorothioate, phosphorodithioate and the like), biotinylation, conjugating or conjugated molecules, linkers, dyes, labels, tags, functional groups (such as for example but not limited to 5'-amino, 5'-thio, 5'-amido, 5'carboxy and the like), inverted linkages, or hydrocarbon moieties which may comprise ether, polyethylene glycol (PEG), ester, hydroxyl, aryl, halo, phosphodiester, bicyclic, heterocyclic or other organic functional group. In certain embodiments, the end modification comprises dimethoxytrityl.

In certain embodiments, the modification comprises a modified base. As used herein, "unmodified" bases include the purine bases adenine (A) and guanine (G), and the pyrimidine bases thymine (T), cytosine (C) and uracil (U). Examples of modified bases include, but are not limited to, synthetic and natural bases such as 2-thioU, 2-thioC, 4-thioU, 6-thioG, 2-aminoA, 2-aminoP, pseudouracil, hypoxanthine, 7-deazaguanine, 7-deaza-8-azaguanine, 7-deazaadenine, 7-deaza-8-azaadenine, 5-methylC, 5-methylU, 5-hydroxymethylcytosine, 5-hydroxymethyluracil, 5,6-dehydrouracil, 5-propynylcytosine, 5-propynyluracil, 5-ethynylcytosine, 5-ethynyluracil, 5-allylU, 5-allylC, 5-aminoallyl-uracil, and 5-aminoallyl-cytosine. In certain embodiments, the modification comprises an abasic nucleotide. In certain embodiments, the modification comprises a nonstandard purine or pyrimidine structure, such as Z or P, isoC or isoG, UNA, 5-methylpyrymidine, x(A,G,C,T) or y(A,G,C,T). In certain embodiments, the modified gRNA comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 modified bases. In other embodiments, the modified gRNA comprises at least 55, 60, 65, 70, 75, 80, 85, 90, 95, 100, 110, 120, 130 or 140 modified bases. In certain embodiments, all bases in a gRNA are modified.

In certain embodiments, the modification comprises a modified sugar. Examples of modified sugars include, but are not limited to, sugars having modifications at the 2' position or modifications at the 4' position. For example, in certain embodiments, the sugar comprises 2'-O—$C_{1-4}$alkyl, such as 2'-O-methyl (2'-OMe). In certain embodiments, the sugar comprises 2'-O—$C_{1-3}$alkyl-O—$C_{1-3}$alkyl, such as 2'-methoxyethoxy (2'-O—$CH_2CH_2OCH_3$) also known as 2'-O-(2-methoxyethyl) or 2'-MOE. In certain embodiments, the sugar comprises 2'-halo, such as 2'-F, 2'-Br, 2'-Cl, or 2'-I.

In certain embodiments, the sugar comprises 2'-NH₂. In certain embodiments, the sugar comprises 2'-H (e.g., a deoxynucleotide). In certain embodiments, the sugar comprises 2'-arabino or 2'-F-arabino. In certain embodiments, the sugar comprises 2'-LNA or 2'-ULNA. In certain embodiments, the sugar comprises a 4'-thioribosyl. In certain embodiments, the modified gRNA comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 modified sugars. In other embodiments, the modified gRNA comprises at least 55, 60, 65, 70, 75, 80, 85, 90, 95, 100, 110, 120, 130 or 140 modified sugars. In certain embodiments, all sugars in a gRNA are modified.

In certain embodiments, the modification comprises a modified backbone (i.e., an internucleotide linkage other than a natural phosphodiester). Examples of modified internucleotide linkages include, but are not limited to, a phosphorothioate internucleotide linkage, a chiral phosphorothioate internucleotide linkage, a phosphorodithioate internucleotide linkage, a boranophosphonate internucleotide linkage, a C₁₋₄alkyl phosphonate internucleotide linkage such as a methylphosphonate internucleotide linkage, a boranophosphonate internucleotide linkage, a phosphonocarboxylate internucleotide linkage such as a phosphonoacetate internucleotide linkage, a phosphonocarboxylate ester internucleotide linkage such as a phosphonoacetate ester internucleotide linkage, a thiophosphonocarboxylate internucleotide linkage such as for example a thiophosphonoacetate internucleotide linkage, a thiophosphonocarboxylate ester internucleotide linkage such as a thiophosphonoacetate ester internucleotide linkage. Various salts, mixed salts and free acid forms are also included. In certain embodiments, the modified gRNA comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 modified internucleotide linkages. In other embodiments, the modified gRNA comprises at least 55, 60, 65, 70, 75, 80, 85, 90, 95, 100, 110, 120, 130 or 140 modified internucleotide linkages. In certain embodiments, all internucleotide linkages in a gRNA are modified.

In certain embodiments, the modification is a 2'-O—C₁₋₄alkyl, 2'-H, 2'-O—C₁₋₃alkyl-O—C₁₋₃alkyl, 2'-F, 2'-NH₂, 2'-arabino, 2'-F-arabino, 2'-LNA, 2'-ULNA, 4'-thioribosyl, 2-thioU, 2-thioC, 4-thioU, 6-thioG, 2-aminoA, 2-aminoP, pseudouracil, hypoxanthine, 7-deazaguanine, 7-deaza-8-azaguanine, 7-deazaadenine, 7-deaza-8-azaadenine, 5-MeC, 5-MeU, 5-hydroxymethylcytosine, 5-hydroxymethyluracil, 5,6-dehydrouracil, 5-propynylcytosine, 5-propynyluracil, 5-ethynylcytosine, 5-ethynyluracil, 5-allylU, 5-allylC, 5-aminoallyl-uracil, 5-aminoallyl-cytosine, an abasic nucleotide, Z, P, UNA, isoC, isoG, 5-methyl-pyrimidine, x(A,G,C,T), y(A,G,C,T), a 3'-phosphorothioate group, a 3'-phosphonoacetate group, a 3'-phosphonoacetate ester group, a 3'-thiophosphonoacetate group, a 3'-thiophosphonoacetate ester group, a 3'-methylphosphonate group, a 3'-boranophosphonate group, a 3'-phosphorodithioate group, or combinations thereof.

In certain embodiments, the modified nucleotide comprises a 2'-O-methyl-3'-phosphorothioate. In certain embodiments, the modified nucleotide comprises a 2'-O-methyl-3'-phosphonoacetate. In certain embodiments, the modified nucleotide comprises a 2'-O-methyl-3'-thiophosphonoacetate. In certain embodiments, the modified nucleotide comprises a Z base. In certain embodiments, the modified nucleotide comprises a 2'-halo-3'-phosphorothioate. In certain embodiments, the modified nucleotide comprises a 2'-halo-3'-phosphonoacetate. In certain embodiments, the modified nucleotide comprises a 2'-halo-3'-thiophosphonoacetate. In certain embodiments, the modified nucleotide comprises a 2'-fluoro-3'-phosphorothioate. In certain embodiments, the modified nucleotide comprises a 2'-fluoro-3'-phosphonoacetate. In certain embodiments, the modified nucleotide comprises a 2'-fluoro-3'-thiophosphonoacetate.

In certain embodiments, the guide RNA comprises an oligonucleotide represented by Formula (I):

$$W-Y \text{ or } Y-W \tag{I}$$

wherein W represents a nucleotide or a stretch of nucleotides of the oligonucleotide comprising at least one modification and Y represents an unmodified portion of the oligonucleotide.

In certain embodiments, W is within the 5' portion of the guide RNA. In certain embodiments, W is at least partially within the first five (5) nucleotides of the 5' portion of the guide RNA. In certain embodiments, W is at least partially within the first three (3) nucleotides of the 5' portion of the guide RNA. In certain embodiments, W is within the 3' portion of the guide RNA. In certain embodiments, W is at least partially within the last five (5) nucleotides of the 3' portion of the guide RNA. In certain embodiments, W is at least partially within the last three (3) nucleotides of the 3' portion of the guide RNA. In certain embodiments, W is within the internal region (i.e., between the 5' end and the 3' end) of the guide RNA.

In certain embodiments, W comprises an end modification, such as a 5' end modification or a 3' end modification as described above. In certain embodiments, the end modification comprises dimethoxytrityl.

In certain embodiments, W comprises a modified base as described above. In certain embodiments, W comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 modified bases. In other embodiments, W comprises at least 55, 60, 65, 70, 75, 80, 85, 90, 95, 100, 110, 120, 130 or 140 modified bases. In certain embodiments, all bases in a gRNA are modified.

In certain embodiments, W comprises a modified sugar as described above. In certain embodiments, W comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 modified sugars. In other embodiments, W comprises at least 55, 60, 65, 70, 75, 80, 85, 90, 95, 100, 110, 120, 130 or 140 modified sugars. In certain embodiments, all sugars in a gRNA are modified.

In certain embodiments, W comprises a modified backbone (i.e., an internucleotide linkage other than a phosphodiester) as described above. In certain embodiments, W comprises more than one, such as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 modified internucleotide linkages. In other embodiments, W comprises at least 55, 60, 65, 70, 75, 80, 85, 90, 95, 100, 110, 120, 130 or 140 modified internucleotide linkages. In certain embodiments, all internucleotide linkages in a gRNA are modified.

In certain embodiments, W comprises a 2'-O—C₁₋₄alkyl, 2'-H, 2'-O—C₁₋₃alkyl-O—C₁₋₃alkyl, 2'-F, 2'-NH₂, 2'-arabino, 2'-F-arabino, 2'-LNA, 2'-ULNA, 4'-thioribosyl, 2-thioU, 2-thioC, 4-thioU, 6-thioG, 2-aminoA, 2-aminoP, pseudouracil, hypoxanthine, 7-deazaguanine, 7-deaza-8-azaguanine, 7-deazaadenine, 7-deaza-8-azaadenine, 5-MeC, 5-MeU, 5-hydroxymethylcytosine, 5-hydroxymethyluracil, 5,6-dehydrouracil, 5-propynylcytosine, 5-propynyluracil, 5-ethynylcytosine, 5-ethynyluracil, 5-allylU, 5-allylC, 5-aminoallyl-uracil, 5-aminoallyl-cytosine, abasic nucleotides, Z, P, UNA, isoC, isoG, 5-methyl-pyrimidine, x(A,G,C,T), y(A,G,C,T), a phosphorothioate internucleotide linkage, a phosphonoacetate internucleotide linkage, a phosphonoacetate ester internucleotide linkage, a thiophosphonoacetate internucleotide linkage, a thiophosphonoacetate ester internucleotide linkage a methylphosphonate internucleotide linkage, a boranophosphonate internucleotide linkage, a phosphorodithioate internucleotide linkage, or combinations thereof.

In certain embodiments, W comprises a 2'-O-methyl and a 3'-phosphorothioate group on the same nucleotide. In certain embodiments, W comprises a 2'-O-methyl and a 3'-phosphonoacetate group on the same nucleotide. In certain embodiments, W comprises a 2'-O-methyl and $3^1$-thiophosphonoacetate group on the same nucleotide. In certain embodiments, W comprises a 2'-F and a 3'-phosphorothioate group on the same nucleotide. In certain embodiments, W comprises a 2'-F and a 3'-phosphonoacetate group on the same nucleotide. In certain embodiments, W comprises a 2'-F and $3^1$-thiophosphonoacetate group on the same nucleotide.

In certain embodiments, W comprises 1, 2, 3, 4, 5, 6, 7, 8, 9, 10, 11, 12, 13, 14, 15, 16, 17, 18, 19 or 20 modified nucleotides. In certain embodiments, each of the modified nucleotides comprises the same modification. In certain embodiments, W comprises a combination of variously modified nucleotides. In certain embodiments, W comprises two or more modified nucleotides. In certain embodiments, W comprises three or more modified nucleotides. In certain embodiments, the modified nucleotides are not arranged contiguously in the sequence, or at least not entirely, as one or more unmodified nucleotides may intercede. In certain embodiments, the modified nucleotides are arranged contiguously. In certain embodiments, W comprises at least one contiguous stretch of modified nucleotides. In certain embodiments, W comprises a contiguous stretch of at least three (3) modified nucleotides. In certain embodiments, W comprises a contiguous stretch of at least four (4) modified nucleotides. In certain embodiments, W comprises a contiguous stretch of at least five (5) modified nucleotides.

In certain embodiments, the guide RNA comprises an oligonucleotide represented by Formula (II):

$$M_m N_n \quad (II)$$

wherein each N independently represents an unmodified ribonucleotide;

wherein each M represents a modified nucleotide and is independently selected from the group consisting of a 2'-O-methyl ribonucleotide, a 3'-P(S) ribonucleotide, a 3'-PACE ribonucleotide, a 3'-thioPACE ribonucleotide, a 2'-O-methyl-3'-P(S)-ribonucleotide, a 2'-O-methyl-3'-PACE ribonucleotide, a 2'-O-methyl-3'-thioPACE ribonucleotide, a Z nucleotide, and a 2'-deoxynucleotide;

wherein each M is at any position of the sequence of the guide RNA;

wherein any given M is the same or different from any other M, and any given N is the same or different from any other N; and wherein each of m and n are independently selected from an integer between 0 and 219, provided that 50<m+n≤220, and m is not 0.

In some embodiments, m+n<150.

In certain embodiments, each M is modified with one or more moieties independently selected from the group consisting of 2'-F, 2-thiouracil, 4-thiouracil, 2-aminoadenine, hypoxanthine, 5-methylcytosine, 5-methyluracil, 5-allylaminouracil, squarate linkage, a triazolo linkage, and a 2-(4-butylamidofluorescein)propane-1,3-diol bis(phosphodiester) linkage. In some embodiments, M comprises a dye attached through a linker.

In certain embodiments, each M is independently selected from the group consisting of a 2'-O-methyl ribonucleotide, a 2'-O-methyl-3'-P(S) ribonucleotide, a 2'-O-methyl-3'-PACE ribonucleotide, and a 2'-O-methyl-3'-thioPACE ribonucleotide. In certain embodiments, each M is independently selected from the group consisting of a 2'-O-methyl-3'-PACE ribonucleotide and a 2'-O-methyl-3'-thioPACE ribonucleotide.

In certain embodiments, where m>1, any given M is the same or different from any other M. In certain embodiments, where m>1, each M has the same modification.

In certain embodiments, each M is a 2'-O-methyl-3'-PACE ribonucleotide, m is selected from an integer between 1 and 10, each N is independently selected from the group consisting of A, U, C, and G, and n is selected from an integer between 1 and 149, provided 50<m+n≤150. In certain embodiments, each M is a 2'-O-methyl-3'-PACE ribonucleotide, m is selected from an integer between 1 and 5, each N is independently selected from the group consisting of A, U, C, and G, and n is selected from an integer between 1 and 149, provided 50<m+n≤150. In certain embodiments, each M is a 2'-O-methyl-3'-PACE ribonucleotide, m is selected from an integer between 2 and 5, each N is independently selected from the group consisting of A, U, C, and G, and n is selected from an integer between 1 and 148, provided 50<m+n≤150. In certain embodiments, m is 1. In certain embodiments, m is 2. In certain embodiments, m is 3. In certain embodiments, m is 4. In certain embodiments, m is 5.

In certain embodiments, each M is a 2'-O-methyl-3'-thioPACE ribonucleotide, m is selected from an integer between 1 and 10, each N is independently selected from the group consisting of A, U, C, and G, and n is selected from an integer between 1 and 149, provided 50<m+n≤150. In certain embodiments, each M is a 2'-O-methyl-3'-thioPACE ribonucleotide, m is selected from an integer between 1 and 5, each N is independently selected from the group consisting of A, U, C, and G, and n is selected from an integer between 1 and 149, provided 50<m+n≤150. In certain embodiments, each M is a 2'-O-methyl-3'-thioPACE ribonucleotide, m is selected from an integer between 2 and 5, each N is independently selected from the group consisting of A, U, C, and G, and n is selected from an integer between 1 and 148, provided 50<m+n≤150. In certain embodiments, m is 1. In certain embodiments, m is 2. In certain embodiments, m is 3. In certain embodiments, m is 4. In certain embodiments, m is 5.

In certain embodiments, each M is a 2'-O-methyl ribonucleotide, m is selected from an integer between 1 and 40, each N is independently selected from the group consisting of A, U, C, and G, and n is selected from an integer between 1 and 149, provided 50<m+n≤150. In certain embodiments, each M is a 2'-O-methyl ribonucleotide, m is selected from an integer between 1 and 25, each N is independently selected from the group consisting of A, U, C, and G, and n is selected from an integer between 1 and 149, provided 50<m+n≤150. In certain embodiments, each M is a 2'-O-methyl ribonucleotide, m is selected from an integer between 1 and 20, each N is independently selected from the group consisting of A, U, C, and G, and n is selected from an integer between 1 and 149, provided 50<m+n≤150. In certain embodiments, m is 1. In certain embodiments, m is 2. In certain embodiments, m is 3. In certain embodiments, m is 4. In certain embodiments, m is 5. In certain embodiments, m is 10. In certain embodiments, m is 15. In certain embodiments, m is 20. In certain embodiments, m is 30. In certain embodiments, m is 40.

In certain embodiments, each M is a 2'-deoxynucleotide, m is selected from an integer between 1 and 30, each N is independently selected from the group consisting of A, U, C, and G, and n is selected from an integer between 1 and 149, provided 50<m+n≤150. In certain embodiments, each M is 2'-deoxynucleotide, m is selected from an integer between 1 and 20, each N is independently selected from the group consisting of A, U, C, and G, and n is selected from an integer between 1 and 149, provided 50<m+n≤150. In certain embodiments, m is 5. In certain embodiments, m is 10. In certain embodiments, m is 15. In certain embodiments, m is 20. In certain embodiments, m is 30.

In certain embodiments, each M is a 2'-O-methyl-3'-P(S) ribonucleotide, m is selected from an integer between 1 and 10, each N is independently selected from the group consisting of A, U, C, and G, and n is selected from an integer between 1 and 149, provided 50<m+n≤150. In certain embodiments, each M is a 2'-O-methyl-3'-P(S) ribonucleotide, m is selected from an integer between 1 and 5, each N is independently selected from the group consisting of A, U, C, and G, and n is selected from an integer between 1 and 149, provided 50<m+n≤150. In certain embodiments, m is 1. In certain embodiments, m is 2. In certain embodiments, m is 3. In certain embodiments, m is 4. In certain embodiments, m is 5.

In certain embodiments, each M is a Z nucleotide, m is selected from an integer between 1 and 10, each N is independently selected from the group consisting of A, U, C, and G, and n is selected from an integer between 1 and 149, provided 50<m+n≤150. In certain embodiments, each M is a Z nucleotide, m is selected from an integer between 1 and 5, each N is independently selected from the group consisting of A, U, C, and G, and n is selected from an integer between 1 and 149, provided 50<m+n≤150. In certain embodiments, m is 1. In certain embodiments, m is 2. In certain embodiments, m is 3. In certain embodiments, m is 4. In certain embodiments, m is 5.

In certain embodiments, the modification is a stability-altering modification. In certain embodiments, the modification increases nuclease resistance of the guide RNA relative to a guide RNA without the modification, thus it enhances the guide RNA stability. In certain embodiments, the stability-altering modification is a stability-enhancing modification. For example, in certain embodiments, the stability-enhancing modification comprises a 2'-O-methyl or a 2'-O—$C_{1-4}$alkyl nucleotide. In certain embodiments, the stability-enhancing modification comprises a 2'-halo nucleotide, such as 2'-F, 2'-Br, 2'-Cl, or 2'-I. In certain embodiments, the stability-enhancing modification comprises a 2'MOE or a 2'-O—$C_{1-3}$alkyl-O—$C_{1-3}$alkyl. In certain embodiments, the stability-enhancing modification comprises a 2'-$NH_2$ nucleotide. In certain embodiments, the stability-enhancing modification comprises a 2'-H (or 2'-deoxy) nucleotide. In certain embodiments, the stability-enhancing modification comprises a 2'-arabino or a 2'-F-arabino. In certain embodiments, the stability-enhancing modification comprises a 4'-thioribosyl sugar moiety. In certain embodiments, the stability-enhancing modification comprises a 3'-phosphorothioate group. In certain embodiments, the stability-enhancing modification comprises a 3'-phosphonoacetate group. In certain embodiments, the stability-enhancing modification comprises a nucleotide containing a 3'-thiophosphonoacetate group. In certain embodiments, the stability-enhancing modification comprises a nucleotide containing a 3'-methylphosphonate group. In certain embodiments, the stability-enhancing modification comprises a nucleotide containing a 3'-boranophosphate group. In certain embodiments, the stability-enhancing modification comprises a nucleotide containing a 3'-phosphorodithioate group. In certain embodiments, the stability-enhancing modification comprises a locked nucleic acid ("LNA") nucleotide. In certain embodiments, the stability-enhancing modification comprises an unlocked nucleic acid ("ULNA") nucleotide.

In certain embodiments, the stability-enhancing modification comprises a 2'-O-methyl and a 3'-phosphorothioate group on the same nucleotide. In certain embodiments, the stability-enhancing modification comprises a 2'-O-methyl and a 3'-phosphonoacetate group on the same nucleotide. In certain embodiments, the stability-enhancing modification comprises a 2'-O-methyl and a 3'-thiophosphonoacetate group on the same nucleotide. In certain embodiments, the stability-enhancing modification comprises a 2'-fluoro and a 3'-phosphorothioate group on the same nucleotide. In certain embodiments, the stability-enhancing modification comprises a 2'-fluoro and a 3'-phosphonoacetate group on the same nucleotide. In certain embodiments, the stability-enhancing modification comprises a 2'-fluoro and a 3'-thiophosphonoacetate group on the same nucleotide.

In certain embodiments, the modification is a specificity-altering modification. In some embodiments, specificity enhancement may be achieved by enhancing on-target binding and/or cleavage, or reducing off-target binding and/or cleavage, or a combination of both. In some other embodiments, specificity reduction may be achieved, for example, by reducing on-target binding and/or cleavage, or increasing off-target binding and/or cleavage, or a combination of both.

In certain embodiments, the specificity-altering modification comprises a 2'-O-methyl. In certain embodiments, the specificity-altering modification comprises a 2'-halo, such as 2'-fluoro.

In certain embodiments, the specificity-altering modification comprises a 2-thiouracil base (2-thioU). In certain embodiments, the specificity-altering modification comprises 2-thioC. In certain embodiments, the specificity-altering modification comprises 4-thioU. In certain embodiments, the specificity-altering modification comprises 6-thioG. In certain embodiments, the specificity-altering modification comprises 2-aminoA. In certain embodiments, the specificity-altering modification comprises a 2-aminopurine. In certain embodiments, the specificity-altering modification comprises pseudouracil. In certain embodiments, the specificity-altering modification comprises hypoxanthine. In certain embodiments, the specificity-altering modification comprises 7-deazaguanine. In certain embodiments, the specificity-altering modification comprises 7-deaza-8-azaguanine. In certain embodiments, the specificity-altering modification comprises 7-deazaadenine. In certain embodiments, the specificity-altering modification comprises 7-deaza-8-azaadenine. In certain embodiments, the specificity-altering modification comprises 5-methylC. In certain embodiments, the specificity-altering modification comprises 5-methylU. In certain embodiments, the specificity-altering modification comprises 5-hydroxymethylcytosine. In certain embodiments, the specificity-altering modification comprises 5-hydroxymethyluracil. In certain embodiments, the specificity-altering modification comprises 5,6-dehydrouracil. In certain embodiments, the specificity-altering modification comprises 5-propynylcytosine. In certain embodiments, the specificity-altering modification comprises 5-propynyluracil. In certain embodiments, the specificity-altering modification comprises 5-ethynylcytosine. In certain embodiments, the specificity-altering modification comprises 5-ethynyluracil. In certain embodiments, the specificity-altering modification comprises 5-allylU. In certain embodiments, the specificity-altering modification comprises 5-allylC. In certain embodiments, the specificity-altering modification comprises 5-aminoallylU. In certain embodiments, the specificity-altering modification comprises 5-aminoallylC. In certain embodiments, the specificity-altering modification comprises an abasic nucleotide. In certain embodiments, the specificity-altering modification comprises a Z base. In certain embodiments, the specificity-altering modification comprises P base. In certain embodiments, the specificity-altering modification comprises a UNA base. In certain embodiments, the specificity-altering modification comprises isoC. In certain embodiments, the specificity-altering modification comprises isoG. In certain embodiments, the specificity-altering modification comprises 5-methyl-pyrimidine. In certain embodiments, the specificity-altering modification comprises x(A,G,C,T). In certain embodiments, the specificity-altering modification comprises y(A,G,C,T).

In certain embodiments, the specificity-altering modification comprises a phosphorothioate internucleotide linkage. In certain embodiments, the specificity-altering modification comprises a phosphonoacetate internucleotide linkage. In certain embodiments, the specificity-altering modification comprises a thiophosphonoacetate internucleotide linkage. In certain embodiments, the specificity-altering modification comprises a methylphosphonate internucleotide linkage. In certain embodiments, the specificity-altering modification comprises a boranophosphate internucleotide linkage. In certain embodiments, the specificity-altering modification comprises a phosphorodithioate internucleotide linkage. In certain embodiments, the specificity-altering modification comprises a ULNA. In certain embodiments, the specificity-altering modification comprises an LNA.

In certain embodiments, the modification alters RNA base pairing by, for example, altering the melting temperature (Tm) of the guide RNA relative to a guide RNA without the modification. In certain embodiments, the modification lowers the Tm of the guide RNA relative to a guide RNA without the modification. In certain embodiments, the modification raises the Tm of the guide RNA relative to a guide RNA without the modification.

In certain embodiments, the specificity-altering modification lowers the Tm of a base pairing interaction. In certain embodiments, the modification that lowers the Tm of the base pairing interaction is a 2'-deoxy, as it is well-known in the art that DNA/DNA base pairs have lower Tm than their respective counterpart in RNA/DNA duplexes. In certain embodiments, the modification that lowers the Tm of the base pairing interaction is 2-thiouracil, which slightly lowers Tm of G-U wobble pair. In certain embodiments, the modification that lowers the Tm of the base pairing interaction is a phosphorothioate internucleotide linkage or a phosphorodithioate internucleotide linkage, which lower the Tm by ~0.5° C. per modification. In certain embodiments, the modification that lowers the Tm of the base pairing interaction is a boranophosphonate internucleotide linkage, which lowers the Tm by ~0.5-0.8° C. per modification. In certain embodiments, the modification that lowers the Tm of the base pairing interaction is a phosphonoacetate internucleotide linkage, which lowers the Tm by ~1.3° C. per modification. In certain embodiments, the modification that lowers the Tm of the base pairing interaction is unlocked nucleic acid ("ULNA"), which lowers the Tm by ~5-8° C. per modification. In certain embodiments, the modification that lowers the Tm of the base pairing interaction is 2'-O-methyl-3'-methylphosphonate.

In certain embodiments, the specificity-altering modification raises the Tm of a base pairing interaction. In certain embodiments, the modification that raises the Tm of the base pairing interaction is a 2'-O-methyl, which raises Tm by ~0.5-0.7° C. per modification. In certain embodiments, the modification that raises the Tm of the base pairing interaction is a 2'-F, which raises Tm by ~1° C. per modification. In certain embodiments, the modification that raises the Tm of the base pairing interaction is a 2-thiouracil, which raises Tm of A-U pair (and, as noted above, slightly lowers Tm of G-U wobble pair). In certain embodiments, the modification that raises the Tm of the base pairing interaction is a 4-thiouracil, which raises Tm of G-U wobble pair and slightly raises Tm of A-U pair. In certain embodiments, the modification that raises the Tm of the base pairing interaction is a 2-amino-adenine, which raises Tm of its base pairing with U by ~1° C. per modification. In certain embodiments, the modification that raises the Tm of the base pairing interaction is a 5-methyl-uracil (5-methylU) (see, e.g., Wang & Kool (1995) *Biochemistry*, 34, 4125-32). In certain embodiments, the modification that raises the Tm of the base pairing interaction is a 5-methyl-cytosine (5-methylC). In certain embodiments, the modification that raises the Tm of the base pairing interaction is a locked nucleic acid ("LNA"), which raises Tm by 2-10° C. per modification.

In certain embodiments, the modification alters transfection efficiency of the guide RNA relative to a guide RNA without the modification. In certain embodiments, the modification increases transfection efficiency of the guide RNA relative to a guide RNA without the modification. In certain embodiments, the modification decreases transfection efficiency of the guide RNA relative to a guide RNA without the modification. In certain embodiments, the modification neutralizes the anionic charge on phosphate to allow passive diffusion into cells. In certain embodiments, the charge-neutralizing modification comprises a phosphonoacetate alkyl ester internucleotide linkage, such as a phosphonoacetate methyl ester internucleotide linkage.

In certain embodiments, the modification alters the immunostimulatory effect of the guide RNA relative to a guide RNA without the modification. It was initially discovered that unmethylated bacterial DNA and synthetic analogs thereof are ligands for TLR9 (see Hemmi et al. (2000) *Nature*, 408, 740-5). The stimulation of TLR9 can be mitigated in the dinucleotide motif for example by modifying the C and G residues. The use of 5-methylcytosine, 2-aminocytosine, 2-thiocytosine, 5-methylisocytosine, P nucleobase (6-(β-D-2'-Deoxyribofuranosyl)-3,4-dihydro-8H-pyrimido[4,5-c][1,2]oxazin-7-one), and 2'-O-methylcytosine all result in loss or decrease in TLR9 stimulation. In certain embodiments, use of 6-thioguanine, 2,6-diaminopurine, 2-aminopurine, xanthosine, inosine, 7-deazaxanthosine, isoguanine, 8-oxoguanine, nebularine, 8-bromoguanine, K-nucleobase (2-amino-N-methoxyadenosine), and/or 2'-O-methylguanine can result in loss or decrease in TLR9 stimulation. In some embodiments, use of phosphodiester modifications can lower or eliminate the TLR9 response. Typically, synthetically incorporated phosphorothioates can decrease the TLR9 response to a limited extent, as is thought to result from the presence of two stereoisomers of each phosphorothioate in synthetic RNA. However, it has been shown that phosphorothioate-modified DNA lacking CpG motifs stimulate TLR9 to a rather small extent. The negative charge on the phosphorus is an important element for recognition by TLR9 and therefore removing the negative charge using alkylphosphonates can result in loss or decrease in TLR9 stimulation. The use of phosphonoacetate (PACE) internucleotide linkages between deoxynucleosides in 5' and 3' terminal sequences can significantly increase the TLR9 response; however, the use of thiophosphonoacetate (thioPACE) internucleotide linkages between deoxynucleosides in 5' and 3' terminal sequences can result in loss or decrease in TLR9 stimulation. In certain embodiments, use of sugar modifications that the favor C3'-endo conformation such as 2'-O-methyl modifications can be incorporated at 5' and 3' termini to decrease the TLR9 response. TLR 7 and TLR8 can be stimulated by molecules containing 7-deazaguanine and by single-stranded RNA (see, e.g., Heil et al. (2004) *Science*, 303, 1526-9). TLR3 has been implicated in cellular immunoresponses to virus-derived double-stranded RNA. In certain embodiments, these TLR responses can be mitigated for example by using 2'-O-methyl modifications, modified phosphodiester linkages containing sulfur, or modifications that decrease internucleotide negative charge such as methylphosphonate and/or phosphonoacetate internucleotide linkages.

In certain embodiments, the modification enhances stability and specificity of the guide RNA relative to a guide RNA without the modification. In certain embodiments, the modification enhances stability and transfection efficiency of the guide RNA relative to a guide RNA without the modification. In certain embodiments, the modification enhances specificity and transfection efficiency of the guide RNA relative to a guide RNA without the modification. In certain embodiments, the modification enhances the overall efficacy of the guide RNA relative to a guide RNA without the modification.

C. Guide RNA with a Combination of Modifications

In one aspect, the present technology provides a guide RNA having a combination of two or more modifications.

In certain embodiments, the two modifications are on the same nucleotide (for example, one nucleotide comprises a 2'-O-methyl and a 3'-thiophosphonoacetate moiety). In other embodiments, the two modifications are on two different nucleotides (for example, one nucleotide has a 2-thioU base and another nucleotide has a 2'-O-methyl group).

In certain embodiments, each modification in the guide RNA is the same. In certain embodiments, at least one modification in the guide RNA is different from at least one other modification in the guide RNA. In certain embodiments, a single nucleotide within the guide RNA possesses two or more modifications.

In certain embodiments, the guide RNA comprises a combination of different types of modifications, and at least one type in the combination exists in multiple places in the guide RNA In certain embodiments, at least one type in the combination appears 1, 2, 3, 4, 5, 6, 7, 8, 9, 10, 11, 12, 13, 14, 15, 16, 17, 18, 19 or 20 times in the guide RNA.

In certain embodiments, at least one type of the modifications in the combination appears in two or more modified nucleotides. In certain embodiments, at least one type of the modifications in the combination appears in three or more modified nucleotides. In certain embodiments, the modified nucleotides are not arranged contiguously in the sequence, or at least not entirely, as one or more unmodified nucleotides may intercede. In certain embodiments, the modified nucleotides are arranged contiguously. In certain embodiments, the guide RNA comprises a stretch of contiguous modified nucleotides of the same type. In certain embodiments, the stretch has at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 modified nucleotides.

In certain embodiments, at least one type of the modifications in the combination is within the 5' portion of the guide RNA. In certain embodiments, at least one type of the modifications in the combination is within the first five (5) nucleotides of the 5' portion of the guide RNA. In certain embodiments, at least one type of the modifications in the combination is within the first three (3) nucleotides of the 5' portion of the guide RNA. In certain embodiments, at least one type of the modifications in the combination is within the 3' portion of the guide RNA. In certain embodiments, at least one type of the modifications in the combination is within the last five (5) nucleotides of the 3' portion of the guide RNA. In certain embodiments, at least one type of the modifications in the combination is within the last three (3) nucleotides of the 3' portion of the guide RNA. In certain embodiments, at least one type of the modifications in the combination is within the internal region (i.e., between the 5' end and the 3' end) of the guide RNA.

In certain embodiments, at least one type of the modifications in the combination is incorporated in the 5' portion or 3' portion of the guide RNA, particularly within the first 5 or 10 nucleotides of the 5' portion or within the last 5 or 10 nucleotides of the 3' portion to, for example, protect the RNA from degradation by nucleases or for other purposes. In certain embodiments, at least one type of the modifications in the combination is in the 5' portion and at least one type of the modifications in the combination is in the 3' portion of the guide RNA, particularly within the first 5 or 10 nucleotides of the 5' portion and within the last 5 or 10 nucleotides of the 3' portion to, for example, protect the RNA from degradation by nucleases or for other purposes. In certain embodiments, a guide RNA comprises 20 or fewer, alternatively 15 or fewer, alternatively 15 or fewer, alternatively 10 or fewer, alternatively 5 or fewer, alternatively 3 or fewer deoxyribonucleotide residues in the 5' portion of the guide RNA.

In certain embodiments, at least one type of the modifications in the combination is within the crRNA segment of the guide RNA. In certain embodiments, at least one type of the modifications in the combination is within the guide sequence of the crRNA. In certain embodiments, at least one type of the modifications in the combination is within the first five (5) nucleotides of the crRNA segment. In certain embodiments, at least one type of the modifications in the combination is within the first three (3) nucleotides of the crRNA segment. In certain embodiments, at least one type of the modifications in the combination is within the tracrRNA segment of the guide RNA. In certain embodiments, at least one type of the modifications in the combination is within the last five (5) nucleotides of the tracrRNA segment of the guide RNA. In certain embodiments, at least one type of the modifications in the combination is within the last three (3) nucleotides of the tracrRNA segment of the guide RNA.

In certain embodiments, a first type of modification in the combination is within the 5' portion of the guide RNA and a second type of modification in the combination is within the internal region (i.e., between the 5' end and the 3' end) of the guide RNA. In certain embodiments, the first type of modification is within the first five (5) nucleotides of the 5' portion of the guide RNA. In certain embodiments, the first type of modification is within the first three (3) nucleotides of the 5' portion of the guide RNA.

In certain embodiments, a first type of modification in the combination is within the internal region (i.e., between the 5' end and the 3' end) of the guide RNA and a second type of modification in the combination is within the 3' portion of the guide RNA. In certain embodiments, the second type of modification is within the last five (5) nucleotides of the 3' portion of the guide RNA. In certain embodiments, the second type of modification is within the last three (3) nucleotides of the 3' portion of the guide RNA.

In certain embodiments, a first type of modification in the combination is within the 5' portion of the guide RNA and a second type of modification in the combination is within the 3' portion of the guide RNA. In certain embodiments, the first type of modification is within the first five (5) nucleotides of the 5' portion of the guide RNA. In certain embodiments, the first type of modification is within the first three (3) nucleotides of the 5' portion of the guide RNA. In certain embodiments, the second type of modification is within the last five (5) nucleotides of the 3' portion of the guide RNA. In certain embodiments, the second type of modification is within the last three (3) nucleotides of the 3' portion of the guide RNA.

In certain embodiments, a first type of modification in the combination is within the 5' portion of the guide RNA, a second type of modification in the combination is within the internal region (i.e., between the 5' end and the 3' end) of the guide RNA, and a third type of modification in the combination is within the 3' portion of the guide RNA. In certain embodiments, the first type of modification is within the first five (5) nucleotides of the 5' portion of the guide RNA. In certain embodiments, the first type of modification is within the first three (3) nucleotides of the 5' portion of the guide RNA. In certain embodiments, the third type of modification is within the last five (5) nucleotides of the 3' portion of the guide RNA. In certain embodiments, the third type of modification is within the last three (3) nucleotides of the 3' portion of the guide RNA.

In certain embodiments, a first type of modification in the combination is within the crRNA segment of the guide RNA and a second type of modification in the combination is within the tracr segment. In certain embodiments, the first type of modification is within the guide sequence of the crRNA. In certain embodiments, the first type of modification is within the first five (5) nucleotides of the crRNA segment. In certain embodiments, the first type of modification is within the first three (3) nucleotides of the crRNA segment. In certain embodiments, the second type of modification is within the last five (5) nucleotides of the tracrRNA segment of the guide RNA. In certain embodiments, the second type of modification is within the last three (3) nucleotides of the tracrRNA segment of the guide RNA.

In certain embodiments, a first type and a second type of modification in the combination are within the crRNA segment of the guide RNA. In certain embodiments, the first type of modification is within the guide sequence of the crRNA. In certain embodiments, the first type of modification is within the first five (5) nucleotides of the crRNA segment. In certain embodiments, the first type of modification is within the first three (3) nucleotides of the crRNA segment.

In certain embodiments, a first type and a second type of modification in the combination are within the crRNA segment of the guide RNA and a third type of modification in the combination is within the tracr segment. In certain embodiments, the first type of modification is within the guide sequence of the crRNA. In certain embodiments, the first type of modification is within the first five (5) nucleotides of the crRNA segment. In certain embodiments, the first type of modification is within the first three (3) nucleotides of the crRNA segment. In certain embodiments, the third type of modification is within the last five (5) nucleotides of the tracrRNA segment of the guide RNA. In certain embodiments, the third type of modification is within the last three (3) nucleotides of the tracrRNA segment of the guide RNA.

In certain embodiments, at least one of the modifications in the combination comprises an end modification, such as a 5' end modification or a 3' end modification as described above. In certain embodiments, the end modification comprises dimethoxytrityl.

In certain embodiments, at least one of the modifications in the combination comprises a modified base. In certain embodiments, the modified gRNA comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 modified bases. In other embodiments, the modified gRNA comprises at least 55, 60, 65, 70, 75, 80, 85, 90, 95, 100, 110, 120, 130 or 140 modified bases. In certain embodiments, all bases in a gRNA are modified.

In certain embodiments, at least one of the modifications in the combination comprises a modified sugar. In certain embodiments, the modified gRNA comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 modified sugars. In other embodiments, the modified gRNA comprises at least 55, 60, 65, 70, 75, 80, 85, 90, 95, 100, 110, 120, 130 or 140 modified sugars. In certain embodiments, all sugars in a gRNA are modified.

In certain embodiments, at least one of the modifications in the combination comprises a modified backbone (i.e., an internucleotide linkage other than a natural phosphodiester). In certain embodiments, the modified gRNA comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 modified internucleotide linkages. In other embodiments, the modified gRNA comprises at least 55, 60, 65, 70, 75, 80, 85, 90, 95, 100, 110, 120, 130 or 140 modified internucleotide linkages. In certain embodiments, all internucleotide linkages in a gRNA are modified.

In certain embodiments, at least one of the modifications in the combination comprises a 2'-O-methyl, a 2'-fluoro, a 2'-amino, a 2'-deoxy, a 2'-arabino, a 2'-F-arabino, a 2-thiouracil, a 2-aminoadenine, a 5-methylcytosine, a 5-aminoallyluracil, a Z base, a 3'-phosphorothioate, a 3'-phosphonoacetate, a 3'-phosphonoacetate ester, a 3'-thiophosphonoacetate, a 3'-thiophosphonoacetate ester, a 3'-methylphosphonate, a 3'-boranophosphonate, a 3'-phosphorodithioate, or combinations thereof. In certain embodiments, at least one of the modifications in the combination comprises a 2'-O-methyl, a 2'-deoxy, a Z base, a phosphorothioate internucleotide linkage, a phosphonoacetate internucleotide linkage, a thiophosphonoacetate internucleotide linkage, or combinations thereof. In certain embodiments, at least one of the modifications in the combination comprises a 2'-F, a 2-thioU, a 4-thioU, a 2-aminoA, a 5-methylC, a 5-methylU, a 5-aminoallylU, or combinations thereof. In certain embodiments, at least one of the modifications in the combination is an "end" modification such as terminal phosphate, a PEG, a terminal amine, a terminal linker such as a hydrocarbon linker, a substituted hydrocarbon linker, a squarate linker, a triazolo linker, an internal linker such as 2-(4-butylamidofluorescein)propane-1,3-diol bis(phosphodiester) linker, a linker conjugated to a dye, a linker conjugated to a non-fluorescent label, a linker conjugated to a tag or a linker conjugated to a solid support such as for example a bead or microarray. In certain embodiments, at least two of the modifications in the combination comprise a 2'-O-methyl nucleotide and phosphorothioate internucleotide linkage, a 2'-O-methyl nucleotide and phosphonoacetate internucleotide linkage, or a 2'-O-methyl nucleotide and thiophosphonoacetate internucleotide linkage. In certain embodiments, at least two of the modifications in the combination comprise a 2'-O-methyl nucleotide and phosphonocarboxylate internucleotide linkage, a 2'-O-methyl nucleotide and phosphonocarboxylate ester internucleotide linkage, a 2'-O-methyl nucleotide and thiophosphonocarboxylate internucleotide linkage, a 2'-O-methyl nucleotide and thiophosphonocarboxylate ester internucleotide linkage, or combinations thereof. In other embodiments, the modifications in the combination further comprise a 2-thiouracil, 2-thiocytosine, 4-thiouracil, 6-thioguanine, 2-aminoadenine, 2-aminopurine, pseudouracil, inosine, 7-deazaguanine, 7-deaza-8-azaguanine, 7-deazaadenine, 7-deaza-8-azaadenine, 5-methylcytosine, 5-methyluracil, 5-hydroxymethylcytosine, 5-hydroxymethyluracil, 5,6-dehydrouracil, 5-propynylcytosine, 5-propynyluracil, 5-ethynylcytosine, 5-ethynyluracil, 5-allyluracil, 5-allylcytosine, 5-aminoallyluracil, 5-aminoallyl-cytosine, or an abasic nucleotide.

In certain embodiments, at least one of the modifications in the combination comprises a 2'-O-methyl-3'-phosphorothioate. In certain embodiments, at least one of the modifications in the combination comprises a 2'-O-methyl-3'-phosphonoacetate. In certain embodiments, at least one of the modifications in the combination comprises a 2'-O-methyl-3'-thiophosphonoacetate. In certain embodiments, at least one of the modifications in the combination comprises a 2'-halo-3'-phosphorothioate. In certain embodiments, at least one of the modifications in the combination comprises a 2'-halo-3'-phosphonoacetate. In certain embodiments, at least one of the modifications in the combination comprises a 2'-halo-3'-thiophosphonoacetate. In certain embodiments, at least one of the modifications in the combination comprises a 2'-fluoro-3'-phosphorothioate. In certain embodiments, at least one of the modifications in the combination comprises a 2'-fluoro-3'-phosphonoacetate. In certain embodiments, at least one of the modifications in the combination comprises a 2'-fluoro-3'-thiophosphonoacetate. Possible combinations of at least two or three modifications are represented in FIG. 6 and FIG. 7 respectively and are incorporated herein by reference.

In certain embodiments, the guide RNA comprises an oligonucleotide represented by Formula (III) or Formula (IV):

W—Y-Q    (III); or

Y—W—X-Q    (IV)

wherein Q and W each independently represent a nucleotide or a stretch of nucleotides of the oligonucleotide comprising at least one modification and Y and X each independently represent an unmodified portion of the oligonucleotide.

In certain embodiments, W is within the 5' portion of the guide RNA. In certain embodiments, W is at least partially within the first five (5) nucleotides of the 5' portion of the guide RNA. In certain embodiments, W is at least partially within the first three (3) nucleotides of the 5' portion of the guide RNA. In certain embodiments, W is within the internal region (i.e., between the 5' end and the 3' end) of the guide RNA.

In certain embodiments, Q is within the 3' portion of the guide RNA. In certain embodiments, Q is at least partially within the last five (5) nucleotides of the 3' portion of the guide RNA. In certain embodiments, Q is at least partially within the last three (3) nucleotides of the 3' portion of the guide RNA. In certain embodiments, Q is within the internal region (i.e., between the 5' end and the 3' end) of the guide RNA.

In certain embodiments, W comprises an end modification as described above, such as a 5' end or a 3' end modification. In certain embodiments, the end modification comprises dimethoxytrityl.

In certain embodiments, at least one of W or Q comprises a modified base as described above. In certain embodiments, at least one of W or Q comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 modified bases. In certain embodiments, at least one of W or Q comprises more than one modified base, such as 2, 3, 4, 5, 6, 7, 8, 9, 10, 11, 12, 13, 14, 15, 16, 17, 18, 19 or 20 modified bases.

In certain embodiments, at least one of W or Q comprises a modified sugar as described above. In certain embodiments, at least one of W or Q comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 modified sugars. In certain embodiments, at least one of W or Q comprises more than one, such as 2, 3, 4, 5, 6, 7, 8, 9, 10, 11, 12, 13, 14, 15, 16, 17, 18, 19 or 20 modified sugars.

In certain embodiments, at least one of W or Q comprises a modified backbone (i.e., an internucleotide linkage other than a phosphodiester) as described above. In certain embodiments, at least one of W or Q comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 modified internucleotide linkages. In certain embodiments, at least one of W or Q comprises more than one, such as 2, 3, 4, 5, 6, 7, 8, 9, 10, 11, 12, 13, 14, 15, 16, 17, 18, 19 or 20 modified internucleotide linkages.

In certain embodiments, at least one of W or Q comprises a 2'-O-methyl nucleotide, a 2'-F nucleotide, a 2'-amino nucleotide, a 2'-deoxy nucleotide, a 2-thiouridine nucleotide, a 2-aminoadeosine nucleotide, a 6-thioguanosine nucleotide, a 5-methylcytidine nucleotide, a 5-aminoallyluridine nucleotide, a Z nucleotide, a 3'-phosphorothioate internucleotide linkage, a 3'-phosphorothioate internucleotide linkage, a 3'-phosphonoacetate internucleotide linkage, a 3'-phosphonoacetate ester internucleotide linkage, a 3'-thiophosphonoacetate internucleotide linkage, a 3'-thiophosphonoacetate ester internucleotide linkage, a 3'-methylphosphonate internucleotide linkage, a 3'-boranophosphonate internucleotide linkage, a 3'-phosphorodithioate internucleotide linkage, or combinations thereof.

In certain embodiments, at least one of W or Q comprises a 2'-O-methyl and a 3'-phosphorothioate group on the same nucleotide. In certain embodiments, at least one of W or Q comprises a 2'-O-methyl and a 3'-phosphonoacetate group linkage on the same nucleotide. In certain embodiments, at least one of W or Q comprises a 2'-O-methyl and 3'-thiophosphonoacetate group on the same nucleotide. In certain embodiments, at least one of W or Q comprises a 2'-F and a 3'-phosphorothioate group on the same nucleotide. In certain embodiments, at least one of W or Q comprises a 2'-F and a 3'-phosphonoacetate group linkage on the same nucleotide. In certain embodiments, at least one of W or Q comprises a 2'-F and 3'-thiophosphonoacetate group on the same nucleotide.

In certain embodiments, at least one of W or Q comprises 1, 2, 3, 4, 5, 6, 7, 8, 9, 10, 11, 12, 13, 14, 15, 16, 17, 18, 19 or 20 modified nucleotides. In certain embodiments, each of the modified nucleotides within at least one of W or Q comprises the same modification or modifications. In certain embodiments, W comprises a modified nucleotide that is different than a modified nucleotide in Q. In certain embodiments, at least one of W or Q comprises two or more modified nucleotides. In certain embodiments, at least one of W or Q comprises three or more modified nucleotides. In certain embodiments, the modified nucleotides are not arranged contiguously in the sequence, or at least not entirely, as one or more unmodified nucleotides may intercede. In certain embodiments, the modified nucleotides are arranged contiguously. In certain embodiments, at least one of W or Q comprises at least one contiguous stretch of modified nucleotides. In certain embodiments, at least one of W or Q comprises a contiguous stretch of at least three (3) modified nucleotides. In certain embodiments, at least one of W or Q comprises a contiguous stretch of at least four (4) modified nucleotides. In certain embodiments, at least one of W or Q comprises a contiguous stretch of at least five (5) modified nucleotides.

In certain embodiments, the guide RNA comprises a nucleotide sequence of Formula (V) or Formula (VI):

  (Formula V); or

  (Formula VI)

wherein each M independently represents a modified ribonucleotide;

wherein each N independently represents an unmodified ribonucleotide;

wherein each M' independently represents a modified ribonucleotide;

wherein each N' independently represents an unmodified ribonucleotide;

wherein each M" independently represents a modified ribonucleotide;

wherein m is an integer between 0 and 40, n is an integer between 0 and 130, m' is an integer between 0 and 10, n' is an integer between 0 and 130, m" is an integer between 0 and 10, provided that m+m'+m" is greater than or equal to 1 and 50<m+n+m'+n'+m"≤150.

In certain embodiments, each M is independently selected from the group consisting of a 2'-O-methyl ribonucleotide, a 2'-O-methyl-3'-P(S) ribonucleotide, a 2'-O-methyl-3'-PACE ribonucleotide, a 2'-O-methyl-3'-thioPACE ribonucleotide, and a 2'-deoxynucleotide. In certain embodiments, each M is independently selected from the group consisting of a 2'-O-methyl ribonucleotide, a 2'-O-methyl-3'-P(S) ribonucleotide, a 2'-O-methyl-3'-PACE ribonucleotide, and a 2'-O-methyl-3'-thioPACE ribonucleotide. In certain embodiments, each M is independently selected from the group consisting of a 2'-O-methyl-3'-PACE ribonucleotide and a 2'-O-methyl-3'-thioPACE ribonucleotide. In certain embodiments, where m>1, any given M is the same or different from any other M. In certain embodiments, where m>1, each M comprises the same modification or modifications.

In certain embodiments, each M' is independently selected from the group consisting of a 2'-O-methyl ribonucleotide, a 2'-O-methyl-3'-P(S) ribonucleotide, a 2'-O-methyl-3'-PACE ribonucleotide, a 2'-O-methyl-3'-thioPACE ribonucleotide, and a 2'-deoxynucleotide. In certain embodiments, each M' is independently selected from the group consisting of a 2'-O-methyl ribonucleotide, a 2'-O-methyl-3'-P(S) ribonucleotide, a 2'-O-methyl-3'-PACE ribonucleotide, and a 2'-O-methyl-3'-thioPACE ribonucleotide. In certain embodiments, each M' is independently selected from the group consisting of a 2'-O-methyl-3'-PACE ribonucleotide and a 2'-O-methyl-3'-thioPACE ribonucleotide. In certain embodiments, where m'>1, any given M' is the same or different from any other M'. In certain embodiments, where m'>1, each M' comprises the same modification or modifications.

In certain embodiments, each M" is independently selected from the group consisting of a 2'-O-methyl ribonucleotide, a 2'-O-methyl-3'-P(S) ribonucleotide, a 2'-O-methyl-3'-PACE ribonucleotide, a 2'-O-methyl-3'-thioPACE ribonucleotide, and a 2'-deoxynucleotide. In certain embodiments, each M" is independently selected from the group consisting of a 2'-O-methyl ribonucleotide, a 2'-O-methyl-3'-P(S) ribonucleotide, a 2'-O-methyl-3'-PACE ribonucleotide, and a 2'-O-methyl-3'-thioPACE ribonucleotide. In certain embodiments, each M" is independently selected from the group consisting of a 2'-O-methyl-3'-PACE ribonucleotide and a 2'-O-methyl-3'-thioPACE ribonucleotide. In certain embodiments, where m">1, any given M" is the same or different from any other M". In certain embodiments, where m'>1, each M" comprises the same modification or modifications.

In certain embodiments, each M is a 2'-O-methyl-3'-PACE ribonucleotide; m is selected from an integer between 1 and 10; each N is independently selected from the group consisting of A, U, C, and G; n is selected from an integer between 10 and 130; each M' is independently selected from the group consisting of a 2'-O-methyl ribonucleotide, a 2'-O-methyl-3'-P(S)ribonucleotide, a 2'-O-methyl-3'-PACE ribonucleotide, a 2'-O-methyl-3'-thioPACE ribonucleotide, a 2'-deoxynucleotide, and a Z nucleotide; m' is selected from an integer between 1 and 10; each N is independently selected from the group consisting of A, U, C, and G; and n' is selected from an integer between 0 and 130. In certain embodiments, each M' is a 2'-O-methyl-3'-PACE ribonucleotide. In certain embodiments, each M' is a 2'-O-methyl-3'-thioPACE ribonucleotide. In certain embodiments, each M' is a 2'-O-methyl ribonucleotide. In certain embodiments, each M' is a 2'-O-methyl-3'-P(S) ribonucleotide. In certain embodiments, each M' is a Z nucleotide.

In certain embodiments, each M is a 2'-O-methyl-3'-thioPACE ribonucleotide; m is selected from an integer between 1 and 10; each N is independently selected from the group consisting of A, U, C, and G; n is selected from an integer between 10 and 130; each M' is independently selected from the group consisting of a 2'-O-methyl ribonucleotide, a 2'-O-methyl-3'-P(S) ribonucleotide, a 2'-O-methyl-3'-PACE ribonucleotide, a 2'-O-methyl-3'-thioPACE ribonucleotide, a 2'-deoxynucleotide, and a Z nucleotide; m' is selected from an integer between 1 and 10; each N is independently selected from the group consisting of A, U, C, and G; and n' is selected from an integer between 0 and 130. In certain embodiments, each M' is a 2'-O-methyl-3'-PACE ribonucleotide. In certain embodiments, each M' is a 2'-O-methyl-3'-thioPACE ribonucleotide. In certain embodiments, each M' is a 2'-O-methyl ribonucleotide. In certain embodiments, each M' is a 2'-O-methyl-3'-P(S) ribonucleotide. In certain embodiments, each M' is a Z nucleotide.

In certain embodiments, each M is a 2'-O-methyl-3'-P(S) ribonucleotide; m is selected from an integer between 1 and 10; each N is independently selected from the group consisting of A, U, C, and G; n is selected from an integer between 10 and 130; each M' is independently selected from the group consisting of a 2'-O-methyl ribonucleotide, a 2'-O-methyl-3'-P(S) ribonucleotide, a 2'-O-methyl-3'-PACE ribonucleotide, a 2'-O-methyl-3'-thioPACE ribonucleotide, a 2'-deoxynucleotide, and a Z nucleotide; m' is selected from an integer between 1 and 10; each N is independently selected from the group consisting of A, U, C, and G; and n' is selected from an integer between 0 and 130. In certain embodiments, each M' is a 2'-O-methyl-3'-PACE ribonucleotide. In certain embodiments, each M' is a 2'-O-methyl-3'-thioPACE ribonucleotide. In certain embodiments, each M' is a 2'-O-methyl ribonucleotide. In certain embodiments, each M' is a 2'-O-methyl-3'-P(S)ribonucleotide. In certain embodiments, each M' is a Z nucleotide.

In certain embodiments, each M is independently selected from the group consisting of a 2'-O-methyl ribonucleotide, a 2'-O-methyl-3'-P(S) ribonucleotide, a 2'-O-methyl-3'-PACE ribonucleotide, a 2'-O-methyl-3'-thioPACE ribonucleotide, a 2'-deoxynucleotide, and a Z nucleotide; m is selected from an integer between 0 and 10; each N is independently selected from the group consisting of A, U, C, and G; n is selected from an integer between 10 and 15; each M' is a 2'-O-methyl ribonucleotide; m' is selected from an integer between 1 and 5; each N is independently selected from the group consisting of A, U, C, and G; and n' is selected from an integer between 0 and 130. In certain embodiments, each M is a 2'-O-methyl-3'-PACE ribonucleotide. In certain embodiments, each M is a 2'-O-methyl-3'-thioPACE ribonucleotide. In certain embodiments, each M is a 2'-O-methyl ribonucleotide. In certain embodiments, each M is a 2'-O-methyl-3'-P(S)ribonucleotide. In certain embodiments, m is 0; n is selected from an integer between 10 and 15, m' is selected from an integer between 1 and 5; and n' is selected from an integer between 0 and 130.

In certain embodiments, at least one of the modifications in the combination is a stability-altering modification. In certain embodiments, at least one of the modifications in the combination increases nuclease resistance of the guide RNA relative to a guide RNA without the modification, thus it enhances the stability of the guide RNA.

In certain embodiments, at least one of the modifications in the combination is a stability-enhancing modification as described above.

In certain embodiments, at least one of the modifications in the combination is a specificity-altering modification as described above.

In certain embodiments, at least one of the modifications in the combination alters RNA base pairing. In certain embodiments, at least one of the modifications in the combination lowers the Tm of a base pairing interaction as described above. In certain embodiments, at least one of the modifications in the combination raises the Tm of a base pairing interaction as described above.

In certain embodiments, at least one of the modifications in the combination alters transfection efficiency of the guide RNA relative to a guide RNA without the modification. In certain embodiments, at least one of the modifications in the combination increases transfection efficiency of the guide RNA relative to a guide RNA without the modification. In certain embodiments, at least one of the modifications in the combination decreases transfection efficiency of the guide RNA relative to a guide RNA without the modification. In certain embodiments, at least one of the transfection-increasing modifications in the combination comprises a phosphonoacetate alkyl ester internucleotide linkage, such as a phosphonoacetate methyl ester internucleotide linkage.

In certain embodiments, at least one of the modifications in the combination enhances stability and specificity of the guide RNA relative to a guide RNA without the modification. In certain embodiments, at least one of the modifications in the combination enhances stability and transfection efficiency of the guide RNA relative to a guide RNA without the modification. In certain embodiments, at least one of the modifications in the combination enhances specificity and transfection efficiency of the guide RNA relative to a guide RNA without the modification.

In certain embodiments, at least one of the modifications in the combination alters the secondary structure of the guide RNA. This modification alters the base-pairing of any of the RNA/RNA internal duplexes in the guide RNA. Some of these modifications increase the base pairing of the RNA/RNA structure or alternatively increase the Tm of the RNA/RNA duplex, whereas other modifications decrease the base pairing (or Tm) of the RNA/RNA duplex or duplexes. Such modifications include base modified nucleotides, particularly UNA nucleotides such as the 2-thiouridine and 2-aminoadenosine pair, the Z/P nucleotide pair, the isoC/isoG pair, the 6-thioG/5-methylpyrimidine pair, and nucleotides with modifications on the sugar or the internucleotide linkages as discussed before.

In certain embodiments, the combination includes at least one modification or a set of modifications that increases nucleases resistance (i.e., stability) with at least one modification or a set of modifications that increases specificity (i.e., reduces off-target effects). In certain embodiments, the combination includes at least one modification or a set of modifications that increases nucleases resistance (i.e., stability) with at least one modification or a set of modifications that raises the Tm of some bases pairing in the guide RNA. In certain embodiments, the combination includes at least one modification or a set of modifications that increases nucleases resistance (i.e., stability) with at least one modification or a set of modifications that lowers the Tm of some bases pairing of the guide RNA. In certain embodiments, the combination includes at least one modification or a set of modifications that increases nuclease resistance (i.e., stability), at least one modification or a set of modifications that increases the Tm of some bases paring in the guide RNA, and at least one modification or a set of modifications that decreases the Tm of some base paring elsewhere in the guide RNA. In certain embodiments, the combination includes at least one modification or a set of modifications that increases nuclease resistance (i.e., stability) and at least one modification or a set of modifications that increases the binding of the guide RNA to Cas protein. In certain embodiments, the combination includes at least one modification or a set of modifications that increases nuclease resistance (i.e., stability) and at least one modification or a set of modifications that decreases the binding of the guide RNA to Cas protein.

In certain embodiments, the guide RNA comprises a combination of the different types of modifications.

D. Guide RNA Structure

In certain embodiments, the guide RNA is able to form a complex with a CRISPR-associated-protein. In certain embodiments, the CRISPR-associated protein is provided by or is derived from a CRISPR-Cas type II system, which has an RNA-guided polynucleotide binding and/or nuclease activity. In certain embodiments, the CRISPR-associated protein is Cas9, a Cas9 mutant, or a Cas9 variant. In certain embodiments, the CRISPR-associated protein is the Cas9 nuclease from *Streptococcus pyogenes*. In certain embodiments, the CRISPR-associated protein is the Cas9 nuclease from *Streptococcus thermophilus*. In certain embodiments, the CRISPR-associated protein is the Cas9 nuclease from *Staphylococcus aureus*. In certain embodiments, the synthetic guide RNA or a synthetic guide RNA:CRISPR-associated protein complex maintains functionality of natural guide RNA or a complex that does not have modified nucleotides. In certain embodiments, the functionality includes binding a target polynucleotide. In certain embodiments, the functionality includes nicking a target polynucleotide. In certain embodiments, the functionality includes cleaving a target polynucleotide. In certain embodiments, the target polynucleotide is within a nucleic acid in vitro. In certain embodiments, the target polynucleotide is within the genome of a cell in vivo or in vitro (such as in cultured cells or cells isolated from an organism). In certain embodiments, the target polynucleotide is a protospacer in DNA.

In certain embodiments, the crRNA segment comprises from 25 to 80 nucleotides. In certain embodiments, the crRNA segment comprises a guide sequence that is capable of hybridizing to a target sequence. In certain embodiments, the guide sequence is complementary to the target sequence or a portion thereof. In certain embodiments, the guide sequence comprises from 15 to 30 nucleotides. In certain embodiments, the crRNA segment comprises a stem sequence. In certain embodiments, the stem sequence comprises from 10 to 50 nucleotides. In certain embodiments, the crRNA segment comprises a 5'-overhang sequence. In certain embodiments, the 5'-overhang sequence comprises from 1 to 10 nucleotides, alternatively 1 to 5 nucleotides, alternatively 1, 2 or 3 nucleotides. In certain embodiments, the crRNA comprises both (i) a guide sequence that is capable of hybridizing to a target sequence and (ii) a stem sequence. In certain embodiments, the crRNA comprises (i) a 5'-overhang sequence, (ii) a guide sequence that is capable of hybridizing to a target sequence, and (iii) a stem sequence. In certain embodiments wherein the crRNA segment comprises a stem sequence, the tracrRNA segment comprises a nucleotide sequence that is partially or completely complementary to the stem sequence of the crRNA segment. In certain embodiments, the tracrRNA segment comprises at least one more duplex structure.

In certain embodiments, the guide RNA is a single guide RNA. In certain embodiments, the guide RNA is a single guide RNA, wherein the crRNA segment and the tracrRNA segment are linked through a loop L. In certain embodiments, the loop L comprises 1, 2, 3, 4, 5, 6, 7, 8, 9, or 10 nucleotides. In certain embodiments, the loop L comprises a nucleotide sequence of GNRA, wherein N represents A, C, G, or U and R represents A or G. In certain embodiments, the loop L comprises a nucleotide sequence of GAAA. In certain embodiments, the guide RNA comprises more than one loop.

The guide RNA comprises a 5' portion (i.e., the 5' half) and a 3' portion (i.e., the 3' half). In certain embodiments, the crRNA segment is 5' (i.e., upstream) of the tracrRNA segment. In certain embodiments, the tracrRNA segment is 5' relative to the crRNA segment.

In certain embodiments, the guide RNA comprises at least two separate RNA strands, for example, a crRNA strand and a separate tracrRNA strand. See, for example, FIG. 5A. In certain embodiments, each of the strands is a synthetic strand comprising one or more modifications. In certain embodiments, at least one of the strands is a synthetic strand comprising one or more modifications. In certain embodiments, the strands function together to guide binding, nicking, or cleaving of a target polynucleotide by a Cas protein, such as Cas9. In certain embodiments, the crRNA sequence and the tracrRNA sequence are on separate stands and hybridize to each other via two complementary sequences to form a stem or duplex.

In certain embodiments, the guide RNA is a single guide RNA comprising a crRNA sequence and a tracrRNA sequence. See, for example, FIG. 5B. In certain embodiments, the crRNA sequence and the tracrRNA sequence are connected by a loop sequence or "loop." In certain embodiments, a single guide RNA comprises a 5' portion and a 3' portion, wherein the crRNA sequence is upstream of the tracrRNA sequence.

In certain embodiments, the total length of the two RNA pieces can be about 50-220 (e.g., about 55-200, 60-190, 60-180, 60-170, 60-160, 60-150, 60-140, 60-130, and 60-120) nucleotides in length, such as about 60, 70, 80, 90, 100, 110, 120, 130, 140, 150, 160, 170, 180, 190, 200, or 220 nucleotides in length. Similarly, the single guide RNA (e.g., FIG. 5B) can be about 50-220 (e.g., about 55-200, 60-190, 60-180, 60-170, 60-160, 60-150, 60-140, 60-130, and 60-120) nucleotides in length, such as about 60, 70, 80, 90, 100, 110, 120, 130, 140, 150, 160, 170, 180, 190, 200, or 220 nucleotides in length.

As shown in FIGS. 5A and 5B, the synthetic guide RNA comprises (i) a crRNA sequence that comprises (a) a guide sequence (e.g., segment $G_1$-$G_n$, where each G represents a nucleotide in the guide sequence) capable of hybridizing to a target sequence in a nucleic acid, (b) a first stem sequence (e.g., segment $X_1$-$X_n$, where each X represents a nucleotide in the first stem sequence) capable of hybridizing partially or completely to a second stem sequence, and, optionally (c) a 5'-overhang sequence (e.g., segment $O_1$-$O_n$, where each O represents a nucleotide in the overhang sequence), and (ii) a tracrRNA sequence that comprises the second stem sequence (e.g., segment $Y_1$-$Y_n$, where each Y represents a nucleotide in the second stem sequence). The tracrRNA sequence further comprises segment $T_1$-$T_n$, where each T represents a nucleotide in the tracrRNA sequence. The synthetic guide RNA shown in FIG. 5A includes one or more modifications. Likewise, the synthetic guide RNA shown in FIG. 5B includes one or more modifications. In certain embodiments, the modification is located at any point along the length of the crRNA, the tracrRNA, or the single guide RNA comprising a crRNA segment, a tracrRNA segment, and, optionally, a loop. In certain embodiments, any nucleotide represented by O, G, X, Y, or T in the synthetic guide RNA shown in FIGS. 5A and 5B may be a modified nucleotide. The guide RNA shown in FIG. 5B represents a single guide RNA (sgRNA) where the crRNA segment and the tracrRNA segment are connected by a loop having the sequence GNRA, wherein N represents A, C, G, or U, and R represents A or G.

In certain embodiments, the crRNA segment of the guide RNA is 25-70 (e.g., 30-60, 35-50, or 40-45) nucleotides in length. In certain embodiments, the guide sequence is 12-30 (e.g., 16-25, 17-20, or 15-18) nucleotides in length. In some embodiments, a 5' portion of the crRNA does not hybridize or only partially hybridizes with the target sequence. For example, there can be a 5'-overhang on the crRNA segment.

In certain embodiments, the single guide RNA comprises a central portion including the stem sequence of the crRNA segment, the stem sequence of the tracrRNA segment, and, optionally, a loop that covalently connects the crRNA segment to the tracrRNA segment. In certain embodiments, the central segment of the single guide RNA is 8-60 (e.g., 10-55, 10-50, or 20-40) nucleotides in length.

In certain embodiments, the tracrRNA segment of the guide RNA is 10-130 (e.g., 10-125, 10-100, 10-75, 10-50, or 10-25) nucleotides in length. In certain embodiments, the tracrRNA segment includes one or more hairpin or duplex structures in addition to any hairpin or duplex structure in the central segment.

In certain embodiments, the tracrRNA is truncated compared to a reference tracrRNA, such as a naturally existing mature tracrRNA. A range of lengths has been shown to function in both the separate type (FIG. 5A) and the chimeric sgRNA type (FIG. 5B). For example, in certain embodiments, tracrRNA may be truncated from its 3' end by at least 1, 2, 3, 4, 5, 6, 7, 8, 9, 10, 15, 20, 25, 30, 35 or 40 nts. In certain embodiments, the tracrRNA molecule may be truncated from its 5' end by at least 1, 2, 3, 4, 5, 6, 7, 8, 9, 10, 15, 20, 25, 30, 35, 40, 45, 50, 55, 60, 65, 70, 75 or 80 nts. In certain embodiments, the tracrRNA molecule may be truncated from both the 5' and 3' end, e.g., by at least 1, 2, 3, 4, 5, 6, 7, 8, 9, 10, 15 or 20 nts from the 5' end and at least 1, 2, 3, 4, 5, 6, 7, 8, 9, 10, 15, 20, 25, 30, 35 or 40 nts from the 3' end. See, e.g., Jinek et al. (2012) *Science*, 337, 816-21; Mali et al. (2013) *Science*, 339:6121, 823-6; Cong et al. (2013) *Science*, 339:6121, 819-23; and Hwang et al. (2013) *Nat. Biotechnol.* 31:3, 227-9; Jinek et al. (2013) *eLife*, 2, e00471. In certain embodiments, the tracrRNA is untruncated.

In certain embodiments, the disclosed modifications are in the crRNA segment or the tracrRNA segment or both. In certain embodiments, the disclosed modifications are in the guide sequence of the crRNA segment. In certain embodiments, the disclosed modifications are in the stem sequence of the crRNA segment. In certain embodiments, the disclosed modifications are in the 5'-overhang sequence of the crRNA segment. In certain embodiments, the disclosed modifications are in the stem sequence of the tracrRNA segment. In certain embodiments, the disclosed modifications are in the loop sequence of the guide RNA. In certain embodiments, the disclosed modifications are in the 5' portion of the guide RNA. In certain embodiments, the disclosed modifications are in the 3' portion of the guide RNA. In certain embodiments, the disclosed modifications are in the 5' portion of the guide RNA and the 3' portion of the guide RNA.

E. Synthesis of Guide RNA

In certain embodiments, guide RNAs, including single guide RNAs (sgRNAs; see FIGS. 1 and 5B) are produced by chemical synthesis using the art of synthetic organic chemistry. A guide RNA that comprises any nucleotide other than the four predominant ribonucleotides, namely A, C, G, and U, whether unnatural or natural, such as a pseudouridine, inosine or a deoxynucleotide, possesses a chemical modification or substitution at the nucleotide which is chemically/structurally distinct from any of the four predominant nucleotides in RNAs.

The synthetic guide RNAs described herein can be chemically synthesized. For example, the synthetic guide RNAs can be synthesized using TC chemistry by the method described in Dellinger et al. (2011) *J. Am. Chem. Soc.*, 133, 11540, U.S. Pat. No. 8,202,983, and US Patent Application 2010/0076183A1, the contents of which are incorporated by reference in their entireties. "TC chemistry" refers to the composition and methods of using RNA monomeric nucleotide precursors protected on the 2'-hydroxyl moiety by a thionocarbamate protecting group, to synthesize unmodified RNA or modified RNA comprising one or more modified nucleotides. The ability to chemically synthesize relatively long RNAs (as long as 200 mers or more) using TC-RNA chemistry allows one to produce guide RNAs with special features capable of outperforming those enabled by the four predominant ribonucleotides (A, C, G and U). Some synthetic guide RNAs described herein can also be made using methods known in the art that include in vitro transcription and cell-based expression. For example, 2'-fluoro NTPs can be incorporated into synthetic guide RNAs produced by cell-based expression.

Synthesis of guide RNAs can also be accomplished by chemical or enzymatic synthesis of RNA sequences that are subsequently ligated together by enzymes, or chemically ligated by chemical ligation, including but not limited to cyanogen bromide chemistry, "click" chemistry as published by R. Kumar et al. (2007) *J. Am. Chem. Soc.*, 129, 6859-64, or squarate conjugation chemistry as described by K. Hill in WO2013176844 titled "Compositions and methods for conjugating oligonucleotides."

As further described below, a guide RNA disclosed herein, including those comprising modified nucleotides and/or modified internucleotide linkages, can be used to perform various CRISPR-mediated functions (including but not limited to editing genes, regulating gene expression, cleaving target sequences, and binding to target sequences) in vitro or in vivo, such as in cell-free assays, in intact cells, or in whole organisms. For in vitro or in vivo applications, the RNA can be delivered into cells or whole organisms in any manner known in the art.

Libraries and Arrays

In one aspect, the present invention provides a set or library of multiple guide RNAs. In certain embodiments, the library contains two or more guide RNAs disclosed herein. The library can contain from about 10 to about $10^7$ individual members, e.g., about 10 to about $10^2$, about $10^2$ to about $10^3$, about $10^3$ to about $10^5$, from about $10^5$ to about $10^7$ members. An individual member of the library differs from other members of the library at least in the guide sequence, i.e., the DNA targeting segment of the gRNA. On the other hand, in certain embodiments, each individual member of a library can contain the same or substantially the same nucleotide sequence for the tracrRNA segment as all the other members of the library. In this way, the library can comprise members that target different polynucleotides or different sequences in one or more polynucleotides.

In certain embodiments, the library comprises at least $10^2$ unique guide sequences. In certain embodiments, the library comprises at least $10^3$ unique guide sequences. In certain embodiments, the library comprises at least $10^4$ unique guide sequences. In certain embodiments, the library comprises at least $10^5$ unique guide sequences. In certain embodiments, the library comprises at least $10^6$ unique guide sequences. In certain embodiments, the library comprises at least $10^7$ unique guide sequences. In certain embodiments, the library targets at least 10 different polynucleotides. In certain embodiments, the library targets at least $10^2$ different polynucleotides. In certain embodiments, the library targets at least $10^3$ different polynucleotides. In certain embodiments, the library targets at least $10^4$ different polynucleotides. In certain embodiments, the library targets at least $10^5$ different polynucleotides. In certain embodiments, the library targets at least $10^6$ different polynucleotides. In certain embodiments, the library targets at least $10^7$ different polynucleotides.

In certain embodiments, the library comprises a collection of guide RNAs having the same sequence and the same modifications in a progressively shifted window that moves across the sequence of the members in the library. In certain embodiments, the windows collectively cover the entire length of the RNA.

In certain embodiments, the library allows one to conduct high-throughput, multi-target genomic manipulations and analyses. In certain embodiments, only the DNA-targeting segments of the guide RNAs are varied, while the Cas protein-binding segment is the same. In certain embodiments, a first portion of the library comprises guide RNAs possessing a Cas-binding segment that recognizes, binds and directs a particular Cas protein and a second portion of the library comprises a different Cas-binding segment that recognizes, binds and directs a different Cas protein (e.g., a Cas protein from a different species), thereby allowing the library to function with two or more orthogonal Cas proteins. In certain embodiments, induced expression of a first orthogonal Cas protein utilizes the portion of the library which interacts with the first orthogonal Cas protein. In certain embodiments, induced expression of a first and second orthogonal Cas protein utilizes the portions of the library which interact with the first and second orthogonal Cas proteins, respectively. In certain embodiments, induced expression of the first and second orthogonal Cas proteins occur at different times. Accordingly, one can carry out large-scale gene editing or gene regulation by specifically manipulating or modifying multiple targets as specified in the library.

In certain embodiments, the library is an "arrayed" library, namely a collection of different features or pools of features in an addressable arrangement. For example, features of an array can be selectively cleaved and transferred to a microtiter plate such that each well in the plate contains a known feature or a known pool of features. In some other embodiments, the library is synthesized in a 48-columns or in a 96-columns microtiter plate format or in a 384-columns plate.

In certain embodiments, synthesis of the guide RNA of this invention may be conducted on a solid support having a surface to which chemical entities may bind. In some embodiments, guide RNAs being synthesized are attached, directly or indirectly, to the same solid support and may form part of an array. An "array" is a collection of separate molecules of known monomeric sequence each arranged in a spatially defined and a physically addressable manner, such that the location of each sequence is known. An "array," or "microarray" used interchangeably herein includes any one-dimensional, two-dimensional or substantially two-dimensional (as well as a three-dimensional) arrangement of addressable regions bearing a particular chemical moiety or moieties (such as ligands, e.g., biopolymers such as polynucleotide or oligonucleotide sequences (nucleic acids), polypeptides (e.g., proteins), carbohydrates, lipids, etc.) associated with that region. An array is "addressable" when it has multiple regions of different moieties (e.g., different polynucleotide sequences) such that a region (i.e., a "feature" of the array) at a particular predetermined location (i.e., an "address") on the array will detect a particular target or class of targets (although a feature may incidentally detect non-targets of that feature). Array features are typically, but need not be, separated by intervening spaces. The number of features that can be contained on an array will largely be determined by the surface area of the substrate, the size of a feature and the spacing between features. Arrays can have densities of up to several hundred thousand or more features per $cm^2$, such as 2,500 to 200,000 features/$cm^2$. The features may or may not be covalently bonded to the substrate.

Suitable solid supports may have a variety of forms and compositions and derive from naturally occurring materials, naturally occurring materials that have been synthetically modified, or synthetic materials. Examples of suitable support materials include, but are not limited to, silicas, silicon and silicon oxides, teflons, glasses, polysaccharides such as agarose (e.g., Sepharose® from Pharmacia) and dextran (e.g., Sephadex® and Sephacyl®, also from Pharmacia), polyacrylamides, polystyrenes, polyvinyl alcohols, copolymers of hydroxyethyl methacrylate and methyl methacrylate, and the like. In some embodiments, the solid support is a plurality of beads.

The initial monomer of the guide RNAs to be synthesized on the substrate surface can be bound to a linker which in turn is bound to a surface hydrophilic group, e.g., a surface hydroxyl moiety present on a silica substrate. In some embodiments, a universal linker is used. In some other embodiments, the initial monomer is reacted directly with, e.g., a surface hydroxyl moiety. Alternatively, guide RNAs can be synthesized first according to the present invention, and attached to a solid substrate post-synthesis by any method known in the art. Thus, the present invention can be used to prepare arrays of guide RNAs wherein the oligonucleotides are either synthesized on the array, or attached to the array substrate post-synthesis. Subsequently, the guide RNAs or a pool or a plurality of pools of guide RNAs can optionally and selectively be cleaved from the array substrate and be used as a library or libraries.

IV. Cas Proteins

As mentioned above, a functional CRISPR-Cas system also requires a protein component (e.g., a Cas protein, which may be a Cas nuclease) that provides a desired activity, such as target binding or target nicking/cleaving. In certain embodiments, the desired activity is target binding. In certain embodiments, the desired activity is target nicking or target cleaving. In certain embodiments, the desired activity also includes a function provided by a polypeptide that is covalently fused to a Cas protein, as disclosed herein. In certain embodiments, the desired activity also includes a function provided by a polypeptide that is covalently fused to a nuclease-deficient Cas protein, as disclosed herein. Examples of such a desired activity include a transcription regulation activity (either activation or repression), an epigenetic modification activity, or a target visualization/identification activity, as described below. The Cas protein can be introduced into an in vitro or in vivo system as a purified or non-purified (i) Cas protein or (ii) mRNA encoded for expression of the Cas protein or (iii) linear or circular DNA encoded for expression of the protein. Any of these 3 methods of providing the Cas protein are well known in the art and are implied interchangeably when mention is made herein of a Cas protein or use of a Cas protein. In certain embodiments, the Cas protein is constitutively expressed from mRNA or DNA. In certain embodiments, the expression of Cas protein from mRNA or DNA is inducible or induced.

In certain embodiments, the Cas protein is chemically synthesized (see e.g., Creighton, "Proteins: Structures and Molecular Principles," W.H. Freeman & Co., NY, 1983), or produced by recombinant DNA technology as described herein. For additional guidance, skilled artisans may consult Frederick M. Ausubel et al., "Current Protocols in Molecular Biology," John Wiley & Sons, 2003; and Sambrook et al., "Molecular Cloning, A Laboratory Manual," Cold Spring Harbor Press, Cold Spring Harbor, N.Y., 2001).

In certain embodiments, the Cas protein is provided in purified or isolated form. In certain embodiments, the Cas protein is provided at about 80%, about 90%, about 95%, or about 99% purity. In certain embodiments, the Cas protein is provided as part of a composition. In certain embodiments, the Cas protein is provided in aqueous compositions suitable for use as, or inclusion in, a composition for an RNA-guided nuclease reaction. Those of skill in the art are well aware of the various substances that can be included in such nuclease reaction compositions.

In certain embodiments, a Cas protein is provided as a recombinant polypeptide. In certain examples, the recombinant polypeptide is prepared as a fusion protein. For example, in certain embodiments, a nucleic acid encoding the Cas protein is linked to another nucleic acid encoding a fusion partner, e.g., glutathione-s-transferase (GST), 6×-His epitope tag, or M13 Gene 3 protein. Suitable host cells can be used to expresses the fusion protein. In certain embodiments, the fusion protein is isolated by methods known in the art. In certain embodiments, the fusion protein can be further treated, e.g., by enzymatic digestion, to remove the fusion partner and obtain the Cas protein. Alternatively, Cas protein:guide RNA complexes can be made with recombinant technology using a host cell system or an in vitro translation-transcription system known in the art. Details of such systems and technology can be found in e.g., WO2014144761 WO2014144592, WO2013176772, US20140273226, and US20140273233, the contents of which are incorporated herein by reference in their entireties.

Wild Type Cas Proteins

In certain embodiments, a Cas protein comprises a protein derived from a CRISPR-Cas type I, type II, or type III system, which has an RNA-guided polynucleotide binding and/or nuclease activity. Non-limiting examples of suitable Cas proteins include Cas3, Cas4, Cas5, Cas5e (or CasD), Cash, Cas6e, Cas6f, Cas7, Cas8a1, Cas8a2, Cas8b, Cas8c, Cas9, Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cu1966. See e.g., WO2014144761 WO2014144592, WO2013176772, US20140273226, and US20140273233, the contents of which are incorporated herein by reference in their entireties.

In certain embodiments, the Cas protein is derived from a type II CRISPR-Cas system. In certain embodiments, the Cas protein is or is derived from a Cas9 protein. In certain embodiments, the Cas protein is or is derived from a bacterial Cas9 protein, including those identified in WO2014144761. In certain embodiments, the Cas protein is or is derived from a *Streptococcus* sp. or *Staphylococcus* sp. Cas9 protein. In certain embodiments, the Cas protein is or is derived from the *Streptococcus thermophilus* Cas9 protein. In certain embodiments, the Cas protein is or is derived from a the *Streptococcus pyogenes* Cas9 protein. In certain embodiments, the Cas protein is or is derived from the *Staphylococcus aureus* Cas9 protein. In certain embodiments, the Cas protein is or is derived from the *Streptococcus thermophilus* Cas9 protein.

In certain embodiments, the wild type Cas protein is a Cas9 protein. In certain embodiments, the wild type Cas9 protein is the Cas9 protein from *S. pyogenes* (SEQ ID NO: 1). In certain embodiments, the protein or polypeptide can comprise, consist of, or consist essentially of a fragment of SEQ ID NO: 1.

In general, a Cas protein includes at least one RNA binding domain, which interacts with the guide RNA. In certain embodiments, the Cas protein is modified to increase nucleic acid binding affinity and/or specificity, alter an enzymatic activity, and/or change another property of the protein. For example, nuclease (i.e., DNase, RNase) domains of the Cas protein can be modified, mutated, deleted, or inactivated. Alternatively, the Cas protein can be truncated to remove domains that are not essential for the function of the protein. In certain embodiments, the Cas protein is truncated or modified to optimize the activity of the effector domain. In certain embodiments, the Cas protein includes a nuclear localization sequence (NLS) that effects importation of the NLS-tagged Cas protein into the nucleus of a living cell. In certain embodiments, the Cas protein includes two or more modifications.

Mutant Cas Proteins

In some embodiments, the Cas protein can be a mutant of a wild type Cas protein (such as Cas9) or a fragment thereof. In other embodiments, the Cas protein can be derived from a mutant Cas protein. For example, the amino acid sequence of the Cas9 protein can be modified to alter one or more properties (e.g., nuclease activity, binding affinity, stability, etc.) of the protein. Alternatively, domains of the Cas9 protein not involved in RNA-guided cleavage can be eliminated from the protein such that the modified Cas9 protein is smaller than the wild type Cas9 protein. For example, reducing the size of the Cas9 coding sequence can allow it to fit within a transfection vector that otherwise cannot accommodate the wild type sequence, such as the AAV vector among others. In some embodiments, the present system utilizes the Cas9 protein from *S. pyogenes*, either as encoded in bacteria or codon-optimized for expression in eukaryotic cells. Shown below is the amino acid sequence of wild type *S. pyogenes* Cas9 protein sequence (SEQ ID No. 1, Uniprot No. Q99ZW2.

MDKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

```
KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDHIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD
```

A Cas9 protein generally has at least two nuclease (e.g., DNase) domains. For example, a Cas9 protein can have a RuvC-like nuclease domain and an HNH-like nuclease domain. The RuvC and HNH domains work together to cut both strands in a target site to make a double-stranded break in the target polynucleotide. (Jinek et al., Science, 337: 816-821). In certain embodiments, a mutant Cas9 protein is modified to contain only one functional nuclease domain (either a RuvC-like or an HNH-like nuclease domain). For example, in certain embodiments, the mutant Cas9 protein is modified such that one of the nuclease domains is deleted or mutated such that it is no longer functional (i.e., the nuclease activity is absent). In some embodiments where one of the nuclease domains is inactive, the mutant is able to introduce a nick into a double-stranded polynucleotide (such protein is termed a "nickase") but not able to cleave the double-stranded polynucleotide. For example, an aspartate to alanine (D10A) conversion in a RuvC-like domain converts the Cas9-derived protein into a nickase. Likewise, a histidine to alanine (H840A) conversion in a HNH domain converts the Cas9-derived protein into a nickase. Likewise, an arsparagine to alanine (N863A) conversion in a HNH domain converts the Cas9-derived protein into a nickase.

In certain embodiments, both the RuvC-like nuclease domain and the HNH-like nuclease domain are modified or eliminated such that the mutant Cas9 protein is unable to nick or cleave the target polynucleotide. In certain embodiments, all nuclease domains of the Cas9-derived protein are modified or eliminated such that the Cas9-derived protein lacks all nuclease activity. In certain embodiments, a Cas9 protein that lacks some or all nuclease activity relative to a wild-type counterpart, nevertheless, maintains target recognition activity to a greater or lesser extent.

In any of the above-described embodiments, any or all of the nuclease domains can be inactivated by one or more deletion mutations, insertion mutations, and/or substitution mutations using well-known methods, such as site-directed mutagenesis, PCR-mediated mutagenesis, and total gene synthesis, as well as other methods known in the art.

In certain embodiments, the "Cas mutant" or "Cas variant" is at least 50% (e.g., any number between 50% and 100%, inclusive, e.g., 50%, 60%, 70%, 80%, 90%, 95%, 98%, and 99%) identical to SEQ ID NO: 1. In certain embodiments, the "Cas mutant" or "Cas variant" binds to an RNA molecule (e.g., a sgRNA). In certain embodiments, the "Cas mutant" or "Cas variant" is targeted to a specific polynucleotide sequence via the RNA molecule.

Fusion Proteins

In certain embodiments, the Cas protein is fused to another protein or polypeptide heterologous to the Cas protein to create a fusion protein. In certain embodiments, the heterologous sequence includes one or more effector domains, such as a cleavage domain, a transcriptional activation domain, a transcriptional repressor domain, or an epigenetic modification domain. Additional examples of the effector domain include a nuclear localization signal, cell-penetrating or translocation domain, or a marker domain. In certain embodiments, the effector domain is located at the N-terminal, the C-terminal, or in an internal location of the fusion protein. In certain embodiments, the Cas protein of the fusion protein is or is derived from a Cas9 protein. In certain embodiments, the Cas protein of the fusion protein is or is derived from a modified or mutated Cas protein in which all the nuclease domains have been inactivated or deleted. In certain embodiments, the Cas protein of the fusion protein is or is derived from a modified or mutated Cas protein that lacks nuclease activity. In certain embodiments, the RuvC and/or HNH domains of the Cas protein are modified or mutated such that they no longer possess nuclease activity.

Cleavage Domains

In certain embodiments, the effector domain of the fusion protein is a cleavage domain. As used herein, a "cleavage domain" refers to a domain that cleaves DNA. The cleavage domain can be obtained from any endonuclease or exonuclease. Non-limiting examples of endonucleases from which a cleavage domain can be derived include restriction endonucleases and homing endonucleases. See, for example, New England Biolabs Catalog or Belfort et al. (1997) *Nucleic Acids Res.* 25, 3379-88. Additional enzymes that cleave DNA are known (e.g., 51 Nuclease; mung bean nuclease; pancreatic DNase I; micrococcal nuclease; yeast HO endonuclease). See also Linn et al. (eds.) "Nucleases," Cold Spring Harbor Laboratory Press, 1993. One or more of these enzymes (or functional fragments thereof) can be used as a source of cleavage domains.

In certain embodiments, the cleavage domain can be derived from a type II-S endonuclease. Type II-S endonucleases cleave DNA specifically at sites that are typically several base pairs away from the DNA recognition site of the endonuclease and, as such, have separable recognition and cleavage domains. These enzymes generally are monomers that transiently associate to form dimers to cleave each strand of DNA at staggered locations. Non-limiting examples of suitable type II-S endonucleases include BfiI, BpmI, BsaI, BsgI, BsmBI, BsmI, BspMI, FokI, MboII, and SapI. In certain embodiments, the cleavage domain of the fusion protein is a FokI cleavage domain or a fragment or derivative thereof. See Miller et al. (2007) *Nat. Biotechnol.*

25, 778-85; Szczpek et al. (2007) *Nat. Biotechnol.* 25, 786-93; Doyon et al. (2011) *Nat. Methods,* 8, 74-81.

Transcriptional Activation Domains

In certain embodiments, the effector domain of the fusion protein is a transcriptional activation domain. In general, a transcriptional activation domain interacts with transcriptional control elements and/or transcriptional regulatory proteins (i.e., transcription factors, RNA polymerases, etc.) to increase and/or activate transcription of a gene. In certain embodiments, the transcriptional activation domain is a herpes simplex virus VP16 activation domain, VP64 (which is a tetrameric derivative of VP16), a NFκB p65 activation domain, p53 activation domains 1 and 2, a CREB (cAMP response element binding protein) activation domain, an E2A activation domain, or an NFAT (nuclear factor of activated T-cells) activation domain. In certain embodiments, the transcriptional activation domain is Gal4, Gcn4, MLL, Rtg3, Gln3, Oaf1, Pip2, Pdr1, Pdr3, Pho4, or Leu3. The transcriptional activation domain may be wild type, or it may be a modified or truncated version of the original transcriptional activation domain.

Transcriptional Repressor Domains

In certain embodiments, the effector domain of the fusion protein is a transcriptional repressor domain. In general, a transcriptional repressor domain interacts with transcriptional control elements and/or transcriptional regulatory proteins (i.e., transcription factors, RNA polymerases, etc.) to decrease and/or prohibit transcription of a gene. In certain embodiments, the transcriptional repressor domains is inducible cAMP early repressor (ICER) domains, Kruppel-associated box A (KRAB-A) repressor domains, YY1 glycine rich repressor domains, Sp1-like repressors, E(spl) repressors, IκB repressor, or MeCP2.

Epigenetic Modification Domains

In certain embodiments, the effector domain of the fusion protein is an epigenetic modification domain. In general, epigenetic modification domains alter gene expression by modifying the histone structure and/or chromosomal structure. In certain embodiments, the epigenetic modification domains is a histone acetyltransferase domain, a histone deacetylase domain, a histone methyltransferase domain, a histone demethylase domain, a DNA methyltransferase domain, or a DNA demethylase domain.

Additional Domains

In certain embodiments, the fusion protein further comprises at least one additional domain. Non-limiting examples of suitable additional domains include nuclear localization signals (NLSs), cell-penetrating or translocation domains, and marker domains. An NLS generally comprises a stretch of basic amino acids. See, e.g., Lange et al. (2007) *J. Biol. Chem.,* 282, 5101-5. For example, in certain embodiments, the NLS is a monopartite sequence, such as PKKKRKV (SEQ ID NO: 2) or PKKKRRV (SEQ ID NO: 3). In certain embodiments, the NLS is a bipartite sequence. In certain embodiments, the NLS is KRPAATKKAGQAKKKK (SEQ ID NO: 4).

In certain embodiments, the fusion protein comprises at least one cell-penetrating domain. In certain embodiments, the cell-penetrating domain is a cell-penetrating peptide sequence derived from the HIV-1 TAT protein. As an example, the TAT cell-penetrating sequence can be GRKKRRQRRRPPQPKKKRKV (SEQ ID NO: 5). In certain embodiments, the cell-penetrating domain is TLM (PLSSIFSRIGDPPKKKRKV; SEQ ID NO: 6), a cell-penetrating peptide sequence derived from the human hepatitis B virus. In certain embodiments, the cell-penetrating domain is MPG (GALFLGWLGAAGSTMGAPKKKRKV; SEQ ID NO: 7 or GALFLGFLGAAGSTMGAWSQPKKKRKV; SEQ ID NO: 8). In certain embodiments, the cell-penetrating domain is Pep-1 (KETWWETWWTEWSQPKKKRKV; SEQ ID NO: 9), VP22, a cell penetrating peptide from Herpes simplex virus, or a polyarginine peptide sequence.

In certain embodiments, the fusion protein comprises at least one marker domain. Non-limiting examples of marker domains include fluorescent proteins, purification tags, and epitope tags. In certain embodiments, the marker domain is a fluorescent protein. Non limiting examples of suitable fluorescent proteins include green fluorescent proteins (e.g., GFP, GFP-2, tagGFP, turboGFP, EGFP, Emerald, Azami Green, Monomeric Azami Green, CopGFP, AceGFP, ZsGreen1), yellow fluorescent proteins (e.g. YFP, EYFP, Citrine, Venus, YPet, PhiYFP, ZsYellow1), blue fluorescent proteins (e.g. EBFP, EBFP2, Azurite, mKalama1, GFPuv, Sapphire, T-sapphire), cyan fluorescent proteins (e.g. ECFP, Cerulean, CyPet, AmCyan1, Midoriishi-Cyan), red fluorescent proteins (mKate, mKate2, mPlum, DsRed monomer, mCherry, mRFP1, DsRed-Express, DsRed2, DsRed-Monomer, HcRed-Tandem, HcRedl, AsRed2, eqFP611, mRasberry, mStrawberry, Jred), orange fluorescent proteins (mOrange, mKO, Kusabira-Orange, Monomeric Kusabira-Orange, mTangerine, tdTomato) and any other suitable fluorescent protein. In certain embodiments, the marker domain is a purification tag and/or an epitope tag. Exemplary tags include, but are not limited to, glutathione-S-transferase (GST), chitin binding protein (CBP), maltose binding protein, thioredoxin (TRX), poly(NANP), tandem affinity purification (TAP) tag, myc, AcV5, AU1, AU5, E, ECS, E2, FLAG, HA, nus, Softag 1, Softag 3, Strep, SBP, Glu-Glu, HSV, KT3, S, S1, T7, V5, VSV-G, 6×His, biotin carboxyl carrier protein (BCCP), and calmodulin.

V. Uses and Methods

In one aspect, the present invention provides a method for cleaving a target polynucleotide with a Cas protein. The method comprises contacting the target polynucleotide with (i) a guide RNA or a set of guide RNA molecules described herein, and (ii) a Cas protein. In certain embodiments, the method results in a double-strand break in the target polynucleotide. In certain embodiments, the Cas protein is a Cas protein having a single-strand nicking activity. In certain embodiments, the method results in a single-strand break in the target polynucleotide. In certain embodiments, a complex comprising a guide RNA and Cas protein having a single-strand nicking activity is used for sequence-targeted single-stranded DNA cleavage, i.e., nicking.

In one aspect, the present invention provides a method for cleaving two or more target polynucleotides with a Cas protein. The method comprises contacting the target polynucleotides with (i) a set of guide RNA molecules described herein, and (ii) a Cas protein. In certain embodiments, the method results in double-strand breaks in the target polynucleotides. In certain embodiments, the Cas protein is a Cas protein having a single-strand nicking activity. In certain embodiments, the method results in single-strand breaks in the target polynucleotides. In certain embodiments, a complex comprising a guide RNA and Cas protein having a single-strand nicking activity is used for sequence-targeted single-stranded DNA cleavage, i.e., nicking.

In one aspect, the present invention provides a method for binding a target polynucleotide with a Cas protein. The method comprises contacting the target polynucleotide with (i) a guide RNA or a set of guide RNA molecules described herein and (ii) a Cas protein, to result in binding of the target polynucleotide with the Cas protein. In certain embodiments, the Cas protein is a Cas variant. In certain embodiments, the Cas variant lacks some or all nuclease activity relative to a counterpart wild-type Cas protein.

In one aspect, the present invention provides a method for binding two or more target polynucleotides with a Cas protein. The method comprises contacting the target polynucleotides with (i) a set of RNA molecules described herein and (ii) a Cas protein, to result in binding of the target polynucleotides with the Cas protein. In certain embodiments, the Cas protein is a Cas variant. In certain embodiments, the Cas variant lacks some or all nuclease activity relative to a counterpart wild-type Cas protein.

In one aspect, the present invention provides a method for targeting a Cas protein to a target polynucleotide. The method comprises contacting the Cas protein with a guide RNA or a set of guide RNA molecules described herein. In certain embodiments, the method results in formation of a guide RNA:Cas protein complex. In certain embodiments, the Cas protein is a wild type Cas9 protein. In certain embodiments, the Cas protein is a mutant or variant of a Cas9 protein. In certain embodiments, the Cas protein is a Cas protein having a single-strand nicking activity. In certain embodiments, the Cas protein is a Cas protein lacking nuclease activity (e.g., a nuclease-deficient mutant of Cas protein). In certain embodiments, the Cas protein is part of a fusion protein (e.g., a fusion protein comprising (i) the Cas protein and (ii) a heterologous polypeptide).

In one aspect, the present invention provides a method for targeting a Cas protein to two or more target polynucleotides. The method comprises contacting the Cas protein with a set of guide RNA molecules described herein. In certain embodiments, the method results in formation of a guide RNA:Cas protein complex. In certain embodiments, the Cas protein is a wild type Cas9 protein. In certain embodiments, the Cas protein is a mutant or variant of a Cas9 protein. In certain embodiments, the Cas protein is a Cas protein having a single-strand nicking activity. In certain embodiments, the Cas protein is a Cas protein lacking nuclease activity (e.g., a nuclease-deficient mutant of Cas protein). In certain embodiments, the Cas protein is part of a fusion protein (e.g., a fusion protein comprising (i) the Cas protein or and (ii) a heterologous polypeptide).

In certain embodiments, the guide RNA is introduced into a cell by transfection. Techniques for RNA transfection are known in the art and include electroporation and lipofection. Effective techniques for RNA transfection depend mostly on cell type. See, e.g., Lujambio et al. (Spanish National Cancer Centre) Cancer Res. February 2007, which describes transfection of HTC-116 colon cancer cells and uses Oligofectamine (Invitrogen) for transfection of commercially obtained, modified miRNA or precursor miRNA. See also, Cho et al. (Seoul National Univ.) Nat. Biotechnol. March 2013, which describes transfection of K562 cells and uses 4D Nucleofection™ (Lonza) electroporation for transfection of transcribed sgRNAs (about 60 nts long). Techniques for transfection of RNA are also known in the art. For example, therapeutic RNA has been delivered in non-pathogenic E. coli coated with Invasin protein (to facilitate uptake into cells expressing β-1 integrin protein) and with the E. coli encoded to express lysteriolysin O pore-forming protein to permit the shRNA to pass from the E. coli into the cytoplasm. See also Cho et al. (Seoul National Univ.) Nat. Biotechnol. March 2013.

In certain embodiments, the guide RNA is introduced or delivered into cells. Technologies that can be used for delivery of guide RNA include those that utilize encapsulation by biodegradable polymers, liposomes, or nanoparticles. Such polymers, liposomes, and nanoparticles can be delivered intravenously. In certain embodiments, for in vivo delivery, guide RNA can be injected into a tissue site or administered systemically. In vivo delivery can also be effected by a beta-glucan delivery system, such as those described in U.S. Pat. Nos. 5,032,401 and 5,607,677, and U.S. Publication No. 2005/0281781, which are hereby incorporated by reference in their entirety. In certain embodiments, guide RNA or a delivery vehicle containing guide RNA is targeted to a particular tissue or body compartment. For example, in certain embodiments, to target exogenous RNA to other tissues, synthetic carriers are decorated with cell-specific ligands or aptamers for receptor uptake, e.g., RNA encased in cyclodextrin nanoparticles coated with PEG and functionalized with human transferrin protein for uptake via the transferrin receptor which is highly expressed in tumor cells. Further approaches are described herein below or known in the art.

The present invention has been tested in human cells as described in Hendel et al., Nat. Biotechnol. (2015) 33:9, 985-9 (which is incorporated in this application in its entirety). In the cited work, modified guide RNA was introduced into K562 cells, human primary T cells, and CD34+ hematopoietic stem and progenitor cells (HSPCs). The modified guide RNA significantly enhanced genome editing efficiencies in human cells, including human primary T cells and CD34+ HSPCs as compared to unmodified guide RNA.

Figure 11A:
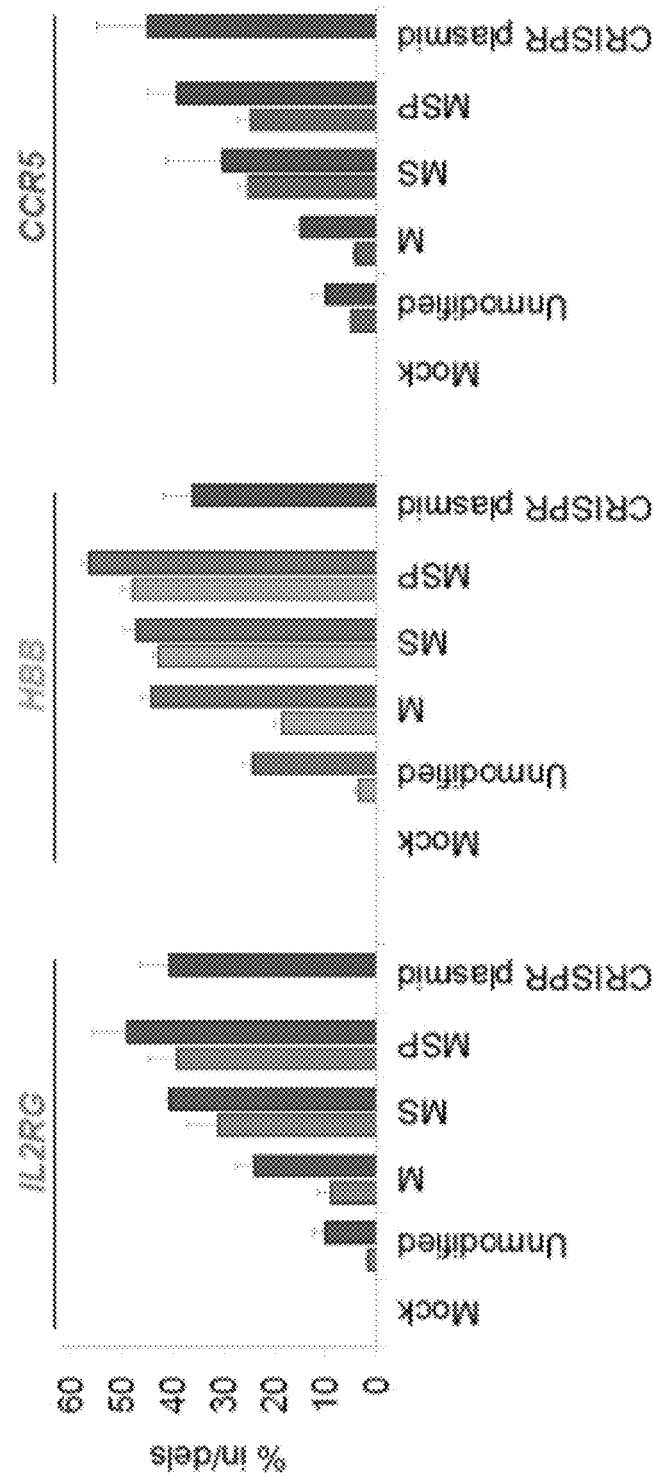
FIGS. 11A and 11B illustrate experimental results showing that gene disruption in human cell lines, with high frequencies of indels and homologous recombination (HR), can be achieved using synthesized and chemically modified sgRNAs disclosed herein, as reported in Hendel et al., *Nat. Biotechnol.* (2015) 33:9, 985-9.
Figure 11B:
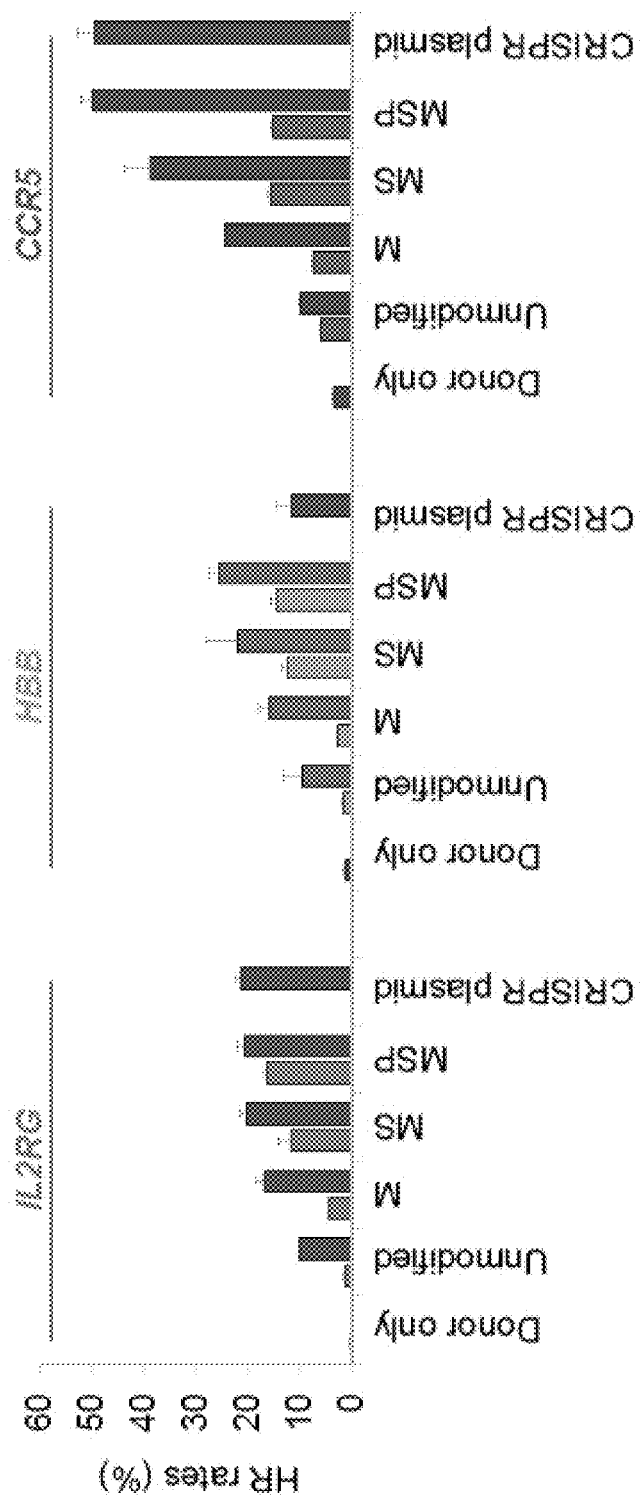
Figure 12C:
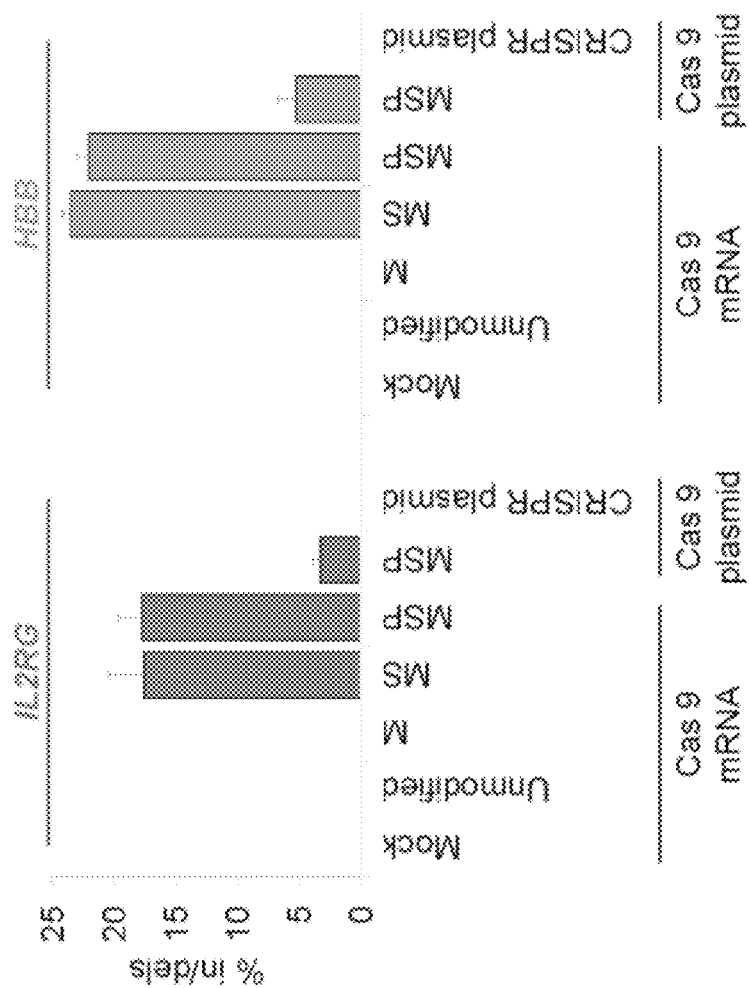
FIGS. 12A, 12B, 12C and 12D illustrate experimental results showing that chemically modified sgRNAs as described herein can be used to achieve high frequencies of gene disruption or targeted genome editing in stimulated primary human T cells as well as in CD34+ hematopoietic stem and progenitor cells (HSPCs), as reported in Hendel et al., *Nat. Biotechnol.* (2015) 33:9, 985-9.

FIGS. 11A and 11B illustrate experimental results showing that gene disruption in human cell lines can be achieved by high frequencies of indels or by cleavage-stimulated homologous recombination using synthesized and chemically modified sgRNAs disclosed herein. Gene disruption by mutagenic NHEJ was measured by deep sequencing of PCR amplicons (FIG. 12A) or gene addition by HR at the three loci IL2RG, HBB and CCR5 in K562 cells induced by Cas9 in combination with synthetic sgRNAs (FIG. 12B). The synthetic sgRNAs were delivered at 1 µg (light shade) or 20 µg (dark shade) per 1 million cells. Cas9 was expressed from a plasmid (2 µg) and for HR experiments 5 µg of GFP-encoding donor plasmid was included. As a positive control, 2 µg of sgRNA plasmid encoding both the sgRNA and the Cas9 protein was used (gray bars). Bars represent average values+s.e.m., n=3.

FIGS. 12A, 12B, 12C and 12D illustrate experimental results showing that chemically modified sgRNAs as described herein can be used to achieve high frequencies of gene disruption or targeted genome editing in stimulated primary human T cells and CD34+ hematopoietic stem and progenitor cells (HSPCs).

Figure 12A:

FIG. 12A illustrates results from primary human T cells nucleofected with 10 µg of a synthetic CCR5 sgRNAs and either 15 µg Cas9 mRNA or 1 µg Cas9-encoding plasmid. 1 µg sgRNA plasmid encoding both the sgRNA and Cas9 protein was included for comparison. The bars represent average indel frequencies for three different donors+s.e.m., n=6, as measured by TIDE (tracking of indels by decomposition) analysis of PCR amplicons spanning the sgRNA target site, and using a mock-treated sample as control reference. Delivery of Cas9 mRNA with the unmodified or the M-modified sgRNA, and nucleofection of the plasmid encoding both the sgRNA and Cas9, did not give rise to allele modification frequencies above background. Co-transfection of the MSP-modified sgRNA with DNA expression plasmid for Cas9 generated 9.3% indel frequency. Cas9 mRNA with either the MS- or MSP-modified sgRNA generated 48.7% and 47.9% indel frequencies, respectively.

FIG. 12B illustrates results from stimulated T cells. The cells were nucleofected as above, but with 15 µg Cas9 protein complexed with a 2.5 molar excess of the indicated synthetic CCR5 sgRNAs. Indel frequencies were measured by TIDE analysis. The bars represent average indel frequencies for three different donors+s.e.m., n=6. A 2.4-fold improvement in indel frequencies of the MS-modified sgRNA over the unmodified sgRNA (30.7% vs. 12.8%) was observed for chemically modified sgRNAs when delivered complexed with Cas9 protein. These results establish that chemically modified sgRNAs can be used for genome editing of stimulated T cells when delivered complexed with Cas9 protein.

FIG. 12C illustrates results from human peripheral blood CD34+HSPCs. 500,000 mobilized cells were nucleofected with 10 µg of the indicated synthetic sgRNAs targeting IL2RG or HBB and either 15 µg Cas9 mRNA or 1 µg Cas9 plasmid. 1 µg of sgRNA plasmid encoding both the sgRNA and Cas9 protein was included for comparison. Bars represent average indel frequencies+s.e.m., n=3, as measured by T7 endonuclease cleavage assay. Indels were not detected at either locus using the unmodified or M-modified sgRNAs when co-transfected with Cas9 mRNA. However, the IL2RG MS- and MSP-modified sgRNAs showed 17.5% and 17.7% indel frequencies, respectively, and 23.4% and 22.0%, respectively, for the HBB MS- and MSP-modified sgRNAs.

Figure 12D:
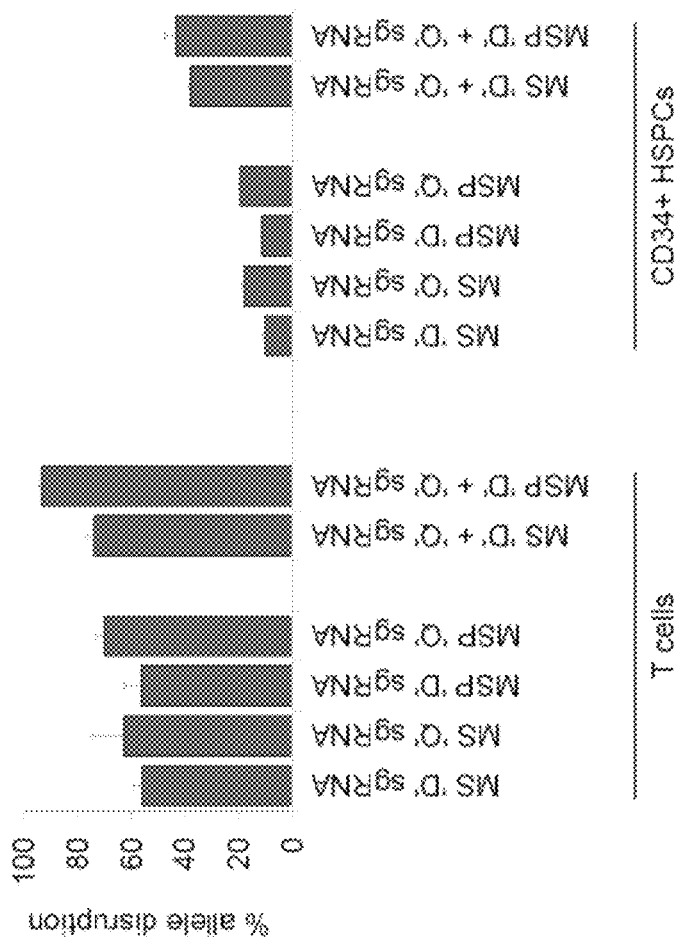
Figure 12B:
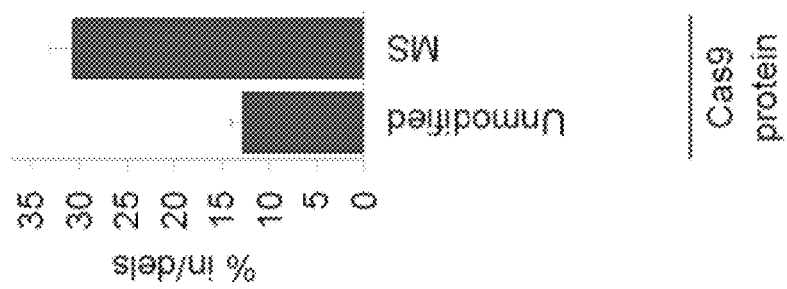

FIG. 12D illustrates results from stimulated T cells or mobilized human peripheral blood CD34+ HSPCs. One million cells were nucleofected with 15 µg Cas9 mRNA and 10 µg of the indicated synthetic CCR5 sgRNAs. A recent study showed that the simultaneous use of two sgRNAs could improve gene disruption in human primary T cells and in CD34+ HSPCs. See, e.g., Mandal et al. (2014) *Cell Stem Cell*, 15, 643-52. MS- and MSP-modified CCR5 sgRNAs were chemically synthesized with the sequences reported in Mandal study (termed 'D' and 'Q'), which cut 205 base pairs apart. When used in combination, the amount of each sgRNA was 5 µg. Indel frequencies for samples with single sgRNAs were measured by TIDE analysis as above and allele disruption frequencies for samples with two sgRNAs were measured by sequencing of cloned PCR products. The bars represent average indel frequencies+s.e.m., n=3. In T cells, the 'D' sgRNA alone gave rise to 56.0% and 56.3% indels for the MS- and MSP-modified sgRNA, respectively, and the 'Q' sgRNA gave rise to 62.6% and 69.6% indels, respectively. When used in combination, the frequencies of allele modification increased, as we observed 73.9% and 93.1% indels for the MS- and MSP-modified sgRNAs, respectively, of which the majority of the modification events were deletions between the two sgRNA target sites. In CD34+HSPCs, observations were similar though the overall frequencies were lower. For the 'D' sgRNA, allele modification frequencies of 9.8% and 11.2% were observed for the MS- and MSP-modified sgRNA, respectively, and 17.8% and 19.2% for the 'Q' sgRNA. When used in combination the frequencies increased to 37.8% and 43.0% for the MS- and MSP-modified sgRNAs, respectively. This shows that the use of two chemically modified sgRNAs is a highly effective way to facilitate gene disruption in primary human T cells and CD34+ HSPCs.

Examples of other uses include genomic editing and gene expression regulation as described below.

Genomic Editing

In one aspect, the present invention provides a method for genomic editing to modify a DNA sequence in vivo or in vitro ("in vitro" includes, without being limited to, a cell-free system, a cell lysate, an isolated component of a cell, and a cell outside of a living organism). The DNA sequence may comprise a chromosomal sequence, an episomal sequence, a plasmid, a mitochondrial DNA sequence, or a functional intergenic sequence, such as an enhancer sequence or a DNA sequence for a non-coding RNA. The method comprises contacting the DNA sequence with (i) a guide RNA or a set of guide RNA molecules described herein, and (ii) a Cas protein. In certain embodiments, the DNA sequence is contacted outside of a cell. In certain embodiments, the DNA sequence is located in the genome within a cell and is contacted in vitro or in vivo. In certain embodiments, the cell is within an organism or tissue. In certain embodiments, the cell is a human cell, a non-human mammalian cell, a stem cell, a non-mammalian vertebrate cell, an invertebrate cell, a plant cell, a single cell organism, or an embryo. In certain embodiments, the guide RNA aids in targeting the Cas protein to a targeted site in the DNA sequence. In certain embodiments, the Cas protein cleaves at least one strand of the DNA sequence at the targeted site. In certain embodiments, the Cas protein cleaves both strands of the DNA sequence at the targeted site.

In certain embodiments, the method further comprises introducing the Cas protein into a cell or another system. In certain embodiments, the Cas protein is introduced as a purified or non-purified protein. In certain embodiments, the Cas protein is introduced via an mRNA encoding the Cas protein. In certain embodiments, the Cas protein is introduced via a linear or circular DNA encoding the Cas protein. In certain embodiments, the cell or system comprises a Cas protein or a nucleic acid encoding a Cas protein.

In certain embodiments, a double-stranded break can be repaired via an error-prone, non-homologous end-joining ("NHEJ") repair process. In certain embodiments, a double-stranded break can be repaired by a homology-directed repair (HDR) process such that a donor sequence in a donor polynucleotide can be integrated into or exchanged with the targeted DNA sequence.

In certain embodiments, the method further comprises introducing at least one donor polynucleotide into the cell or system. In certain embodiments, the donor polynucleotide comprises at least one homologous sequence having substantial sequence identity with a sequence on either side of the targeted site in the DNA sequence. In certain embodiments, the donor polynucleotide comprises a donor sequence that can be integrated into or exchanged with the DNA sequence via homology-directed repair, such as homologous recombination.

In certain embodiments, the donor polynucleotide includes an upstream homologous sequence and a downstream homologous sequence, each of which have substantial sequence identity to sequences located upstream and downstream, respectively, of the targeted site in the DNA sequence. These sequence similarities permit, for example, homologous recombination between the donor polynucleotide and the targeted DNA sequence such that the donor sequence can be integrated into (or exchanged with) the DNA sequence targeted.

In certain embodiments, the target site(s) in the DNA sequence spans or is adjacent to a mutation, e.g., point mutation, a translocation or an inversion which may cause or be associated with a disorder. In certain embodiments, the method comprises correcting the mutation by introducing into the cell or system at least one donor polynucleotide comprising (i) a wild type counterpart of the mutation and (ii) at least one homologous sequence having substantial sequence identity with a sequence on one side of the targeted site in the DNA sequence. In certain embodiments, the donor polynucleotide comprises a homologous sequence having substantial sequence identity with a sequence on both sides of the targeted site in the DNA sequence.

In certain embodiments, the donor polynucleotide comprises an exogenous sequence that can be integrated into or exchanged with the targeted DNA sequence via a homology-directed repair process, such as homologous recombination. In certain embodiments, the exogenous sequence comprises a protein coding gene, which, optionally, is operably linked to an exogenous promoter control sequence. Thus, in certain embodiments, upon integration of the exogenous sequence, a cell can express a protein encoded by the integrated gene. In certain embodiments, the exogenous sequence is integrated into the targeted DNA sequence such that its expression in the recipient cell or system is regulated by the exogenous promoter control sequence. Integration of an exogenous gene into the targeted DNA sequence is termed a "knock in." In other embodiments, the exogenous sequence can be a transcriptional control sequence, another expression control sequence, an RNA coding sequence, and the like.

In certain embodiments, the donor polynucleotide comprises a sequence that is essentially identical to a portion of the DNA sequence at or near the targeted site, but comprises at least one nucleotide change. For example, in certain embodiments, the donor sequence comprises a modified or mutated version of the DNA sequence at or near the targeted site such that, upon integration or exchange with the targeted site, the resulting sequence at the targeted site comprises at least one nucleotide change. In certain embodiments, the at least one nucleotide change is an insertion of one or more nucleotides, a deletion of one or more nucleotides, a substitution of one or more nucleotides, or combinations thereof. As a consequence of the integration of the modified sequence, the cell may produce a modified gene product from the targeted DNA sequence.

In certain embodiments, the methods are for multiplex applications. In certain embodiments, the methods comprise introducing a library of guide RNAs into the cell or system. In certain embodiments, the library comprises at least 100 unique guide sequences. In certain embodiments, the library comprises at least 1,000 unique guide sequences. In certain embodiments, the library comprises at least 10,000 unique guide sequences. In certain embodiments, the library comprises at least 100,000 unique guide sequences. In certain embodiments, the library comprises at least 1,000,000 unique guide sequences. In certain embodiments, the library targets at least 10 different polynucleotides or at least 10 different sequences within one or more polynucleotides. In certain embodiments, the library targets at least 100 different polynucleotides or at least 100 different sequences within one or more polynucleotides. In certain embodiments, the library targets at least 1,000 different polynucleotides or at least 1,000 different sequences within one or more polynucleotides. In certain embodiments, the library targets at least 10,000 different polynucleotides or at least 10,000 different sequences within one or more polynucleotides. In certain embodiments, the library targets at least 100,000 different polynucleotides or at least 100,000 different sequences within one or more polynucleotides. In certain embodiments, the library targets at least 1,000,000 different polynucleotides or at least 1,000,000 different sequences within one or more polynucleotides.

Genomic Editing in Human and Mammalian Cells

Embodiments of the present invention are useful in methods for genomic editing to modify a target polynucleotide, for example a DNA sequence, in a mammalian cell.

In certain embodiments, the DNA sequence is a chromosomal sequence. In certain embodiments, the DNA sequence is a protein-coding sequence. In certain embodiments, the DNA sequence is a functional intergenic sequence, such as an enhancer sequence or a non-coding sequence. In certain embodiments, the DNA is part of a human gene. In some such embodiments, the human gene is the clathrin light chain (CLTA1) gene, the human interleukin 2 receptor gamma (IL2RG) gene, the human cytotoxic T-lymphocyte-associated protein 4 (CLTA4) gene, the human protocadherin alpha 4 (PCDHA4) gene, the human engrailed homeobox 1 (EN1) gene), the human hemoglobin beta (HBB) gene, which can harbor mutations responsible for sickle cell anemia and thalassemias, or the human chemokine (C-C motif) receptor 5 (CCR5) gene which encodes a co-receptor of HIV.

In certain embodiments, the mammalian cell is a human cell. In some such embodiments, the human cell is a primary human cell. In further embodiments, the primary human cell is a human primary T cell. The human primary T cell may be stimulated or unstimulated. In certain embodiments, the human cell is a stem/progenitor cell, such as a CD34+ hematopoietic stem and progenitor cell (HSPC). In certain embodiments, the human cell is from a cultured cell line, for example such as can be obtained commercially. Exemplary cell lines include K562 cells, a human myelogenous leukemia line.

In certain embodiments, the cell is within a living organism. In certain other embodiments, the cell is outside of a living organism.

The method comprises contacting the DNA sequence with (i) a guide RNA or a set of guide RNA molecules described herein, and (ii) a Cas protein.

In certain embodiments, the method further comprises introducing or delivering the guide RNA into the cell. In some such embodiments, the guide RNA is introduced into a cell by transfection. Techniques for RNA transfection are known in the art and include electroporation and lipofection. In other embodiments, the guide RNA is introduced into a cell (and, more particularly, a cell nucleus) by nucleofection. Techniques for nucleofection are known in the art and may utilize nucleofection devices such as the Lonza Nucleofector 2b or the Lonza 4D-Nucleofector and associated reagents.

In certain embodiments, the method further comprises introducing or delivering the Cas protein into the cell. In some such embodiments, the Cas protein is introduced as a purified or non-purified protein. In other embodiments, the Cas protein is introduced via an mRNA encoding the Cas protein. In some such embodiments, the mRNA encoding the Cas protein is introduced into the cell by transfection. In other embodiments, the mRNA encoding the Cas protein is introduced into a cell (and, more particularly, a cell nucleus) by nucleofection.

In certain embodiments, the method employs ribonucleoprotein (RNP)-based delivery such that the Cas protein is introduced into the cell in a complex with the guide RNA. For example, a Cas9 protein may be complexed with a guide RNA in a Cas9:gRNA complex, which allows for co-delivery of the gRNA and Cas protein. For example, the Cas:gRNA complex may be nucleofected into cells.

In certain embodiments, the method employs an all-RNA delivery platform. For example, in some such embodiments, the guide RNA and the mRNA encoding the Cas protein are introduced into the cell simultaneously or substantially simultaneously (e.g., by co-transfection or co-nucleofection). In certain embodiments, co-delivery of Cas mRNA and modified gRNA results in higher editing frequencies as compared to co-delivery of Cas mRNA and unmodified gRNA. In particular, gRNA having 2'-O-methyl-3'-phosphorothioate (MS), or 2'-O-methyl-3'-thioPACE (MSP) incorporated at three terminal nucleotides at both the 5' and 3' ends, provide higher editing frequencies as compared to unmodified gRNA.

In certain embodiments, the guide RNA and the mRNA encoding the Cas protein are introduced into the cell sequentially; that is, the guide RNA and the mRNA encoding the Cas protein are introduced into the cell at different times. The time period between the introduction of each agent may range from a few minutes (or less) to several hours or days. For example, in some such embodiments, gRNA is delivered first, followed by delivery of Cas mRNA 4, 8, 12 or 24 hours later. In other such embodiments, Cas mRNA is delivered first, followed by delivery of gRNA 4, 8, 12 or 24 hours later. In some particular embodiments, delivery of modified gRNA first, followed by delivery of Cas mRNA results in higher editing frequencies as compared to delivery of unmodified gRNA followed by delivery of Cas mRNA.

In certain embodiments, the gRNA is introduced into the cell together with a DNA plasmid encoding the Cas protein. In some such embodiments, the gRNA and the DNA plasmid encoding the Cas protein are introduced into the cell by nucleofection. In some particular embodiments, an RNP-based delivery platform or an all-RNA delivery platform provides lower cytotoxicity in primary cells than a DNA plasmid-based delivery system.

In certain embodiments, the method provides significantly enhanced genome editing efficiencies in human cells, including human primary T cells and CD34+HSPCs.

In certain embodiments, modified gRNA increases the frequency of insertions or deletions (indels), which may be indicative of mutagenic NHEJ and gene disruption, relative to unmodified gRNA. In particular, modified gRNA having 2'-O-methyl-3'-phosphorothioate (MS) or 2'-O-methyl-3'-thioPACE (MSP) incorporated at three terminal nucleotides at both the 5' and 3' ends, increases the frequency of indels relative to unmodified gRNA.

In certain embodiments, co-delivery of modified gRNA and Cas mRNA to human primary T cells increases the frequency of indels as compared to co-delivery of unmodified gRNA and Cas mRNA. In particular, modified gRNA having 2'-O-methyl-3'-phosphorothioate (MS) or 2'-O-methyl-3'-thioPACE (MSP) incorporated at three terminal nucleotides at both the 5' and 3' ends, increases the frequency of indels in human primary T cells relative to unmodified gRNA.

In certain embodiments, modified gRNA improves gRNA stability relative to unmodified gRNA. As one example, gRNA having 2'-O-methyl (M) incorporated at three terminal nucleotides at both the 5' and 3' ends, modestly improves stability against nucleases and also improves base pairing thermostability over unmodified gRNA. As another example, gRNA having 2'-O-methyl-3'-phosphorothioate (MS) or 2'-O-methyl-3'-thioPACE (MSP) incorporated at three terminal nucleotides at both the 5' and 3' ends, dramatically improves stability against nucleases relative to unmodified gRNA. It is contemplated that gRNA end modifications enhance intracellular stability against exonucleases, thus enabling increased efficacy of genome editing when Cas mRNA and gRNA are co-delivered or sequentially delivered into human cells.

In certain embodiments, modified gRNA stimulates gene targeting, which, in turn, allows for gene editing by, for example, homologous recombination or NHEJ. In particular, gRNA having 2'-O-methyl-3'-phosphorothioate (MS), or 2'-O-methyl-3'-thioPACE (MSP) incorporated at three terminal nucleotides at both the 5' and 3' ends, stimulates higher levels of homologous recombination than unmodified gRNA.

In certain embodiments, modified gRNA retains high specificity. In certain embodiments, the ratio of on-target to off-target indel frequencies is improved with modified gRNA as compared to unmodified gRNA. In certain embodiments, modified gRNA delivered in an RNP complex with a Cas protein provides significantly better on-target: off-target ratios compared to a DNA plasmid-based delivery system.

Gene Expression Regulation

In certain embodiments, the guide RNA described herein is used for regulating transcription or expression of a gene of interest. For example, in certain embodiments, a fusion protein comprising a Cas protein (e.g., a nuclease-deficient Cas9) and a transcription activator polypeptide is used to increase transcription of a gene. Similarly, in certain embodiments, a fusion protein comprising a Cas protein (e.g., a nuclease-deficient Cas9) and a repressor polypeptide is used to knock-down gene expression by interfering with transcription of the gene.

In at least one aspect, the present invention provides a method for regulating the expression of a gene of interest in vivo or in vitro. The method comprises introducing into a cell or another system (i) a synthetic guide RNA described herein, and (ii) a fusion protein. In certain embodiments, the fusion protein comprises a Cas protein and an effector domain, such as a transcriptional activation domain, a transcriptional repressor domain, or an epigenetic modification domain. In certain embodiments, the fusion protein comprises a mutated Cas protein, such as a Cas9 protein that is a null nuclease. In certain embodiments, the Cas protein contains one or more mutations, such as D10A, H840A and/or N863A.

In certain embodiments, the fusion protein is introduced into the cell or system as a purified or non-purified protein. In certain embodiments, the fusion protein is introduced into the cell or system via an mRNA encoding the fusion protein. In certain embodiments, the fusion protein is introduced into the cell or system via a linear or circular DNA encoding the fusion protein.

In certain embodiments, the guide RNA aids in directing the fusion protein to a specific target polynucleotide comprising a chromosomal sequence, an episomal sequence, a plasmid, a mitochondrial DNA sequence, or a functional intergenic sequence, such as an enhancer or the DNA sequence for a non-coding RNA. In certain embodiments, the effector domain regulates expression of a sequence in the target polynucleotide. A guide RNA for modulating gene expression can be designed to target any desired endogenous gene or sequence encoding a functional RNA. A genomic target sequence can be selected in proximity of the transcription start site of the endogenous gene, or alternatively, in proximity of the translation initiation site of the endogenous gene. In certain embodiments, the target sequence is in a region of the DNA that is traditionally termed the "promoter proximal" region of a gene. In certain embodiments, the target sequence lies in a region from about 1,000 base pairs upstream of the transcription start site to about 1,000 base pairs downstream of the transcription start site. In certain embodiments, the target sequence is remote from the start site for transcription of the gene (e.g., on another chromosome).

In certain embodiments, the methods are for multiplex applications. In certain embodiments, the methods comprise introducing a library of guide RNAs into the cell or system. In certain embodiments, the library comprises at least 100, at least 1,000, at least 10,000, at least 100,000, or at least 1,000,000 unique guide sequences. In certain embodiments, the library targets at least 10 different polynucleotides or at least 10 different sequences within one or more polynucleotides. In certain embodiments, the library targets at least 100 different polynucleotides or at least 100 different sequences within one or more polynucleotides. In certain embodiments, the library targets at least 1,000 different polynucleotides or at least 1,000 different sequences within one or more polynucleotides. In certain embodiments, the library targets at least 10,000 different polynucleotides or at least 10,000 different sequences within one or more polynucleotides. In certain embodiments, the library targets at least 100,000 different polynucleotides or at least 100,000 different sequences within one or more polynucleotides. In certain embodiments, the library targets at least 1,000,000 different polynucleotides or at least 1,000,000 different sequences within one or more polynucleotides.

Kits

In one aspect, the present invention provides kits containing reagents for performing the above-described methods, including producing gRNA:Cas protein complex and/or supporting its activity for binding, nicking or cleaving target polynucleotide. In certain embodiments, one or more of the reaction components, e.g., one or more guide RNAs and Cas proteins, for the methods disclosed herein, can be supplied in the form of a kit for use. In certain embodiments, the kit comprises a Cas protein or a nucleic acid encoding the Cas protein, and one or more guide RNAs described herein or a set or library of guide RNAs. In certain embodiments, the kit includes one or more other reaction components. In certain embodiments, an appropriate amount of one or more reaction components is provided in one or more containers or held on a substrate.

Examples of additional components of the kits include, but are not limited to, one or more different polymerases, one or more host cells, one or more reagents for introducing foreign nucleic acid into host cells, one or more reagents (e.g., probes or PCR primers) for detecting expression of the guide RNA and/or the Cas mRNA or protein or for verifying the status of the target nucleic acid, and buffers, transfection reagents or culture media for the reactions (in 1× or more concentrated forms). In certain embodiments, the kit includes one or more of the following components: biochemical and physical supports; terminating, modifying and/or digesting reagents; osmolytes; and apparati for reaction, transfection and/or detection.

The reaction components used can be provided in a variety of forms. For example, the components (e.g., enzymes, RNAs, probes and/or primers) can be suspended in an aqueous solution or bound to a bead or as a freeze-dried or lyophilized powder or pellet. In the latter case, the components, when reconstituted, form a complete mixture of components for use in an assay. The kits of the invention can be provided at any suitable temperature. For example, for storage of kits containing protein components or complexes thereof in a liquid, it is preferred that they are provided and maintained below 0° C., preferably at about −20° C., possibly in a freeze-resistant solution containing glycerol or other suitable antifreeze.

A kit or system may contain, in an amount sufficient for at least one assay, any combination of the components described herein. In some applications, one or more reaction components may be provided in pre-measured single use amounts in individual, typically disposable, tubes or equivalent containers. With such an arrangement, a RNA-guided nuclease reaction can be performed by adding a target nucleic acid, or a sample or cell containing the target nucleic acid, to the individual tubes directly. The amount of a component supplied in the kit can be any appropriate amount and may depend on the market to which the product is directed. The container(s) in which the components are supplied can be any conventional container that is capable of holding the supplied form, for instance, microfuge tubes, microtiter plates, ampoules, bottles, or integral testing devices, such as fluidic devices, cartridges, lateral flow, or other similar devices.

The kits can also include packaging materials for holding the container or combination of containers. Typical packaging materials for such kits and systems include solid matrices (e.g., glass, plastic, paper, foil, micro-particles and the like) that hold the reaction components or detection probes in any of a variety of configurations (e.g., in a vial, microtiter plate well, microarray, and the like). The kits may further include instructions recorded in a tangible form for use of the components.

EXAMPLES

Example 1

To evaluate the ability of the chemically synthesized guide RNAs to target and cleave a DNA target sequence, an in vitro cleavage assay was developed. Briefly, as shown in FIG. 3, ~4-kb PAM-addressable DNA targets were prepared by preparative PCR amplification of plasmid-borne human sequences (here, a sequence from the human clathrin light chain CLTA gene). In a 20-uL reaction volume, 50 fmoles of linearized DNA target in the presence of 50 nM sgRNA, 39 nM recombinant purified Cas9 protein (*S. pyogenes*; Agilent) and 10 mM $MgCl_2$ at pH 7.6 was incubated at 37° C. for 30 min. Upon completion, 0.5 uL of RNace It (Agilent) was added, and incubation was continued at 37° C. for 5 min and then at 70° C. for 15 min. Subsequently 0.5 µL of Proteinase K (Mol. Bio. grade, NEB) was added and incubated at 37° C. for 15 min. Aliquots were loaded into a DNA 7500 LabChip and were analyzed on a Bioanalyzer 2200. The workup steps served to release Cas9 from binding to target DNA, which were assayed for cleavage.

A series of guide RNAs as listed in FIG. 4 were chemically synthesized. Briefly, individual RNA strands were synthesized and HPLC purified. All oligonucleotides were quality control approved on the basis of chemical purity by HPLC analysis and full-length strand purity by mass spectrometry analysis. Each of these guide RNAs was designed to target the human CLTA gene.

The results are shown in FIG. 4. As shown in the Table 1 of FIG. 4, all but one of the chemically synthesized guide RNAs targeted and cleaved the CLTA-encoded DNA target sequence with significant cleavage rates. The one exception was "CLTA_37_Deoxy" guide RNA, which had a contiguous sequence of 37 deoxyribonucleotides at its 5' end.

As disclosed herein, a variety of chemical modifications were tested at specific positions in the sequence of a guide RNA. Surprisingly, the tested positions in the guide sequence of the guide RNA (a.k.a. the spacer sequence in the guide RNA) tolerated most of the modifications tested, including combinations of multiple modifications within single nucleotides in the guide RNA, even when modifications were instantiated in the target-binding sequences.

The results revealed that guide RNAs containing modifications at specific positions were tolerated by active Cas protein and gRNA:Cas protein complexes, as the modifications did not prevent target-specific cleavage of the target polynucleotide. In all the guide RNA sequences listed in the Table 1 of FIG. 4, the first 20 nucleotides at the 5' end are complementary to the target sequence in target DNA. The modifications that were tested and found to be tolerated at specific positions include 2'-O-methylribonucleotide (=2'OMe), 2'-deoxyribonucleotide, racemic phosphorothioate internucleotide linkage(s) (=P(S)), 3'-phosphonoacetate (=PACE), 3'-thiophosphonoacetates (=thioPACE), Z nucleotides, and combinations of these.

It is contemplated that the chemical modifications disclosed and tested herein, particularly at the tested positions (as listed in the Table 1 of FIG. 4), will be tolerated at equivalent positions in a variety of guide RNAs. In certain embodiments, the chemical modifications disclosed and tested herein are tolerated in any position in a guide RNA.

As disclosed herein, chemically modified nucleotides were incorporated into guide RNAs in an effort to improve certain properties. Such properties include improved nuclease resistance of the guide RNA, reduced off-target effects of a gRNA:Cas protein complex (also known as improved specificity), improved efficacy of gRNA:Cas protein complex when cleaving, nicking or binding a target polynucleotide, improved transfection efficiency, and/or improved organelle localization such as nuclear localization.

While the use of modified RNA is known (e.g., to block nucleotlytic degradation in certain applications), it is widely known that one cannot simply incorporate modifications at any or all positions in an RNA sequence and expect it to function, particularly when the RNA sequence needs to complex with a protein or an enzyme to exert certain functions. Thus, it was not predictable whether these guide RNAs could tolerate chemical modifications at a variety of nucleotide positions while performing sufficient or improved function in a CRISPR-Cas system. In fact, it was unexpected that the guide RNA can tolerate specific modifications to the extent instantiated and tested, especially at several of the positions tested.

Example 2

To evaluate the ability of the chemically synthesized guide RNAs to target and cleave a DNA target sequence, an in vitro cleavage assay similar to that described in Example 1 was used. Target DNA constructs were for human DNA targets (sequences from the human clathrin light chain (CLTA1) gene, the human Interleukin 2 Receptor Gamma (IL2RG) gene, the human cytotoxic T-lymphocyte-associated protein 4 (CLTA4) gene, the human protocadherin alpha 4 (PCDHA4) gene, and the human engrailed homeobox 1 (EN1) gene), along with off-target DNA constructs differing from the target DNA by one or more nucleotides.

Table 3 sets forth the guide RNA constructs and their sequences, along with DNA constructs used for assessing the ability of those guide RNA constructs to target and cleave. In all the guide RNA sequences listed in the Table 3, the first 20 nucleotides at the 5' end are complementary to the target sequence in target DNA. ON target constructs comprise the 20 nt target sequence. OFF target constructs comprise most of the same 20 nucleotides as the target DNA, with 1, 2 or 3 nucleotide differences. Accordingly, the guide RNA is mostly, but not completely, complementary to the sequence of the OFF target constructs. The OFF target constructs are based on gene sequences known to occur in the human genome.

TABLE 3

| Entry # | Guide RNA Construct | Target DNA Construct | RNA sequence (5'→3')<br>2-piece dual-guide scaffold<br>Unmodified dual-guide RNA (dgRNA) | RNA length |
|---|---|---|---|---|
| 1 | CLTA1 crRNA + tracrRNA | CLTA1 ON1-target | AGUCCUCAUCUCCCUCAAGCGUUUAAGAGCUAUGCUGUUUUGAAUGGUCC CAAAAC (SEQ ID NO: 25) +<br>GGAACCAUUCAAAACAGCAAGCAUAGCAAGUUUAAAUAAGGCUAGUCCGUUAUCA ACUUGUAAAAGUGGCACCGAGUCGGUGCUUUUUU (SEQ ID NO: 26) | 56 + 86 |
| 2 | CLTA1 crRNA + tracrRNA | CLTA1 ON1-target | AGUCCUCAUCUCCCUCAAGCGUUUAAGAGCUAUGCUGUUUUGAAUGGUCC CAAAAC (SEQ ID NO: 25) +<br>GGAACCAUUCAAAACAGCAAGCAUAGCAAGUUUAAAUAAGGCUAGUCCGUUAUCA ACUUGUAAAAGUGGCACCGAGUCGGUGCUUUUUU (SEQ ID NO: 26) | 56 + 86 |
| 3 | CLTA1 crRNA + tracrRNA | CLTA1 OFF1-target | AGUCCUCAUCUCCCUCAAGCGUUUAAGAGCUAUGCUGUUUUGAAUGGUCC CAAAAC (SEQ ID NO: 25) +<br>GGAACCAUUCAAAACAGCAAGCAUAGCAAGUUUAAAUAAGGCUAGUCCGUUAUCA ACUUGUAAAAGUGGCACCGAGUCGGUGCUUUUUU (SEQ ID NO: 26) | 56 + 86 |
| 4 | CLTA1 crRNA + tracrRNA | CLTA1 OFF1-target | AGUCCUCAUCUCCCUCAAGCGUUUAAGAGCUAUGCUGUUUUGAAUGGUCC CAAAAC + (SEQ ID NO: 25)<br>GGAACCAUUCAAAACAGCAAGCAUAGCAAGUUUAAAUAAGGCUAGUCCGUUAUCA ACUUGUAAAAGUGGCACCGAGUCGGUGCUUUUUU (SEQ ID NO: 26) | 56 + 86 |
| 5 | CLTA1 crRNA + tracrRNA | CLTA1 OFF2-target | AGUCCUCAUCUCCCUCAAGCGUUUAAGAGCUAUGCUGUUUUGAAUGGUCC CAAAAC (SEQ ID NO: 25) +<br>GGAACCAUUCAAAACAGCAAGCAUAGCAAGUUUAAAUAAGGCUAGUCCGUUAUCA ACUUGUAAAAGUGGCACCGAGUCGGUGCUUUUUU (SEQ ID NO: 26) | 56 + 86 |
| 6 | CLTA1 crRNA + tracrRNA | CLTA1 OFF2-target | AGUCCUCAUCUCCCUCAAGCGUUUAAGAGCUAUGCUGUUUUGAAUGGUCC CAAAAC (SEQ ID NO: 25) +<br>GGACCAUUCAAAACAGCAAGCAUAGCAAGUUUAAAUAAGGCUAGUCCGUUAUCA ACUUGUAAAAGUGGCACCGAGUCGGUGCUUUUUU (SEQ ID NO: 26) | 56 + 86 |
| 7 | CLTA1 crRNA + tracrRNA | CLTA1 OFF3-target | AGUCCUCAUCUCCCUCAAGCGUUUAAGAGCUAUGCUGUUUUGAAUGGUCC CAAAAC (SEQ ID NO: 25) +<br>GGAACCAUUCAAAACAGCAAGCAUAGCAAGUUUAAAUAAGGCUAGUCCGUUAUCA ACUUGUAAAAGUGGCACCGAGUCGGUGCUUUUUU (SEQ ID NO: 26) | -56 + 86 |
| 8 | CLTA1 crRNA + tracrRNA | CLTA1 OFF3-target | AGUCCUCAUCUCCCUCAAGCGUUUAAGAGCUAUGCUGUUUUGAAUGGUCC CAAAAC (SEQ ID NO: 25) +<br>GGACCAUUCAAAACAGCAAGCAUAGCAAGUUUAAAUAAGGCUAGUCCGUUAUCA ACUUGUAAAAGUGGCACCGAGUCGGUGCUUUUUU (SEQ ID NO: 26) | 56 + 86 |
| 9 | CLTA1 crRNA + tracrRNA | CLTA1 target | AGUCCUCAUCUCCCUCAAGCGUUUAAGAGCUAUGCUGUUUUGAAUGGUCC CAAAAC (SEQ ID NO: 25) +<br>GGAACCAUUCAAAACAGCAAGCAUAGCAAGUUUAAAUAAGGCUAGUCCGUUAUCA ACUUGUAAAAGUGGCACCGAGUCGGUGCUUUUUU (SEQ ID NO: 26) | 56 + 86 |
| 10 | IL2RG_crRNA + tracrRNA | IL2RGrrig ON-target | UGGUAAUGAUGGCUUCAACAAGUUUAAGAGCUAUGCUGUUUUGAUGGUC CCAAAAC (SEQ ID NO: 27) +<br>GGAACCAUUCAAAACAGCAAGCAUAGCAAGUUUAAAUAAGGCUAGUCCGUUAUCA ACUUGUAAAAGUGGCACCGAGUCGGUGCUUUUUU (SEQ ID NO: 28) | 56 + 86 |

TABLE 3-continued

| Entry # | Guide RNA Construct | Target DNA Construct | RNA sequence (5'→3') | RNA length |
|---|---|---|---|---|
| Fluorophore-coupled dgRNA | | | | |
| 11 | CLTA1 crRNA + tracrRNA_aminoallylU57 + Cy5 | CLTA1 ON1-target | AGUCCUCAUCUCCCUCAAGCGUUUAAGAGCUAUGCUGUUUUGAAUGGUCC CAAAAC (SEQ ID NO: 29) + GGAACCAUUCAAACAGCAAGCAUAGCAAGUUUAAAAUAAGGCUAGUCCGUUAUCA ACUUG(aminoallylU + Cy5)AAAAGUGGCACCGAGUCGGUGCUUUUUUU (SEQ ID NO: 30) | 56 + 86 |
| 2'OMethyl-modified dgRNA | | | | |
| 12 | IL2RG crRNA_5', 3'-3x(2'OMe) + tracrRNA_5', 3'-3x(2'OMe) | IL2RGmg ON-target | <u>UGG</u>UAAUGAUGGCUUCAACAGUUUUAGAGCUAUGCUGUUUUGAAUGGUC CCA<u>AAA</u>C (SEQ ID NO: 31) + <u>GGA</u>ACCAUUCAAACAGCAAGCAUAGCAAGUUUAAAAUAAGGCUAGUCCGUUAUCA ACUUGUAAAAGUGGCACCGAGUCGGUGCUUU<u>UUU</u> (SEQ ID NO: 32) | 56 + 86 |
| 2'OMethyl, 3'Phosphorothioate-modified dgRNA | | | | |
| 13 | IL2RG crRNA_5', 3'-3x(2'OMe), 3'P(S)) + tracrRNA_5', 3'-3x(2'OMe), 3'P(S)) | IL2RGmg ON-target | U<u>sGsGs</u>UAAUGAUGGCUUCAACAGUUUUAGAGCUAUGCUGUUUUGAAUGG UCCCA<u>AsAsAs</u>C (SEQ ID NO: 33) + <u>GsGsAs</u>ACCAUUCAAACAGCAAGCAUAGCAAGUUUAAAAUAAGGCUAGUCCGUUAU CAACUUGUAAAAGUGGCACCGAGUCGGUGCUUU<u>UsUsU</u> (SEQ ID NO: 34) | 56 + 86 |
| 2'OMethyl, 3'PhosphorothioPACE-modified dgRNA | | | | |
| 14 | IL2RG crRNA_5', 3'-3x(2'OMe), 3'thioPACE) + tracrRNA_5', 3'-3x(2'OMe), 3'thioPACE) | IL2RGmg ON-target | U*sG*sG*sUAAUGAUGGCUUCAACAGUUUUAGAGCUAUGCUGUUUUGAAU GGUCCCAA*sA*sA*sC (SEQ ID NO: 35) + G*sG*sA*sACCAUUCAAACAGCAAGCAUAGCAAGUUUAAAAUAAGGCUAGUCCGU UAUCAACUUGUAAAAGUGGCACCGAGUCGGUGCUUU<u>U</u>*s<u>U</u>*s<u>U</u>*sU (SEQ ID NO: 36) | 56 + 86 |
| 15 | IL2RG crRNA_5', 3'-1x(2'OMe), 3'thioPACE) + tracrRNA_5', 3'-1x(2'OMe), 3'thioPACE) | IL2RGmg ON-target | U*sGUAAUGAUGGCUUCAACAGUUUUAGAGCUAUGCUGUUUUGAAUGGU CCCAAAA*sC (SEQ ID NO: 37) + G*sGAACCAUUCAAACAGCAAGCAUAGCAAGUUUAAAAUAAGGCUAGUCCGUUAU CAACUUGUAAAAGUGGCACCGAGUCGGUGCUUUU*sU (SEQ ID NO: 38) | 56 + 86 |
| 2-thioU-modified dgRNA | | | | |
| 16 | CLTA1 2thioU + 3 crRNA + tracrRNA | CLTA1 ON1-target | AG(2sU)CCUCAUCUCCCUCAAGCGUUUAAGAGCUAUGCUGUUUUGAAUGGU CCCAAAAC (SEQ ID NO: 39) + GGAACCAUUCAAACAGCAAGCAUAGCAAGUUUAAAAUAAGGCUAGUCCGUUAUCA ACUUGUAAAAGUGGCACCGAGUCGGUGCUUUUUU (SEQ ID NO: 26) | 56 + 86 |
| 17 | CLTA1 2thioU + 3 crRNA + tracrRNA | CLTA1 ON1-target | AG(2sU)CCUCAUCUCCCUCAAGCGUUUAAGAGCUAUGCUGUUUUGAAUGGU CCCAAAAC (SEQ ID NO: 39) + GGAACCAUUCAAACAGCAAGCAUAGCAAGUUUAAAAUAAGGCUAGUCCGUUAUCA ACUUGUAAAAGUGGCACCGAGUCGGUGCUUUUUU (SEQ ID NO: 26) | 56 + 86 |

TABLE 3-continued

| Entry # | Guide RNA Construct | Target DNA Construct | RNA sequence (5'→3') | RNA length |
|---|---|---|---|---|
| 18 | CLTA1_2thioU + 3 crRNA + tracrRNA | CLTA1 OFF1-target | AG(2sU)CCUAUCUCCCUCAAGCGUUUAAGAGCUAUGCUGUUUUGAUGGU CCCAAAAC (SEQ ID NO: 39) + GGAACCAUUCAAAACAGCAUAGCAAGUUUAAAUAAGGCUAGCCGUUAUCA ACUUGUAAAGUGGCACCGAGUCGGUGCUUUUUU (SEQ ID NO: 26) | 56 + 86 |
| 19 | CLTA1_2thioU + 3 crRNA + tracrRNA | CLTA1 OFF1-target | AG(2sU)CCUAUCUCCCUCAAGCGUUUAAGAGCUAUGCUGUUUUGAAUGGU CCCAAAAC (SEQ ID NO: 39) + GGAACCAUUCAAAACAGCAUAGCAAGUUUAAAUAAGCUAGCCGUUAUCA ACUUGUAAAGUGGCACCGAGUCCGUGCUUUUUU (SEQ ID NO: 26) | 56 + 86 |
| 20 | CLTA1_2thioU + 3 crRNA + tracrRNA | CLTA1 OFF2-target | AG(2sU)CCUAUCUCCCUCAAGCGUUUAAGAGCUAUGCUGUUUUGAAUGGU CCCAAAAC (SEQ ID NO: 39) + GGAACCAUUCAAAACAGCAAGUUUAAAUAAGGCUAGCCGUUAUCA ACUUGUAAAGUGGCACCGAGUCGGUGCUUUUUU (SEQ ID NO: 26) | 56 + 86 |
| 21 | CLTA1_2thioU + 3 crRNA + tracrRNA | CLTA1 OFF2-target | AG(2sU)CCUAUCUCCCUCAAGCGUUUAAGAGCUAUGCUGUUUUGAAUGGU CCCAAAAC (SEQ ID NO: 39) + GGAACCAUUCAAAACAGCAAGUUUAAAUAAGGCUAGCCGUUAUCA ACUUGUAAAGUGGCACCGAGUCGGUGCUUUUUU (SEQ ID NO: 26) | 56 + 86 |
| 22 | CLTA1_2thioU + 3 crRNA + tracrRNA | CLTA1 OFF3-target | AG(2sU)CCUAUCUCCCUCAAGCGUUUAAGAGCUAUGCUGUUUUGAAUGGU CCCAAAAC (SEQ ID NO: 39) + GGAACCAUUCAAAACAGCAAGUUUAAAUAAGGCUAGCCGUUAUCA ACUUGUAAAGUGGCACCGAGUCGGUGCUUUUUU (SEQ ID NO: 26) | 56 + 86 |
| 23 | CLTA1_2thioU + 3 crRNA + tracrRNA | CLTA1 OFF3-target | AG(2sU)CCUAUCUCCCUCAAGCGUUUAAGAGCUAUGCUGUUUUGAAUGGU CCCAAAAC (SEQ ID NO: 39) + GGAACCAUUCAAAACAGCAAGUUUAAAUAAGGCUAGCCGUUAUCA ACUUGUAAAGUGGCACCGAGUCGGUGCUUUUUU (SEQ ID NO: 26) | 56 + 86 |
| 24 | CLTA1_2thioU + 9 crRNA + tracrRNA | CLTA1 ON1-target | AGUCCUCA(2sU)CUCCCUCAAGCGUUUAAGAGCUAUGCUGUUUUGAAUGGU CCCAAAAC (SEQ ID NO: 40) + GGAACCAUUCAAAACAGCAAGUUUAAAUAAGGCUAGCCGUUAUCA ACUUGUAAAGUGGCACCGAGUCGGUGCUUUUUU (SEQ ID NO: 26) | 56 + 86 |
| 25 | CLTA1_2thioU + 9 crRNA + tracrRNA | CLTA1 ON1-target | AGUCCUCA(2sU)CUCCCUCAAGCGUUUAAGAGCUAUGCUGUUUUGAAUGGU CCCAAAAC (SEQ ID NO: 40) + GGAACCAUUCAAAACAGCAAGUUUAAAUAAGGCUAGCCGUUAUCA ACUUGUAAAGUGGCACCGAGUCGGUGCUUUUUU (SEQ ID NO: 26) | 56 + 86 |
| 26 | CLTA1_2thioU + 9 crRNA + tracrRNA | CLTA1 OFF1-target | AGUCCUCA(2sU)CUCCCUCAAGCGUUUAAGAGCUAUGCUGUUUUGAAUGGU CCCAAAAC (SEQ ID NO: 40) + GGAACCAUUCAAAACAGCAAGUUUAAAUAAGGCUAGCCGUUAUCA ACUUGUAAAGUGGCACCGAGUCGGUGCUUUUUU (SEQ ID NO: 26) | 56 + 86 |
| 27 | CLTA1_2thioU + 9 crRNA + tracrRNA | CLTA1 OFF1-target | AGUCCUCA(2sU)CUCCCUCAAGCGUUUAAGAGCUAUGCUGUUUUGAAUGGU CCCAAAAC (SEQ ID NO: 40) + GGAACCAUUCAAAACAGCAAGUUUAAAUAAGGCUAGCCGUUAUCA ACUUGUAAAGUGGCACCGAGUCGGUGCUUUUUU (SEQ ID NO: 26) | 56 + 86 |
| 28 | CLTA1_2thioU + 9 crRNA + tracrRNA | CLTA1 OFF2-target | AGUCCUCA(2sU)CUCCCUCAAGCGUUUAAGAGCUAUGCUGUUUUGAAUGGU CCCAAAAC (SEQ ID NO: 40) + GGAACCAUUCAAAACAGCAAGUUUAAAUAAGGCUAGCCGUUAUCA ACUUGUAAAGUGGCACCGAGUCGGUGCUUUUUU (SEQ ID NO: 26) | 56 + 86 |
| 29 | CLTA1_2thioU + 9 crRNA + tracrRNA | CLTA1 OFF2-target | AGUCCUCA(2sU)CUCCCUCAAGCGUUUAAGAGCUAUGCUGUUUUGAAUGGU CCCAAAAC (SEQ ID NO: 40) + GGAACCAUUCAAAACAGCAAGUUUAAAUAAGGCUAGCCGUUAUCA ACUUGUAAAGUGGCACCGAGUCGGUGCUUUUUU (SEQ ID NO: 26) | 56 + 86 |

TABLE 3-continued

| Entry # | Guide RNA Construct | Target DNA Construct | RNA sequence (5'→3') | RNA length |
|---|---|---|---|---|
| 30 | CLTA1_2thioU + 9 crRNA + tracrRNA | CLTA1 OFF3-target | AGUCCUCA(2sU)CUCCCUCAAGCGUUUAAGAGCUAUGCUGUUUUGAUGGU (SEQ ID NO: 40) + GGAACCAUUCAAAACAGCAUAGCAAGUUUAAAUAAGCUAGUCCGUUAUCA CCCAAAAC (SEQ ID NO: 26) | 56 + 86 |
| 31 | CLTA1_2thioU + 9 crRNA + tracrRNA | CLTA1 OFF3-target | AGUCCUCA(2sU)CUCCCUCAAGCGUUUAAGAGCUAUGCUGUUUUGAUGGU (SEQ ID NO: 40) + ACUUGUAAAAGUGGCACCGAGUCGGUGCUUUUUU (SEQ ID NO: 26) | 56 + 86 |
| 32 | CLTA1_2thioU + 11 crRNA + tracrRNA | CLTA1 ON1-target | AGUCCUCAUC(2sU)CCCUCAAGCGUUUAAGAGCUAUGCUGUUUUGAAUGGU (SEQ ID NO: 41) + GGAACCAUUCAAAACAGCAAGCAUAGCAAGUUUAAAUAAGCUAGUCCGUUAUCA CCCAAAAC (SEQ ID NO: 26) | 56 + 86 |
| 33 | CLTA1_2thioU + 11 crRNA + tracrRNA | CLTA1 ON1-target | AGUCCUCAUC(2sU)CCCUCAAGCCU UUAAGAGCUAUGCUGUUUUGAAUGGU (SEQ ID NO: 41) + ACUUGUAAAAGUGGCACCGAGUCGGUGCUUUUUU (SEQ ID NO: 26) | 56 + 86 |
| 34 | CLTA1_2thioU + 11 crRNA + tracrRNA | CLTA1 OFF1-target | AGUCCUCAUC(2sU)CCCUCAAGCCAUAGCAAGUUUAAAUAAGCUAGUCCGUUAUCA (SEQ ID NO: 41) + GGAACCAUUCAAAACAGCAAGCAUAGCAAGUUUAAAUAAGCUAGUCCGUUAUCA CCCAAAAC (SEQ ID NO: 26) | 56 + 86 |
| 35 | CLTA1_2thioU + 11 crRNA + tracrRNA | CLTA1 OFF1-target | AGUCCUCAUC(2sU)CCCUCAAGCCU UUAAGAGCUAUGCUGUUUUGAAUGGU (SEQ ID NO: 41) + ACUUGUAAAAGUGGCACCGAGUCGGUGCUUUUUU (SEQ ID NO: 26) | 56 + 86 |
| 36 | CLTA1_2thioU + 11 crRNA + tracrRNA | CLTA1 OFF2-target | AGUCCUCAUC(2sU)CCCUCAAGCGUUUAAGAGCUAUGCUGUUUUGAAUGGU (SEQ ID NO: 41) + GGAACCAUUCAAAACAGCAAGCAUAGCAAGUUUAAAUAAGCUAGUCCGUUAUCA CCCAAAAC (SEQ ID NO: 26) | 56 + 86 |
| 37 | CLTA1_2thioU + 11 crRNA + tracrRNA | CLTA1 OFF2-target | AGUCCUCAUC(2sU)CCCUCAAGCGUUUAAGAGCUAUGCUGUUUUGAAUGGU (SEQ ID NO: 41) + ACUUGUAAAAGUGGCACCGAGUCGGUGCUUUUUU (SEQ ID NO: 26) | 56 + 86 |
| 38 | CLTA1_2thioU + 11 crRNA + tracrRNA | CLTA1 OFF3-target | AGUCCUCAUC(2sU)CCCUCAAGCGUUUAAGAGCUAUGCUGUUUUGAAUGGU (SEQ ID NO: 41) + GGAACCAUUCAAAACAGCAAGCAUAGCAAGUUUAAAUAAGCUAGUCCGUUAUCA CCCAAAAC (SEQ ID NO: 26) | 56 + 86 |
| 39 | CLTA1_2thioU + 11 crRNA + tracrRNA | CLTA1 OFF3-target | AGUCCUCAUC(2sU)CCCUCAAGCGUUUAAGAGCUAUGCUGUUUUGAAUGGU (SEQ ID NO: 41) + ACUUGUAAAAGUGGCACCGAGUCGGUGCUUUUUU (SEQ ID NO: 26) | 56 + 86 |

Single-guide scaffold
Unmodified single-guide RNA (sgRNA)

| Entry # | Guide RNA Construct | Target DNA Construct | RNA sequence (5'→3') | RNA length |
|---|---|---|---|---|
| 40 | CLTA1 sgRNA (Batch #1) | CLTA1 ON1-target | AGUCCUCUCCCUCAAGCGUUUAAGCUGUUUAACAGCAUAGCA AGUUUAAAUAAGGCUAGUCCGUUAUCAACUUGAAAAAGUGGCACCGAGUC GGUGCUUUUUU (SEQ ID NO: 42) | 113 |
| 41 | CLTA1 sgRNA (Batch #1) | CLTA1 ON1-target | AGUCCUCAUCUCCCUCAAGCGUUUAUCAACGUUUAAGAGCUAUGCA AGUUUAAAUAAGGCUAGUCCGUUAUCAACUUGAAAAAGUGGCACCGAGUC GGUGCUUUUUU (SEQ ID NO: 42) | 113 |

TABLE 3-continued

| Entry # | Guide RNA Construct | Target DNA Construct | RNA sequence (5'→3') | RNA length |
|---|---|---|---|---|
| 42 | CLTA1 sgRNA (Batch #2) | CLTA1 ON1-target | AGUCCUCAUCUCCCUCAAGCGUUUAAGAGCUAUGCUGUUUAACAGCAUAGCAAGUUAAAUAAGGCUAGUCCGUUAUCAACUUGAAAAAGUGGCACCGAGUCGGUGCUUUUUU (SEQ ID NO: 42) | 113 |
| 43 | CLTA1 sgRNA (Batch #2) | CLTA1 ON1-target | AGUCCUCAUCUCCCUCAAGCGUUUAAGAGCUAUGCUGUUUAACAGCAUAGCAAGUUAAAUAAGGCUAGUCCGUUAUCAACUUGAAAAAGUGGCACCGAGUCGGUGCUUUUUU (SEQ ID NO: 42) | 113 |
| 44 | CLTA1 sgRNA (Batch #3) | CLTA1 ON1-target | AGUCCUCAUCUCCCUCAAGCGUUUAAGAGCUAUGCUGUUUAACAGCAUAGCAAGUUAAAUAAGGCUAGUCCGUUAUCAACUUGAAAAAGUGGCACCGAGUCGGUGCUUUUUU (SEQ ID NO: 42) | 113 |
| 45 | CLTA1 sgRNA (Batch #3) | CLTA1 ON1-target | AGUCCUCAUCUCCCUCAAGCGUUUAAGAGCUAUGCUGUUUAACAGCAUAGCAAGUUAAAUAAGGCUAGUCCGUUAUCAACUUGAAAAAGUGGCACCGAGUCGGUGCUUUUUU (SEQ ID NO: 42) | 113 |
| 46 | CLTA1 sgRNA (Batch #3) | CLTA1 ON1-target | AGUCCUCAUCUCCCUCAAGCGUUUAAGAGCUAUGCUGUUUAACAGCAUAGCAAGUUAAAUAAGGCUAGUCCGUUAUCAACUUGAAAAAGUGGCACCGAGUCGGUGCUUUUUU (SEQ ID NO: 42) | 113 |
| 47 | CLTA1 sgRNA (Batch #3) | CLTA1mg ON1-target | AGUCCUCAUCUCCCUCAAGCGUUUAAGAGCUAUGCUGUUUAACAGCAUAGCAAGUUAAAUAAGGCUAGUCCGUUAUCAACUUGAAAAAGUGGCACCGAGUCGGUGCUUUUUU (SEQ ID NO: 42) | 113 |
| 48 | CLTA1 sgRNA (Batch #3) | CLTA1mg ON1-target | AGUCCUCAUCUCCCUCAAGCGUUUAAGAGCUAUGCUGUUUAACAGCAUAGCAAGUUAAAUAAGGCUAGUCCGUUAUCAACUUGAAAAAGUGGCACCGAGUCGGUGCUUUUUU (SEQ ID NO: 42) | 113 |
| 49 | CLTA1 sgRNA (Batch #3) | CLTA1mg ON1-target | AGUCCUCAUCUCCCUCAAGCGUUUAAGAGCUAUGCUGUUUAACAGCAUAGCAAGUUAAAUAAGGCUAGUCCGUUAUCAACUUGAAAAAGUGGCACCGAGUCGGUGCUUUUUU (SEQ ID NO: 42) | 113 |
| 50 | CLTA1 sgRNA (Batch #3) | CLTA1mg OFF1-target | AGUCCUCAUCUCCCUCAAGCGUUUAAGAGCUAUGCUGUUUAACAGCAUAGCAAGUUAAAUAAGGCUAGUCCGUUAUCAACUUGAAAAAGUGGCACCGAGUCGGUGCUUUUUU (SEQ ID NO: 42) | 113 |
| 51 | CLTA1 sgRNA (Batch #3) | CLTA1mg OFF3-target | AGUCCUCAUCUCCCUCAAGCGUUUAAGAGCUAUGCUGUUUAACAGCAUAGCAAGUUAAAUAAGGCUAGUCCGUUAUCAACUUGAAAAAGUGGCACCGAGUCGGUGCUUUUUU (SEQ ID NO: 42) | 113 |
| 52 | CLTA1 sgRNA (crude) | CLTA1 ON1-target | AGUCCUCAUCUCCCUCAAGCGUUUAAGAGCUAUGCUGUUUAACAGCAUAGCAAGUUAAAUAAGGCUAGUCCGUUAUCAACUUGAAAAAGUGGCACCGAGUCGGUGCUUUUUU (SEQ ID NO: 42) | 113 |
| 53 | CLTA1_Bos sgRNA | CLTA1mg ON1-target | AGUCCUCAUCUCCCUCAAGCGUUAUAGAGCUAGUAAAGCAAGUUAAAAUAAGGCUAGUCCGUUAUCAACUUGAAAUAGUGGCACCGAGUCGGUGCUUUU (SEQ ID NO: 43) | 100 |
| 54 | CLTA1_Bos sgRNA | CLTA1mg ON1-target | AGUCCUCAUCUCCCUCAAGCGUUAUAGAGCUAGUAAAGCAAGUUAAAAUAAGGCUAGUCCGUUAUCAACUUGAAAUAGUGGCACCGAGUCGGUGCUUUU (SEQ ID NO: 43) | 100 |
| 55 | CLTA1_Bos sgRNA | CLTA1mg ON1-target | AGUCCUCAUCUCCCUCAAGCGUUAUAGAGCUAGUAAAGCAAGUUAAAAUAAGGCUAGUCCGUUAUCAACUUGAAAUAGUGGCACCGAGUCGGUGCUUUU (SEQ ID NO: 43) | 100 |
| 56 | CLTA1_Bos sgRNA | CLTA1mg OFF1-target | AGUCCUCAUCUCCCUCAAGCGUUAUAGAGCUAGUAAAGCAAGUUAAAAUAAGGCUAGUCCGUUAUCAACUUGAAAUAGUGGCACCGAGUCGGUGCUUUU (SEQ ID NO: 43) | 100 |
| 57 | CLTA1_Bos sgRNA | CLTA1mg OFF3-target | AGUCCUCAUCUCCCUCAAGCGUUAUAGAGCUAGUAAAGCAAGUUAAAAUAAGGCUAGUCCGUUAUCAACUUGAAAUAGUGGCACCGAGUCGGUGCUUUU (SEQ ID NO: 43) | 100 |

TABLE 3-continued

| Entry # | Guide RNA Construct | Target DNA Construct | RNA sequence (5'→3') | RNA length |
|---|---|---|---|---|
| 58 | CLTA4 sgRNA | CLTA4 ON-target | GCAGAUGUAGUGUUUCCACAGUUUAAGAGCUAUGCUGGAAACAGCAUAGCAAGUUUAAAUAAGGCUAGUCCGUUAUCAACUUGAAAAAGUGGCACCGAGUCGGUGCUUUUUU (SEQ ID NO: 44) | 113 |
| 59 | CLTA4 sgRNA | CLTA4 ON-target | GCAGAUGUAGUGUUUCCACAGUUUAAGAGCUAUGCUGGAAACAGCAUAGCAAGUUUAAAUAAGGCUAGUCCGUUAUCAACUUGAAAAAGUGGCACCGAGUCGGUGCUUUUUU (SEQ ID NO: 44) | 113 |
| 60 | CLTA4 sgRNA | CLTA4 ON-target | GCAGAUGUAGUGUUUCCACAGUUUAAGAGCUAUGCUGGAAACAGCAUAGCAAGUUUAAAUAAGGCUAGUCCGUUAUCAACUUGAAAAAGUGGCACCGAGUCGGUGCUUUUUU (SEQ ID NO: 44) | 113 |
| 61 | CLTA4 sgRNA | CLTA4mg ON-target | GCAGAUGUAGUGUUUCCACAGUUUAAGAGCUAUGCUGGAAACAGCAUAGCAAGUUUAAAUAAGGCUAGUCCGUUAUCAACUUGAAAAAGUGGCACCGAGUCGGUGCUUUUUU (SEQ ID NO: 44) | 113 |
| 62 | CLTA4 sgRNA | CLTA4mg ON-target | GCAGAUGUAGUGUUUCCACAGUUUAAGAGCUAUGCUGGAAACAGCAUAGCAAGUUUAAAUAAGGCUAGUCCGUUAUCAACUUGAAAAAGUGGCACCGAGUCGGUGCUUUUUU (SEQ ID NO: 44) | 113 |
| 63 | CLTA4 sgRNA | CLTA4mg OFF5-target | GCAGAUGUAGUGUUUCCACAGUUUAAGAGCUAUGCUGGAAACAGCAUAGCAAGUUUAAAUAAGGCUAGUCCGUUAUCAACUUGAAAAAGUGGCACCGAGUCGGUGCUUUUUU (SEQ ID NO: 44) | 113 |
| 64 | CLTA1_Truncated_18 mer | CLTA1mg ON-target | UCCUCAUCUCCCAAGCGUUUAAGAGCUAUGCUGGUAACAGCAUAGCAAGUUUAAAUAAGGCUAGUCCGUUAUCAACUUGAAAAAGUGGCACCGAGUCGGUGCUUUUUU (SEQ ID NO: 45) | 111 |
| 65 | CLTA1_Truncated_18 mer | CLTA1mg ON-target | UCCUCAUCUCCCAAGCGUUUAAGAGCUAUGCUGGUAACAGCAUAGCAAGUUUAAAUAAGGCUAGUCCGUUAUCAACUUGAAAAAGUGGCACCGAGUCGGUGCUUUUUU (SEQ ID NO: 45) | 111 |
| 66 | CLTA1_Truncated_18 mer | CLTA1mg OFF1-target | UCCUCAUCUCCCAAGCGUUUAAGAGCUAUGCUGGUAACAGCAUAGCAAGUUUAAAUAAGGCUAGUCCGUUAUCAACUUGAAAAAGUGGCACCGAGUCGGUGCUUUUUU (SEQ ID NO: 45) | 111 |
| 67 | CLTA1_Truncated_18 mer | CLTA1mg OFF3-target | UCCUCAUCUCCCAAGCGUUUAAGAGCUAUGCUGGUAACAGCAUAGCAAGUUUAAAUAAGGCUAGUCCGUUAUCAACUUGAAAAAGUGGCACCGAGUCGGUGCUUUUUU (SEQ ID NO: 45) | 110 |
| 68 | CLTA1_Truncated_17 mer | CLTA1mg ON-target | CCUCAUCUCCCAAGCGUUUAAGAGCUAUGCUGGUAACAGCAUAGCAAGUUUAAAUAAGGCUAGUCCGUUAUCAACUUGAAAAAGUGGCACCGAGUCGGUGCUUUUUU (SEQ ID NO: 46) | 110 |
| 69 | CLTA1_Truncated_17 mer | CLTA1mg ON-target | CCUCAUCUCCCAAGCGUUUAAGAGCUAUGCUGGUAACAGCAUAGCAAGUUUAAAUAAGGCUAGUCCGUUAUCAACUUGAAAAAGUGGCACCGAGUCGGUGCUUUUUU (SEQ ID NO: 46) | 110 |
| 70 | CLTA1_Truncated_17 mer | CLTA1mg OFF1-target | CCUCAUCUCCCAAGCGUUUAAGAGCUAUGCUGGUAACAGCAUAGCAAGUUUAAAUAAGGCUAGUCCGUUAUCAACUUGAAAAAGUGGCACCGAGUCGGUGCUUUUUU (SEQ ID NO: 46) | 110 |
| 71 | CLTA1_Truncated_17 mer | CLTA1mg OFF3-target | CCUCAUCUCCCAAGCGUUUAAGAGCUAUGCUGGUAACAGCAUAGCAAGUUUAAAUAAGGCUAGUCCGUUAUCAACUUGAAAAAGUGGCACCGAGUCGGUGCUUUUUU (SEQ ID NO: 46) | 110 |
| 72 | CLTA1_1xExtraG | CLTA1mg ON-target | GAGUCCCAUCUCCCUCAAGCGUUUAAGAGCUAUGCUGGUAACAGCAUAGCAAGUUUAAAUAAGGCUAGUCCGUUAUCAACUUGAAAAAGUGGCACCGAGUCGGUGCUUUUUU (SEQ ID NO: 47) | 114 |
| 73 | CLTA1_1xExtraG | CLTA1mg ON-target | GAGUCCCAUCUCCCUCAAGCGUUUAAGAGCUAUGCUGGUAACAGCAUAGCAAGUUUAAAUAAGGCUAGUCCGUUAUCAACUUGAAAAAGUGGCACCGAGUCGGUGCUUUUUU (SEQ ID NO: 47) | 114 |

TABLE 3-continued

| Entry # | Guide RNA Construct | Target DNA Construct | RNA sequence (5'→3') | RNA length |
|---|---|---|---|---|
| 74 | CLTA1_1xExtraG | CLTA1mg OFF1-target | GAGUCCUCAUCUCCCUCAAGCGUUUAAGAGCUAUGCUGGUAACAGCAUAGC AAGUUAAAAUAAGGCUAGUCCGUUAUCAACUUGAAAAAGUGGCACCGAGU CGGUGCUUUUUU (SEQ ID NO: 47) | 114 |
| 75 | CLTA1_1xExtraG | CLTA1mg OFF3-target | GAGUCCUCAUCUCCCUCAAGCGUUUAAGAGCUAUGCUGGUAACAGCAUAGC AAGUUAAAAUAAGGCUAGUCCGUUAUCAACUUGAAAAAGUGGCACCGAGU CGGUGCUUUUUU (SEQ ID NO: 47) | 114 |
| 76 | CLTA1_2xExtraG | CLTA1mg ON1-target | GGAGUCCUCAUCUCCCUCAAGCGUUUAAGAGCUAUGCUGGUAACAGCAUAG CAAGUUAAAAUAAGGCUAGUCCGUUAUCAACUUGAAAAAGUGGCACCGAG UCGGUGCUUUUUU (SEQ ID NO: 48) | 115 |
| 77 | CLTA1_2xExtraG | CLTA1mg ON1-target | GGAGUCCUCAUCUCCCUCAAGCGUUUAAGAGCUAUGCUGGUAACAGCAUAG CAAGUUAAAAUAAGGCUAGUCCGUUAUCAACUUGAAAAAGUGGCACCGAG UCGGUGCUUUUUU (SEQ ID NO: 48) | 115 |
| 78 | CLTA1_2xExtraG | CLTA1mg OFF1-target | GGAGUCCUCAUCUCCCUCAAGCGUUUAAGAGCUAUGCUGGUAACAGCAUAG CAAGUUAAAAUAAGGCUAGUCCGUUAUCAACUUGAAAAAGUGGCACCGAG UCGGUGCUUUUUU (SEQ ID NO: 48) | 115 |
| 79 | CLTA1_2xExtraG | CLTA1mg OFF3-target | GGAGUCCUCAUCUCCCUCAAGCGUUUAAGAGCUAUGCUGGUAACAGCAUAG CAAGUUAAAAUAAGGCUAGUCCGUUAUCAACUUGAAAAAGUGGCACCGAG UCGGUGCUUUUUU (SEQ ID NO: 48) | 115 |
| 80 | CLTA1_63U, 64U | CLTA1mg ON1-target | AGUCCUCAUCUCCCUCAAGCGUUUAAGAGCUGGUAACAGCAGCAUAGCA AGUUAAAAUUCUAGUCCGUUAUCAACUUGAAAAAGUGGCACCGAGUC GGUGCUUUUUU (SEQ ID NO: 49) | 113 |
| 81 | CLTA163A, 64A | CLTA1mg ON1-target | AGUCCUCAUCUCCCUCAAGCGUUUAAGAGCUAUGCUGGUAACAGCAGCAUAGCA AGUUAAAAUAAGGCUAGUCCGUUAUCAACUUGAAAAAGUGGCACCGAGUC GGUGCUUUUUU (SEQ ID NO: 50) | 113 |
| 82 | CLTA1_63A, 64A, 70U, 71U | CLTA1mg ON1-target | AGUCCUCAUCUCCCUCAAGCGUUUAAGAGCUAUGCUGGUAACAGCAGCAUAGCA AGUUAAAAUAAGGCUAGUUGUAUCAACUUGAAAAAGUGGCACCGAGUC GGUGCUUUUUU (SEQ ID NO: 51) | 113 |
| 83 | CLTA1_cis-block(1-5)_polyU_sgRNA | CLTA1mg ON1-target | GGACUUUUUUAGUCCUCAUCUCCCUCAAGCGUUUUAGAGCUAGAAAUAG CAAGUUAAAAUAAGGCUAGUCCGUUAUCAACUUGAAAAAGUGGCACCGAG UCGGUGCUUU (SEQ ID NO: 52) | 111 |
| 84 | CLTA1_cis-block(1-5)_polyU_sgRNA | CLTA1mg ON1-target | GGACUUUUUUAGUCCUCAUCUCCCUCAAGCGUUUUAGAGCUAGAAAUAG CAAGUUAAAAUAAGGCUAGUCCGUUAUCAACUUGAAAAAGUGGCACCGAG UCGGUGCUUU (SEQ ID NO: 52) | 111 |
| 85 | CLTA1_cis-block(1-5)_polyU_sgRNA | CLTA1mg ON1-target | GGACUUUUUUAGUCCUCAUCUCCCUCAAGCGUUUUAGAGCUAGAAAUAG CAAGUUAAAAUAAGGCUAGUCCGUUAUCAACUUGAAAAAGUGGCACCGAG UCGGUGCUUU (SEQ ID NO: 52) | 111 |
| 86 | CLTA1_cis-block(1-5)_polyU_sgRNA | CLTA1mg OFF3-target | GGACUUUUUUAGUCCUCAUCUCCCUCAAGCGUUUUAGAGCUAGAAAUAG CAAGUUAAAAUAAGGCUAGUCCGUUAUCAACUUGAAAAAGUGGCACCGAG UCGGUGCUUU (SEQ ID NO: 52) | 111 |
| 87 | CLTA1_cis-block(1-10)_polyU_sgRNA | CLTA1mg ON1-target | GAUGAGGACUUUUUUUAGUCCUCAUCCCCUCAAGCGUUUUAGAGCUAGA AAUAGCAAGUUAAAAUAAGGCUAGUCCGUUAUCAACUUGAAAAAGUGGCA CCGAGUCGGUGCUUUU (SEQ ID NO: 53) | 116 |
| 88 | CLTA1_cis-block(1-10)_polyU_sgRNA | CLTA1mg ON1-target | GAUGAGGACUUUUUUUAGUCCUCAUCUCCCUCAAGCGUUAUCUAGAGUGGCA AAUAGCAAGUAAAAUAAGGCUAGUCCGUUAUCAACUGAAAAAGUGGCA CCGAGUCGGUGCUUUU (SEQ ID NO: 53) | 116 |
| 89 | CLTA1_cis-block(1-10)_polyU_sgRNA | CLTA1mg OFF1-target | GAUGAGGACUUUUUUUAGUCCUCAUCUCCCUCAAGCGUUAUCUAGAGUGGCA AAUAGCAAGUAAAAUAAGGCUAGUCCGUUAUCAACUGAAAAAGUGGCA CCGAGUCGGUGCUUUU (SEQ ID NO: 53) | 116 |

TABLE 3-continued

| Entry # | Guide RNA Construct | Target DNA Construct | RNA sequence (5'→3') | RNA length |
|---|---|---|---|---|
| 90 | CLTA1_cis-block(1-10)_polyU_sgRNA | CLTA1mg OFF3-target | GAUGAGGACUUUUUAGUCCUCAUCCCUCAAGCGUUUUAGAGCUAGA AAUAGCAAGUUAAAUAAGGCUAGUCCGUUAUCAACUUGAAAAAGUGGCA CCGAGUCGUGCUUUU (SEQ ID NO: 53) | 116 |
| 91 | CLTA1_cis-block(16-20)_polyU_sgRNA | CLTA1mg ON1-target | GCUUGUUUUAGUCCUCAUCCCUCAAGCGUUUUAGAGCUAGAAAUAG CAAGUUAAAUAAGGCUAGUCCGUUAUCAACUUGAAAAAGUGGCACCGAG UCGUGCUUUU (SEQ ID NO: 54) | 111 |
| 92 | CLTA1_cis-block(16-20)_polyU_sgRNA | CLTA1mg ON1-target | GCUUGUUUUAGUCCUCAUCCCUCAAGCGUUUUAGAGCUAGAAAUAG CAAGUUAAAUAAGGCUAGUCCGUUAUCAACUUGAAAAAGUGGCACCGAG UCGUGCUUUU (SEQ ID NO: 54) | 111 |
| 93 | CLTA1_cis-block(16-20)_polyU_sgRNA | CLTA1mg OFF1-target | GCUUGUUUUAGUCCUCAUCCCUCAAGCGUUUUAGAGCUAGAAAUAG CAAGUUAAAUAAGGCUAGUCCGUUAUCAACUUGAAAAAGUGGCACCGAG UCGUGCUUUU (SEQ ID NO: 54) | 111 |
| 94 | CLTA1_cis-block(16-20)_polyU_sgRNA | CLTA1mg OFF3-target | GCUUGUUUUAGUCCUCAUCCCUCAAGCGUUUUAGAGCUAGAAAUAG CAAGUUAAAUAAGGCUAGUCCGUUAUCAACUUGAAAAAGUGGCACCGAG UCGUGCUUUU (SEQ ID NO: 54) | 111 |

DMT-modified sgRNA

| 95 | CLTA1_DMT-ON sgRNA | CLTA1 ON1-target | (dmt)AGUCCUCAUCUCCCUCAAGCGUUUAAGAGCUAUGCUGGAAACAGCAU AGCAGUUUAAAAUAAGGCUAGUCCGUAUAUCAACUUGAAAAAGUGGCACCG AGUCGGUGCUUUUU (SEQ ID NO: 55) | 113 |
| 96 | CLTA1_DMT-ON/OFF sgRNA | CLTA1 ON1-target | AGUCCUCAUCUCCCUCAAGCGUUUAAGAGCUAUGCUGGUAACAGCA AGUUUAAAAUAAGGCUAGUCCGUAUCAACUUGAAAAAGUGGCACCGAGUC GGUGCUUUUUU (SEQ ID NO: 56) | 113 |

Fluorophore-modified sgRNA

| 97 | CLTA1_IntFl_sgLoop | CLTA1 ON1-target | AGUCCUCAUCUCCCUCAAGCGUUUAAGAGCUAUGCUGG(F1)AACAGCAUAGC AAGUUAAAUAAGGCUAGUCCGUAUCAACUUGAAAAAGUGGCACCGAGU CGGUGCUUUUUU (SEQ ID NO: 57) | 113 |
| 98 | CLTA1_IntFl_sgLoop | CLTA1mg ON1-target | AGUCCUCAUCUCCCUCAAGCGUUUAAGAGCUAUGCUGG(F1)AACAGCAUAGC AAGUUAAAUAAGGCUAGUCCGUAUCAACUUGAAAAAGUGGCACCGAGU CGGUGCUUUUUU (SEQ ID NO: 57) | 113 |
| 99 | CLTA1_IntFl_sgLoop | CLTA1mg ON1-target | AGUCCUCAUCUCCCUCAAGCGUUUAAGAGCUAUGCUGG(F1)AACAGCAUAGC AAGUUAAAUAAGGCUAGUCCGUAUCAACUUGAAAAAGUGGCACCGAGU CGGUGCUUUUUU (SEQ ID NO: 57) | 113 |
| 100 | CLTA1_IntFl_sgLoop | CLTA1mg OFF1-target | AGUCCUCAUCUCCCUCAAGCGUUUAAGAGCUAUGCUGG(F1)AACAGCAUAGC AAGUUAAAUAAGGCUAGUCCGUAUCAACUUGAAAAAGUGGCACCGAGU CGGUGCUUUUUU (SEQ ID NO: 57) | 113 |
| 101 | CLTA1_IntFl_sgLoop | CLTA1mg OFF3-target | AGUCCUCAUCUCCCUCAAGCGUUUAAGAGCUAUGCUGG(F1)AACAGCAUAGC AAGUUAAAUAAGGCUAGUCCGUAUCAACUUGAAAAAGUGGCACCGAGU CGGUGCUUUUUU (SEQ ID NO: 57) | 113 |
| 102 | CLTA1_IntFl_sgLoop_5', 3x(2'OMe) | CLTA1mg ON1-target | <u>AGU</u>CCUCAUCUCCCUCAAGCGUUUAAGAGCUAUGCUGG(F1)AACAGCAUAGC AAGUUAAAUAAGGCUAGUCCGUAUCAACUUGAAAAAGUGGGCACCGAGU CGGUGCUUUU<u>UUU</u> (SEQ ID NO: 58) | 113 |
| 103 | CLTA1_IntFl_sgLoop_5', 3x(2'OMe) | CLTA1mg ON1-target | <u>AGU</u>CCUCAUCUCCCUCAAGCGUUUAAGAGCUAUGCUGG(F1)AACAGCAUAGC AAGUUAAAUAAGGCUAGUCCGUAUCAACUUGAAAAAGUGGGCACCGAGU CGGUGCUUUU<u>UUU</u> (SEQ ID NO: 58) | 113 |

TABLE 3-continued

| Entry # | Guide RNA Construct | Target DNA Construct | RNA sequence (5'→3') | RNA length |
|---|---|---|---|---|
| 104 | CLTA1_IntF1_sgLoop_5', 3x(2'OMe) | CLTA1mg OFF1-target | AGUCCUCAUCUCCCUCAAGCGUUUAAGAGCUAUGCUGG(F1)AACAGCAUA AGUUUAAAUAAGGCUAGUCCGUUAUCAACUUGAAAAAGUGGCACCGAG CGGUGCUUUUUU (SEQ ID NO: 58) | 113 |
| 105 | CLTA1_IntF1_sgLoop_5', 3x(2'OMe) | CLTA1mg OFF3-target | AGUCCUCAUCUCCCUCAAGCGUUUAAGAGCUAUGCUGG(F1)AACAGCAUAGC AAGUUUAAAUAAGGCUAGUCCGUUAUCAACUUGAAAAAGUGGCACCGAGU CGGUGCUUUUUU (SEQ ID NO: 58) | 113 |
| 106 | CLTA1_IntF1_sgLoop_5', 3x(2'OMe) | CLTA1mg ON1-target | AsGsUsCCCUCAUCUCCCCUCAAGCGUUUAAGAGCUAUGCUUGG(F1)AACAGCAUA GCAAGUUUAAAUAAGGCUAGUCCGUUAUCAACUUGAAAAAGUGGCACCGA GUCCGUGCUUUUUsUsUsU (SEQ ID NO: 59) | 113 |
| 107 | CLTA1_IntF1_sgLoop_5', 3x(2'OMe), 3'P(S) | CLTA1mg ON1-target | AsGsUsCCCUCAUCUCCCCUCAAGCGUUUAAGAGCUAUGCUGG(F1)AACAGCAUA GCAAGUUUAAAUAAGGCUAGUCCGUUAUCAACUUGAAAAAGUGGCACCGA GUCCGUGCUUUUUsUsUsU (SEQ ID NO: 59) | 113 |
| 108 | CLTA1_IntF1_sgLoop_5', 3x(2'OMe), 3'P(S) | CLTA1mg OFF1-target | AsGsUsCCCUCAUCUCCCCUCAAGCGUUUAAGAGCUAUGCUGG(F1)AACAGCAUA GCAAGUUUAAAUAAGGCUAGUCCGUUAUCAACUUGAAAAAGUGGCACCGA GUCCGUGCUUUUUsUsUsU (SEQ ID NO: 59) | 113 |
| 109 | CLTA1_IntF1_sgLoop_5', 3x(2'OMe), 3'P(S) | CLTA1mg OFF3-target | AsGsUsCCCUCAUCUCCCCUCAAGCGUUUAAGAGCUAUGCUGG(F1)AACAGCAUA GCAAGUUUAAAUAAGGCUAGUCCGUUAUCAACUUGAAAAAGUGGCACCGA GUCCGUGCUUUUUsUsUsU (SEQ ID NO: 59) | 113 |
| 110 | CLTA1_IntF1_sgLoop_5', 3x(2'OMe), 3'thioPACE | CLTA1mg ON1-target | A*sg*sU*sCCCAUCUCCCUCAAGCGUUUAAGAGCUAUGCUGG(F1)AACAGC AUAGCAAGUUUAAAUAAGGCUAGUCCGUUAUCAACUUGAAAAAGUGGCAC CGAGUCGGUGCUUUU*sU*sU*sU (SEQ ID NO: 60) | 113 |
| 111 | CLTA1_IntF1_sgLoop_5', 3x(2'OMe), 3'thioPACE | CLTA1mg OFF1-target | A*sG*sU*sCCCUCAUCUCCCUCAAGCGUUUAAGAGCUAUGCUGG(F1)AACAGC AUAGCAAGUUUAAAUAAGGCUAGUCCGUUAUCAACUUGAAAAAGUGGCAC CGAGUCGGUGCUUUU*sU*sU*sU (SEQ ID NO: 60) | 113 |
| 112 | CLTA1_IntF1_sgLoop_5', 3x(2'OMe), 3'thioPACE | CLTA1mg ON1-target | A*sG*sU*sCCCUCAUCUCCCUCAAGCGUUUAAGAGCUAUGCUGG(F1)AACAGC AUAGCAAGUUUAAAUAAGGCUAGUCCGUUAUCAACUUGAAAAAGUGGCAC CGAGUCGGUGCUUUU*sU*sU*sU (SEQ ID NO: 60) | 113 |
| 113 | CLTA1_IntF1_sgLoop_5', 3x(2'OMe), 3'thioPACE | CLTA1mg OFF3-target | A*sG*sU*sCCCUCAUCUCCCUCAAGCGUUUAAGAGCUAUGCUGG(F1)AACAGC AUAGCAAGUUUAAAUAAGGCUAGUCCGUUAUCAACUUGAAAAAGUGGCAC CGAGUCGGUGCUUUU*sU*sU*sU (SEQ ID NO: 60) | 113 |
| 114 | CLTA4_3xF1-Int_3x(2'OMe), 3'thioPACE | CLTA4mg ON-target | Uo*s(F1o)GCAGAUGUAGUGUCCGGUUA(F1)CAACUUGAAAAAGUGGCACCGAGUCGG UGCU(F1)U*sU (SEQ ID NO: 61) | 102 |
| 115 | CLTA4_3xF1-Int_3x(2'OMe), 3'thioPACE | CLTA4mg OFF5-target | Uo*s(F1o)GCAGAUGUAGUGUCCGGUUCCACAGUUGAAGAGCUAG(F1)CAACUUGAAAAAGUGGCACCGAGUCGG UGCU(F1)U*sU (SEQ ID NO: 61) | 102 |
| 116 | CLTA4_3xF1-Loops_3x(2'OMe), 3'thioPACE | CLTA4mg ON-target | G*sGssCAGAUGUAGUGUCCACAGUUAaGAGCUAG(F1)AAUAGCAAGUUuAA AUAAGGCUAGUCCGUUAUCAACUUG(F1)AAAAGUGGCACCGAG(F1)AAUAGCAAGUUuAA UUU*sU (SEQ ID NO: 62) | 100 |
| 117 | CLTA4_3xF1-Loops_3x(2'OMe), 3'thioPACE | CLTA4mg OFF5-target | G*sGssCAGAUGUAGUGUCCACAGUUAaGAGCUAG(F1)AAUAGCAAGUUuAA AUAAGGCUAGUCCGUUAUCAACUUG(F1)AAAAGUGGCACCGAG(F1)AAUAGCAAGUUuAA UUU*sU (SEQ ID NO: 62) | 100 |

3'Phosphorothioate-modified sgRNA

| Entry # | Guide RNA Construct | Target DNA Construct | RNA sequence (5'→3') | RNA length |
|---|---|---|---|---|
| 118 | CLTA1_5'-2xP(S) sgRNA | CLTA1 ON1-target | AsGsUCCCUCAUCUCCCUCAAGCGUUUAAGAGCUAUGCUGGAAACAGCAUAGC AAGUUUAAAUAAGGCUAGUCCGUUAUCAACUUGAAAAGUGGCACCGAGU CGGUGCUUUUUU (SEQ ID NO: 63) | 113 |

TABLE 3-continued

| Entry # | Guide RNA Construct | Target DNA Construct | RNA sequence (5'→3') | RNA length |
|---|---|---|---|---|
| 119 | CLTA1_5'-3xP(S) sgRNA | CLTA1 ON1-target | AsGsUsCCUCAUCUCCCUCAAGCGUUUAAGAGCUAUGCUGGAAACAGCAUAGCAAGUUUAAAUAAGGCUAGUCCGUUAUCAACUUGAAAAAGUGGCACCGAGUCGUGCUUUUUUU (SEQ ID NO: 64) | 113 |
| 120 | CLTA1_5'-4xP(S) sgRNA | CLTA1 ON1-target | AsGsUsCsCUCAUCUCCCUCAAGCGUUUAAGAGCUAUGCUGGAAACAGCAUAGCAAGUUUAAAUAAGGCUAGUCCGUUAUCAACUUGAAAAAGUGGCACCGAGUCGUGCUUUUUUU (SEQ ID NO: 65) | 113 |
| 121 | CLTA1_3'-4xP(S) sgRNA | CLTA1 ON1-target | AGUCCUCAUCUCCCUCAAGCGUUUAAGAGCUAUGCUGGAAACAGCAUAGCAAGUUUAAAUAAGGCUAGUCCGUUAUCAACUUGAAAAAGUGGCACCGAGUCGGUGCUUUsUsUsU (SEQ ID NO: 66) | 113 |

2'Omethyl-modified sgRNA

| Entry # | Guide RNA Construct | Target DNA Construct | RNA sequence (5'→3') | RNA length |
|---|---|---|---|---|
| 122 | CLTA1_2'OMe + 20 sgRNA | CLTA1 ON1-target | AGUCCUCAUCUCCCUCAAGCGUUUAAGAGCUAUGCUGGUAACAGCAUAGCAAGUUUAAAUAAGGCUAGUCCGUUAUCAACUUGAAAAAGUGGCACCGAGUCGGUGCUUUUUUU (SEQ ID NO: 67) | 113 |
| 123 | CLTA1_2'OMe + 19 sgRNA | CLTA1 ON1-target | AGUCCUCAUCUCCCUCAAGCGUUUAAGAGCUAUGCUGGUAACAGCAUAGCAAGUUUAAAUAAGGCUAGUCCGUUAUCAACUUGAAAAAGUGGCACCGAGUCGGUGCUUUUUUU (SEQ ID NO: 68) | 113 |
| 124 | CLTA1_2'OMe + 19 sgRNA | CLTA1mg ON1-target | AGUCCUCAUCUCCCUCAAGCGUUUAAGAGCUAUGCUGGUAACAGCAUAGCAAGUUUAAAUAAGGCUAGUCCGUUAUCAGCUUGAAAAAGUGGCACCGAGUCGGUGCUUUUUUU (SEQ ID NO: 68) | 113 |
| 125 | CLTA1_2'OMe + 19 sgRNA | CLTA1mg OFF1-target | AGUCCUCAUCUCCCUCAAGCGUUUAAGAGCUAUGCUGGUAACAGCAUAGCAAGUUUAAAUAAGGCUAGUCCGUUAUCAGCUUGAAAAAGUGGCACCGAGUCGGUGCUUUUUUU (SEQ ID NO: 68) | 113 |
| 126 | CLTA1_2'OMe + 19 sgRNA | CLTA1mg OFF3-target | AGUCCUCAUCUCCCUCAAGCGUUUAAGAGCUAUGCUGGUAACAGCAUAGCAAGUUUAAAUAAGGCUAGUCCGUUAUCAGCUUGAAAAAGUGGCACCGAGUCGGUGCUUUUUUU (SEQ ID NO: 68) | 113 |
| 127 | CLTA1_2'OMe + 19 sgRNA | CLTA1 ON1-target | AGUCCUCAUCUCCCUCAAGCGUUUAAGAGCUAUGCUGGUAACAGCAUAGCAAGUUUAAAUAAGGCUAGUCCGUUAUCAACUUGAAAAAGUGGCACCGAGUCGGUGCUUUUUUU (SEQ ID NO: 68) | 113 |
| 128 | CLTA1_2'OMe + 18 sgRNA | CLTA1 ON1-target | AGUCCUCAUCUCCCUCAAGCGUUUAAGAGCUAUGCUGGUAACAGCAUAGCAAGUUUAAAUAAGGCUAGUCCGUUAUCAACUUGAAAAAGUGGCACCGAGUCGGUGCUUUUUUU (SEQ ID NO: 69) | 113 |
| 129 | CLTA1_2'OMe + 18 sgRNA | CLTA1mg ON1-target | AGUCCUCAUCUCCCUCAAGCGUUUAAGAGCUAUGCUGGUAACAGCAUAGCAAGUUUAAAUAAGGCUAGUCCGUUAUCAGCUUGAAAAAGUGGCACCGAGUCGGUGCUUUUUUU (SEQ ID NO: 69) | 113 |
| 130 | CLTA1_2'OMe + 18 sgRNA | CLTA1mg OFF1-target | AGUCCUCAUCUCCCUCAAGCGUUUAAGAGCUAUGCUGGUAACAGCAUAGCAAGUUUAAAUAAGGCUAGUCCGUUAUCAGCUUGAAAAAGUGGCACCGAGUCGGUGCUUUUUUU (SEQ ID NO: 69) | 113 |
| 131 | CLTA1_2'OMe + 18 sgRNA | CLTA1mg OFF1-target | AGUCCUCAUCUCCCUCAAGCGUUUAAGAGCUAUGCUGGUAACAGCAUAGCAAGUUUAAAUAAGGCUAGUCCGUUAUCAGCUUGAAAAAGUGGCACCGAGUCGGUGCUUUUUUU (SEQ ID NO: 69) | 113 |
| 132 | CLTA1_2'OMe + 18 sgRNA | CLTA1mg OFF3-target | AGUCCUCAUCUCCCUCAAGCGUUUAAGAGCUAUGCUGGUAACAGCAUAGCAAGUUUAAAUAAGGCUAGUCCGUUAUCAGCUUGAAAAAGUGGCACCGAGUCGGUGCUUUUUUU (SEQ ID NO: 69) | 113 |
| 133 | CLTA1_2'OMe + 17 sgRNA | CLTA1 ON1-target | AGUCCUCAUCUCCCUCAAGCGUUUAAGAGCUAUGCUGGUAACAGCAUAGCAAGUUUAAAUAAGGCUAGUCCGUUAUCAACUUGAAAAAGUGGCACCGAGUCGGUGCUUUUUUU (SEQ ID NO: 70) | 113 |

TABLE 3-continued

| Entry # | Guide RNA Construct | Target DNA Construct | RNA sequence (5'→3') | RNA length |
|---|---|---|---|---|
| 134 | CLTA1_2'OMe + 17 sgRNA | CLTA1mg ON1-target | AGUCCUCAUCUCCUCAAGCGUUUAAGAGCUAUGCUGGUAACAGCAUAGCA AGUUUAAAUAAGGCUAGUCCGUUAUCAACUGAAAAAGUGGCACCGAGUC GGUGCUUUUUU (SEQ ID NO: 70) | 113 |
| 135 | CLTA1_2'OMe + 17 sgRNA | CLTA1mg ON1-target | AGUCCUCAUCUCCUCAAGCGUUUAAGAGCUAUGCUGGUAACAGCAUAGCA AGUUUAAAUAAGGCUAGUCCGUUAUCAACUGAAAAAGUGGCACCGAGUC GGUGCUUUUUU (SEQ ID NO: 70) | 113 |
| 136 | CLTA1_2'OMe + 17 sgRNA | CLTA1mg OFF1-target | AGUCCUCAUCUCCUCAAGCGUUUAAGAGCUAUGCUGGUAACAGCAUAGCA AGUUUAAAUAAGGCUAGUCCGUUAUCAACUGAAAAAGUGGCACCGAGUC GGUGCUUUUUU (SEQ ID NO: 70) | 113 |
| 137 | CLTA1_2'OMe + 17 sgRNA | CLTA1mg OFF3-target | AGUCCUCAUCUCCUCAAGCGUUUAAGAGCUAUGCUGGUAACAGCAUAGCA AGUUUAAAUAAGGCUAGUCCGUUAUCAACUGAAAAAGUGGCACCGAGUC GGUGCUUUUUU (SEQ ID NO: 70) | 113 |
| 138 | CLTA1_2'OMe + 17,18 sgRNA | CLTA1 ON1-target | AGUCCUCAUCUCCUCAAGCGUUUAAGAGCUAUGCUGGUAACAGCAUAGCA AGUUUAAAUAAGGCUAGUCCGUUAUCAACUUGAAAAAGUGGCACCGAGUC GGUGCUUUUUU (SEQ ID NO: 71) | 113 |
| 139 | CLTA1_2'OMe + 17,18 sgRNA | CLTA1mg ON1-target | AGUCCUCAUCUCCUCAAGCGUUUAAGAGCUAUGCUGGUAACAGCAUAGCA AGUUUAAAUAAGGCUAGUCCGUUAUCAACUUGAAAAAGUGGCACCGAGUC GGUGCUUUUUU (SEQ ID NO: 71) | 113 |
| 140 | CLTA1_2'OMe + 17,18 sgRNA | CLTA1mg OFF1-target | AGUCCUCAUCUCCUCAAGCGUUUAAGAGCUAUGCUGGUAACAGCAUAGCA AGUUUAAAUAAGGCUAGUCCGUUAUCAACUUGAAAAAGUGGCACCGAGUC GGUGCUUUUUU (SEQ ID NO: 71) | 113 |
| 141 | CLTA1_2'OMe + 17,18 sgRNA | CLTA1mg OFF3-target | AGUCCUCAUCUCCUCAAGCGUUUAAGAGCUAUGCUGGUAACAGCAUAGCA AGUUUAAAUAAGGCUAGUCCGUUAUCAACUUGAAAAAGUGGCACCGAGUC GGUGCUUUUUU (SEQ ID NO: 71) | 113 |
| 142 | CLTA1_2'OMe + 17,18 sgRNA | CLTA1 ON1-target | AGUCCUCAUCUCCUCAAGCGUUUAAGAGCUAUGCUGGUAACAGCAUAGCA AGUUUAAAUAAGGCUAGUCCGUUAUCAACUUGAAAAAGUGGCACCGAGUC GGUGCUUUUUU (SEQ ID NO: 71) | 113 |
| 143 | CLTA1 5', 3'-3x(2'OMe) sgRNA | CLTA1 ON1-target | AGUCCUCAUCUCCUCAAGCGUUUAAGAGCUAUGCUGGUAACAGCAUAGC AGUUUAAAUAAGGCUAGUCCGUUAUCAACUGAAAAAGUGGCACCGAGUC GGUGCUUUUUU (SEQ ID NO: 72) | 113 |
| 144 | CLTA4 5', 3'-3x(2'OMe) sgRNA | CLTA4mg ON-target | GCAGAUGUAGUGUUUCCAGUUUAAGAGCUAUGCUGGAAACAGCAUAGC AGUUUAAAUAAGGCUAGUCCGUUAUCAACUUGAAAAAGUGGCACCGAGU CGGUGCUUUUUU (SEQ ID NO: 73) | 113 |
| 145 | CLTA4 5', 3'-3x(2'OMe) sgRNA | CLTA4mg OFF5-target | GCAGAUGUAGUGUUUCCAGUUUAAGAGCUAUGCUGGAAACAGCAUAGC AGUUUAAAUAAGGCUAGUCCGUUAUCAACUUGAAAAAGUGGCACCGAGU CGGUGCUUUUUU (SEQ ID NO: 73) | 113 |
| 146 | CLTA1 5'-20x(2'OMe) sgRNA | CLTA1 ON1-target | AGUCCUCAUCUCCUCAAGCGUUUAAGAGCUAUGCUGGUAACAGCAUAGCA AGUUUAAAUAAGGCUAGUCCGUUAUCAACUUGAAAAAGUGGCACCGAGUC GGUGCUUUUUU (SEQ ID NO: 74) | 113 |
| 147 | CLTA1 5'-20x(2'OMe) sgRNA | CLTA1mg ON1-target | AGUCCUCAUCUCCUCAAGCGUUUAAGAGCUAUGCUGGUAACAGCAUAGCA AGUUUAAAUAAGGCUAGUCCGUUAUCAACUUGAAAAAGUGGCACCGAGUC GGUGCUUUUUU (SEQ ID NO: 74) | 113 |
| 148 | CLTA1 5'-20x(2'OMe) sgRNA | CLTA1mg ON1-target | AGUCCUCAUCUCCUCAAGCGUUUAAGAGCUAUGCUGGUAACAGCAUAGCA AGUUUAAAUAAGGCUAGUCCGUUAUCAACUUGAAAAAGUGGCACCGAGUC GGUGCUUUUUU (SEQ ID NO: 74) | 113 |
| 149 | CLTA1 5'-20x(2'OMe) sgRNA | CLTA1mg OFF1-target | AGUCCUCAUCUCCUCAAGCGUUUAAGAGCUAUGCUGGUAACAGCAUAGCA AGUUUAAAUAAGGCUAGUCCGUUAUCAACUUGAAAAAGUGGCACCGAGUC GGUGCUUUUUU (SEQ ID NO: 74) | 113 |

TABLE 3-continued

| Entry # | Guide RNA Construct | Target DNA Construct | RNA sequence (5'→3') | RNA length |
|---|---|---|---|---|
| 150 | CLTA1_5'-20x(2'OMe)_sgRNA | CLTA1mg OFF3-target | AGUCCUCAUCUCCCUCAAGCGUUUAAGAGCUAUGCUGGUAACAGCAUAGCA AGUUAAAUAAGGCUAGUCCGUUAUCAACUUGAAAAAGUGGCACCGAGUC GGUGCUUUUUU (SEQ ID NO: 74) | 113 |
| 151 | CLTA1_5'-26x(2'OMe)_sgRNA | CLTA1 ON1-target | AGUCCUCAUCUCCCUCAAGCGUUUAAGAGCUAUGCUGGUAACAGCAUAGC AAGUUAAAUAAGGCUAGUCCGUUAUCAACUUGAAAAAGUGGCACCGAGU CGGUGCUUUUUUU (SEQ ID NO: 75) | 113 |
| 152 | CLTA1_5'-37x(2'OMe)_sgRNA | CLTA1 ON1-target | AGUCCUCAUCUCCCUCAAGCGUUUAAGAGCUAUGCUGGUAACAGCAUAGC AAGUUAAAUAAGGCUAGUCCGUUAUCAACUUGAAAAAGUGGCACCGAGU CGGUGCUUUUUU (SEQ ID NO: 76) | 113 |
| 153 | CLTA1_41x(2'OMeC/U)_QB3 | CLTA1mg ON1-target | AGUCCUCAUCUCCCUCAAGCGUUUAAGAGCUAUGCUGGUAACAGCAUAGCA AGUUAAAUAAGGCUAGUCCGUUAUCAACUUGAAAAAGUGGCACCGAGUC GGUGCUUUUUUU (SEQ ID NO: 77) | 113 |
| 154 | CLTA1_47x(2'OMeC/U)_QB3 | CLTA1 ON1-target | AGUCCUCAUCU̱CCCUCAAGCGUUUAAGAGCUAUGCUGGUAACAGCAUAGCA AGUUAAAUAAGGCUAGUCCGUUAUCAACUUGAAAAAGUGGC̱ACCGAGUC GGUGCUUUUUU (SEQ ID NO: 78) | 113 |
| 155 | CLTA1_47x(2'OMeC/U)_QB3 | CLTA1 ON1-target | AGUCCUCAUCUCCCUCAAGCGUUUAAGAGCUAUGCUGGUAACAGCAUAGCA AGUUAAAUAAGGCUAGUCCGUUAUCAACUUGAAAAAGUGGCACCGAGUC GGUGCUUUUUU (SEQ ID NO: 79) | 113 |
| 156 | CLTA1_47x(2'OMeC/U)_QB3 | CLTA1mg ON1-target | AGUCCUCAUCUCCCUCAAGCGUUUAAGAGCUAUGCUGGUAACAGCAUAGCA AGUUAAAUAAGGCUAGUCCGUUAUCAACUUGAAAAAGUGGCACCGAGUC GGUGCUUUUUU (SEQ ID NO: 79) | 113 |
| 157 | CLTA1_47x(2'OMeC/U)_QB3 | CLTA1 ON1-target | AGUCCUCAUCUCCCUCAAGCGUUUAAGAGCUAUGCUGGUAACAGCAUAGCA AGUUAAAUAAGGCUAGUCCGUUAUCAACUUGAAAAAGUGGCACCGAGUC GGUGCUUUUUU (SEQ ID NO: 79) | 113 |
| 158 | CLTA1_47x(2'OMeC/U)_QB3 | CLTA1mg OFF3-target | AGUCCUCAUCUCCCUCAAGCGUUUAAGAGCUAUGCUGGUAACAGCAUAGCA AGUUAAAUAAGGCUAGUCCGUUAUCAACUUGA)AAAAGUGGCACCGAGUC GGUGCUUUUUU (SEQ ID NO: 80) | 113 |
| 159 | CLTA1_47x(2'OMeG/A)_QB3 | CLTA1 ON1-target | AGUCCUCAUCUCCCUCAAGCGUUUAAGAGCUAUGCUGGUAACAGCAUAGCA AGUUAAAUAAGGCUAGUCCGUUAUCAACUUGAAAAAGUGGCACCGAGUC GGUGCUUUUUU (SEQ ID NO: 80) | 113 |
| 160 | CLTA1_47x(2'OMeG/A)_QB3 | CLTA1mg ON1-target | AGUCCUCAUCUCCCUCAAGCGUUUAAGAGCUAUGCUGGUAACAGCAUAGCA AGUUAAAUAAGGCUAGUCCGUUAUCAACUUGAAAAAGUGGCACCGAGUC GGUGCUUUUUU (SEQ ID NO: 80) | 113 |
| 161 | CLTA1_47x(2'OMeG/A)_QB3 | CLTA1 ON1-target | AGUCCUCAUCUCCCUCAAGCGUUUAAGAGCUAUGCUGGUAACAGCAUAGCA AGUUAAAUAAGGCUAGUCCGUUAUCAACUUGAAAAAGUGGCACCGAGUC GGUGCUUUUUU (SEQ ID NO: 80) | 113 |
| 162 | CLTA1_47x(2'OMeG/A)_QB3 | CLTA1mg OFF1-target | AGUCCUCAUCUCCCUCAAGCGUUUAAGAGCUAUGCUGGUAACAGCAUAGCA AGUUAAAUAAGGCUAGUCCGUUAUCAACUUGAAAAAGUGGCACCGAGUC GGUGCUUUUUU (SEQ ID NO: 80) | 113 |
| 163 | CLTA1_47x(2'OMeG/A)_QB3 | CLTA1mg OFF3-target | AGUCCUCAUCUCCCUCAAGCGUUUAAGAGCUAUGCUGGUAACAGCAUAGCA AGUUAAAUAAGGCUAGUCCGUUAUCAACUUGAAAAAGUGGCACCGAGUC GGUGCUUUUUU (SEQ ID NO: 80) | 113 |
| 164 | CLTA1_43x(2'OMeG/A)_Bos | CLTA1 ON1-target | AGUCCUCAUCUCCCUCAAGCGUUUAGAGCUAGUAAAUAGCAAGUAAAAUA AGGCUAGUCCGUUAUCAACUUGAAAAAGUGGCACCGAGUCGGUGCUUUUU (SEQ ID NO: 81) | 100 |
| 165 | CLTA1_43x(2'OMeG/A)_Bos | CLTA1mg ON1-target | AGUCCUCAUCUCCCUCAAGCGUUUAGAGCUAGUAAAUAGCAAGUAAAAUA AGGCUAGUCCGUUAUCAACUUGAAAAAGUGGCACCGAGUCGGUGCUUUUU (SEQ ID NO: 81) | 100 |

TABLE 3-continued

| Entry # | Guide RNA Construct | Target DNA Construct | RNA sequence (5'→3') | RNA length |
|---|---|---|---|---|
| 166 | CLTA1_43x(2'OMeG/A)_Bos | CLTA1mg ON1-target | AGUCCUCAUCCCUCAAGCGUUUUAGAGCUAGUAAUAGCAAGUUAAAUA AGGCUAGUCCGUUAUCAACUUGAAAAAGUGGCACCGAGUCGGUGCUUUU (SEQ ID NO: 81) | 100 |
| 167 | CLTA1_43x(2'OMeG/A)_Bos | CLTA1mg OFF1-target | AGUCCUCACUCCCUCAAGCGUUUUAGAGCUAGUAAUAGCAAGUUAAAUA AGGCUAGUCCGUUAUCAACUUGAAAAAGUGGCACCGAGUCGGUGCUUUU (SEQ ID NO: 81) | 100 |
| 168 | CLTA1_43x(2'OMeG/A)_Bos | CLTA1mg OFF3-target | AGUCCCUCACUCCCUCAAGCGUUUUAGAGCUAGUAAUAGCAAGUUAAAUA AGGCUAGUCCGUUAUCAACUUGAAAAAGUGGCACCGAGUCGGUGCUUUU (SEQ ID NO: 81) | 100 |
| 169 | CLTA4 sgRNA_5', 3'-3x(2'OMe) | CLTA4 ON-target | GCAGAUGUAGUGUUUCCACAGUUUAAGAGCUAGUCCGGAAACAGCAUAGC AAGUUAAAUAAGGCUAGUCCGUUAUCAACUUGAAAAAGUGGCACCGAGU CGGUGCUUUUUUU (SEQ ID NO: 82) | 113 |
| 170 | CLTA4 sgRNA_5', 3'-3x(2'OMe) | CLTA4 ON-target | GCAGAUGUAGUGUUUCCACAGUCCGUUAUCAAGAGCUAGUCCGGAAACAGCAUAGC AAGUUAAAUAAGGCUAGUCCGUUAUCAACUUGAAAAAGUGGCACCGAGU CGGUGCUUUUUUU (SEQ ID NO: 82) | 113 |
| 171 | CLTA4_47x(2'OMeC/U)_QB3 | CLTA4 ON-target | GCAGAUGUAGUGUUUCCACAGUUUAAGAGCUAGUCCGGUAACAGCAUAGC AAGUUAAAUAAGGCUAGUCCGUUAUCAACUUGAAAAAGUGGCACCGAGU CGGUGCUUUUUU (SEQ ID NO: 83) | 113 |
| 172 | CLTA4_47x(2'OMeC/U)_QB3 | CLTA4 ON-target | GCAGAUGUAGUGUUUCCACAGUUUAAGAGCUAGUCCGGUAACAGCAUAGC AAGUUAAAUAAGGCUAGUCCGUUAUCAACUUGAAAAAGUGGCACCGAGU CGGUGCUUUUUU (SEQ ID NO: 83) | 113 |
| 173 | CLTA4_47x(2'OMeC/U)_QB3 | CLTA4 ON-target | GCAGAUGUAGUGUUUCCACAGUUUAAGAGCUAGUCCGGUAACAGCAUAGC AAGUUAAAUAAGGCUAGUCCGUUAUCAACUUGAAAAAGUGGCACCGAGU CGGUGCUUUUUU (SEQ ID NO: 83) | 113 |
| 174 | CLTA4_49x(2'OMeG/A)_Bos | CLTA4 ON-target | GCAGAUGUAGUCCGUUUCCACAGUUUAAGAGCUAGUAAUAGCAAGUAAAU AAGGCUAGUCCGUUAUCAACUUGAAAAAGGGGCACCGAGUCGGUGCUUUU (SEQ ID NO: 84) | 100 |
| 175 | CLTA4_49x(2'OMeG/A)_Bos | CLTA4 ON-target | GCAGAUGUAGUCCGUUUCCACAGUUUAAGAGCUAGUAAUAGCAAGUAAAU AAGGCUAGUCCGUUAUCAACUUGAAAAAGGGGCACCGAGUCGGUGCUUUU (SEQ ID NO: 84) | 100 |
| 176 | CLTA4_49x(2'OMeC/U)_Bos | CLTA4 ON-target | GCAGAUGUAGUGUUUCCACAGUUUAAGAGCUAGUAAUAGCAAGUAAAU AAGGCUAGUCCGUUAUCAACUUGAAAAAGUGGCACCGAGUCGGUGCUUUU (SEQ ID NO: 85) | 100 |
| 177 | CLTA4_39x(2'OMeC/U)_Bos | CLTA4 ON-target | GCAGAUGUAGUGUUUCCACAGUUUAAGAGCUAGUAAUAGCAAGUAAAU AAGGCUAGUCCGUUAUCAACUUGAAAAAGUGGCACCGAGUCGGUGCUUUU (SEQ ID NO: 85) | 100 |
| 178 | CLTA4_39x(2'OMeC/U)_Bos | CLTA4 ON-target | GCAGAUGUAGUGUUUCCACAGUUUAAGAGCUAGUAAUAGCAAGUAAAU AAGGCUAGUCCGUUAUCAACUUGAAAAAGUGGCACCGAGUCGGUGCUUUU (SEQ ID NO: 85) | 100 |
| 179 | CLTA4_39x(2'OMeC/U)_Bos | CLTA4 ON-target | GCAGAUGUAGUGUUUCCACAGUUUAAGAGCUAGUAAUAGCAAGUAAAU AAGGCUAGUCCGUUAUCAACUUGAAAAAGUGGCACCGAGUCGGUGCUUUU (SEQ ID NO: 85) | 100 |

2'Deoxy-modified sgRNA

| 180 | CLTA1_5'-20x(21deoxy) | CLTA1 ON1-target | AGTCCTCATCTCCCTCAAGCGUUUUAGAGCUAGUAACAGCAUAGCAA GUUAAAUAAGGCUAGUCCGUUAUCAACUUGAAAAAGUGGCACCGAGUCG GUGCUUUUUUU (SEQ ID NO: 86) | 113 |

TABLE 3-continued

| Entry # | Guide RNA Construct | Target DNA Construct | RNA sequence (5'→3') | RNA length |
|---|---|---|---|---|
| 181 | CLTA1_5'-26x(2'deoxy) | CLTA1 ON1-target | AGTCCTCATCTCCCTCAAGCGTTTAAGAGCUAUGCUGGUAACAGCAUAGCAAG UUUAAAUAAGGCUAGUCCGUUAUCAACUUGAAAAAGUGGCACCGAGUCGG UGCUUUUUUU (SEQ ID NO: 87) | 113 |
| 182 | CLTA1_5'-37x(2'deoxy) | CLTA1 ON1-target | AGTCTCTCATCTCCCTCAAGCGTTTAAGAGCTATGCTGUAACAGCAUAGCAAG UUUAAAUAAGGCUAGUCCGUUAUCAACUUGAAAAAGUGGCACCGAGUCGG UGCUUUUUUU (SEQ ID NO: 88) | 113 |

2'Deoxy, 3'PACE-modified sgRNA

| 183 | CLTA4_2'deoxy3'PACE + 15 | CLTA4mg ON-target | GCAGAUGUAGUGUU*CCACAGUUUAAGCUAUGCUGUAACAGCAUAG CAAGUUUAAAUAAGG̲CUAGUCCGUUAUCAACUUGAAAAAGUGGCACCGAG UCGGUGCUUUUUUU (SEQ ID NO: 89) | 113 |
| 184 | CLTA4_2'deoxy3'PACE + 15 | CLTA4 OFF5-target | GCAGAUGUAGUGUU̲*CCACAGUUUAAGCUAUGCUGUAACAGCAUAG CAAGUUUAAAUAAGGCUAGUCCGUUAUCAACUUGAAAAAGUGGCACCGAG UCGGUGCUUUUUUU (SEQ ID NO: 89) | 113 |

2'OMethyl, 3'PACE-modified sgRNA

| 185 | 5'-1x(2'OMe, 3'PACE)_CLTA1 sgRNA | CLTA1mg ON1-target | A̲*GUCCCAUCUCCCAAGCGUUUAAGAGCUAUGCUGUAACAGCAUAGC AAGUUUAAAUAAGGCUAGUCCGUUAUCAACUUGAAAAAGUGGCACCGAGU CGGUGCUUUUUUU (SEQ ID NO: 90) | 113 |
| 186 | 5'-1x(2'OMe, 3'PACE)_CLTA1 sgRNA | CLTA1mg ON1-target | A̲*GUCCCAUCUCCCAAGCGUUUAAGAGCUAUGCUGUAACAGCAUAGC AAGUUUAAAUAAGGCUAGUCCGUUAUCAACUUGAAAAAGUGGCACCGAGU CGGUGCUUUUUUU (SEQ ID NO: 90) | 113 |
| 187 | 5'-2x(2'OMe, 3'PACE)_CLTA1 sgRNA | CLTA1 ON1-target | A*G̲*UCCCUCAUCUCCCAAGCGUUUAAGAGCUAUGCUGUAACAGCAUAG CAAGUUUAAAUAAGGCUAGUCCGUUAUCAACUUGAAAAAGUGGCACCGAG UCGGUGCUUUUUUU (SEQ ID NO: 91) | 113 |
| 188 | 5'-2x(2'OMe, 3'PACE)_CLTA1 sgRNA | CLTA1 ON1-target | A̲*G̲*UCCCUCAUCUCCCAAGCGUUUAAGAGCUAUGCUGUAACAGCAUAG CAAGUUUAAAUAAGGCUAGUCCGUUAUCAACUUGAAAAAGUGGCACCGAG UCGGUGCUUUUUUU (SEQ ID NO: 91) | 113 |
| 189 | 5'-3x(2'OMe, 3'PACE)_CLTA1 sgRNA | CLTA1mg ON1-target | A̲*G̲*U̲*CCCUCAUCUCCCAAGCGUUUAAGAGCUAUGCUGUAACAGCAUAG CAAGUUUAAAUAAGGCUAGUCCGUUAUCAACUUGAAAAAGUGGCACCGAG UCGGUGCUUUUUUU (SEQ ID NO: 91) | 113 |
| 190 | 5'-3x(2'OMe, 3'PACE)_CLTA1 sgRNA | CLTA1mg ON1-target | A̲*G̲*U̲*CCCUCAUCUCCCAAGCGUUUAAGAGCUAUGCUGUAACAGCAUAG CAAGUUUAAAUAAGGCUAGUCCGUUAUCAACUUGAAAAAGUGGCACCGAG UCGGUGCUUUUUUU (SEQ ID NO: 91) | 113 |
| 191 | 5'-3x(2'OMe, 3'PACE)_CLTA1 sgRNA | CLTA1 ON1-target | G*G*A*GUCCCAUCUCCCAAGCGUUUAAGAGCUAUGCUGGUAACAGCA UAGCAAGUUUAAAUAAGGCUAGUCCGUUAUCCGUUAUCAACUUGAAAAAGUGGCACC GAGUCGGUGCUUUUUUU (SEQ ID NO: 92) | 115 |
| 192 | 5'-3x(2'OMe, 3'PACE)_CLTA1 sgRNA | CLTA1mg ON1-target | G*G*A̲*GUCCCCAUCUCCCAAGCGUUUAAGAGCUAUGCUGGUAACAGCA UAGCAAGUUUAAAUAAGGCUAGUCCGUUAUCAACUUGAAAAAGUGGCACC GAGUCGGUGCUUUUUUU (SEQ ID NO: 92) | 115 |
| 193 | 5'-4x(2'OMe, 3'PACE)_CLTA1 sgRNA | CLTA1mg ON1-target | A*G*U*C̲*CUCAUCUCCCAAGCGUUUAAGAGCUAUGCUGGUAACAGCAU AGCAAGUUUAAAUAAGGCUAGUCCGUUAUCAACUUGAAAAAGUGGCACCG AGUCCGGUGCUUUUUUU (SEQ ID NO: 93) | 113 |
| 194 | 5'-4x(2'OMe, 3'PACE)_CLTA1 sgRNA | CLTA1mg ON1-target | A̲*G̲*U̲*C̲*CUCAUCUCCCAAGCGUUUAAGAGCUAUGCUGGUAACAGCAU AGCAAGUUUAAAUAAGGCUAGUCCGUUAUCAACUUGAAAAAGUGGCACCG AGUCCGGUGCUUUUUUU (SEQ ID NO: 93) | 113 |

TABLE 3-continued

| Entry # | Guide RNA Construct | Target DNA Construct | RNA sequence (5'→3') | RNA length |
|---|---|---|---|---|
| 195 | 5'-4x(2'OMe, 3'PACE)_CLTA1 sgRNA | CLTA1mg ON1-target | A*G*U*C*CUCACUCCCCUCAAGCGUUUAAGAGCUAUGCUGGUAACAGCAU AGCAAGUUUAAAUAAGGCUAGUCCGUUAUCAACUUGAAAAAGUGGCACC AGUCGGUGCUUUUUU (SEQ ID NO: 93) | 113 |
| 196 | 5'-5x(2'OMe, 3'PACE)_CLTA1 sgRNA | CLTA1mg ON1-target | G*G*A*G*U*CCUCAUCCCCUCAAGCGUUUAAGAGCUAUGCUGGUAACAG CAUAGCAAGUUUAAAUAAGGCUAGUCCGUUAUCAACUUGAAAAAGUGCA CCGAGUCGGUGCUUUUUU (SEQ ID NO: 94) | 115 |
| 197 | 5'-5x(2'OMe, 3'PACE)_CLTA1 sgRNA | CLTA1mg ON1-target | G*G*A*G*U*CCUCAUCCCCUCAAGCGUUUAAGAGCUAUGCUGGUAACAG CAUAGCAAGUUUAAAUAAGGCUAGUCCGUUAUCAACUUGAAAAAGUGGCA CCGAGUCGGUGCUUUUUU (SEQ ID NO: 94) | 115 |
| 198 | CLTA1_3'-4x(2'OMe, 3'PACE) sgRNA | CLTA1 ON1-target | AGUCCUCACUCCCCUCAAGCGUUUAAGAGCUAUGCUGGUAACAGCAUAGCA AGUUUAAAUAAGGCUAGUCCGUUAUCAACUUGAAAAAGUGGCACCGAGUC GGUGCUUU*U*U*U*U (SEQ ID NO: 95) | 113 |
| 199 | C_LTA_1_3'-4x(2'OMe, 3'PACE) sgRNA | CLTA1 ON1-target | AGUUUAAAUAAGGCUAGUCCGUUUAAGAGCUAUGCUGGUAACAGCAUAGCA AGUUUAAAUAAGGCUAGUCCGUUAUCAACUUGAAAAAGUGCACCGAGUC GGUGCUUU*U*U*U*U (SEQ ID NO: 95) | 113 |
| 200 | CLTA1_3'-4x(2'OMe, 3'PACE) sgRNA | CLTA1 ON1-target | AGUCCUCACUCCCCUCAAGCGUUUAAGAGCUAUGCUGGUAACAGCAUAGCA AGUUUAAAUAAGGCUAGUCCGUUAUCAACUUGAAAAAGUGGCACCGAGUC GGUGCUUU*U*U*U*U (SEQ ID NO: 95) | 113 |
| 201 | CLTA1_3'-4x(2'OMe, 3'PACE) sgRNA | CLTA1 ON1-target | AGUCCUCACUCCCCUCAAGCGUUUAAGAGCUAUGCUGGUAACAGCAUAGCA AGUUUAAAUAAGGCUAGUCCGUUAUCAACUUGAAAAAGUGGCACCGAGUC GGUGCUUU*U*U*U*U (SEQ ID NO: 95) | 113 |
| 202 | CLTA1_3'-5x(2'OMe, 3'PACE) sgRNA | CLTA1 ON1-target | AGUCCUCACUCCCCUCAAGCGUUUAAGAGCUAUGCUGGUAACAGCAUAGCA AGUUUAAAUAAGGCUAGUCCGUUAUCAACUUGAAAAAGUGGCACCGAGUC GGUGCUU*U*U*U*U*U (SEQ ID NO: 96) | 113 |
| 203 | CLTA1_3'-5x(2'OMe, 3'PACE) sgRNA | CLTA1 ON1-target | AGUCCUCACUCCCCUCAAGCGUUUAAGAGCUAUGCUGGUAACAGCAUAGCA AGUUUAAAUAAGGCUAGUCCGUUAUCAACUUGAAAAAGUGGCACCGAGUC GGUGCUU*U*U*U*U*U (SEQ ID NO: 96) | 113 |
| 204 | CLTA1_3'-5x(2'OMe, 3'PACE) sgRNA | CLTA1 ON1-target | AGUCCUCACUCCCCUCAAGCGUUUAAGAGCUAUGCUGGUAACAGCAUAGCA AGUUUAAAUAAGGCUAGUCCGUUAUCAACUUGAAAAAGUGGCACCGAGUC GGUGCUU*U*U*U*U*U (SEQ ID NO: 96) | 113 |
| 205 | CLTA1_3'-5x(2'OMe, 3'PACE) sgRNA | CLTA1 ON1-target | AGUCCUCACUCCCCUCAAGCGUUUAAGAGCUAUGCUGGUAACAGCAUAGCA AGUUUAAAUAAGGCUAGUCCGUUAUCAACUUGAAAAAGUGGCACCGAGUC GGUGCUU*U*U*U*U*U (SEQ ID NO: 96) | 113 |
| 206 | 5'-3x(2'OMe, 3'PACE)_plus1 overhg_CLTA1 | CLTA1 ON1-target | C_o*A*G*UCCUCAUCCCCUCAAGCGUUUAAGAGCUAUGCUGGUAACAGCAU AGCAAGUUUAAAUAAGGCUAGUCCGUUAUCAACUUGAAAAAGUGGCACCG AGUCGGUGCUUUUUU (SEQ ID NO: 97) | 114 |
| 207 | 5'-3x(2'OMe, 3'PACE)_plus1 overhg_CLTA1 | CLTA1 ON1-target | C_o*A*G*UCCUCAUCCCCUCAAGCGUUUAAGAGCUAUGCUGGUAACAGCAU AGCAAGUUUAAAUAAGGCUAGUCCGUUAUCAACUUGAAAAAGUGGCACCG AGUCGGUGCUUUUUU (SEQ ID NO: 97) | 114 |
| 208 | 5'-3x(2'OMe, 3'PACE)_plus1 overhg_CLTA1 | CLTA1 ON1-target | C_o*A*G*UCCUCAUCCCCUCAAGCGUUUAAGAGCUAUGCUGGUAACAGCAU AGCAAGUUUAAAUAAGGCUAGUCCGUUAUCAACUUGAAAAAGUGGCACCG AGUCGGUGCUUUUUU (SEQ ID NO: 97) | 114 |
| 209 | 5'-3x(2'OMe, 3'PACE)_plus1 NC_overhg_CLTA1 | CLTA1 ON1-target | G_o*A*G*UCCUCAUCCCCUCAAGCGUUUAAGAGCUAUGCUGGUAACAGCAU AGCAAGUUUAAAUAAGGCUAGUCCGUUAUCAACUUGAAAAAGUGGCACCG AGUCGGUGCUUUUUU (SEQ ID NO: 98) | 114 |
| 210 | 5'-3x(2'OMe, 3'PACE)_plus1 NC_overhg_CLTA1 | CLTA1 ON1-target | G_o*A*G*UCCUCAUCCCCUCAAGCGUUUAAGAGCUAUGCUGGUAACAGCAU AGCAAGUUUAAAUAAGGCUAGUCCGUUAUCAACUUGAAAAAGUGGCACCG AGUCGGUGCUUUUUU (SEQ ID NO: 98) | 114 |

TABLE 3-continued

| Entry # | Guide RNA Construct | Target DNA Construct | RNA sequence (5'→3') | RNA length |
|---|---|---|---|---|
| 211 | 5'-3x(2'OMe, 3'PACE)_plus1 NC_overhg_CLTA1 | CLTA1mg ON1-target | G₀*A*G*UCCUCAUCCCUCCCUCAAGCGUUUAAGAGCUAUGCUGGUAACAGCAU AGCAGCAUAGCAAGUUUAAAUAAGGCUAGUCCGUUAUCAACUUGAAAAAGUGGCACCG AGUCGGGUGCUUUUUUU (SEQ ID NO: 98) | 114 |
| 212 | 5'-5x(2'OMe, 3'PACE)_plus2 overhg_CLTA1 | CLTA1 ON1-target | U₀*C₀*A*G*U*CCUCAUCUCCCUCCCUCAAGCGUUUAAGAGCUAUGCUGGUAACA GCAUAGCAAGUUUAAAUAAGGCUAGUCCGUUAUCAACUUGAAAAAGUGGC ACCGAGUCCGUGCUUUUUU (SEQ ID NO: 99) | 115 |
| 213 | 5'-5x(2'OMe, 3'PACE)_plus2 overhg_CLTA1mg | CLTA1mg ON1-target | U₀*C₀*A*G*U*CCUCAUCUCCCUCCCUCAAGCGUUUAAGAGCUAUGCUGGUAACA GCAUAGCAAGUUUAAAUAAGGCUAGUCCGUUAUCAACUUGAAAAAGUGGC ACCGAGUCCGUGCUUUUUU (SEQ ID NO: 99) | 115 |
| 214 | 5'-5x(2'OMe, 3'PACE)_plus2 NC_overhg_CLTA1 | CLTA1 ON1-target | U₀*C₀*A*G*U*CCUCAUCUCCCUCCCUCAAGCGUUUAAGAGCUAUGCUGGUAACA GCAUAGCAAGUUUAAAUAAGGCUAGUCCGUUAUCAACUUGAAAAAGUGGC ACCGAGUCCGUGCUUUUUU (SEQ ID NO: 99) | 115 |
| 215 | 5'-5x(2'OMe, 3'PACE)_plus2 NC_overhg_CLTA1mg | CLTA1mg ON1-target | A₀*G₀*A*G*U*CCUCAUCUCCCUCCCUCAAGCGUUUAAGAGCUAUGCUGGUAACA GCAUAGCAAGUUUAAAUAAGGCUAGUCCGUUAUCAACUUGAAAAAGUGGC ACCGAGUCCGUGCUUUUUU (SEQ ID NO: 100) | 115 |
| 216 | 5'-5x(2'OMe, 3'PACE)_plus2 overhg_CLTA1 | CLTA1 ON1-target | A₀*G₀*A*G*U*CCUCAUCUCCCUCCCUCAAGCGUUUAAGAGCUAUGCUGGUAACA GCAUAGCAAGUUUAAAUAAGGCUAGUCCGUUAUCAACUUGAAAAAGUGGC ACCGAGUCCGUGCUUUUUU (SEQ ID NO: 100) | 115 |
| 217 | 5'-5x(2'OMe, 3'PACE)_plus2 overhg_CLTA1mg | CLTA1mg ON1-target | A₀*G₀*A*G*U*CCUCAUCUCCCUCCCUCAAGCGUUUAAGAGCUAUGCUGGUAACA GCAUAGCAAGUUUAAAUAAGGCUAGUCCGUUAUCAACUUGAAAAAGUGGC ACCGAGUCCGUGCUUUUUU (SEQ ID NO: 100) | 115 |
| 218 | 5'-7x(2'OMe, 3'PACE)_plus3 overhg_CLTA1_3'-4x(2'OMe, 3'PACE) | CLTA1 ON1-target | C₀*U₀*C₀*A*G*U*C*CUCAUCUCCCUCCCUCAAGCGUUUAAGAGCUAUGCUGGUA ACAGCAUAGCAAGUUUAAAUAAGGCUAGUCCGUUAUCAACUUGAAAAAGU GGCACCGAGUCCGUGCUUU*U*U*U*U (SEQ ID NO: 101) | 116 |
| 219 | 5'-7x(2'OMe, 3'PACE)_plus3 overhg_CLTA1mg_3'-4x(2'OMe, 3'PACE) | CLTA1mg ON1-target | C₀*U₀*C₀*A*G*U*C*CUCAUCUCCCUCCCUCAAGCGUUUAAGAGCUAUGCUGGUA ACAGCAUAGCAAGUUUAAAUAAGGCUAGUCCGUUAUCAACUUGAAAAAGU GGCACCGAGUCCGUGCUUU*U*U*U*U (SEQ ID NO: 101) | 116 |
| 220 | 5'-7x(2'OMe, 3'PACE)_plus3 NC_overhg_CLTA1_3'-4x(2'OMe, 3'PACE) | CLTA1 ON1-target | C₀*U₀*C₀*A*G*U*C*CUCAUCUCCCUCCCUCAAGCGUUUAAGAGCUAUGCUGGUA ACAGCAUAGCAAGUUUAAAUAAGGCUAGUCCGUUAUCAACUUGAAAAAGU GGCACCGAGUCCGUGCUUU*U*U*U*U (SEQ ID NO: 101) | 116 |
| 221 | 5'-7x(2'OMe, 3'PACE)_plus3 NC_overhg_CLTA1mg_3'-4x(2'OMe, 3'PACE) | CLTA1mg ON1-target | G₀*A₀*G₀*A*G*U*C*CUCAUCUCCCUCCCUCAAGCGUUUAAGAGCUAUGCUGGUA ACAGCAUAGCAAGUUUAAAUAAGGCUAGUCCGUUAUCAACUUGAAAAAGU GGCACCGAGUCCGUGCUUU*U*U*U*U (SEQ ID NO: 101) | 116 |
| 222 | 5'-7x(2'OMe, 3'PACE)_plus3 overhg_CLTA1_3'-4x(2'OMe, 3'PACE) | CLTA1 ON1-target | G₀*A₀*G₀*A*G*U*C*CUCAUCUCCCUCCCUCAAGCGUUUAAGAGCUAUGCUGGUA ACAGCAUAGCAAGUUUAAAUAAGGCUAGUCCGUUAUCAACUUGAAAAAGU GGCACCGAGUCCGUGCUUU*U*U*U*U (SEQ ID NO: 101) | 116 |
| 223 | 5'-7x(2'OMe, 3'PACE)_plus3 NC_overhg_CLTA1mg_3'-4x(2'OMe, 3'PACE) | CLTA1mg ON1-target | G₀*A₀*G₀*A*G*U*C*CUCAUCUCCCUCCCUCAAGCGUUUAAGAGCUAUGCUGGUA ACAGCAUAGCAAGUUUAAAUAAGGCUAGUCCGUUAUCAACUUGAAAAAGU GGCACCGAGUCCGUGCUUU*U*U*U*U (SEQ ID NO: 101) | 116 |
| 224 | CLTA1_2'OMe, 3'PACE + 20 sgRNA | CLTA1 ON1-target | AGUCCUCAUCUCCCUCCCUCAAGC*GUUUAAGAGCUAUGCUGGUAACAGCAUAGC AAGUUUAAAUAAGGCUAGUCCGUUAUCAACUUGAAAAAGUGGGCCACCGAGU CGGUGCUUUUUUU (SEQ ID NO: 102) | 113 |

TABLE 3-continued

| Entry # | Guide RNA Construct | Target DNA Construct | RNA sequence (5'→3') | RNA length |
|---|---|---|---|---|
| 225 | CLTA1_2'OMe, 3'PACE + 20 sgRNA | CLTA1mg ON1-target | AGUCCUCAUCUCCCUCAAGC*GUUUAAGAGCUAUGCUGGUAACAGCAUAGC AAGUUUAAAUAAGGCUAGUCCGUUAUCAACUUGAAAAAGUGGCACCGAGU CGGUGCUUUUUU (SEQ ID NO: 102) | 113 |
| 226 | CLTA1_2'OMe, 3'PACE + 20 sgRNA | CLTA1mg ON1-target | AGUCCUCAUCUCCCUCAAG*CGUUUAAGAGCUAUGCUGGUAACAGCAUAGC AAGUUUAAAUAAGGCUAGUCCGUUAUCAACUUGAAAAAGUGGCACCGAGU CGGUGCUUUUUU (SEQ ID NO: 102) | 113 |
| 227 | CLTA1_2'OMePACE + 19 sgRNA | CLTA1 ON1-target | AGUCCUCAUCUCCCUCAAG*CGUUUAAGAGCUAUGCUGUAACAGCAUAGC AAGUUUAAAUAAGGCUAGUCCGUUAUCAACUUGAAAAAGUGGGCACCGAGU CGGUGCUUUUUU (SEQ ID NO: 103) | 113 |
| 228 | CLTA1_2'OMePACE + 19 sgRNA | CLTA1mg ON1-target | AGUCCUCAUCUCCCUCAAG*CGUUUAAGAGCUAUGCUGGUAACAGCAUAGC AAGUUUAAAUAAGGCUAGUCCGUUAUCAACUUGAAAAAGUGGCACCGAGU CGGUGCUUUUUU (SEQ ID NO: 103) | 113 |
| 229 | CLTA1_2'OMePACE + 19 sgRNA | CLTA1mg ON1-target | AGUCCUCAUCUCCCUCAAG*CGUUUAAGAGCUAUGCUGGUAACAGCAUAGC AAGUUUAAAUAAGGCUAGUCCGUUAUCAACUUGAAAAAGUGGCACCGAGU CGGUGCUUUUUU (SEQ ID NO: 103) | 113 |
| 230 | CLTA1_2'OMePACE + 19 sgRNA | CLTA1 OFF1-target | AGUCCUCAUCUCCCUCAAG*CGUUUAAGAGCUAUGCUGGUAACAGCAUAGC AAGUUUAAAUAAGGCUAGUCCGUUAUCAACUUGAAAAAGUGGCACCGAGU CGGUGCUUUUUU (SEQ ID NO: 103) | 113 |
| 231 | CLTA1_2'OMePACE + 19 sgRNA | CLTA1mg OFF3-target | AGUCCUCAUCUCCCUCAAG*CGUUUAAGAGCUAUGCUGGUAACAGCAUAGC AAGUUUAAAUAAGGCUAGUCCGUUAUCAACUUGAAAAAGUGGCACCGAGU CGGUGCUUUUUU (SEQ ID NO: 103) | 113 |
| 232 | CLTA1_2'OMePACE + 18 sgRNA | CLTA1 ON1-target | AGUCCUCAUCUCCCUCA*GCGUUUAAGAGCUAUGCUGGUAACAGCAUAGC AAGUUUAAAUAAGGCUAGUCCGUUAUCAACUUGAAAAAGUGGCACCGAGU CGGUGCUUUUUU (SEQ ID NO: 104) | 113 |
| 233 | CLTA1_2'OMePACE + 18 sgRNA | CLTA1mg ON1-target | AGUCCUCAUCUCCCUCAA*GCGUUUAAGAGCUAUGCUGGUAACAGCAUAGC AAGUUUAAAUAAGGCUAGUCCGUUAUCAACUUGAAAAAGUGGCACCGAGU CGGUGCUUUUUU (SEQ ID NO: 104) | 113 |
| 234 | CLTA1_2'OMePACE + 18 sgRNA | CLTA1mg ON1-target | AGUCCUCAUCUCCCUCA<u>A</u>GCGUUUAAGAGCUAUGCUGGUAACAGCAUAGC AAGUUUAAAUAAGGCUAGUCCGUUAUCAACUUGAAAAAGUGGCACCGAGU CGGUGCUUUUUU (SEQ ID NO: 104) | 113 |
| 235 | CLTA1_2'OMePACE + 17 sgRNA | CLTA1 ON1-target | AGUCCUCAUCUCCCUCA*AGCGUUUAAGAGCUAUGCUGGUAACAGCAUAGC AAGUUUAAAUAAGGCUAGUCCGUUAUCAACUUGAAAAAGUGGCACCGAGU CGGUGCUUUUUU (SEQ ID NO: 105) | 113 |
| 236 | CLTA1_2'OMePACE + 17 sgRNA | CLTA1mg ON1-target | AGUCCUCAUCUCCCUCA*AGCGUUUAAGAGCUAUGCUGGUAACAGCAUAGC AAGUUUAAAUAAGGCUAGUCCGUUAUCAACUUGAAAAAGUGGCACCGAGU CGGUGCUUUUUU (SEQ ID NO: 105) | 113 |
| 237 | CLTA1_2'OMePACE + 17 sgRNA | CLTA1 ON1-target | AGUCCUCAUCUCCCUCA<u>A</u>AGCGUUUAAGAGCUAUGCUGGUAACAGCAUAGC AAGUUUAAAUAAGGCUAGUCCGUUAUCAACUUGAAAAAGUGGCACCGAGU CGGUGCUUUUUU (SEQ ID NO: 105) | 113 |
| 238 | CLTA1_2'OMePACE + 17,1 8 sgRNA | CLTA1 ON1-target | AGUCCUCAUCUCCCUCA*<u>A</u>*GCGUUUAAGAGCUAUGCUGGUAACAGCAUAG CAAGUUUAAAUAAGGCUAGUCCGUUAUCAACUUGAAAAAGUGGUAACAGCAUAG UCGGUGCUUUUUU (SEQ ID NO: 106) | 113 |
| 239 | CLTA1_2'OMePACE + 17,1 8 sgRNA | CLTA1mg ON1-target | AGUCCUCAUCUCCCUCA*<u>A</u>*GCGUUUAAGAGCUAUGCUGGUAACAGCAUAG CAAGUUUAAAUAAGGCUAGUCCGUUAUCAACUUGAAAAAGUGGUAACAGCAUAG UCGGUGCUUUUUU (SEQ ID NO: 106) | 113 |
| 240 | CLTA1_2'OMePACE + 17,1 8 sgRNA | CLTA1mg ON1-target | AGUCCUCAUCUCCCUCA*<u>A</u>*GCGUUUAAGAGCUAUGCUGGUAACAGCAUAG CAAGUUUAAAUAAGGCUAGUCCGUUAUCAACUUGAAAAAGUGGUAACAGCAUAG UCGGUGCUUUUUU (SEQ ID NO: 106) | 113 |

TABLE 3-continued

2'OMethyl, 3'Phosphorothioate-modified sgRNA

| Entry # | Guide RNA Construct | Target DNA Construct | RNA sequence (5'→3') | RNA length |
|---|---|---|---|---|
| 241 | CLTA1_5', 3'-3x(2'OMe, 3'P(S)) | CLTA1 ON1-target | AsGsUsCCUCAUCUCCCCAAGCGUUUAAGAGCUAUGCUGGUAACAGCAUAG CAAGUUUAAAUAAGGCUAGUCCGUUAUCAACUUGAAAAAGUGGCACCGAG UCGGUGCUUUUsUsUsU (SEQ ID NO: 107) | 113 |
| 242 | CLTA1_5', 3'-3x(2'OMe, 3'P(S)) | CLTA1mg ON1-target | AsGsUsCCUCAUCUCCCCAAGCGUUUAAGAGCUAUGCUGGUAACAGCAUAG CAAGUUUAAAUAAGGCUAGUCCGUUAUCAACUUGAAAAAGUGGCACCGAG UCGGUGCUUUUsUsUsU (SEQ ID NO: 107) | 113 |
| 243 | CLTA1_5', 3'-3x(2'OMe, 3'P(S)) | CLTA1mg ON1-target | AsGsUsCCUCAUCUCCCCAAGCGUUUAAGAGCUAUGCUGGUAACAGCAUAG CAAGUUUAAAUAAGGCUAGUCCGUUAUCAACUUGAAAAAGUGGCACCGAG UCGGUGCUUUUsUsUsU (SEQ ID NO: 107) | 113 |
| 244 | CLTA1_5', 3'-3x(2'OMe, 3'P(S)) | CLTA1mg ON1-target | AsGsUsCCUCAUCUCCCCAAGCGUUUAAGAGCUAUGCUGGUAACAGCAUAG CAAGUUUAAAUAAGGCUAGUCCGUUAUCAACUUGAAAAAGUGGCACCGAG UCGGUGCUUUUsUsUsU (SEQ ID NO: 107) | 113 |
| 245 | CLTA1_5', 3'-3x(2'OMe, 3'P(S)) | CLTA1 OFF1-target | AsGsUsCCCUCAUCUCCCCAAGCGUUUAAGAGCUAUGCUGGUAACAGCAUAG CAAGUUUAAAUAAGGCUAGUCCGUUAUCAACUUGAAAAAGUGGCACCGAG UCGGUGCUUUUsUsUsU (SEQ ID NO: 107) | 113 |
| 246 | CLTA4_5', 3'-3x(2'OMe, 3'P(S)) | CLTA1mg OFF3-target | GsCsAsGAUGUAGUGUUUCCACAGUCCUAGUCCGUUAUCAACUUGAAACAGCAUA GCAAGUUUAAAUAAGGCUAGUCCGUUAUCAACUUGAAAAAGUGGCACCGA GUCCGUGCUUUUsUsUsU (SEQ ID NO: 107) | 113 |
| 247 | CLTA4_5', 3'-3x(2'OMe, 3'P(S)) | CLTA4 target | GsCsAsGAUGUAGUGUUUCCACAGUCCUAGUCCGUUAUCAACUUGAAACAGCAUA GCAAGUUUAAAUAAGGCUAGUCCGUUAUCAACUUGAAAAAGUGGCACCGA GUCCGUGCUUUUsUsUsU (SEQ ID NO: 107) | 113 |
| 248 | CLTA4_5', 3'-3x(2'OMe, 3'P(S)) | CLTA4 target | GsCsAsGAUGUAGUGUUUCCACAGUCCUAGUCCGUUAUCAACUUGAAACAGCAUA GCAAGUUUAAAUAAGGCUAGUCCGUUAUCAACUUGAAAAAGUGGCACCGA GUCCGUGCUUUUsUsUsU (SEQ ID NO: 107) | 113 |
| 249 | CLTA4_5', 3'-3x(2'OMe, 3'P(S)) | CLTA4mg ON-target | GsCsAsGAUGUAGUGUUUCCACAGUCCUAGUCCGUUAUCAACUUGAAACAGCAUA GCAAGUUUAAAUAAGGCUAGUCCGUUAUCAACUUGAAAAAGUGGCACCGA GUCCGUGCUUUUsUsUsU (SEQ ID NO: 107) | 113 |
| 250 | CLTA4_5', 3'-3x(2'OMe, 3'P(S)) | CLTA4mg ON-target | GsCsAsGAUGUAGUGUUUCCACAGUCCUAGUCCGUUAUCAACUUGAAACAGCAUA GCAAGUUUAAAUAAGGCUAGUCCGUUAUCAACUUGAAAAAGUGGCACCGA GUCCGUGCUUUUsUsUsU (SEQ ID NO: 107) | 113 |
| 251 | CLTA4_5', 3'-3x(2'OMe, 3'P(S)) | CLTA4mg OFF5-target | GsCsAsGAUGUAGUGUUUCCACAGUCCUAGUCCGUUAUCAACUUGAAACAGCAUA GCAAGUUUAAAUAAGGCUAGUCCGUUAUCAACUUGAAAAAGUGGCACCGA GUCCGUGCUUUUsUsUsU (SEQ ID NO: 107) | 113 |
| 252 | CLTA4_5', 3'-3x(2'OMe, 3'P(S)), 3'-5x(2'OMe, 3'P(S)) | CLTA4mg ON-target | GsCsAsGAUGUAGUGUUUCCACAGUCCUAGUCCGUUAUCAACUUGAAACAGCAUA GCAAGUUUAAAUAAGGCUAGUCCGUUAUCAACUUGAAAAAGUGGCACCGA GUCCGUGCUUUUsUsUsUsU (SEQ ID NO: 108) | 113 |
| 253 | CLTA4_5', 3'-3x(2'OMe, 3'P(S)), 3'-5x(2'OMe, 3'P(S)) | CLTA4mg ON-target | GsCsAsGAUGUAGUGUUUCCACAGUCCUAGUCCGUUAUCAACUUGAAACAGCAUA GCAAGUUUAAAUAAGGCUAGUCCGUUAUCAACUUGAAAAAGUGGCACCGA GUCCGUGCUUUUsUsUsUsU (SEQ ID NO: 108) | 113 |
| 254 | CLTA4_5', 3'-3x(2'OMe, 3'P(S)), 3'-5x(2'OMe, 3'P(S)) | CLTA4mg ON-target | GsCsAsGAUGUAGUGUUUCCACAGUCCUAGUCCGUUAUCAACUUGAAACAGCAUA GCAAGUUUAAAUAAGGCUAGUCCGUUAUCAACUUGAAAAAGUGGCACCGA GUCCGUGCUUUUsUsUsUsU (SEQ ID NO: 108) | 113 |
| 255 | CLTA4_5', 3'-5x(2'OMe, 3'P(S)) | CLTA4mg ON-target | GsCsAsGsAsUGUAGUGUUUCCAGAGUCCGUAUUAAGAGCUAUGCUGGAAACAGCAU AGCAAGUUUAAAUAAGGCUAGUCCGUUAUCAACUUGAAAAAGUGGCACCG AGUCGGUGCUUUUsUsUsUsU (SEQ ID NO: 109) | 113 |

TABLE 3-continued

| Entry # | Guide RNA Construct | Target DNA Construct | RNA sequence (5'→3') | RNA length |
|---|---|---|---|---|
| 256 | CLTA4_5', 3'-5x(2'OMe, 3'P(S)) | CLTA4mg ON-target | GsCsAsGsAsUGUAGUGUUUCCAAGUUUAAGAGCUAUGCUGGAAACAGCAU AGCAAGUUUAAAUAAGGCUAGUCCGUUAUCAACUUGAAAAAGUGGCACCG AGUCGGUGCUUsUsUsUsU (SEQ ID NO: 109) | 113 |
| 257 | CLTA4_5', 3'-5x(2'OMe, 3'P(S)) | CLTA4mg OFF5-target | GsCsAsGsAsUGUAGUGUUUCCAAGUUUAAGAGCUAUGCUGGAAACAGCAU AGCAAGUUUAAAUAAGGCUAGUCCGUUAUCAACUUGAAAAAGUGGCACCG AGUCGGUGCUUsUsUsUsU (SEQ ID NO: 109) | 113 |

2'OMethyl, 3'PhosphorothioPACE-modified sgRNA

| | | | | |
|---|---|---|---|---|
| 258 | CLTA1_5', 3'-3x(2'OMe, 3'thioPACE) | CLTA1 ON1-target | A*sG*sU*sCCCUCAUCCCCUCAAGCGUUUAAGAGCUAUGCUGGUAACAGCA UAGCAAGUUAAAUAAGGCUAGUCCGUUAUCAACUUGAAAAAGUGGCACC GAGUCGGUGCUUU*sU*sU*sU (SEQ ID NO: 110) | 113 |
| 259 | CLTA1_5', 3'-3x(2'OMe, 3'thioPACE) | CLTA1mg ON1-target | A*sG*sU*sCCCUCAUCCCCUCAAGCGUUUAAGAGCUAUGCUGGUAACAGCA UAGCAAGUUAAAUAAGGCUAGUCCGUUAUCAACUUGAAAAAGUGGCACC GAGUCGGUGCUUU*sU*sU*sU (SEQ ID NO: 110) | 113 |
| 260 | CLTA1_5', 3'-3x(2'OMe, 3'thioPACE) | CLTA1mg ON1-target | A*sG*sU*sCCCUCAUCCCCUCAAGCGUUUAAGAGCUAUGCUGGUAACAGCA UAGCAAGUUAAAUAAGGCUAGUCCGUUAUCAACUUGAAAAAGUGGCACC GAGUCGGUGCUUU*sU*sU*sU (SEQ ID NO: 110) | 113 |
| 261 | CLTA1_5', 3'-3x(2'OMe, 3'thioPACE) | CLTA1mg OFF1-target | A*sG*sU*sCCCUCAUCCCCUCAAGCGUUUAAGAGCUAUGCUGGUAACAGCA UAGCAAGUUAAAUAAGGCUAGUCCGUUAUCAACUUGAAAAAGUGGCACC GAGUCGGUGCUUU*sU*sU*sU (SEQ ID NO: 110) | 113 |
| 262 | CLTA1_5', 3'-3x(2'OMe, 3'thioPACE) | CLTA1mg OFF3-target | A*sG*sU*sCCCUCAUCCCCUCAAGCGUUUAAGAGCUAUGCUGGUAACAGCA UAGCAAGUUAAAUAAGGCUAGUCCGUUAUCAACUUGAAAAAGUGGCACC GAGUCGGUGCUUU*sU*sU*sU (SEQ ID NO: 110) | 113 |
| 263 | CLTA1_5', 3'-1x(2'OMe, 3'thioPACE) | CLTA1mg ON1-target | A*sGUCCCUCAUCCCCUCAAGCGUUUAAGAGCUAUGCUGGUAACAGCAUAG CAAGUUAAAUAAGGCUAGUCCGUUAUCAACUUGAAAAAGUGGCACCGAG UCGGUGCUUUUU*sU (SEQ ID NO: 111) | 113 |
| 264 | CLTA1_5', 3'-1x(2'OMe, 3'thioPACE) | CLTA1mg ON1-target | A*sGUCCCUCAUCCCCUCAAGCGUUUAAGAGCUAUGCUGGUAACAGCAUAG CAAGUUAAAUAAGGCUAGUCCGUUAUCAACUUGAAAAAGUGGCACCGAG UCGGUGCUUUUU*sU (SEQ ID NO: 111) | 113 |
| 265 | CLTA1_5', 3'-1x(2'OMe, 3'thioPACE) | CLTA1mg OFF1-target | A*sGUCCCUCAUCCCCUCAAGCGUUUAAGAGCUAUGCUGGUAACAGCAUAG CAAGUUAAAUAAGGCUAGUCCGUUAUCAACUUGAAAAAGUGGCACCGAG UCGGUGCUUUUU*sU (SEQ ID NO: 111) | 113 |
| 266 | CLTA1_5', 3'-1x(2'OMe, 3'thioPACE) | CLTA1mg OFF3-target | A*sGUCCCUCAUCCCCUCAAGCGUUUAAGAGCUAUGCUGGUAACAGCAUAG CAAGUUAAAUAAGGCUAGUCCGUUAUCAACUUGAAAAAGUGGCACCGAG UCGGUGCUUUUU*sU (SEQ ID NO: 111) | 113 |
| 267 | CLTA1_5', 3'-3x(2'OMe, 3'thioPACE) 75 mer | CLTA1 ON1-target | A*sG*sU*sCCCUCAUCCCCUCAAGCGUUUAAGAGCUAUGCUGGUAACAGCA UAGCAAGUUUAAAUAAGGCUAGUCCG*sU*sU*sU (SEQ ID NO: 112) | 75 |
| 268 | CLTA1_5', 3'-1x(2'OMe, 3'thioPACE) 74 mer | CLTA1mg ON1-target | A*sGUCCCUCAUCCCCUCAAGCGUUUAAGAGCUAUGCUGGUAACAGCAUAG CAAGUUAAAUAAGGCUAGUCCGU*sU (SEQ ID NO: 112) | 74 |
| 269 | CLTA1_5', 3'-1x(2'OMe, 3'thioPACE) 75 mer | CLTA1mg ON1-target | A*sGUCCCUCAUCCCCUCAAGCGUUUAAGAGCUAUGCUGGUAACAGCAUAG CAAGUUAAAUAAGGCUAGUCCGUU*sA (SEQ ID NO: 112) | 75 |
| 270 | CLTA1_5', 3'-1x(2'OMe, 3'thioPACE) 77 mer | CLTA1mg ON1-target | A*sGUCCCUCAUCCCCUCAAGCGUUUAAGAGCUAUGCUGGUAACAGCAUAG CAAGUUAAAUAAGGCUAGUCCGUUAU*sC (SEQ ID NO: 113) | 77 |
| 271 | CLTA1_5', 3'-1x(2'OMe, 3'thioPACE) 77 mer + G | CLTA1mg ON1-target | G*sAGUCCCUCAUCCCCUCAAGCGUUUAAGAGCUAUGCUGGUAACAGCAUA GCAAGUUAAAUAAGGCUAGUCCGUUAU*sC (SEQ ID NO: 114) | 78 |
| 272 | CLTA4_5', 3'-3x(2'OMe, 3'thioPACE) | CLTA4 ON-target | G*sC*sA*sGAUGUAGUGUUUCCAGUUUAAGAGCUAUGCUGGAAACAGCA UAGCAAGUUUAAAUAAGGCUAGUCCGUUAUCAACUUGAAAAAGUGGCACC GAGUCGGUGCUUU*sU*sU*sU (SEQ ID NO: 115) | 113 |

TABLE 3-continued

| Entry # | Guide RNA Construct | Target DNA Construct | RNA sequence (5'→3') | RNA length |
|---|---|---|---|---|
| 273 | CLTA4_5', 3'-3x(2'OMe, 3'thioPACE) | CLTA4 ON-target | G*sC*sA*sGAUGUAGUGUUUCCACAGUUUAAGAGCUAUGCUGGAAACAGCA UAGCAAGUUUAAAUAAGGCUAGUCCGUUAUCAACUGAAAAAGUGGCACC GAGUCGGUGCUUUU*sU*sU*sU (SEQ ID NO: 115) | 113 |
| 274 | CLTA4_5', 3'-3x(2'OMe, 3'thioPACE) | CLTA4 ON-target | G*sC*sA*sGAUGUAGUGUUUCCACAGUUUAAGAGCUAUGCUGGAAACAGCA UAGCAAGUUUAAAUAAGGCUAGUCCGUUAUCAACUGAAAAAGUGGCACC GAGUCGGUGCUUUU*sU*sU*sU (SEQ ID NO: 115) | 113 |
| 275 | CLTA4_5', 3'-3x(2'OMe, 3'thioPACE) | CLTA4mg OFF5-target | G*sC*sA*sGAUGUAGUGUUUCCACAGUUUAAGAGCUAUGCUGGAAACAGCA UAGCAAGUUUAAAUAAGGCUAGUCCGUUAUCAACUGAAAAAGUGGCACC GAGUCGGUGCUUUU*sU*sU*sU (SEQ ID NO: 115) | 113 |
| 276 | CLTA4_5', 3'-1x(2'OMe, 3'thioPACE) | CLTA4mg ON-target | G*sCAGAUGUAGUGUUUCCACAGUUUAAGAGCUAUGCUGGAAACAGCAUAG CAAGUUUAAAUAAGGCUAGUCCGUUAUCAACUGAAAAAGUGGCACCGAG UCGGUGCUUUUU*sU (SEQ ID NO: 116) | 113 |
| 277 | CLTA4_5', 3'-1x(2'OMe, 3'thioPACE) | CLTA4mg ON-target | G*sCAGAUGUAGUGUUUCCACAGUUUAAGAGCUAUGCUGGAAACAGCAUAG CAAGUUUAAAUAAGGCUAGUCCGUUAUCAACUGAAAAAGUGGCACCGAG UCGGUGCUUUUU*sU (SEQ ID NO: 116) | 113 |
| 278 | CLTA4_5', 3'-1x(2'OMe, 3'thioPACE) | CLTA4mg ON-target | G*sCAGAUGUAGUGUUUCCACAGUUUAAGAGCUAUGCUGGAAACAGCAUAG CAAGUUUAAAUAAGGCUAGUCCGUUAUCAACUGAAAAAGUGGCACCGAG UCGGUGCUUUUU*sU (SEQ ID NO: 116) | 113 |
| 279 | CLTA4_5', 3'-1x(2'OMe, 3'thioPACE) | CLTA4mg OFF5-target | G*sCAGAUGUAGUGUUUCCACAGUUUAAGAGCUAUGCUGGAAACAGCAUAG CAAGUUUAAAUAAGGCUAGUCCGUUAUCAACUGAAAAAGUGGCACCGAG UCGGUGCUUUUU*sU (SEQ ID NO: 116) | 113 |
| 2-aminoA-modified sgRNA (including unmodified controls) | | | | |
| 280 | EN1 | EN1mg ON-target | GAUGUUGUCGAUGAAAAGUGUUAAGAGCUAUGCUGGUAACAGCAUAGC AAGUUUAAAUAAGGCUAGUCCGUUAUCAACUGAAAAGCUAUGCAUAGC CGGUGCUUUUUU (SEQ ID NO: 117) | 113 |
| 281 | EN1 | EN1mg OFF-target | GAUGUUGUCGAUGAAAAGUGUUAAGAGCUAUGCUGGUAACAGCAUAGC AAGUUUAAAUAAGGCUAGUCCGUUAUCAACUGAAAAGCUAUGCAUAGC CGGUGCUUUUUU (SEQ ID NO: 117) | 113 |
| 282 | EN1_2aminoA + 16 | EN1mg ON-target | GAUGUUGUCGAUGAA(2aA)AAGUGUUAAGAGCUAUGCUGGUAACAGCAU AGCAAGUUUAAAUAAGGCUAGUCCGUUAUCAACUUGAAAAAGUGGCACCG AGUCGGUGCUUUUUU (SEQ ID NO: 118) | 113 |
| 283 | EN1_2aminoA + 16 | EN1mg OFF-target | GAUGUUGUCGAUGAA(2aA)AAGUGUUAAGAGCUAUGCUGGUAACAGCAU AGCAAGUUUAAAUAAGGCUAGUCCGUUAUCAACUUGAAAAAGUGGCACCG AGUCGGUGCUUUUUU (SEQ ID NO: 118) | 113 |
| 284 | PCDHA4 | PCDHA4mg ON-target | GAUUUAGACGAAGGAUUGAAGUUUAAGAGCUAUGCUGGUAACAGCAUAGC AAGUUUAAAUAAGGCUAGUCCGUUAUCAACUUGAAAAAGUGGCACCGAGU CGGUGCUUUUUU (SEQ ID NO: 119) | 113 |
| 285 | PCDHA4 | PCDHA4mg OFF-target | GAUUUAGACGAAGGAUUGAAGUUUAAGAGCUAUGCUGGUAACAGCAUAGC AAGUUUAAAUAAGGCUAGUCCGUUAUCAACUUGAAAAAGUGGCACCGAGU CGGUGCUUUUUU (SEQ ID NO: 119) | 113 |
| 286 | PCDHA4_2aminoA + 15 | PCDHA4mg ON-target | GAUUUAGACGAAGG(2aA)UUGAAGUUUAAGAGCUAUGCUGGUAACAGCAU AGCAAGUUUAAAUAAGGCUAGUCCGUUAUCAACUUGAAAAAGUGGCACCG AGUCGGUGCUUUUUU (SEQ ID NO: 120) | 113 |
| 287 | PCDHA4_2aminoA + 15 | PCDHA4mg OFF-target | GAUUUAGACGAAGG(2aA)UUGAAGUUUAAGAGCUAUGCUGGUAACAGCAU AGCAAGUUUAAAUAAGGCUAGUCCGUUAUCAACUUGAAAAAGUGGCACCG AGUCGGUGCUUUUUU (SEQ ID NO: 120) | 113 |

TABLE 3-continued

| Entry # | Guide RNA Construct | Target DNA Construct | RNA sequence (5'→3') | RNA length |
|---|---|---|---|---|
| | | | 5-methylU-modified sgRNA | |
| 288 | CLTA4_21x(5-MeU) | CLTA4mg ON-target | GCAGA(5mU)G(5mU)AG(5mU)G(5mU)(5mU)CCACAGUUUAAGAGC(5mU)A(5mU)GC(5mU)GG(5mU)AACAGCA(5mU)AGCAAGUUUAAAUAAGG CUAGUCCGUUAUCAAC(5mU)(5mU)GAAAAAG(5mU)GGCACCGAGUCGG (5mU)GC(5mU)(5mU)(5mU)(5mU)(5mU)(5mU)U (SEQ ID NO: 121) | 113 |
| 289 | CLTA4_21x(5-MeU) | CLTA4mg OFF5-target | GCAGA(5mU)G(5mU)AG(5mU)G(5mU)(5mU)CCAAGUUUAAGAGC(5mU)A(5mU)GC(5mU)GG(5mU)AACAGCA(5mU)AGCAAGUUUAAAUAAGG CUAGUCCGUUAUCAAC(5mU)(5mU)GAAAAAG(5mU)GGCACCGAGUCGG (5mU)GC(5mU)(5mU)(5mU)(5mU)(5mU)(5mU)U (SEQ ID NO: 121) | 113 |
| | | | Z base-modified sgRNA | |
| 290 | CLTA1_22_70,71 | CLTA1 ON-target | AGUCCUCAUCUCCCUCAAGCGUUUAAGAGCUAUGCGUAACAGCAUAGCA AGUUUAAAUAAGGCUAGUZZGUUAUCAACUUGAAAAAGUGGCACCGAGUC GGUGCUUUUUU (SEQ ID NO: 122) | 113 |
| 291 | CLTA1_22_95,96 | CLTA1 ON-target | AGUCCUCAUCUCCCUCAAGCGUUUAAGAGCUAUGCGUAACAGCAUAGCA AGUUUAAAUAAGGCUAGUCCGUUAUCAACUUGAAAAAGUGGCAZZGAGUC GGUGCUUUUUU (SEQ ID NO: 122) | 113 |
| | | | sgRNA modified to disfavor misfolding | |
| 292 | CLTA1_opti_short_5', 3'-1x(2'OMe, 3'thioPACE)_2'OMe_54,57 | CLTA1mg ON-target | <u>A</u>*sGUCCCAUCUCCCUCAAGCGUUUAAGAGCUAGUAAUAGCAAGUUUAAA UAAGGU<u>UA</u>AUCCGUUAUCAACAAGAA<u>A</u>AUUGUGGCACCGAGUCGGUGCUU<u>U</u>*sU (SEQ ID NO: 123) | 100 |
| 293 | CLTA1_opti_short_5', 3'-1x(2'OMe, 3'thioPACE)_2'OMe_64,67 | CLTA1mg ON-target | <u>A</u>*sGUCCCAUCUCCCUCAAGCGUUUAAGAGCUAUGCGUAACAGCAUAG CAAGUUUAAAUAAGGU<u>UA</u>AUCCGUUAUCAACAAGAAAAUUGUGGCACCGAG UCGGUGCUUUU<u>U</u>*sU (SEQ ID NO: 124) | 113 |

N<sub>o</sub> = 5'-overhang (5' to the 20-nt guide sequence); "NC" means the overhang is not complementary to protospacer-adjacent sequence IntFl = Fluorophore incorporated at an internal position in the RNA sequence <u>N</u> = 2'OMe
N = 2'deoxy
Ns = 3'P(S)
N* = 3'-PACE
N*s = 3'-thioPACE
<u>N</u>* = 2'OMe, 3'-PACE
<u>N</u>*s = 2'OMe, 3'-thioPACE
<u>N</u>s = 2'OMe, 3'P(S)
(2sU) = 2-thioU
(2aA) = 2-aminoA
(5mU) = 5-methylU
Z = Z base The DNA target constructs in Table 3 had the following sequences:

```
CLTA1 ON1-      AGAATTTAACTGTGGTCACATTTGCTTTATCGACTGGCTTCATCTCACAGCTCATC
target:         TTACGCAAGTTCGATGAGTATGCCAGTCACTTTCAATTTGGTTGAATGTTCCCGTG
                ACATGCGAGTTCTGTCGACCATGTGCCGCGGATTGAATTCCTCAAGGGTGGTGATA
                GATGCTACGGTGGTGATGCGCATGCGCTCAGTCCTCATCTCCCTCAAGCAGGCCCC
                GCTGGTGGGTCGGAGTCCCTAGTGAAGCCACCAATATAGTGGTCGTGTCAAGCAAC
                TGTCCACGCTCCACCCTCGAGGTCGTAACATAAACGTACTAAGGCACGAGTAAACA
                AGATCGATAGCAAGAACATGGTATAGACTGACGGAGAGCTCGCCATTAGTCTGA
                (SEQ ID NO: 10)

CLTA1 OFF1-     AGAATTTAACTGTGGTCACATTTGCTTTATCGACTGGCTTCATCTCACAGCTCATC
target:         TTACGCAAGTTCGATGAGTATGCCAGTCACTTTCAATTTGGTTGAATGTTCCCGTG
                ACATGCGAGTTCTGTCGACCATGTGCCGCGGATTGAATTCCTCAAGGGTGGTGATA
                GATGCTACGGTGGTGATGCGTATGCACTCAGTCCTCAACTCCCTCAAGCAGGCGAC
                CCCTGGGGGTCGGAGTCCCTAGTGAAGCCACCAATATAGTGGTCGTGTCAAGCAAC
                TGTCCACGCTCCACCCTCGAGGTCGTAACATAAACGTACTAAGGCACGAGTAAACA
                AGATCGATAGCAAGAACATGGTATAGACTGACGGAGAGCTCGCCATTAGTCTGA
                (SEQ ID NO: 11)

CLTA1 OFF2-     AGAATTTAACTGTGGTCACATTTGCTTTATCGACTGGCTTCATCTCACAGCTCATC
target:         TTACGCAAGTTCGATGAGTATGCCAGTCACTTTCAATTTGGTTGAATGTTCCCGTG
                ACATGCGAGTTCTGTCGACCATGTGCCGCGGATTGAATTCCTCAAGGGTGGTGATA
                GATGCTACGGTGGTGATGCAATAAATTTCAGCCCTCATTTCCCTCAAGCAGGGGTT
                ACTTTAGGGTCGGAGTCCCTAGTGAAGCCACCAATATAGTGGTCGTGTCAAGCAAC
                TGTCCACGCTCCACCCTCGAGGTCGTAACATAAACGTACTAAGGCACGAGTAAACA
                AGATCGATAGCAAGAACATGGTATAGACTGACGGAGAGCTCGCCATTAGTCTGA
                (SEQ ID NO: 12)

CLTA1 OFF3-     AGAATTTAACTGTGGTCACATTTGCTTTATCGACTGGCTTCATCTCACAGCTCATC
target:         TTACGCAAGTTCGATGAGTATGCCAGTCACTTTCAATTTGGTTGAATGTTCCCGTG
                ACATGCGAGTTCTGTCGACCATGTGCCGCGGATTGAATTCCTCAAGGGTGGTGATA
                GATGCTACGGTGGTGATGCTCTCCAGCCCACTCCTCATCCCCCTCAAGCCGGTCCC
                AGGCTGGGGTCGGAGTCCCTAGTGAAGCCACCAATATAGTGGTCGTGTCAAGCAAC
                TGTCCACGCTCCACCCTCGAGGTCGTAACATAAACGTACTAAGGCACGAGTAAACA
                AGATCGATAGCAAGAACATGGTATAGACTGACGGAGAGCTCGCCATTAGTCTGA
                (SEQ ID NO: 13)

CLTA1mg ON1-    GCGTTTCTGGGTGAGCAAAAACAGGAAGGCAAAATGCCGCAAAAAAGGGAATAAGG
target:         GCGACACGGAAATGTTGAATACTCATACTCTTCCTTTTTCAATATTATTGAAGCAT
                TTATCAGGGTTATTGTCTCATGAGCGGATACATATTTGAATGTATTTAGAAAAATA
                AACAAATAGGGGTTCCGCGCACATTTCCCCGAAAAGTGCCACCTAAATTGTAAGCG
                TTAATATTTTGTTAAAATTCGCGTTAAATTTTTGTTAAATCAGCTCATTTTTTAAC
                CAATAGGCCGAAATCGGCAAAATCCCTTATAAATCAAAAGAATAGACCGAGATAGG
                GTTGAGTGTTGTTCCAGTTTGGAACAAGAGTCCACTATTAAAGAACGTGGACTCCA
                ACGTCAAAGGGCGAAAAACCGTCTATCAGGGCGATGGCCCACTACGTGAACCATCA
                CCCTAATCAAGTTTTTTGGGGTCGAGGTGCCGTAAAGCACTAAATCGGAACCCTAA
                AGGGAGCCCCCGATTTAGAGCTTGACGGGGAAAGCCGGCGAACGTGGCGAGAAAGG
                AAGGGAAGAAAGCGAAAGGAGCGGGCGCTAGGGCGCTGGCAAGTGTAGCGGTCACG
                CTGCGCGTAACCACCACACCCGCCGCGCTTAATGCGCCGCTACAGGGCGCGTCCCA
                TTCGCCATTCAGGCTGCGCAACTGTTGGGAAGGGCGATCGGTGCGGGCCTCTTCGC
                TATTACGCCAGCTGGCGAAAGGGGGATGTGCTGCAAGGCGATTAAGTTGGGTAACG
                CCAGGGTTTTCCCAGTCACGACGTTGTAAAACGACGGCCAGTGAGCGCGCGTAATA
                CGACTCACTATAGGGCGAATTGGGTACGATCGATGCGGCCTCGCAGGCCAAAGATG
                TCTCCCGCATGCGCTCAGTCCTCATCTCCCTCAAGCAGGCCCTGCTGGTGCACTGA
                AGAGCCACCCTGTGCGCGTGATATGCAGCTCCAGCTTTTGTTCCCTTTAGTGAGGG
                TTAATTGCGCGCTTGGCGTAATCATGGTCATAGCTGTTTCCTGTGTGAAATTGTTA
                TCCGCTCACAATTCCACACAACATACGAGCCGGAAGCATAAAGTGTAAAGCCTGGG
                GTGCCTAATGAGTGAGCTAACTCACATTAATTGCGTTGCGCTCACTGCCCGCTTTC
                CAGTCGGGAAACCTGTCGTGCCAGCTGCATTAATGAATCGGCCAACGCGCGGGGAG
                AGGCGGTTTGCGTATTGGGCGCTCTTCCGCTTCCTCGCTCACTGACTCGCTGCGCT
                CGGTCGTTCGGCTGCGGCGAGCGGTATCAGCTCACTCAAAGGCGGTAATACGGTTA
                TCCACAGAATCAGGGGATAACGCAGGAAAGAACATGTGAGCAAAAGGCCAGCAAAA
                GGCCAGGAACCGTAAAAAGGCCGCGTTGCTGGCGTTTTTCCATAGGCTCCGCCCCC
                CTGACGAGCATCACAAAAATCGACGCTCAAGTCAGAGGTGGCGAAACCCGACAGGA
                CTATAAAGATACCAGGCGTTTCCCCCTGGAAGCTCCCTCGTGCGCTCTCCTGTTCC
                GACCCTGCCGCTTACCGGATACCTGTCCGCCTTTCTCCCTTCGGGAAGCGTGGCGC
                TTTCTCATAGCTCACGCTGTAGGTATCTCAGTTCGGTGTAGGTCGTTCGCTCCAAG
                CTGGGCTGTGTGCACGAACCCCCCGTTCAGCCCGACCGCTGCGCCTTATCCGGTAA
                CTATCGTCTTGAGTCCAACCCGGTAAGACACGACTTATCGCCACTGGCAGCAGCCA
                CTGGTAACAGGATTAGCAGAGCGAGGTATGTAGGCGGTGCTACAGAGTTCTTGAAG
                TGGTGGCCTAACTACGGCTACACTAGAAGGACAGTATTTGGTATCTGCGCTCTGCT
                GAAGCCAGTTACCTTCGGAAAAAGAGTTGGTAGCTCTTGATCCGGCAAACAAACCA
                CCGCTGGTAGCGGTGGTTTTTTGTTTGCAAGCAGCAGATTACGCGCAGAAAAAA
                GGATCTCAAGAAGATCCTTTGATCTTTTCTACGGGGTCTGACGCTCAGTGGAACGA
                AAACTCACGTTAAGGGATTTTGGTCATGAGATTNTCAAAAAGGATCTTCACCTAGA
                TCCTTTTAAATTAAAAATGAAGTTTTAAATCAATCTAAAGTATATATGAGTAAACT
                TGGTCTGACAGTTACCAATGCTTAATCAGTGAGGCACCTATCTCAGCGATCTGTCT
                ATTTCGTTCATCCATAGTTGCCTGACTCCCCGTCGTGTAGATAACTACGATACGGG
                AGGGCTTACCATCTGGCCCCAGTGCTGCAATGATACCGCGAGACCCACGCTCACCG
```

```
                GCTCCAGATTTATCAGCAATAAACCAGCCAGCCGGAAGGGCCGAGCGCAGAAGTGG
                TCCTGCAACTTTATCCGCCTCCATCCAGTCTATTAATTGTTGCCGGGAAGCTAGAG
                TAAGTAGTTCGCCAGTTAATAGTTTGCGCAACGTTGTTGCCATTGCTACAGGCATC
                GTGGTGTCACGCTCGTCGTTTGGTATGGCTTCATTCAGCTCCGGTTCCCAACGATC
                AAGGCGAGTTACATGATCCCCCATGTTGTGCAAAAAAGCGGTTAGCTCCTTCGGTC
                CTCCGATCGTTGTCAGAAGTAAGTTGGCCGCAGTGTTATCACTCATGGTTATGGCA
                GCACTGCATAATTCTCTTACTGTCATGCCATCCGTAAGATGCTTTTCTGTGACTGG
                TGAGTACTCAACCAAGTCATTCTGAGAATAGTGTATGCGGCGACCGAGTTGCTCTT
                GCCCGGCGTCAATACGGGATAATACCGCGCCACATAGC
                (SEQ ID NO: 14)

CLTA1mg_OFF1-   GCGTTTCTGGGTGAGCAAAAACAGGAAGGCAAAATGCCGCAAAAAAGGGAATAAGG
target:         GCGACACGGAAATGTTGAATACTCATACTCTTCCTTTTTCAATATTATTGAAGCAT
                TTATCAGGGTTATTGTCTCATGAGCGGATACATATTTGAATGTATTTAGAAAAATA
                AACAAATAGGGGTTCCGCGCACATTTCCCCGAAAAGTGCCACCTAAATTGTAAGCG
                TTAATATTTTGTTAAAATTCGCGTTAAATTTTTGTTAAATCAGCTCATTTTTTAAC
                CAATAGGCCGAAATCGGCAAAATCCCTTATAAATCAAAAGAATAGACCGAGATAGG
                GTTGAGTGTTGTTCCAGTTTGGAACAAGAGTCCACTATTAAAGAACGTGGACTCCA
                ACGTCAAAGGGCGAAAAACCGTCTATCAGGGCGATGGCCCACTACGTGAACCATCA
                CCCTAATCAAGTTTTTTGGGGTCGAGGTGCCGTAAAGCACTAAATCGGAACCCTAA
                AGGGAGCCCCCGATTTAGAGCTTGACGGGGAAAGCCGGCGAACGTGGCGAGAAAGG
                AAGGGAAGAAAGCGAAAGGAGCGGGCGCTAGGGCGCTGGCAAGTGTAGCGGTCACG
                CTGCGCGTAACCACCACACCCGCCGCGCTTAATGCGCCGCTACAGGGCGCGTCCCA
                TTCGCCATTCAGGCTGCGCAACTGTTGGGAAGGGCGATCGGTGCGGGCCTCTTCGC
                TATTACGCCAGCTGGCGAAAGGGGGATGTGCTGCAAGGCGATTAAGTTGGGTAACG
                CCAGGGTTTTCCCAGTCACGACGTTGTAAAACGACGGCCAGTGAGCGCGCGTAATA
                CGACTCACTATAGGGCGAATTGGGTACGATCGATGCGGCCTCGCAGGGCAAAGAGG
                TCTCCTGTATGCACTCAGTCCTCAACTCCCTCAAGCAGGCGACCCTTGGTGCACTG
                ACAAACCGCTCCTGCGCGTGATATGCAGCTCCAGCTTTTGTTCCCTTTAGTGAGGG
                TTAATTGCGCGCTTGGCGTAATCATGGTCATAGCTGTTTCCTGTGTGAAATTGTTA
                TCCGCTCACAATTCCACACAACATACGAGCCGGAAGCATAAAGTGTAAAGCCTGGG
                GTGCCTAATGAGTGAGCTAACTCACATTAATTGCGTTGCGCTCACTGCCCGCTTTC
                CAGTCGGGAAACCTGTCGTGCCAGCTGCATTAATGAATCGGCCAACGCGCGGGGAG
                AGGCGGTTTGCGTATTGGGCGCTCTTCCGCTTCCTCGCTCACTGACTCGCTGCGCT
                CGGTCGTTCGGCTGCGGCGAGCGGTATCAGCTCACTCAAAGGCGGTAATACGGTTA
                TCCACAGAATCAGGGGATAACGCAGGAAAGAACATGTGAGCAAAAGGCCAGCAAAA
                GGCCAGGAACCGTAAAAAGGCCGCGTTGCTGGCGTTTTTCCATAGGCTCCGCCCCC
                CTGACGAGCATCACAAAAATCGACGCTCAAGTCAGAGGTGGCGAAACCCGACAGGA
                CTATAAAGATACCAGGCGTTTCCCCCTGGAAGCTCCCTCGTGCGCTCTCCTGTTCC
                GACCCTGCCGCTTACCGGATACCTGTCCGCCTTTCTCCCTTCGGGAAGCGTGGCGC
                TTTCTCATAGCTCACGCTGTAGGTATCTCAGTTCGGTGTAGGTCGTTCGCTCCAAG
                CTGGGCTGTGTGCACGAACCCCCCGTTCAGCCCGACCGCTGCGCCTTATCCGGTAA
                CTATCGTCTTGAGTCCAACCCGGTAAGACACGACTTATCGCCACTGGCAGCAGCCA
                CTGGTAACAGGATTAGCAGAGCGAGGTATGTAGGCGGTGCTACAGAGTTCTTGAAG
                TGGTGGCCTAACTACGGCTACACTAGAAGGACAGTATTTGGTATCTGCGCTCTGCT
                GAAGCCAGTTACCTTCGGAAAAAGAGTTGGTAGCTCTTGATCCGGCAAACAAACCA
                CCGCTGGTAGCGGTGGTTTTTTTGTTTGCAAGCAGCAGATTACGCGCAGAAAAAAA
                GGATCTCAAGAAGATCCTTTGATCTTTTCTACGGGGTCTGACGCTCAGTGGAACGA
                AAACTCACGTTAAGGGATTTTGGTCATGAGATTATCAAAAAGGATCTTCACCTAGA
                TCCTTTTAAATTAAAAATGAAGTTTTAAATCAATCTAAAGTATATATGAGTAAACT
                TGGTCTGACAGTTACCAATGCTTAATCAGTGAGGCACCTATCTCAGCGATCTGTCT
                ATTTCGTTCATCCATAGTTGCCTGACTCCCCGTCGTGTAGATAACTACGATACGGG
                AGGGCTTACCATCTGGCCCCAGTGCTGCAATGATACCGCGAGACCCACGCTCACCG
                GCTCCAGATTTATCAGCAATAAACCAGCCAGCCGGAAGGGCCGAGCGCAGAAGTGG
                TCCTGCAACTTTATCCGCCTCCATCCAGTCTATTAATTGTTGCCGGGAAGCTAGAG
                TAAGTAGTTCGCCAGTTAATAGTTTGCGCAACGTTGTTGCCATTGCTACAGGCATC
                GTGGTGTCACGCTCGTCGTTTGGTATGGCTTCATTCAGCTCCGGTTCCCAACGATC
                AAGGCGAGTTACATGATCCCCCATGTTGTGCAAAAAAGCGGTTAGCTCCTTCGGTC
                CTCCGATCGTTGTCAGAAGTAAGTTGGCCGCAGTGTTATCACTCATGGTTATGGCA
                GCACTGCATAATTCTCTTACTGTCATGCCATCCGTAAGATGCTTTTCTGTGACTGG
                TGAGTACTCAACCAAGTCATTCTGAGAATAGTGTATGCGGCGACCGAGTTGCTCTT
                GCCCGGCGTCAATACGGGATAATACCGCGCCACATAGC
                (SEQ ID NO: 15)

CLTA1mg_OFF3    GCGTTTCTGGGTGAGCAAAAACAGGAAGGCAAAATGCCGCAAAAAAGGGAATAAGG
target:         GCGACACGGAAATGTTGAATACTCATACTCTTCCTTTTTCAATATTATTGAAGCAT
                TTATCAGGGTTATTGTCTCATGAGCGGATACATATTTGAATGTATTTAGAAAAATA
                AACAAATAGGGGTTCCGCGCACATTTCCCCGAAAAGTGCCACCTAAATTGTAAGCG
                TTAATATTTTGTTAAAATTCGCGTTAAATTTTTGTTAAATCAGCTCATTTTTTAAC
                CAATAGGCCGAAATCGGCAAAATCCCTTATAAATCAAAAGAATAGACCGAGATAGG
                GTTGAGTGTTGTTCCAGTTTGGAACAAGAGTCCACTATTAAAGAACGTGGACTCCA
                ACGTCAAAGGGCGAAAAACCGTCTATCAGGGCGATGGCCCACTACGTGAACCATCA
                CCCTAATCAAGTTTTTTGGGGTCGAGGTGCCGTAAAGCACTAAATCGGAACCCTAA
                AGGGAGCCCCCGATTTAGAGCTTGACGGGGAAAGCCGGCGAACGTGGCGAGAAAGG
                AAGGGAAGAAAGCGAAAGGAGCGGGCGCTAGGGCGCTGGCAAGTGTAGCGGTCACG
                CTGCGCGTAACCACCACACCCGCCGCGCTTAATGCGCCGCTACAGGGCGCGTCCCA
                TTCGCCATTCAGGCTGCGCAACTGTTGGGAAGGGCGATCGGTGCGGGCCTCTTCGC
                TATTACGCCAGCTGGCGAAAGGGGGATGTGCTGCAAGGCGATTAAGTTGGGTAACG
                CCAGGGTTTTCCCAGTCACGACGTTGTAAAACGACGGCCAGTGAGCGCGCGTAATA
```

| | |
|---|---|
| | CGACTCACTATAGGGCGAATTGGGTACGATCGATGCGGCCTCAGGAGAGGGAGCCA<br>TGCTCATCTCCAGCCCACTCCTCATCCCCCTCAAGC<u>CGG</u>TCCCAGGCTGAGAGGCT<br>AAAGCTTGTCTTTGCGCGTGATATGCAGCTCCAGCTTTTGTTCCCTTTAGTGAGGG<br>TTAATTGCGCGCTTGGCGTAATCATGGTCATAGCTGTTTCCTGTGTGAAATTGTTA<br>TCCGCTCACAATTCCACACAACATACGAGCCGGAAGCATAAAGTGTAAAGCCTGGG<br>GTGCCTAATGAGTGAGCTAACTCACATTAATTGCGTTGCGCTCACTGCCCGCTTTC<br>CAGTCGGGAAACCTGTCGTGCCAGCTGCATTAATGAATCGGCCAACGCGCGGGGAG<br>AGGCGGTTTGCGTATTGGGCGCTCTTCCGCTTCCTCGCTCACTGACTCGCTGCGCT<br>CGGTCGTTCGGCTGCGGCGAGCGGTATCAGCTCACTCAAAGGCGGTAATACGGTTA<br>TCCACAGAATCAGGGGATAACGCAGGAAAGAACATGTGAGCAAAAGGCCAGCAAAA<br>GGCCAGGAACCGTAAAAAGGCCGCGTTGCTGGCGTTTTTCCATAGGCTCCGCCCCC<br>CTGACGAGCATCACAAAAATCGACGCTCAAGTCAGAGGTGGCGAAACCCGACAGGA<br>CTATAAAGATACCAGGCGTTTCCCCCTGGAAGCTCCCTCGTGCGCTCTCCTGTTCC<br>GACCCTGCCGCTTACCGGATACCTGTCCGCCTTTCTCCCTTCGGGAAGCGTGGCGC<br>TTTCTCATAGCTCACGCTGTAGGTATCTCAGTTCGGTGTAGGTCGTTCGCTCCAAG<br>CTGGGCTGTGTGCACGAACCCCCCGTTCAGCCCGACCGCTGCGCCTTATCCGGTAA<br>CTATCGTCTTGAGTCCAACCCGGTAAGACACGACTTATCGCCACTGGCAGCAGCCA<br>CTGGTAACAGGATTAGCAGAGCGAGGTATGTAGGCGGTGCTACAGAGTTCTTGAAG<br>TGGTGGCCTAACTACGGCTACACTAGAAGGACAGTATTTGGTATCTGCGCTCTGCT<br>GAAGCCAGTTACCTTCGGAAAAAGAGTTGGTAGCTCTTGATCCGGCAAACAAACCA<br>CCGCTGGTAGCGGTGGTTTTTTTGTTTGCAAGCAGCAGATTACGCGCAGAAAAAAA<br>GGATCTCAAGAAGATCCTTTGATCTTTTCTACGGGGTCTGACGCTCAGTGGAACGA<br>AAACTCACGTTAAGGGATTTTGGTCATGAGATTATCAAAAAGGATCTTCACCTAGA<br>TCCTTTTAAATTAAAAATGAAGTTTTAAATCAATCTAAAGTATATATGAGTAAACT<br>TGGTCTGACAGTTACCAATGCTTAATCAGTGAGGCACCTATCTCAGCGATCTGTCT<br>ATTTCGTTCATCCATAGTTGCCTGACTCCCCGTCGTGTAGATAACTACGATACGGG<br>AGGGCTTACCATCTGGCCCCAGTGCTGCAATGATACCGCGAGACCCACGCTCACCG<br>GCTCCAGATTTATCAGCAATAAACCAGCCAGCCGGAAGGGCCGAGCGCAGAAGTGG<br>TCCTGCAACTTTATCCGCCTCCATCCAGTCTATTAATTGTTGCCGGGAAGCTAGAG<br>TAAGTAGTTCGCCAGTTAATAGTTTGCGCAACGTTGTTGCCATTGCTACAGGCATC<br>GTGGTGTCACGCTCGTCGTTTGGTATGGCTTCATTCAGCTCCGGTTCCCAACGATC<br>AAGGCGAGTTACATGATCCCCCATGTTGTGCAAAAAAGCGGTTAGCTCCTTCGGTC<br>CTCCGATCGTTGTCAGAAGTAAGTTGGCCGCAGTGTTATCACTCATGGTTATGGCA<br>GCACTGCATAATTCTCTTACTGTCATGCCATCCGTAAGATGCTTTTCTGTGACTGG<br>TGAGTACTCAACCAAGTCATTCTGAGAATAGTGTATGCGGCGACCGAGTTGCTCTT<br>GCCCGGCGTCAATACGGGATAATACCGCGCCACATAGC<br>(SEQ ID NO: 16) |
| CLTA4 ON-<br>target: | GCCGGGCAAGAGCAACTCGGTCGCCGCATACACTATTCTCAGAATGACTTGGTTGA<br>GTACTCACCAGTCACAGAAAAGCATCTTACGGATGGCATGACAGTAAGAGAATTAT<br>GCAGTGCTGCCATAACCATGAGTGATAACACTGCGGCCAACTTACTTCTGACAACG<br>ATCGGAGGACCGAAGGAGCTAACCGCTTTTTTGCACAACATGGGGGATCATGTAAC<br>TCGCCTTGATCGTTGGGAACCGGAGCTGAATGAAGCCATACCAAACGACGAGCGTG<br>ACACCACGATGCCTGTAGCAATGGCAACAACGTTGCGCAAACTATTAACTGGCGAA<br>CTACTTACTCTAGCTTCCCGGCAACAATTAATAGACTGGATGGAGGCGGATAAAGT<br>TGCAGGACCACTTCTGCGCTCGGCCCTTCCGGCTGGCTGGTTTATTGCTGATAAAT<br>CTGGAGCCGGTGAGCGTGGGTCTCGCGGTATCATTGCAGCACTGGGGCCAGATGGT<br>AAGCCCTCCCGTATCGTAGTTATCTACACGACGGGGAGTCAGGCAACTATGGATGA<br>ACGAAATAGACAGATCGCTGAGATAGGTGCCTCACTGATTAAGCATTGGTAACTGT<br>CAGACCAAGTTTACTCATATATACTTTAGATTGATTTAAAACTTCATTTTTAATTT<br>AAAAGGATCTAGGTGAAGATCCTTTTTGATAATCTCATGACCAAAATCCCTTAACG<br>TGAGTTTTCGTTCCACtGaGCGTCAGACCCCGTAGAAAAGATCAAAGGATCTTCTT<br>GAGATCCTTTTTTTCTGCGCGTAATCTGCTGCTTGCAAACAAAAAAACCACCGCTA<br>CCAGCGGTGGTTTGTTTGCCGGATCAAGAGCTACCAACTCTTTTTCCGAAGGTAAC<br>TGGCTTCAGCAGAGCGCAGATACCAAATACTGTTCTTCTAGTGTAGCCGTAGTTAG<br>GCCACCACTTCAAGAACTCTGTAGCACCGCCTACATACCTCGCTCTGCTAATCCTGT<br>TACCAGTGGCTGCTTGCCAGTGGCGATAAGTCGTGTCTTACCGGGTTGGACTCAAG<br>ACGATAGTTACCGGATAAGGCGCAGCGGTCGGGCTGAACGGGGGGTTCGTGCACAC<br>AGCCCAGCTTGGAGCGAACGACCTACACCGAACTGAGATACCTACAGCGTGAGCTA<br>TGAGAAAGCGCCACGCTTCCCGAAGGGAGAAAGGCGGACAGGTATCCGGTAAGCGG<br>CAGGGTCGGAACAGGAGAGCGCACGAGGGAGCTTCCAGGGGGAAACGCCTGGTATC<br>TTTATAGTCCTGTCGGGTTTCGCCACCTCTGACTTGAGCGTCGATTTTTGTGATGC<br>TCGTCAGGGGGCGGAGCCTATGGAAAAACGCCAGCAACGCGGCCTTTTTACGGTT<br>CCTGGCCTTTTGCTGGCCTTTTGCTCACATGTTCTTTCCTGCGTTATCCCCTGATT<br>CTGTGGATAACCGTATTACCGCCTTTGAGTGAGCTGATACCGCTCGCCGCAGCCGA<br>ACGACCGAGCGCAGCGAGTCAGTGAGCGAGGAAGCGGAAGAGCGCCCAATACGCAA<br>ACCGCCTCTCCCCGCGCGTTGGCCGATTCATTAATGCAGCTGGCACGACAGGTTTC<br>CCGACTGGAAAGCGGGCAGTGAGCGCAACGCAATTAATGTGAGTTAGCTCACTCAT<br>TAGGCACCCCAGGCTTTACACTTTATGCTTCCGGCTCGTATGTTGTGTGGAATTGT<br>GAGCGGATAACAATTTCACACAGGAAACAGCTATGACCATGATTACGCCAAGCGCG<br>CAATTAACCCTCACTAAAGGGAACAAAAGCTGGGTACCGGGCCCCCCCTCGACACC<br>AGTTGCATTCGATTCCTGTTTGTAATTGTCCAATTCCTGCAGCCCGGGGATCGGC<br>AGATGTAGTGTTTCCACA<u>GGGG</u>GATCCACTAGTTCTAGAGCGGCCGCCACCGCGGTG<br>GAGCTCCAATTCGCCCTATAGTGAGTCGTATTACGCGCGCTCACTGGCCGTCGTTT<br>TACAACGTCGTGACTGGGAAAACCCTGGCGTTACCCAACTTAATCGCCTTGCAGCA<br>CATCCCCCTTTCGCCAGCTGGCGTAATAGCGAAGAGGCCCGCACCGATCGCCCTTC<br>CCAACAGTTGCGCAGCCTGAATGGCGAATGGAAATTGTAAGCGTTAATATTTTGTT<br>AAAATTCGCGTTAAATTTTTGTTAAATCAGCTCATTTTTTAACCAATAGGCCGAAA<br>TCGGCAAAATCCCTTATAAATCAAAAGAATAGACCGAGATAGGGTTGAGTGTTGTT |

```
CCAGTTTGGAACAAGAGTCCACTATTAAAGAACGTGGACTCCAACGTCAAAGGGCG
AAAAACCGTCTATCAGGGCGATGGCCCACTACGTGAACCATCACCCTAATCAAGTT
TTTTGGGGTCGAGGTGCCGTAAAGCACTAAATCGGAACCCTAAAGGGAGCCCCCGA
TTTAGAGCTTGACGGGAAAGCCGGCGAACGTGGCGAGAAAGGAAGGGAAGAAAGC
GAAAGGAGCGGGCGCTAGGGCGCTGGCAAGTGTAGCGGTCACGCTGCGCGTAACCA
CCACACCCGCCGCGCTTAATGCGCCGCTACAGGGCGCGTCAGGTGGCACTTTTCGG
GGAAATGTGCGCGGAACCCCTATTTGTTTATTTTTCTAAATACATTCAAATATGTA
TCCGCTCATGAGACAATAACCCTGATAAATGCTTCAATAATATTGAAAAAGGAAGA
GTATGAGTATTCAACATTTCCGTGTCGCCCTTATTCCCTTTTTTGCGGCATTTTGC
CTTCCTGTTTTTGCTCACCCAGAAACGCTGGTGAAAGTAAAAGATGCTGAAGATCA
GTTGGGTGCACGAGTGGGTTACATCGAACTGGATCTCAACAGCGGTAAGATCCTTG
AGAGTTTTCGCCCCGAAGAACGTTTTCCAATGATGAGCACTTTTAAAGTTCTGCTA
TGTGGCGCGGTATTATCCCGTATTGAC
(SEQ ID NO: 17)
```

CLTA4mg ON-target:
```
GCGTTTCTGGGTGAGCAAAACAGGAAGGCAAATGCCGCAAAAAAGGGAATAAGG
GCGACACGGAAATGTTGAATACTCATACTCTTCCTTTTTCAATATTATTGAAGCAT
TTATCAGGGTTATTGTCTCATGAGCGGATACATATTTGAATGTATTTAGAAAAATA
AACAAATAGGGGTTCCGCGCACATTTCCCCGAAAAGTGCCACCTAAATTGTAAGCG
TTAATATTTTGTTAAAATTCGCGTTAAATTTTTGTTAAATCAGCTCATTTTTTAAC
CAATAGGCCGAAATCGGCAAAATCCCTTATAAATCAAAGAATAGACCGAGATAGG
GTTGAGTGTTGTTCCAGTTTGGAACAAGAGTCCACTATTAAAGAACGTGGACTCCA
ACGTCAAAGGGCGAAAAACCGTCTATCAGGGCGATGGCCCACTACGTGAACCATCA
CCCTAATCAAGTTTTTTGGGGTCGAGGTGCCGTAAAGCACTAAATCGGAACCCTAA
AGGGAGCCCCCGATTTAGAGCTTGACGGGAAAGCCGGCGAACGTGGCGAGAAAGG
AAGGGAAGAAAGCGAAAGGAGCGGGCGCTAGGGCGCTGGCAAGTGTAGCGGTCACG
CTGCGCGTAACCACCACACCCGCCGCGCTTAATGCGCCGCTACAGGGCGCGTCCCA
TTCGCCATTCAGGCTGCGCAACTGTTGGGAAGGGCGATCGGTGCGGGCCTCTTCGC
TATTACGCCAGCTGGCGAAAGGGGGATGTGCTGCAAGGCGATTAAGTTGGGTAACG
CCAGGGTTTTCCCAGTCACGACGTTGTAAAACGACGGCCAGTGAGCGCGCGTAATA
CGACTCACTATAGGGCGAATTGGGTACGATCGATGCGGCCTCAAGAGCTTCACTGA
GTAGGATTAAGATATTGCAGATGTAGTGTTTCCACAGGGTGGCTCTTCAGTGCACC
AGCGGAACCTGCTGCGCGTGATATGCAGCTCCAGCTTTTGTTCCCTTTAGTGAGGG
TTAATTGCGCGCTTGGCGTAATCATGGTCATAGCTGTTTCCTGTGTGAAATTGTTA
TCCGCTCACAATTCCACACAACATACGAGCCGGAAGCATAAAGTGTAAAGCCTGGG
GTGCCTAATGAGTGAGCTAACTCACATTAATTGCGTTGCGCTCACTGCCCGCTTTC
CAGTCGGGAAACCTGTCGTGCCAGCTGCATTAATGAATCGGCCAACGCGCGGGGAG
AGGCGGTTTGCGTATTGGGCGCTCTTCCGCTTCCTCGCTCACTGACTCGCTGCGCT
CGGTCGTTCGGCTGCGGCGAGCGGTATCAGCTCACTCAAAGGCGGTAATACGGTTA
TCCACAGAATCAGGGGATAACGCAGGAAAGAACATGTGAGCAAAAGGCCAGCAAAA
GGCCAGGAACCGTAAAAAGGCCGCGTTGCTGGCGTTTTTCCATAGGCTCCGCCCCC
CTGACGAGCATCACAAAAATCGACGCTCAAGTCAGAGGTGGCGAAACCCGACAGGA
CTATAAAGATACCAGGCGTTTCCCCCTGGAAGCTCCCTCGTGCGCTCTCCTGTTCC
GACCCTGCCGCTTACCGGATACCTGTCCGCCTTTCTCCCTTCGGGAAGCGTGGCGC
TTTCTCATAGCTCACGCTGTAGGTATCTCAGTTCGGTGTAGGTCGTTCGCTCCAAG
CTGGGCTGTGTGCACGAACCCCCCGTTCAGCCCGACCGCTGCGCCTTATCCGGTAA
CTATCGTCTTGAGTCCAACCCGGTAAGACACGACTTATCGCCACTGGCAGCAGCCA
CTGGTAACAGGATTAGCAGAGCGAGGTATGTAGGCGGTGCTACAGAGTTCTTGAAG
TGGTGGCCTAACTACGGCTACACTAGAAGGACAGTATTTGGTATCTGCGCTCTGCT
GAAGCCAGTTACCTTCGGAAAAAGAGTTGGTAGCTCTTGATCCGGCAAACAAACCA
CCGCTGGTAGCGGTGGTTTTTTTGTTTGCAAGCAGCAGATTACGCGCAGAAAAAAA
GGATCTCAAGAAGATCCTTTGATCTTTTCTACGGGGTCTGACGCTCAGTGGAACGA
AAACTCACGTTAAGGGATTTTGGTCATGAGATTATCAAAAAGGATCTTCACCTAGA
TCCTTTTAAATTAAAAATGAAGTTTTAAATCAATCTAAAGTATATATGAGTAAACT
TGGTCTGACAGTTACCAATGCTTAATCAGTGAGGCACCTATCTCAGCGATCTGTCT
ATTTCGTTCATCCATAGTTGCCTGACTCCCCGTCGTGTAGATAACTACGATACGGG
AGGGCTTACCATCTGGCCCCAGTGCTGCAATGATACCGCGAGACCCACGCTCACCG
GCTCCAGATTTATCAGCAATAAACCAGCCAGCCGGAAGGGCCGAGCGCAGAAGTGG
TCCTGCAACTTTATCCGCCTCCATCCAGTCTATTAATTGTTGCCGGGAAGCTAGAG
TAAGTAGTTCGCCAGTTAATAGTTTGCGCAACGTTGTTGCCATTGCTACAGGCATC
GTGGTGTCACGCTCGTCGTTTGGTATGGCTTCATTCAGCTCCGGTTCCCAACGATC
AAGGCGAGTTACATGATCCCCCATGTTGTGCAAAAAAGCGGTTAGCTCCTTCGGTC
CTCCGATCGTTGTCAGAAGTAAGTTGGCCGCAGTGTTATCACTCATGGTTATGGCA
GCACTGCATAATTCTCTTACTGTCATGCCATCCGTAAGATGCTTTTCTGTGACTGG
TGAGTACTCAACCAAGTCATTCTGAGAATAGTGTATGCGGCGACCGAGTTGCTCTT
GCCCGGCGTCAATACGGGATAATACCGCGCCACATAGC
(SEQ ID NO: 18)
```

CLTA4mg OFF5-target:
```
GCGTTTCTGGGTGAGCAAAACAGGAAGGCAAATGCCGCAAAAAAGGGAATAAGG
GCGACACGGAAATGTTGAATACTCATACTCTTCCTTTTTCAATATTATTGAAGCAT
TTATCAGGGTTATTGTCTCATGAGCGGATACATATTTGAATGTATTTAGAAAAATA
AACAAATAGGGGTTCCGCGCACATTTCCCCGAAAAGTGCCACCTAAATTGTAAGCG
TTAATATTTTGTTAAAATTCGCGTTAAATTTTTGTTAAATCAGCTCATTTTTTAAC
CAATAGGCCGAAATCGGCAAAATCCCTTATAAATCAAAGAATAGACCGAGATAGG
GTTGAGTGTTGTTCCAGTTTGGAACAAGAGTCCACTATTAAAGAACGTGGACTCCA
ACGTCAAAGGGCGAAAAACCGTCTATCAGGGCGATGGCCCACTACGTGAACCATCA
CCCTAATCAAGTTTTTTGGGGTCGAGGTGCCGTAAAGCACTAAATCGGAACCCTAA
AGGGAGCCCCCGATTTAGAGCTTGACGGGAAAGCCGGCGAACGTGGCGAGAAAGG
AAGGGAAGAAAGCGAAAGGAGCGGGCGCTAGGGCGCTGGCAAGTGTAGCGGTCACG
```

```
                    CTGCGCGTAACCACCACACCCGCCGCGCTTAATGCGCCGCTACAGGGCGCGTCCCA
                    TTCGCCATTCAGGCTGCGCAACTGTTGGGAAGGGCGATCGGTGCGGGCCTCTTCGC
                    TATTACGCCAGCTGGCGAAAGGGGATGTGCTGCAAGGCGATTAAGTTGGGTAACG
                    CCAGGGTTTTCCCAGTCACGACGTTGTAAAACGACGGCCAGTGAGCGCGCGTAATA
                    CGACTCACTATAGGGCGAATTGGGTACGATCGATGCGGCCTCTCTGAATAGAGTTG
                    GGAAGAGATGCATACAACATATGTAGTATTTCCACAGGGAATACAATGGACAAATG
                    ACCTCAAGAGCAGGCGCGTGATATGCAGCTCCAGCTTTTGTTCCCTTTAGTGAGGG
                    TTAATTGCGCGCTTGGCGTAATCATGGTCATAGCTGTTTCCTGTGTGAAATTGTTA
                    TCCGCTCACAATTCCACACAACATACGAGCCGGAAGCATAAAGTGTAAAGCCTGGG
                    GTGCCTAATGAGTGAGCTAACTCACATTAATTGCGTTGCGCTCACTGCCCGCTTTC
                    CAGTCGGGAAACCTGTCGTGCCAGCTGCATTAATGAATCGGCCAACGCGCGGGGAG
                    AGGCGGTTTGCGTATTGGGCGCTCTTCCGCTTCCTCGCTCACTGACTCGCTGCGCT
                    CGGTCGTTCGGCTGCGGCGAGCGGTATCAGCTCACTCAAAGGCGGTAATACGGTTA
                    TCCACAGAATCAGGGGATAACGCAGGAAAGAACATGTGAGCAAAAGGCCAGCAAAA
                    GGCCAGGAACCGTAAAAAGGCCGCGTTGCTGGCGTTTTTCCATAGGCTCCGCCCCC
                    CTGACGAGCATCACAAAAATCGACGCTCAAGTCAGAGGTGGCGAAACCCGACAGGA
                    CTATAAAGATACCAGGCGTTTCCCCCTGGAAGCTCCCTCGTGCGCTCTCCTGTTCC
                    GACCCTGCCGCTTACCGGATACCTGTCCGCCTTTCTCCCTTCGGGAAGCGTGGCGC
                    TTTCTCATAGCTCACGCTGTAGGTATCTCAGTTCGGTGTAGGTCGTTCGCTCCAAG
                    CTGGGCTGTGTGCACGAACCCCCCGTTCAGCCCGACCGCTGCGCCTTATCCGGTAA
                    CTATCGTCTTGAGTCCAACCCGGTAAGACACGACTTATCGCCACTGGCAGCAGCCA
                    CTGGTAACAGGATTAGCAGAGCGAGGTATGTAGGCGGTGCTACAGAGTTCTTGAAG
                    TGGTGGCCTAACTACGGCTACACTAGAAGGACAGTATTTGGTATCTGCGCTCTGCT
                    GAAGCCAGTTACCTTCGGAAAAAGAGTTGGTAGCTCTTGATCCGGCAAACAAACCA
                    CCGCTGGTAGCGGTGGTTTTTTTGTTTGCAAGCAGCAGATTACGCGCAGAAAAAAA
                    GGATCTCAAGAAGATCCTTTGATCTTTTCTACGGGGTCTGACGCTCAGTGGAACGA
                    AAACTCACGTTAAGGGATTTTGGTCATGAGATTATCAAAAAGGATCTTCACCTAGA
                    TCCTTTTAAATTAAAAATGAAGTTTTAAATCAATCTAAAGTATATATGAGTAAACT
                    TGGTCTGACAGTTACCAATGCTTAATCAGTGAGGCACCTATCTCAGCGATCTGTCT
                    ATTTCGTTCATCCATAGTTGCCTGACTCCCCGTCGTGTAGATAACTACGATACGGG
                    AGGGCTTACCATCTGGCCCCAGTGCTGCAATGATACCGCGAGACCCACGCTCACCG
                    GCTCCAGATTTATCAGCAATAAACCAGCCAGCCGGAAGGGCCGAGCGCAGAAGTGG
                    TCCTGCAACTTTATCCGCCTCCATCCAGTCTATTAATTGTTGCCGGGAAGCTAGAG
                    TAAGTAGTTCGCCAGTTAATAGTTTGCGCAACGTTGTTGCCATTGCTACAGGCATC
                    GTGGTGTCACGCTCGTCGTTTGGTATGGCTTCATTCAGCTCCGGTTCCCAACGATC
                    AAGGCGAGTTACATGATCCCCCATGTTGTGCAAAAAAGCGGTTAGCTCCTTCGGTC
                    CTCCGATCGTTGTCAGAAGTAAGTTGGCCGCAGTGTTATCACTCATGGTTATGGCA
                    GCACTGCATAATTCTCTTACTGTCATGCCATCCGTAAGATGCTTTTCTGTGACTGG
                    TGAGTACTCAACCAAGTCATTCTGAGAATAGTGTATGCGGCGACCGAGTTGCTCTT
                    GCCCGGCGTCAATACGGGATAATACCGCGCCACATAGC
                    (SEQ ID NO: 19)

IL2RGmg_ON          GCGTTTCTGGGTGAGCAAAACAGGAAGGCAAATGCCGCAAAAAAGGGAATAAGG
target:             GCGACACGGAAATGTTGAATACTCATACTCTTCCTTTTTCAATATTATTGAAGCAT
                    TTATCAGGGTTATTGTCTCATGAGCGGATACATATTTGAATGTATTTAGAAAAATA
                    AACAAATAGGGGTTCCGCGCACATTTCCCCGAAAAGTGCCACCTAAATTGTAAGCG
                    TTAATATTTTGTTAAAATTCGCGTTAAATTTTTGTTAAATCAGCTCATTTTTTAAC
                    CAATAGGCCGAAATCGGCAAAATCCCTTATAAATCAAAAGAATAGACCGAGATAGG
                    GTTGAGTGTTGTTCCAGTTTGGAACAAGAGTCCACTATTAAAGAACGTGGACTCCA
                    ACGTCAAAGGGCGAAAAACCGTCTATCAGGGCGATGGCCCACTACGTGAACCATCA
                    CCCTAATCAAGTTTTTTGGGGTCGAGGTGCCGTAAAGCACTAAATCGGAACCCTAA
                    AGGGAGCCCCCGATTTAGAGCTTGACGGGGAAAGCCGGCGAACGTGGCGAGAAAGG
                    AAGGGAAGAAAGCGAAAGGAGCGGGCGCTAGGGCGCTGGCAAGTGTAGCGGTCACG
                    CTGCGCGTAACCACCACACCCGCCGCGCTTAATGCGCCGCTACAGGGCGCGTCCCA
                    TTCGCCATTCAGGCTGCGCAACTGTTGGGAAGGGCGATCGGTGCGGGCCTCTTCGC
                    TATTACGCCAGCTGGCGAAAGGGGATGTGCTGCAAGGCGATTAAGTTGGGTAACG
                    CCAGGGTTTTCCCAGTCACGACGTTGTAAAACGACGGCCAGTGAGCGCGCGTAATA
                    CGACTCACTATAGGGCGAATTGGGTACGATCGATGCGGCCTCGGCAGCTGCAGGA
                    ATAAGAGGGATGTGAATGGTAATGATGGCTTCAACATGGCGCTTGCTCTTCATTCC
                    CTGGGTGTAGTCTGCGCGTGATATGCAGCTCCAGCTTTTGTTCCCTTTAGTGAGGG
                    TTAATTGCGCGCTTGGCGTAATCATGGTCATAGCTGTTTCCTGTGTGAAATTGTTA
                    TCCGCTCACAATTCCACACAACATACGAGCCGGAAGCATAAAGTGTAAAGCCTGGG
                    GTGCCTAATGAGTGAGCTAACTCACATTAATTGCGTTGCGCTCACTGCCCGCTTTC
                    CAGTCGGGAAACCTGTCGTGCCAGCTGCATTAATGAATCGGCCAACGCGCGGGGAG
                    AGGCGGTTTGCGTATTGGGCGCTCTTCCGCTTCCTCGCTCACTGACTCGCTGCGCT
                    CGGTCGTTCGGCTGCGGCGAGCGGTATCAGCTCACTCAAAGGCGGTAATACGGTTA
                    TCCACAGAATCAGGGGATAACGCAGGAAAGAACATGTGAGCAAAAGGCCAGCAAAA
                    GGCCAGGAACCGTAAAAAGGCCGCGTTGCTGGCGTTTTTCCATAGGCTCCGCCCCC
                    CTGACGAGCATCACAAAAATCGACGCTCAAGTCAGAGGTGGCGAAACCCGACAGGA
                    CTATAAAGATACCAGGCGTTTCCCCCTGGAAGCTCCCTCGTGCGCTCTCCTGTTCC
                    GACCCTGCCGCTTACCGGATACCTGTCCGCCTTTCTCCCTTCGGGAAGCGTGGCGC
                    TTTCTCATAGCTCACGCTGTAGGTATCTCAGTTCGGTGTAGGTCGTTCGCTCCAAG
                    CTGGGCTGTGTGCACGAACCCCCCGTTCAGCCCGACCGCTGCGCCTTATCCGGTAA
                    CTATCGTCTTGAGTCCAACCCGGTAAGACACGACTTATCGCCACTGGCAGCAGCCA
                    CTGGTAACAGGATTAGCAGAGCGAGGTATGTAGGCGGTGCTACAGAGTTCTTGAAG
                    TGGTGGCCTAACTACGGCTACACTAGAAGGACAGTATTTGGTATCTGCGCTCTGCT
                    GAAGCCAGTTACCTTCGGAAAAAGAGTTGGTAGCTCTTGATCCGGCAAACAAACCA
                    CCGCTGGTAGCGGTGGTTTTTTTGTTTGCAAGCAGCAGATTACGCGCAGAAAAAAA
                    GGATCTCAAGAAGATCCTTTGATCTTTTCTACGGGGTCTGACGCTCAGTGGAACGA
```

```
                    AAACTCACGTTAAGGGATTTTGGTCATGAGATTATCAAAAGGATCTTCACCTAGA
                    TCCTTTTAAATTAAAAATGAAGTTTTAAATCAATCTAAAGTATATATGAGTAAACT
                    TGGTCTGACAGTTACCAATGCTTAATCAGTGAGGCACCTATCTCAGCGATCTGTCT
                    ATTTCGTTCATCCATAGTTGCCTGACTCCCCGTCGTGTAGATAACTACGATACGGG
                    AGGGCTTACCATCTGGCCCCAGTGCTGCAATGATACCGCGAGACCCACGCTCACCG
                    GCTCCAGATTTATCAGCAATAAACCAGCCAGCCGGAAGGGCCGAGCGCAGAAGTGG
                    TCCTGCAACTTTATCCGCCTCCATCCAGTCTATTAATTGTTGCCGGGAAGCTAGAG
                    TAAGTAGTTCGCCAGTTAATAGTTTGCGCAACGTTGTTGCCATTGCTACAGGCATC
                    GTGGTGTCACGCTCGTCGTTTGGTATGGCTTCATTCAGCTCCGGTTCCCAACGATC
                    AAGGCGAGTTACATGATCCCCCATGTTGTGCAAAAAAGCGGTTAGCTCCTTCGGTC
                    CTCCGATCGTTGTCAGAAGTAAGTTGGCCGCAGTGTTATCACTCATGGTTATGGCA
                    GCACTGCATAATTCTCTTACTGTCATGCCATCCGTAAGATGCTTTTCTGTGACTGG
                    TGAGTACTCAACCAAGTCATTCTGAGAATAGTGTATGCGGCGACCGAGTTGCTCTT
                    GCCCGGCGTCAATACGGGATAATACCGCGCCACATAGC
                    (SEQ ID NO: 20)

EN1mg_ON           GCGTTTCTGGGTGAGCAAAAACAGGAAGGCAAATGCCGCAAAAAAGGGAATAAGG
target:             GCGACACGGAAATGTTGAATACTCATACTCTTCCTTTTTCAATATTATTGAAGCAT
                    TTATCAGGGTTATTGTCTCATGAGCGGATACATATTTGAATGTATTTAGAAAAATA
                    AACAAATAGGGGTTCCGCGCACATTTCCCCGAAAAGTGCCACCTAAATTGTAAGCG
                    TTAATATTTTGTTAAAATTCGCGTTAAATTTTTGTTAAATCAGCTCATTTTTTAAC
                    CAATAGGCCGAAATCGGCAAAATCCCTTATAAATCAAAAGAATAGACCGAGATAGG
                    GTTGAGTGTTGTTCCAGTTTGGAACAAGAGTCCACTATTAAAGAACGTGGACTCCA
                    ACGTCAAAGGGCGAAAAACCGTCTATCAGGGCGATGGCCCACTACGTGAACCATCA
                    CCCTAATCAAGTTTTTTGGGGTCGAGGTGCCGTAAAGCACTAAATCGGAACCCTAA
                    AGGGAGCCCCCGATTTAGAGCTTGACGGGGAAAGCCGGCGAACGTGGCGAGAAAGG
                    AAGGGAAGAAAGCGAAAGGAGCGGGCGCTAGGGCGCTGGCAAGTGTAGCGGTCACG
                    CTGCGCGTAACCACCACACCCGCCGCGCTTAATGCGCCGCTACAGGGCGCGTCCCA
                    TTCGCCATTCAGGCTGCGCAACTGTTGGGAAGGGCGATCGGTGCGGGCCTCTTCGC
                    TATTACGCCAGCTGGCGAAAGGGGGATGTGCTGCAAGGCGATTAAGTTGGGTAACG
                    CCAGGGTTTTCCCAGTCACGACGTTGTAAAACGACGGCCAGTGAGCGCGCGTAATA
                    CGACTCACTATAGGGCGAATTGGGTACGATCGATGCGGCCTCCTCCTTACTGCAGC
                    CGAAGTCCGGCCTCAGGATGTTGTCGATGAAAAAGTTGGTGGTGCGGTGCAGCTGG
                    GCCGCTGGCTGCGGCGCGTGATATGCAGCTCCTGTTTTGTTCCCTTAGTGAGGG
                    TTAATTGCGCGCTTGGCGTAATCATGGTCATAGCTGTTTCCTGTGTGAAATTGTTA
                    TCCGCTCACAATTCCACACAACATACGAGCCGGAAGCATAAAGTGTAAAGCCTGGG
                    GTGCCTAATGAGTGAGCTAACTCACATTAATTGCGTTGCGCTCACTGCCCGCTTTC
                    CAGTCGGGAAACCTGTCGTGCCAGCTGCATTAATGAATCGGCCAACGCGCGGGGAG
                    AGGCGGTTTGCGTATTGGGCGCTCTTCCGCTTCCTCGCTCACTGACTCGCTGCGCT
                    CGGTCGTTCGGCTGCGGCGAGCGGTATCAGCTCACTCAAAGGCGGTAATACGGTTA
                    TCCACAGAATCAGGGGATAACGCAGGAAAGAACATGTGAGCAAAAGGCCAGCAAAA
                    GGCCAGGAACCGTAAAAAGGCCGCGTTGCTGGCGTTTTTCCATAGGCTCCGCCCCC
                    CTGACGAGCATCACAAAAATCGACGCTCAAGTCAGAGGTGGCGAAACCCGACAGGA
                    CTATAAAGATACCAGGCGTTTCCCCCTGGAAGCTCCCTCGTGCGCTCTCCTGTTCC
                    GACCCTGCCGCTTACCGGATACCTGTCCGCCTTTCTCCCTTCGGGAAGCGTGGCGC
                    TTTCTCATAGCTCACGCTGTAGGTATCTCAGTTCGGTGTAGGTCGTTCGCTCCAAG
                    CTGGGCTGTGTGCACGAACCCCCCGTTCAGCCCGACCGCTGCGCCTTATCCGGTAA
                    CTATCGTCTTGAGTCCAACCCGGTAAGACACGACTTATCGCCACTGGCAGCAGCCA
                    CTGGTAACAGGATTAGCAGAGCGAGGTATGTAGGCGGTGCTACAGAGTTCTTGAAG
                    TGGTGGCCTAACTACGGCTACACTAGAAGGACAGTATTTGGTATCTGCGCTCTGCT
                    GAAGCCAGTTACCTTCGGAAAAAGAGTTGGTAGCTCTTGATCCGGCAAACAAACCA
                    CCGCTGGTAGCGGTGGTTTTTTTGTTTGCAAGCAGCAGATTACGCGCAGAAAAAAA
                    GGATCTCAAGAAGATCCTTTGATCTTTTCTACGGGGTCTGACGCTCAGTGGAACGA
                    AAACTCACGTTAAGGGATTTTGGTCATGAGATTATCAAAAGGATCTTCACCTAGA
                    TCCTTTTAAATTAAAAATGAAGTTTTAAATCAATCTAAAGTATATATGAGTAAACT
                    TGGTCTGACAGTTACCAATGCTTAATCAGTGAGGCACCTATCTCAGCGATCTGTCT
                    ATTTCGTTCATCCATAGTTGCCTGACTCCCCGTCGTGTAGATAACTACGATACGGG
                    AGGGCTTACCATCTGGCCCCAGTGCTGCAATGATACCGCGAGACCCACGCTCACCG
                    GCTCCAGATTTATCAGCAATAAACCAGCCAGCCGGAAGGGCCGAGCGCAGAAGTGG
                    TCCTGCAACTTTATCCGCCTCCATCCAGTCTATTAATTGTTGCCGGGAAGCTAGAG
                    TAAGTAGTTCGCCAGTTAATAGTTTGCGCAACGTTGTTGCCATTGCTACAGGCATC
                    GTGGTGTCACGCTCGTCGTTTGGTATGGCTTCATTCAGCTCCGGTTCCCAACGATC
                    AAGGCGAGTTACATGATCCCCCATGTTGTGCAAAAAAGCGGTTAGCTCCTTCGGTC
                    CTCCGATCGTTGTCAGAAGTAAGTTGGCCGCAGTGTTATCACTCATGGTTATGGCA
                    GCACTGCATAATTCTCTTACTGTCATGCCATCCGTAAGATGCTTTTCTGTGACTGG
                    TGAGTACTCAACCAAGTCATTCTGAGAATAGTGTATGCGGCGACCGAGTTGCTCTT
                    GCCCGGCGTCAATACGGGATAATACCGCGCCACATAGC
                    (SEQ ID NO: 21)

EN1mg_OFF          GCGTTTCTGGGTGAGCAAAAACAGGAAGGCAAATGCCGCAAAAAAGGGAATAAGG
target:             GCGACACGGAAATGTTGAATACTCATACTCTTCCTTTTTCAATATTATTGAAGCAT
                    TTATCAGGGTTATTGTCTCATGAGCGGATACATATTTGAATGTATTTAGAAAAATA
                    AACAAATAGGGGTTCCGCGCACATTTCCCCGAAAAGTGCCACCTAAATTGTAAGCG
                    TTAATATTTTGTTAAAATTCGCGTTAAATTTTTGTTAAATCAGCTCATTTTTTAAC
                    CAATAGGCCGAAATCGGCAAAATCCCTTATAAATCAAAAGAATAGACCGAGATAGG
                    GTTGAGTGTTGTTCCAGTTTGGAACAAGAGTCCACTATTAAAGAACGTGGACTCCA
                    ACGTCAAAGGGCGAAAAACCGTCTATCAGGGCGATGGCCCACTACGTGAACCATCA
                    CCCTAATCAAGTTTTTTGGGGTCGAGGTGCCGTAAAGCACTAAATCGGAACCCTAA
                    AGGGAGCCCCCGATTTAGAGCTTGACGGGGAAAGCCGGCGAACGTGGCGAGAAAGG
```

```
                AAGGGAAGAAAGCGAAAGGAGCGGGCGCTAGGGCGCTGGCAAGTGTAGCGGTCACG
                CTGCGCGTAACCACCACACCCGCCGCGCTTAATGCGCCGCTACAGGGCGCGTCCCA
                TTCGCCATTCAGGCTGCGCAACTGTTGGGAAGGGCGATCGGTGCGGGCCTCTTCGC
                TATTACGCCAGCTGGCGAAAGGGGGATGTGCTGCAAGGCGATTAAGTTGGGTAACG
                CCAGGGTTTTCCCAGTCACGACGTTGTAAAACGACGGCCAGTGAGCGCGCGTAATA
                CGACTCACTATAGGGCGAATTGGGTACGATCGATGCGGCCTCGTCCTTTCGCCGGC
                CGAACTCGGGCCGCAGGATGTTGTCGATGAAGAAGTTGGTGATGCGGTGCGGGTGC
                TGGTGGTTGCCGGGCGCGTGATATGCAGCTCCAGCTTTTGTTCCCTTTAGTGAGGG
                TTAATTGCGCGCTTGGCGTAATCATGGTCATAGCTGTTTCCTGTGTGAAATTGTTA
                TCCGCTCACAATTCCACACAACATACGAGCCGGAAGCATAAAGTGTAAAGCCTGGG
                GTGCCTAATGAGTGAGCTAACTCACATTAATTGCGTTGCGCTCACTGCCCGCTTTC
                CAGTCGGGAAACCTGTCGTGCCAGCTGCATTAATGAATCGGCCAACGCGCGGGGAG
                AGGCGGTTTGCGTATTGGGCGCTCTTCCGCTTCCTCGCTCACTGACTCGCTGCGCT
                CGGTCGTTCGGCTGCGGCGAGCGGTATCAGCTCACTCAAAGGCGGTAATACGGTTA
                TCCACAGAATCAGGGGATAACGCAGGAAAGAACATGTGAGCAAAAGGCCAGCAAAA
                GGCCAGGAACCGTAAAAAGGCGCGTTGCTGGCGTTTTTCCATAGGCTCCGCCCCC
                CTGACGAGCATCACAAAAATCGACGCTCAAGTCAGAGGTGGCGAAACCCGACAGGA
                CTATAAAGATACCAGGCGTTTCCCCCTGGAAGCTCCCTCGTGCGCTCTCCTGTTCC
                GACCCTGCCGCTTACCGGATACCTGTCCGCCTTTCTCCCTTCGGGAAGCGTGGCGC
                TTTCTCATAGCTCACGCTGTAGGTATCTCAGTTCGGTGTAGGTCGTTCGCTCCAAG
                CTGGGCTGTGTGCACGAACCCCCCGTTCAGCCCGACCGCTGCGCCTTATCCGGTAA
                CTATCGTCTTGAGTCCAACCCGGTAAGACACGACTTATCGCCACTGGCAGCAGCCA
                CTGGTAACAGGATTAGCAGAGCGAGGTATGTAGGCGGTGCTACAGAGTTCTTGAAG
                TGGTGGCCTAACTACGGCTACACTAGAAGGACAGTATTTGGTATCTGCGCTCTGCT
                GAAGCCAGTTACCTTCGGAAAAAGAGTTGGTAGCTCTTGATCCGGCAAACAAACCA
                CCGCTGGTAGCGGTGGTTTTTTTGTTTGCAAGCAGCAGATTACGCGCAGAAAAAAA
                GGATCTCAAGAAGATCCTTTGATCTTTTCTACGGGGTCTGACGCTCAGTGGAACGA
                AAACTCACGTTAAGGGATTTTGGTCATGAGATTATCAAAAAGGATCTTCACCTAGA
                TCCTTTTAAATTAAAAATGAAGTTTTAAATCAATCTAAAGTATATATGAGTAAACT
                TGGTCTGACAGTTACCAATGCTTAATCAGTGAGGCACCTATCTCAGCGATCTGTCT
                ATTTCGTTCATCCATAGTTGCCTGACTCCCCGTCGTGTAGATAACTACGATACGGG
                AGGGCTTACCATCTGGCCCCAGTGCTGCAATGATACCGCGAGACCCACGCTCACCG
                GCTCCAGATTTATCAGCAATAAACCAGCCAGCCGGAAGGGCCGAGCGCAGAAGTGG
                TCCTGCAACTTTATCCGCCTCCATCCAGTCTATTAATTGTTGCCGGGAAGCTAGAG
                TAAGTAGTTCGCCAGTTAATAGTTTGCGCAACGTTGTTGCCATTGCTACAGGCATC
                GTGGTGTCACGCTCGTCGTTTGGTATGGCTTCATTCAGCTCCGGTTCCCAACGATC
                AAGGCGAGTTACATGATCCCCCATGTTGTGCAAAAAAGCGGTTAGCTCCTTCGGTC
                CTCCGATCGTTGTCAGAAGTAAGTTGGCCGCAGTGTTATCACTCATGGTTATGGCA
                GCACTGCATAATTCTCTTACTGTCATGCCATCCGTAAGATGCTTTTCTGTGACTGG
                TGAGTACTCAACCAAGTCATTCTGAGAATAGTGTATGCGGCGACCGAGTTGCTCTT
                GCCCGGCGTCAATACGGGATAATACCGCGCCACATAGC
                (SEQ ID NO: 22)

PCDHA4mg_ON     GCGTTTCTGGGTGAGCAAAAACAGGAAGGCAAAATGCCGCAAAAAAGGGAATAAGG
target:         GCGACACGGAAATGTTGAATACTCATACTCTTCCTTTTTCAATATTATTGAAGCAT
                TTATCAGGGTTATTGTCTCATGAGCGGATACATATTTGAATGTATTTAGAAAAATA
                AACAAATAGGGGTTCCGCGCACATTTCCCCGAAAAGTGCCACCTAAATTGTAAGCG
                TTAATATTTTGTTAAAATTCGCGTTAAATTTTTGTTAAATCAGCTCATTTTTTAAC
                CAATAGGCCGAAATCGGCAAAATCCCTTATAAATCAAAAGAATAGACCGAGATAGG
                GTTGAGTGTTGTTCCAGTTTGGAACAAGAGTCCACTATTAAAGAACGTGGACTCCA
                ACGTCAAAGGGCGAAAAACCGTCTATCAGGGCGATGGCCCACTACGTGAACCATCA
                CCCTAATCAAGTTTTTTGGGGTCGAGGTGCCGTAAAGCACTAAATCGGAACCCTAA
                AGGGAGCCCCCGATTTAGAGCTTGACGGGGAAAGCCGGCGAACGTGGCGAGAAAGG
                AAGGGAAGAAAGCGAAAGGAGCGGGCGCTAGGGCGCTGGCAAGTGTAGCGGTCACG
                CTGCGCGTAACCACCACACCCGCCGCGCTTAATGCGCCGCTACAGGGCGCGTCCCA
                TTCGCCATTCAGGCTGCGCAACTGTTGGGAAGGGCGATCGGTGCGGGCCTCTTCGC
                TATTACGCCAGCTGGCGAAAGGGGGATGTGCTGCAAGGCGATTAAGTTGGGTAACG
                CCAGGGTTTTCCCAGTCACGACGTTGTAAAACGACGGCCAGTGAGCGCGCGTAATA
                CGACTCACTATAGGGCGAATTGGGTACGATCGATGCGGCCTCGGAACATTGGTAAT
                TAAACTTAACGCCTCAGATTTAGACGAAGGATTGAATGGGACATTGTTTATTCAT
                TCTCGAATGATACGCGCGTGATATGCAGCTCCAGCTTTTGTTCCCTTTAGTGAGGG
                TTAATTGCGCGCTTGGCGTAATCATGGTCATAGCTGTTTCCTGTGTGAAATTGTTA
                TCCGCTCACAATTCCACACAACATACGAGCCGGAAGCATAAAGTGTAAAGCCTGGG
                GTGCCTAATGAGTGAGCTAACTCACATTAATTGCGTTGCGCTCACTGCCCGCTTTC
                CAGTCGGGAAACCTGTCGTGCCAGCTGCATTAATGAATCGGCCAACGCGCGGGGAG
                AGGCGGTTTGCGTATTGGGCGCTCTTCCGCTTCCTCGCTCACTGACTCGCTGCGCT
                CGGTCGTTCGGCTGCGGCGAGCGGTATCAGCTCACTCAAAGGCGGTAATACGGTTA
                TCCACAGAATCAGGGGATAACGCAGGAAAGAACATGTGAGCAAAAGGCCAGCAAAA
                GGCCAGGAACCGTAAAAAGGCGCGTTGCTGGCGTTTTTCCATAGGCTCCGCCCCC
                CTGACGAGCATCACAAAAATCGACGCTCAAGTCAGAGGTGGCGAAACCCGACAGGA
                CTATAAAGATACCAGGCGTTTCCCCCTGGAAGCTCCCTCGTGCGCTCTCCTGTTCC
                GACCCTGCCGCTTACCGGATACCTGTCCGCCTTTCTCCCTTCGGGAAGCGTGGCGC
                TTTCTCATAGCTCACGCTGTAGGTATCTCAGTTCGGTGTAGGTCGTTCGCTCCAAG
                CTGGGCTGTGTGCACGAACCCCCCGTTCAGCCCGACCGCTGCGCCTTATCCGGTAA
                CTATCGTCTTGAGTCCAACCCGGTAAGACACGACTTATCGCCACTGGCAGCAGCCA
                CTGGTAACAGGATTAGCAGAGCGAGGTATGTAGGCGGTGCTACAGAGTTCTTGAAG
                TGGTGGCCTAACTACGGCTACACTAGAAGGACAGTATTTGGTATCTGCGCTCTGCT
                GAAGCCAGTTACCTTCGGAAAAAGAGTTGGTAGCTCTTGATCCGGCAAACAAACCA
                CCGCTGGTAGCGGTGGTTTTTTTGTTTGCAAGCAGCAGATTACGCGCAGAAAAAAA
```

```
                    GGATCTCAAGAAGATCCTTTGATCTTTTCTACGGGGTCTGACGCTCAGTGGAACGA
                    AAACTCACGTTAAGGGATTTTGGTCATGAGATTATCAAAAAGGATCTTCACCTAGA
                    TCCTTTTAAATTAAAAATGAAGTTTTAAATCAATCTAAAGTATATATGAGTAAACT
                    TGGTCTGACAGTTACCAATGCTTAATCAGTGAGGCACCTATCTCAGCGATCTGTCT
                    ATTTCGTTCATCCATAGTTGCCTGACTCCCCGTCGTGTAGATAACTACGATACGGG
                    AGGGCTTACCATCTGGCCCCAGTGCTGCAATGATACCGCGAGACCCACGCTCACCG
                    GCTCCAGATTTATCAGCAATAAACCAGCCAGCCGGAAGGGCCGAGCGCAGAAGTGG
                    TCCTGCAACTTTATCCGCCTCCATCCAGTCTATTAATTGTTGCCGGGAAGCTAGAG
                    TAAGTAGTTCGCCAGTTAATAGTTTGCGCAACGTTGTTGCCATTGCTACAGGCATC
                    GTGGTGTCACGCTCGTCGTTTGGTATGGCTTCATTCAGCTCCGGTTCCCAACGATC
                    AAGGCGAGTTACATGATCCCCCATGTTGTGCAAAAAAGCGGTTAGCTCCTTCGGTC
                    CTCCGATCGTTGTCAGAAGTAAGTTGGCCGCAGTGTTATCACTCATGGTTATGGCA
                    GCACTGCATAATTCTCTTACTGTCATGCCATCCGTAAGATGCTTTTCTGTGACTGG
                    TGAGTACTCAACCAAGTCATTCTGAGAATAGTGTATGCGGCGACCGAGTTGCTCTT
                    GCCCGGCGTCAATACGGGATAATACCGCGCCACATAGC
                    (SEQ ID NO: 23)

PCDHA4mg_           GCGTTTCTGGGTGAGCAAAAACAGGAAGGCAAAATGCCGCAAAAAAGGGAATAAGG
OFFtEut             GCGACACGGAAATGTTGAATACTCATACTCTTCCTTTTTCAATATTATTGAAGCAT
                    TTATCAGGGTTATTGTCTCATGAGCGGATACATATTTGAATGTATTTAGAAAAATA
                    AACAAATAGGGGTTCCGCGCACATTTCCCCGAAAAGTGCCACCTAAATTGTAAGCG
                    TTAATATTTTGTTAAAATTCGCGTTAAATTTTTGTTAAATCAGCTCATTTTTTAAC
                    CAATAGGCCGAAATCGGCAAAATCCCTTATAAATCAAAAGAATAGACCGAGATAGG
                    GTTGAGTGTTGTTCCAGTTTGGAACAAGAGTCCACTATTAAAGAACGTGGACTCCA
                    ACGTCAAAGGGCGAAAAACCGTCTATCAGGGCGATGGCCCACTACGTGAACCATCA
                    CCCTAATCAAGTTTTTTGGGGTCGAGGTGCCGTAAAGCACTAAATCGAACCCTAA
                    AGGGAGCCCCCGATTTAGAGCTTGACGGGGAAAGCCGGCGAACGTGGCGAGAAGG
                    AAGGGAAGAAAGCGAAAGGAGCGGGCGCTAGGGCGCTGGCAAGTGTAGCGGTCACG
                    CTGCGCGTAACCACCACACCCGCCGCGCTTAATGCGCCGCTACAGGGCGCGTCCCA
                    TTCGCCATTCAGGCTGCGCAACTGTTGGGAAGGGCGATCGGTGCGGGCCTCTTCGC
                    TATTACGCCAGCTGGCGAAAGGGGGATGTGCTGCAAGGCGATTAAGTTGGGTAACG
                    CCAGGGTTTTCCCAGTCACGACGTTGTAAAACGACGGCCAGTGAGCGCGCGTAATA
                    CGACTCACTATAGGGCGAATTGGGTACGATGATGCGGCCTCGGAACGCTGGTGAT
                    TCATCCCAATGCCTCAGATTTAGACGAAGGCTTGAATGGGGATATTATTTACTCCT
                    TCTCCAGTGATGTGCGCGTGATATGCAGCTCCAGCTTTTGTTCCCTTTAGTGAGGG
                    TTAATTGCGCGCTTGGCGTAATCATGGTCATAGCTGTTTCCTGTGTGAAATTGTTA
                    TCCGCTCACAATTCCACACAACATACGAGCCGGAAGCATAAAGTGTAAAGCCTGGG
                    GTGCCTAATGAGTGAGCTAACTCACATTAATTGCGTTGCGCTCACTGCCCGCTTTC
                    CAGTCGGGAAACCTGTCGTGCCAGCTGCATTAATGAATCGGCCAACGCGCGGGGAG
                    AGGCGGTTTGCGTATTGGGCGCTCTTCCGCTTCCTCGCTCACTGACTCGCTGCGCT
                    CGGTCGTTCGGCTGCGGCGAGCGGTATCAGCTCACTCAAAGGCGGTAATACGGTTA
                    TCCACAGAATCAGGGGATAACGCAGGAAAGAACATGTGAGCAAAAGGCCAGCAAAA
                    GGCCAGGAACCGTAAAAAGGCCGCGTTGCTGGCGTTTTTCCATAGGCTCCGCCCCC
                    CTGACGAGCATCACAAAAATCGACGCTCAAGTCAGAGGTGGCGAAACCCGACAGGA
                    CTATAAAGATACCAGGCGTTTCCCCCTGGAAGCTCCCTCGTGCGCTCTCCTGTTCC
                    GACCCTGCCGCTTACCGGATACCTGTCCGCCTTTCTCCCTTCGGGAAGCGTGGCGC
                    TTTCTCATAGCTCACGCTGTAGGTATCTCAGTTCGGTGTAGGTCGTTCGCTCCAAG
                    CTGGGCTGTGTGCACGAACCCCCCGTTCAGCCCGACCGCTGCGCCTTATCCGGTAA
                    CTATCGTCTTGAGTCCAACCCGGTAAGACACGACTTATCGCCACTGGCAGCAGCCA
                    CTGGTAACAGGATTAGCAGAGCGAGGTATGTAGGCGGTGCTACAGAGTTCTTGAAG
                    TGGTGGCCTAACTACGGCTACACTAGAAGGACAGTATTTGGTATCTGCGCTCTGCT
                    GAAGCCAGTTACCTTCGGAAAAAGAGTTGGTAGCTCTTGATCCGGCAAACAAACCA
                    CCGCTGGTAGCGGTGGTTTTTTTGTTTGCAAGCAGCAGATTACGCGCAGAAAAAAA
                    GGATCTCAAGAAGATCCTTTGATCTTTTCTACGGGGTCTGACGCTCAGTGGAACGA
                    AAACTCACGTTAAGGGATTTTGGTCATGAGATTATCAAAAAGGATCTTCACCTAGA
                    TCCTTTTAAATTAAAAATGAAGTTTTAAATCAATCTAAAGTATATATGAGTAAACT
                    TGGTCTGACAGTTACCAATGCTTAATCAGTGAGGCACCTATCTCAGCGATCTGTCT
                    ATTTCGTTCATCCATAGTTGCCTGACTCCCCGTCGTGTAGATAACTACGATACGGG
                    AGGGCTTACCATCTGGCCCCAGTGCTGCAATGATACCGCGAGACCCACGCTCACCG
                    GCTCCAGATTTATCAGCAATAAACCAGCCAGCCGGAAGGGCCGAGCGCAGAAGTGG
                    TCCTGCAACTTTATCCGCCTCCATCCAGTCTATTAATTGTTGCCGGGAAGCTAGAG
                    TAAGTAGTTCGCCAGTTAATAGTTTGCGCAACGTTGTTGCCATTGCTACAGGCATC
                    GTGGTGTCACGCTCGTCGTTTGGTATGGCTTCATTCAGCTCCGGTTCCCAACGATC
                    AAGGCGAGTTACATGATCCCCCATGTTGTGCAAAAAAGCGGTTAGCTCCTTCGGTC
                    CTCCGATCGTTGTCAGAAGTAAGTTGGCCGCAGTGTTATCACTCATGGTTATGGCA
                    GCACTGCATAATTCTCTTACTGTCATGCCATCCGTAAGATGCTTTTCTGTGACTGG
                    TGAGTACTCAACCAAGTCATTCTGAGAATAGTGTATGCGGCGACCGAGTTGCTCTT
                    CCCGGCGTCAATACGGGATAATACCGCGCCACATAGC
                    (SEQ ID NO: 24)
```

In a 20-uL reaction volume, 50 fmoles of linearized DNA target in the presence of 50 nM sgRNA, 39 nM recombinant purified Cas9 protein (*S. pyogenes*; Agilent) and 10 mM or 0.8 mM $MgCl_2$ at pH 7.6 was incubated at 37° C. for 30 min. Upon completion, 0.5 uL of RNace It (Agilent) was added, and incubation was continued at 37° C. for 5 min and then at 70° C. for 15 min. Subsequently 0.5 μL of Proteinase K (Mol. Bio. grade, NEB) was added and incubated at 37° C. for 15 min. Aliquots were loaded into a DNA 1000 or DNA 7500 LabChip and were analyzed on a Bioanalyzer 2200, or alternatively were loaded into a Genomic DNA ScreenTape and were analyzed on a TapeStation. The workup steps served to release Cas9 from binding of target DNA, which was assayed for cleavage. Cleavage yields were calculated by the formula: a/(a+b)×100 where a is the sum of the band intensities of the two cleavage products and b is the remaining uncleaved DNA if present. A cleavage percentage of 100% means that all of the target DNA construct was cleaved.

A series of guide RNAs were chemically synthesized. The guide RNA oligomers were synthesized on an ABI 394 Synthesizer (Life Technologies, Carlsbad, Calif., USA) using 2'-O-thionocarbamate-protected nucleoside phosphoramidites according to procedures described in Dellinger et al. (2011) *J. Am. Chem. Soc.*, 133, 11540-56. 2'-O-methyl phosphoramidites were incorporated into RNA oligomers under the same conditions as the 2'-O-thionocarbamate protected phosphoramidites. The 2'-O-methyl-3-O-(diisopropylamino)phosphinoacetic acid-1,1-dimethylcyanoethyl ester-5'-O-dimethoxytrityl nucleosides used for synthesis of thiophosphonoacetate (thioPACE)-modified RNAs were synthesized essentially according to published methods. See Dellinger et al. (2003) 1 Am. Chem. Soc., 125, 940-50; and Threlfall et al. (2012) *Org. Biomol. Chem.*, 10, 746-54. For phosphorothioate-containing oligomers, the iodine oxidation step after the coupling reaction was replaced by a sulfurization step using a 0.05 M solution of 3-((N,N-dimethylaminomethylidene)amino)-3H-1,2,4-dithiazole-5-thione in a pyridine-acetonitrile (3:2) mixture for 6 min.

All the oligonucleotides were purified using reversed-phase high-performance liquid chromatography (HPLC) and analyzed by liquid chromatography-mass spectrometry (LC-MS) using an Agilent 1290 Infinity series LC system coupled to an Agilent 6520 Q-TOF (time-of-flight) mass spectrometer (Agilent Technologies, Santa Clara, Calif., USA). The yields for the synthesis and purification of the sgRNAs were estimated using deconvolution of mass spectra obtained from LC-MS-derived total ion chromatograms. The chemical synthesis of the 100-mer sgRNAs typically yielded 25-35% full-length product from a nominal 1 micromole scale synthesis. Reversed-phase HPLC purification using ion pairing buffer conditions typically gave 20% yield from the crude product with an estimated purity of the final sgRNA in the range of 90% to 95%.

The results are shown in Table 4. "% Target cleaved" indicates the percentage of the target DNA construct which was cleaved. Experiments were run with and without addition of a molar excess of targetless competitor DNA (tcDNA) which potentially competes with the target DNA, so the potential impact of the added nonspecific DNA upon the assay could be seen.

TABLE 4

| Entry # | $[Mg^{2+}]$ (mM) | tcDNA | % Target cleaved | % CV | % Cleaved vs. CONTROL | % CV CONTROL |
|---|---|---|---|---|---|---|
| 2-piece dual-guide scaffold Unmodified dual-guide RNA (dgRNA) | | | | | | |
| 1 | 0.8 | N | 99% | — | | |
| 2 | 0.8 | Y | 99% | 5% | | |
| 3 | 0.8 | N | 96% | — | | |
| 4 | 0.8 | Y | 100% | 5% | | |
| 5 | 0.8 | N | 96% | — | | |
| 6 | 0.8 | Y | 0% | 5% | | |
| 7 | 0.8 | N | 99% | — | | |
| 8 | 0.8 | Y | 100% | 5% | | |
| 9 | 10 | N | 94%, 93% | — | | |
| 10 | 0.8 | Y | 88% | — | | |
| Fluorophore-coupled dgRNA | | | | | | |
| 11 | 10 | N | 92%, 93% | — | 94%, 93% | — |
| 2'OMethyl-modified dgRNA | | | | | | |
| 12 | 0.8 | Y | 87% | — | 88% | — |
| 2'OMethyl,3'Phosphorothioate-modified dgRNA | | | | | | |
| 13 | 0.8 | Y | 87% | — | 88% | — |
| 2'OMethyl,3'PhosphorothioPACE-modified dgRNA | | | | | | |
| 14 | 0.8 | Y | 89% | — | 88% | — |
| 15 | 0.8 | Y | 86% | — | 88% | — |
| 2-thioU-modified dgRNA | | | | | | |
| 16 | 0.8 | N | 96% | — | 99% | — |
| 17 | 0.8 | Y | 95% | 5% | 99% | 5% |
| 18 | 0.8 | N | 95% | — | 96% | — |
| 19 | 0.8 | Y | 100% | 5% | 100% | 5% |
| 20 | 0.8 | N | 97% | — | 96% | — |
| 21 | 0.8 | Y | 0% | 5% | 0% | 5% |
| 22 | 0.8 | N | 98% | — | 99% | — |
| 23 | 0.8 | Y | 99% | 5% | 100% | 5% |
| 24 | 0.8 | N | 94% | — | 99% | — |
| 25 | 0.8 | Y | 83% | 5% | 99% | 5% |
| 26 | 0.8 | N | 93% | — | 96% | — |
| 27 | 0.8 | Y | 94% | 5% | 100% | 5% |
| 28 | 0.8 | N | 90% | — | 96% | — |
| 29 | 0.8 | Y | 0% | 5% | 0% | 5% |
| 30 | 0.8 | N | 95% | — | 99% | — |
| 31 | 0.8 | Y | 94% | 5% | 100% | 5% |
| 32 | 0.8 | N | 92% | — | 99% | — |
| 33 | 0.8 | Y | 84% | 5% | 99% | 5% |
| 34 | 0.8 | N | 90% | — | 96% | — |
| 35 | 0.8 | Y | 94% | 5% | 100% | 5% |
| 36 | 0.8 | N | 70% | — | 96% | — |
| 37 | 0.8 | Y | 0% | 5% | 0% | 5% |
| 38 | 0.8 | N | 96% | — | 99% | — |
| 39 | 0.8 | Y | 59% | 5% | 100% | 5% |
| Single-guide scaffold Unmodified single-guide RNA (sgRNA) | | | | | | |
| 40 | 10 | N | 93% | — | | |
| 41 | 10 | N | 94% | — | | |
| 42 | 10 | N | 94% | — | | |
| 43 | 10 | N | 92% | — | | |
| 44 | 10 | N | 90%, 92% | — | | |
| 45 | 10 | N | 92% | — | | |
| 46 | 10 | N | 93% | — | | |
| 47 | 0.8 | N | 86% | — | | |
| 48 | 0.8 | N | 87% | — | | |
| 49 | 0.8 | Y | 87% | — | | |
| 50 | 0.8 | N | 82% | — | | |
| 51 | 0.8 | N | 92% | — | | |
| 52 | 10 | N | 60% | — | | |
| 53 | 0.8 | N | 90% | — | | |
| 54 | 0.8 | N | 90% | — | | |
| 55 | 0.8 | Y | 79% | — | | |
| 56 | 0.8 | N | 79% | — | | |
| 57 | 0.8 | N | 94% | — | | |
| 58 | 10 | N | 73% | — | | |
| 59 | 0.8 | N | 84% | — | | |
| 60 | 0.8 | Y | ≥85% | — | | |
| 61 | 0.8 | Y | 89% | — | | |
| 62 | 0.8 | N | 87%, 82% | — | | |
| 63 | 0.8 | N | 23%, 22% | — | | |
| 64 | 0.8 | N | 78% | — | 87% | — |
| 65 | 0.8 | Y | 76% | — | 87% | — |
| 66 | 0.8 | N | 65% | — | 87% | — |
| 67 | 0.8 | N | 81% | — | 87% | — |
| 68 | 0.8 | N | 85% | — | 87% | — |
| 69 | 0.8 | Y | 71% | — | 87% | — |
| 70 | 0.8 | N | 32% | — | 87% | — |
| 71 | 0.8 | N | 84% | — | 87% | — |
| 72 | 0.8 | N | 91% | — | 87% | — |
| 73 | 0.8 | Y | 79% | — | 87% | — |
| 74 | 0.8 | N | 88% | — | 87% | — |
| 75 | 0.8 | N | 93% | — | 87% | — |
| 76 | 0.8 | N | 87% | — | 87% | — |
| 77 | 0.8 | Y | 79% | — | 87% | — |
| 78 | 0.8 | N | 89% | — | 87% | — |
| 79 | 0.8 | N | 88% | — | 87% | — |
| 80 | 0.8 | N | 3% | — | 86% | — |

TABLE 4-continued

| Entry # | [Mg²⁺] (mM) | tcDNA | % Target cleaved | % CV | % Cleaved vs. CONTROL | % CV CONTROL |
|---|---|---|---|---|---|---|
| 81 | 0.8 | N | 5% | — | 86% | — |
| 82 | 0.8 | N | 89% | — | 86% | — |
| 83 | 0.8 | N | 68% | — | 87% | — |
| 84 | 0.8 | Y | 50% | — | 87% | — |
| 85 | 0.8 | N | 69% | — | 87% | — |
| 86 | 0.8 | N | 69% | — | 87% | — |
| 87 | 0.8 | N | 76% | — | 87% | — |
| 88 | 0.8 | Y | 42% | — | 87% | — |
| 89 | 0.8 | N | 72% | — | 87% | — |
| 90 | 0.8 | N | 78% | — | 87% | — |
| 91 | 0.8 | N | 85% | — | 87% | — |
| 92 | 0.8 | Y | 51% | — | 87% | — |
| 93 | 0.8 | N | 82% | — | 87% | — |
| 94 | 0.8 | " | 83% | — | 87% | — |
| DMT-modified sgRNA | | | | | | |
| 95 | 10 | N | 93% | — | 92% | — |
| 96 | 10 | N | 93% | — | 92% | — |
| Fluorophore-modified sgRNA | | | | | | |
| 97 | 10 | N | 91%, 91% | — | 90%, 92% | — |
| 98 | 0.8 | N | 86% | — | 87% | — |
| 99 | 0.8 | Y | 77% | — | 87% | — |
| 100 | 0.8 | N | 87% | — | 87% | — |
| 101 | 0.8 | N | 86% | — | 87% | — |
| 102 | 0.8 | N | 91% | — | 87% | — |
| 103 | 0.8 | Y | 82% | — | 87% | — |
| 104 | 0.8 | N | 90% | — | 87% | — |
| 105 | 0.8 | N | 92% | — | 87% | — |
| 106 | 0.8 | N | 91% | — | 87% | — |
| 107 | 0.8 | Y | 82% | — | 87% | — |
| 108 | 0.8 | N | 90% | — | 87% | — |
| 109 | 0.8 | N | 91% | — | 87% | — |
| 110 | 0.8 | N | 92% | — | 87% | — |
| 111 | 0.8 | Y | 84% | — | 87% | — |
| 112 | 0.8 | N | 92% | — | 87% | — |
| 113 | 0.8 | N | 89% | — | 87% | — |
| 114 | 0.8 | N | 84%, 84% | — | 87%, 82% | — |
| 115 | 0.8 | N | 12%, 6% | — | 23%, 22% | — |
| 116 | 0.8 | N | 93%, 90% | — | 87%, 82% | — |
| 117 | 0.8 | N | 8%, 9% | — | 23%, 22% | — |
| 3'Phosphorothioate-modified sgRNA | | | | | | |
| 118 | 10 | N | 95% | — | 90%, 92% | — |
| 119 | 10 | N | 94% | — | 90%, 92% | — |
| 120 | 10 | N | 97% | — | 90%, 92% | — |
| 121 | 10 | N | 94% | — | 90%, 92% | — |
| 2'OMethyl-modified sgRNA | | | | | | |
| 122 | 10 | N | 91% | — | 94% | — |
| 123 | 10 | N | 92% | — | 93% | — |
| 124 | 0.8 | N | 86% | — | 87% | — |
| 125 | " | Y | 77% | — | 87% | — |
| 126 | " | N | 85% | — | 87% | — |
| 127 | 0.8 | N | 88% | — | 87% | — |
| 128 | 10 | N | 92% | — | 94% | — |
| 129 | 0.8 | N | 83% | — | 87% | — |
| 130 | 0.8 | Y | 78% | — | 87% | — |
| 131 | 0.8 | N | 83% | — | 87% | — |
| 132 | 0.8 | N | 85% | — | 87% | — |
| 133 | 10 | N | 92% | — | 94% | — |
| 134 | 0.8 | N | 86% | — | 87% | — |
| 135 | 0.8 | Y | 78% | — | 87% | — |
| 136 | 0.8 | N | 83% | — | 87% | — |
| 137 | 0.8 | N | 88% | — | 87% | — |
| 138 | 10 | N | 91% | — | 94% | — |
| 139 | 0.8 | N | 84% | — | 87% | — |
| 140 | 0.8 | Y | 81% | — | 87% | — |
| 141 | 0.8 | N | 83% | — | 87% | — |
| 142 | 0.8 | N | 87% | — | 87% | — |
| 143 | 10 | N | 89% | — | 92% | — |
| 144 | 0.8 | N | 91%, 88% | — | 87%, 82% | — |
| 145 | 0.8 | N | 24%, 25% | — | 23%, 22% | — |
| 146 | 10 | N | 93%, 92% | — | 90%, 92% | — |
| 147 | 0.8 | N | 22% | — | 87% | — |
| 148 | 0.8 | Y | 3% | — | 87% | — |
| 149 | 0.8 | N | 12% | — | 87% | — |
| 150 | 0.8 | N | 5% | — | 87% | — |
| 151 | 10 | N | 0%, 0% | — | 90%, 92% | — |
| 152 | 10 | N | 0%, 0% | — | 90%, 92% | — |
| 153 | 0.8 | N | 85% | — | 86% | — |
| 154 | 0.8 | N | 87% | — | 86% | — |
| 155 | 0.8 | N | 89% | — | 87% | — |
| 156 | 0.8 | Y | 78% | — | 87% | — |
| 157 | 0.8 | N | 84% | — | 87% | — |
| 158 | 0.8 | N | 93% | — | 87% | — |
| 159 | 0.8 | N | 90% | — | 86% | — |
| 160 | 0.8 | N | 90% | — | 87% | — |
| 161 | 0.8 | Y | 86% | — | 87% | — |
| 162 | 0.8 | N | 90% | — | 87% | — |
| 163 | 0.8 | N | 91% | — | 87% | — |
| 164 | 0.8 | N | 92% | — | 90% | — |
| 165 | 0.8 | N | 89% | — | 87% | — |
| 166 | 0.8 | Y | 80% | — | 87% | — |
| 167 | 0.8 | N | 90% | — | 87% | — |
| 168 | 0.8 | N | 94% | — | 87% | — |
| 169 | 0.8 | N | 90% | — | 84% | — |
| 170 | 0.8 | Y | ≥85% | — | ≥85% | — |
| 171 | 0.8 | N | 7% | — | 84% | — |
| 172 | 0.8 | Y | 0% | — | ≥85% | — |
| 173 | 10 | N | 15% | — | 73% | — |
| 174 | 0.8 | N | 85% | — | 84% | — |
| 175 | 0.8 | Y | 75% | — | ≥85% | — |
| 176 | 10 | N | 86% | — | 73% | — |
| 177 | 0.8 | " | 0% | — | 84% | — |
| 178 | 0.8 | Y | 0% | — | ≥85% | — |
| 179 | 10 | N | 15% | — | 73% | — |
| 2'Deoxy-modified sgRNA | | | | | | |
| 180 | 10 | N | 27%, 19% | — | 90%, 92% | — |
| 181 | 10 | N | 0%, 0% | — | 90%, 92% | — |
| 182 | 10 | N | 0%, 0% | — | 90%, 92% | — |
| 2'Deoxy,3'PACE-modified sgRNA | | | | | | |
| 183 | 0.8 | N | 72%, 77% | — | 87%, 82% | — |
| 184 | 0.8 | N | 8%, 9% | — | 23%, 22% | — |
| 2'OMethyl,3'PACE-modified sgRNA | | | | | | |
| 185 | 0.8 | N | 82% | — | 87% | — |
| 186 | 0.8 | Y | 72% | — | 87% | — |
| 187 | 10 | Y | 95% | — | 93% | — |
| 188 | 10 | Y | 95% | — | 94% | — |
| 189 | 0.8 | Y | 91% | — | 87% | — |
| 190 | 0.8 | Y | 84% | — | 87% | — |
| 191 | 0.8 | Y | 85% | — | 87% | — |
| 192 | 0.8 | Y | 77% | — | 87% | — |
| 193 | 10 | Y | 88% | — | 94% | — |
| 194 | 0.8 | Y | 70% | — | 87% | — |
| 195 | 0.8 | Y | 56% | — | 87% | — |
| 196 | 0.8 | Y | 40% | — | 87% | — |
| 197 | 0.8 | Y | 23% | — | 87% | — |
| 198 | 10 | Y | 88% | — | 93% | — |
| 199 | 10 | Y | 89% | — | 94% | — |
| 200 | 0.8 | Y | 84% | — | 87% | — |
| 201 | 0.8 | Y | 75% | — | 87% | — |
| 202 | 10 | Y | 90% | — | 93% | — |
| 203 | 10 | Y | 90% | — | 94% | — |
| 204 | 0.8 | Y | 86% | — | 87% | — |
| 205 | 0.8 | Y | 82% | — | 87% | — |
| 206 | 10 | Y | 88% | — | 93% | — |
| 207 | 0.8 | Y | 82% | — | 87% | — |
| 208 | 0.8 | Y | 78% | — | 87% | — |
| 209 | 10 | Y | 77% | — | 93% | — |
| 210 | 0.8 | Y | 71% | — | 87% | — |
| 211 | " | Y | 69% | — | " | — |
| 212 | 10 | N | 80% | — | 93% | — |
| 213 | 0.8 | N | 56% | — | 87% | — |
| 214 | 0.8 | Y | 41% | — | " | — |
| 215 | 10 | Y | 78% | — | 93% | — |
| 216 | 0.8 | Y | 58% | — | 87% | — |
| 217 | 0.8 | Y | 44% | — | " | — |
| 218 | 10 | Y | 80% | — | 93% | — |
| 219 | 0.8 | Y | 39% | — | 87% | — |
| 220 | 0.8 | Y | 13% | — | " | — |

TABLE 4-continued

| Entry # | [Mg²⁺] (mM) | tcDNA | % Target cleaved | % CV | % Cleaved vs. CONTROL | % CV CONTROL |
|---|---|---|---|---|---|---|
| 221 | 10 | Y | 74% | — | 93% | — |
| 222 | 0.8 | Y | 36% | — | 87% | — |
| 223 | 0.8 | Y | 19% | — | 87% | — |
| 224 | 10 | Y | 86% | — | 93% | — |
| 225 | 0.8 | Y | 84% | — | 87% | — |
| 226 | 0.8 | Y | 80% | — | " | — |
| 227 | 10 | Y | 88% | — | 93% | — |
| 228 | 0.8 | Y | 83% | — | 87% | — |
| 229 | 0.8 | Y | 82% | — | 87% | — |
| 230 | 0.8 | N | 80% | — | 87% | — |
| 231 | 0.8 | N | 84% | — | 87% | — |
| 232 | 10 | N | 88% | — | 93% | — |
| 233 | 0.8 | N | 85% | — | 87% | — |
| 234 | 0.8 | Y | 73% | — | 87% | — |
| 235 | 10 | Y | 82% | — | 93% | — |
| 236 | 0.8 | Y | 89% | — | 87% | — |
| 237 | 0.8 | Y | 76% | — | 87% | — |
| 238 | 10 | Y | 65% | — | 93% | — |
| 239 | 0.8 | Y | 84% | — | 87% | — |
| 240 | 0.8 | Y | 56% | — | 87% | — |
| 2'OMethyl,3'Phosphorothioate-modified sgRNA | | | | | | |
| 241 | 10 | N | 92% | — | 92% | — |
| 242 | 0.8 | N | 84% | — | 87% | — |
| 243 | 0.8 | Y | 88% | — | 87% | — |
| 244 | 0.8 | N | 85% | — | 87% | — |
| 245 | 0.8 | N | 91% | — | 87% | — |
| 246 | 0.8 | N | 91% | — | 84% | — |
| 247 | 0.8 | Y | ≥85% | — | ≥85% | — |
| 248 | 0.8 | N | 84% | — | 84% | — |
| 249 | 0.8 | Y | 90% | — | 89% | — |
| 250 | 0.8 | N | 90%, 87% | — | 87%, 82% | — |
| 251 | 0.8 | N | 16%, 19% | — | 23%, 22% | — |
| 252 | 0.8 | N | 93% | — | 89% | — |
| 253 | 0.8 | N | 90%, 90% | — | 87%, 82% | — |
| 254 | 0.8 | N | 17%, 22% | — | 23%, 22% | — |
| 255 | 0.8 | N | 93% | — | 89% | — |
| 256 | 0.8 | N | 91%, 91% | — | 87%, 82% | — |
| 257 | 0.8 | N | 13%, 16% | — | 23%, 22% | — |
| 2'OMethyl,3'PhosphorothioPACE-modified sgRNA | | | | | | |
| 258 | 10 | N | 89% | — | 92% | — |
| 259 | 0.8 | N | 84% | — | 87% | — |
| 260 | 0.8 | Y | 80% | — | 87% | — |
| 261 | 0.8 | N | 77% | — | 87% | — |
| 262 | 0.8 | N | 83% | — | 87% | — |
| 263 | 0.8 | N | 92% | — | 87% | — |
| 264 | 0.8 | Y | 79% | — | 87% | — |
| 265 | 0.8 | N | 88% | — | 87% | — |
| 266 | 0.8 | N | 94% | — | 87% | — |
| 267 | 10 | N | 74% | — | 93% | — |
| 268 | 0.8 | N | 11% | — | 86% | — |
| 269 | 0.8 | N | 15% | — | " | — |
| 270 | 0.8 | N | 49% | — | " | — |
| 271 | 0.8 | N | 31% | — | " | — |
| 272 | 0.8 | N | 91% | — | 84% | — |
| 273 | 0.8 | Y | 77% | — | ≥85% | — |
| 274 | 0.8 | N | 90%, 91% | — | 87%, 82% | — |
| 275 | 0.8 | N | 9%, 8% | — | 23%, 22% | — |
| 276 | 0.8 | N | 90% | — | 84% | — |
| 277 | 0.8 | Y | ≥85% | — | ≥85% | — |
| 278 | 0.8 | N | 86%, 88% | — | 87%, 82% | — |
| 279 | 0.8 | N | 11%, 7% | — | 23%, 22% | — |
| 2-aminoA-modified sgRNA (including unmodified controls) | | | | | | |
| 280 | 0.8 | Y | 88%, 88% | — | | |
| 281 | 0.8 | Y | 76%, 75% | — | | |
| 282 | 0.8 | Y | 87%, 91% | — | 88%, 88% | — |
| 283 | 0.8 | Y | 90%, 90% | — | 76%, 75% | — |
| 284 | 0.8 | Y | 85%, 87% | — | | |
| 285 | 0.8 | Y | 88%, 88% | — | | |
| 286 | 0.8 | Y | 93%, 96% | — | 85%, 87% | — |
| 287 | 0.8 | Y | 82%, 79% | — | 88%, 88% | — |
| 5-methylU-modified sgRNA | | | | | | |
| 288 | 0.8 | N | 86%, 83% | — | 87%, 82% | — |
| 289 | 0.8 | N | 11%, 11% | — | 23%, 22% | — |
| Z base-modified sgRNA | | | | | | |
| 290 | 10 | N | 19% | — | 92% | — |
| 291 | 10 | N | 93% | — | " | — |
| sgRNA modified to disfavor misfolding | | | | | | |
| 292 | 0.8 | N | 93% | — | 90% | — |
| 293 | 0.8 | N | 93% | — | 86% | — |

The results revealed that guide RNAs containing modifications at specific positions were tolerated by active Cas protein and gRNA:Cas protein complexes, as the modifications did not prevent target-specific cleavage of the on-target polynucleotide. The modifications that were tested and found to be tolerated at specific positions include 2'-O-methylribonucleotide (=2'OMe), 2'-deoxyribonucleotide, racemic phosphorothioate internucleotide linkage, 3'-phosphonoacetate (=PACE), 3'-thiophosphonoacetate (=thioPACE), Z nucleotide, 2-thiouracil, 2-aminoadenine, 5-methyluracil, 5-aminoallyluracil coupled to Cy5 fluorophore, 2-(4-butylamidofluorescein)propane-1,3-diol bis (phosphodiester) linker, and combinations of these.

It is contemplated that the chemical modifications disclosed and tested herein, particularly at the tested positions (as listed in Tables 3 and 4), will be tolerated at equivalent positions in a variety of guide RNAs.

As disclosed herein, chemically modified nucleotides were incorporated into guide RNAs in an effort to improve certain properties. Such properties include improved nuclease resistance of the guide RNA (also known as improved stability), reduced off-target effects of a gRNA:Cas protein complex (also known as improved specificity), improved efficacy of gRNA:Cas protein complex when cleaving, nicking or binding a target polynucleotide, improved transfection efficiency, and/or improved organelle localization.

The assay results in Tables 3 and 4 indicate that: (1) In guide RNAs, many positions can tolerate a variety of chemical modifications; (2) 5' and 3' ends of guide RNAs will tolerate a wide variety of end-protecting modifications, and such modifications are useful to inhibit exonucleolytic RNA degradation; (3) 2-ThioU can be used to deter off-target interactions involving G-U wobble pairings, thereby increasing the specificity of guide pairing by inhibiting off-target hybridization interactions; (4) 5' Extensions are generally well-tolerated; (5) Surface exposed regions of the guide RNA (as inferred from published crystal structures) are tolerant of extensively modifying U's to 5-methylU's, which potentially make the modified RNA more likely to elude immune responses such as stimulated by unmodified RNA; and (6) For RNA folding, G-C pairs are stronger and more stable than A-U pairs. At least one guide RNA is tolerant of replacing some G-C pairs with 2'-O-methylA-2'-O-methylU pairs that are more stable thermodynamically than unmodified A-U pairs.

More particularly, the present example shows that 2'-O-methyl modifications are tolerated at the 5' and 3' ends of dual-guide RNAs (as shown by entry 12 in Tables 3 and 4) and single-guide RNAs (entries 143-146, 169-170), thus allowing end-protection to stabilize gRNAs against exonucleases. 2'-O-methyl modifications are tolerated at most but not all internal positions, thus allowing stabilization against various nucleases including endonucleases (entries 146, 153-168, 174-179). However, the present example also demonstrates that not every position in guide RNAs will tolerate 2'-O-methyls (as shown by entries 151-152 and 171-173), suggesting that too many consecutive 2'-O-methyl modifications at the 5' end (e.g., 26 or more consecutive 2'-O-methyl-modified nucleotides), or too many 2'-O-methyl modifications of C and U nucleotides downstream (3') of the 5'-terminal 20mer guide sequence is not well tolerated (e.g., the inhibitory effect of one or both 2'-O-methyluracils at sequence positions +56 and +69 in entries 171-173 as revealed by the positions tested in entries 154-156).

The present example shows that 2'-O-methyl modifications throughout the 20mer guide sequence are tolerated during in vitro uses in buffer containing 10 mM $Mg^{2+}$ (entry 146), but such extensive modification is not well tolerated under physiological conditions (entries 147-150) as present in cells. Thus, in some embodiments, a gRNA comprising 15 or more, alternatively 17 or more, alternatively 18 or more, alternatively 20 2'-O-methyl modifications throughout the 20mer guide sequence is used for in vitro methods as described herein, such as genomic editing to modify a DNA sequence in vitro, regulating the expression of a gene of interest in vitro, cleaving a DNA target sequence in vitro, and other uses.

The present example shows that extensive incorporation of 2'-deoxy modifications is not well tolerated and can be substantially completely inhibitory (entries 180-182). However, 2'-deoxy modifications can be well-tolerated at some locations (entry 183), therefore such modification can be useful for inhibiting nucleases.

The present example also shows that fluorophore or dye labels are tolerated in every loop of the three known stem-loops in CRISPR-Cas9 guide RNAs (entry 116). Such labels are also tolerated in a 5' overhang on the guide sequence (entry 114), tolerated at additional locations in sgRNAs (entry 114), and tolerated in a loop in tracrRNA used in dual-guide applications (entry 11). In this example, two different types of fluorophores were tested: a phosphodiester-linked fluorophore (no ribose ring) that essentially takes the place of a nucleotide (entries 114 & 116), and a dye label (Cy5) covalently coupled to 5-aminoallylU incorporated in a guide RNA (entry 11).

The present example also shows that Z bases are tolerated in synthetic guide RNAs, particularly as modifications of synthetic guide RNAs in which some C's are replaced with Z bases (entries 290-291). The present example also shows that several other bases are tolerated at various positions, as shown in Tables 3 and 4.

The present example further shows that the 5' and 3' ends of guide RNAs can tolerate a wide variety of end-protecting modifications. Such modifications can be used to inhibit exonucleolytic RNA degradation. Support for the tolerance of such modifications can be found in Hendel et al., *Nat. Biotechnol.* (2015) 33:9, 985-9. Additional support for modifications at the 5' and 3' ends of guide RNAs is provided by entries 143-144, 185-223, 241-257, 258-266, and 272-279 in Tables 3 and 4. In some embodiments, the guide RNA comprises 7 or fewer modified nucleotides at a 5' end or a 3' end or at each of 5' and 3' ends, alternatively 6 or fewer, alternatively 5 or fewer, alternatively 4 or fewer, alternatively 3 or fewer, alternatively 2 or fewer, alternatively 1. Dual-guide RNAs can be protected similarly (entries 12-15).

The present example further shows that 2-thioU can be used to deter off-target interactions involving G-U wobble pairings, thereby increasing the specificity of guide sequence pairing by inhibiting off-target hybridization interactions (entries 16-39). One of the base pairs involved in hybridization between the guide RNA and CLTA1 OFF-target 3 (also referred to as "CLTA1 OFF3-target" or "CLTA1 OFF3") is a G-U wobble pair. Replacing the corresponding U in the guide RNA with a 2-thioU reduces cleavage from 100% (entry 8) to 59% (entry 39). Replacing other U's with 2-thioU's (e.g., at sequence position +3 or +9, entries 23 and 31) does not have the same effect, presumably because those U's do not involve G-U wobble pairing when fully hybridized to each of the OFF-target sites tested. Accordingly, 2-thioU can increase target specificity of guide RNAs when off-target sites involve G-U wobble pairing.

The present example also shows that 5'-overhang sequences attached to the guide sequence are generally well-tolerated (see entries 83-95, 114, and 206-223). For example, a bulky dimethoxytrityl (dmt) group at the 5' end was well tolerated (entry 95). The chromatographic properties of dmt can be used to facilitate purification of full-length synthetic RNAs from incompletely elongated byproducts which are generally produced during synthesis. Accordingly, in some embodiments, the synthetic guide RNA comprises a 5'-overhang sequence, for example, comprising a short polynucleotide sequence of 15 or fewer nucleotides which is complementary to the guide sequence and is covalently linked at its 3' end to the 5' end of the guide sequence by a polymeric linker such as a polynucleotide or similarphosphodiester-based linker, in which the linker can be 5 or more consecutive uridine nucleotides, alternatively 6 or 7.

The present example also shows that surface exposed regions of the guide RNA (as inferred from crystal structures published by others) are tolerant of extensively modifying uracils nucleotides to 5-methyluracils (5-methylU's) (entry 288), which can make the modified RNA more likely to elude immune responses such as stimulated by unmodified RNA. In particular, the 5' and 3' ends of a synthetic guide RNA are potentially immunostimulatory, and the present example shows that 5' and 3' ends are tolerant of 5-methylU modifications (entry 288).

The present example also shows that a synthetic guide RNA is tolerant of replacing some G-C pairs with 2'-O-methylA-2'-O-methylU pairs which are more stable thermodynamically than unmodified A-U pairs (see the non-terminal-2'-O-methylU and complementary-2'-O-methylA modifications in entries 292-293). This is advantageous because it is known that, for folded RNAs, G-C pairs are stronger and more stable than A-U pairs. Replacement of G-C pairs with such thermostabilized A-U pairs in synthetic guide RNAs allows for improved folding of active structures by preventing misfolded structures that involve unintended G-C pair(s), as can be predicted by RNA folding algorithms in common use.

EXEMPLARY EMBODIMENTS

Exemplary embodiments provided in accordance with the presently disclosed subject matter include, but are not limited to, the claims and the following embodiments:

A1. A synthetic guide RNA comprising:
  a crRNA segment comprising (i) a guide sequence capable of hybridizing to a target sequence, (ii) a stem sequence; and
  a tracrRNA segment comprising a nucleotide sequence that is partially or completely complementary to the stem sequence, wherein the synthetic guide RNA comprises at least one modified nucleotide, and wherein the synthetic guide RNA has gRNA functionality.

A2. The synthetic guide RNA of embodiment A1, comprising a 2'-deoxy moiety.

A3. The synthetic guide RNA of embodiment A1 or A2, comprising a 2'-halo moiety selected from 2'-fluoro, 2'-chloro, 2'-bromo and 2'-iodo.

A4. The synthetic guide RNA of any one of the preceding embodiments, comprising a phosphorothioate group.

A5. The synthetic guide RNA of any one of the preceding embodiments, comprising a PACE group.

A6. The synthetic guide RNA of any one of the preceding embodiments, comprising a thioPACE group.

A7. The synthetic guide RNA of any one of embodiments A2-A6, comprising a 2'-O-methyl moiety.

A8. The synthetic guide RNA of any one of the preceding embodiments, comprising a 2-thiouracil.

A9. The synthetic guide RNA of any one of the preceding embodiments, comprising a 4-thiouracil.

A10. The synthetic guide RNA of any one of the preceding embodiments, comprising a 2-aminoadenine.

A11. The synthetic guide RNA of any one of the preceding embodiments, comprising a hypoxanthine.

A12. The synthetic guide RNA of any one of the preceding embodiments, comprising a 5-methylcytosine.

A13. The synthetic guide RNA of any one of the preceding embodiments, comprising a 5-methyluracil.

A14. The synthetic guide RNA of any one of the preceding embodiments, comprising a 5-aminoallyl-uracil.

A15. The synthetic guide RNA of any one of the preceding embodiments, comprising a Z ribonucleotide.

A16. The synthetic guide RNA of any one of the preceding embodiments, comprising a Z deoxyribonucleotide.

A17. The synthetic guide RNA of any one of the preceding embodiments, comprising a squarate conjugation.

A18. The synthetic guide RNA of any one of the preceding embodiments, comprising a dye linker.

A19. The synthetic guide RNA of embodiment A18, wherein the dye linker is 2-(4-butylamidofluorescein)propane-1,3-diol bis(phosphodiester) linker.

A20. The synthetic guide RNA of any one of the preceding embodiments, comprising a nucleotide with 2'-O-methyl and 3'-phosphorothioate.

A21. The synthetic guide RNA of any one of the preceding embodiments, comprising a nucleotide with 2'-O-methyl and 3"-PACE.

A22. The synthetic guide RNA of any one of the preceding embodiments, comprising a nucleotide with 2'-O-methyl and 3'-thioPACE.

A23. The synthetic guide RNA of any one of the preceding embodiments, comprising a nucleotide with 2'-deoxy and 3'-PACE.

A24. The synthetic guide RNA of any one of the preceding embodiments, comprising a 5-methylcytidine.

A25. The synthetic guide RNA of any one of the preceding embodiments, comprising a methylphosphonate.

A26. The synthetic guide RNA of any one of the preceding embodiments, comprising an ester of PACE, wherein the ester is optionally a methyl ester.

A27. The synthetic guide RNA of any one of the preceding embodiments, comprising a a single RNA strand comprising both the cr RNA segment and the tracr RNA segment.

A28. The synthetic guide RNA of any one of embodiments A1-A26, comprising two RNA strands, and the cr RNA segment and the tracr RNA segment are in different RNA strands.

A29. The synthetic guide RNA of any one of the preceding embodiments, comprising a modified nucleotide at a 5' end, 3' end, or both 5' end and 3' end of each RNA strand.

A30. The synthetic guide RNA of any one of the preceding embodiments, comprising a modified nucleotide in the guide sequence.

A31. The synthetic guide RNA of any one of the preceding embodiments, comprising a modified nucleotide 5' to the guide sequence.

A32. The synthetic guide RNA of any one of the preceding embodiments, comprising a modified nucleotide in the stem sequence.

A33. The synthetic guide RNA of any one of the preceding embodiments, comprising a modified nucleotide in the scaffold region.

A34. The synthetic guide RNA of any one of the preceding embodiments, comprising at least one unnatural, orthogonal base pair in the scaffold region, wherein the base pair is independently selected from isoG-isoC and Z base-P base.

A35. The synthetic guide RNA of any one of the preceding embodiments, comprising a 2'-amino group.

A36. The synthetic guide RNA of any one of the preceding embodiments, comprising a phosphorodithioate linkage group.

A37. The synthetic guide RNA of any one of the preceding embodiments, comprising a boranophosphonate linkage group.

A38. The synthetic guide RNA of any one of the preceding embodiments, comprising an unlocked nucleic acid modification (ULNA).

A39. The synthetic guide RNA of any one of the preceding embodiments, comprising a locked nucleic acid modification (LNA).

A40. The synthetic guide RNA of any one of the preceding embodiments, comprising an unstructured nucleic acid modification (UNA).

A41. The synthetic guide RNA of any one of the preceding embodiments, comprising a pseudoU.

A42. The synthetic guide RNA of any one of the preceding embodiments, comprising a 2'-MOE.

A43. The synthetic guide RNA of any one of the preceding embodiments, comprising a 2'-arabino.

A44. The synthetic guide RNA of any one of the preceding embodiments, comprising a 4'-thioribose.

A45. The synthetic guide RNA of any one of the preceding embodiments, comprising a squarate linkage A46. The synthetic guide RNA of any one of the preceding embodiments, comprising a triazaolo linkage.

A47. A method for cleaving or nicking a target polynucleotide comprising contacting the target polynucleotide with a CRISPR-associated protein and the synthetic guide RNA of any one of the preceding embodiments, and cleaving or nicking the target polynucleotide.

A48. The method of embodiment A47, wherein the cleaving or nicking takes place in vitro.

A49. The method of embodiment A47, wherein the cleaving or nicking takes place in a cell.

A50. The method of embodiment A47, wherein the cleaving or nicking takes place in vivo.

A51. The method of any one of embodiments A47-A50, wherein the CRISPR-associated protein is Cas9.

A52. The method of any one of embodiments A47-A51, wherein the cleaving or nicking results in gene editing.

A53. The method of any one of embodiments A47-A52, wherein the cleaving or nicking results in alteration of gene expression.

A54. A method for binding a target polynucleotide comprising contacting the target polynucleotide with a CRISPR-associated protein and the synthetic guide RNA of any one of the preceding embodiments, A55. The method of embodiment A54, wherein the CRISPR-associated protein comprises a mutant which does not have a cleavage or nicking activity.

A56. The method of embodiment A54 or A55, wherein the the CRISPR-associated protein is a fusion protein comprising a protein component not naturally existing in a CRISPR system.

A57. The method of any one of embodiments A54 to A56, resulting in a change of expression of the target polynucleotide.

A58. The method of any one of embodiments A54 to A57 useful to tag the target polynucleotide.

FURTHER EXEMPLARY EMBODIMENTS

B1. A synthetic guide RNA comprising:
(a) a crRNA segment comprising (i) a guide sequence capable of hybridizing to a target sequence in a polynucleotide, (ii) a stem sequence; and
(b) a tracrRNA segment comprising a nucleotide sequence that is partially or completely complementary to the stem sequence, wherein the synthetic guide RNA comprises one or more modifications, and wherein the synthetic guide RNA has gRNA functionality.

B2. The synthetic guide RNA of embodiment 1, comprising a 2'-O-methyl moiety, a 2'-deoxy moiety, a Z base, a phosphorothioate internucleotide linkage, a phosphonoacetate internucleotide linkage, a thiophosphonoacetate internucleotide linkage, or combinations thereof.

B3. The synthetic guide RNA of embodiment 1 or 2, comprising one or more modifications selected from the group consisting of a 2'-O-methyl nucleotide with a 3'-phosphorothioate group, a 2'-O-methyl nucleotide with a 3'-phosphonocarboxylate group, a 2'-O-methyl nucleotide with a 3'-phosphonoacetate group, a 2'-O-methyl nucleotide with a 3'-thiophosphonocarboxylate group, a 2'-O-methyl nucleotide with a 3'-thiophosphonoacetate group, a 2'-deoxy nucleotide with a 3'-phosphonoacetate group, a 2'-deoxy nucleotide with a 3'-thiophosphonoacetate group, and a Z base.

B4. The synthetic guide RNA of embodiment 1, 2 or 3, comprising one or more modifications selected from the group consisting of a 2'-fluororibosyl, a 2-thiouracil base, a 4-thiouracil base, a 2-aminoadenine base, an hypoxanthine base, a 5-methylcytosine base, a 5-methyluracil base, a methylphosphonate internucleotide linkage, a 5-aminoallyluracil base, a squarate linkage, a triazolo linkage, a dye conjugated to a nucleotide, and combinations thereof.

B5. The synthetic guide RNA of any of the preceding embodiments, comprising a modification selected from the group consisting of a 2'-MOE, 2'-amino, 2'-F-arabino, 2'-LNA, 2'-ULNA, 3'-methylphosphonate, 3'-boranophosphonate, 3'-phosphorodithioate, 2'-OMe-3'-P(S)$_2$, 2'-OMe-3'-P(CH$_3$), 2'-OMe-3'-P(BH$_3$), 4'-thioribosyl, L-sugar, 2-thiocytosine, 6-thioguanine, 2-aminopurine, pseudouracil, 7-deazaguanine, 7-deaza-8-azaguanine, 7-deazaadenine, 7-deaza-8-azaadenine, 5-hydroxymethylcytosine, 5-hydroxymethyluracil, 5,6-dehydrouracil, 5-propynylcytosine, 5-propynyluracil, 5-ethynylcytosine, 5-ethynyluracil, 5-allyluracil, 5-allylcytosine, 5-allylaminocytosine, P nucleobase, isocytosine (isoC), isoguanine (isoG),UNA, x(A,G,C,T), y(A,G,C,T), abasic nucleotide, PEG, hydrocarbon linker, halo-substituted hydrocarbon linker, heteroatom (O,N,S)-substituted hydrocarbon linker, (keto, carboxy, amido, thionyl, carbamoyl, or thionocarbamoyl)-containing hydrocarbon linker, spermine linker, and combinations thereof.

B6. The synthetic guide RNA of any one of the preceding embodiments, comprising a stability-enhancing modification.

B7. The synthetic guide RNA of any one of the preceding embodiments, comprising at least two modifications; wherein a first modification is a stability-enhancing modification and a second modification is a specificity-altering modification.

B8. The synthetic guide RNA of embodiment 6 or 7, wherein the stability-enhancing modification is located in the guide sequence.

B9. The synthetic guide RNA of embodiment 6 or 7, wherein the stability-enhancing modification is located upstream of the guide sequence.

B10. The synthetic guide RNA of embodiment 6 or 7, wherein the stability-enhancing modification is located within the first five and/or the last five nucleotides of the crRNA segment.

B11. The synthetic guide RNA of embodiment 6 or 7, wherein the stability-enhancing modification is located in the tracrRNA segment.

B12. The synthetic guide RNA of embodiment 6 or 7, wherein the stability-enhancing modification is located within the first five and/or the last five nucleotides of the tracrRNA segment.

B13. The synthetic guide RNA of any one of embodiments 6-12, wherein the stability-enhancing modification comprises a 2'-O-methyl moiety, a 2'-fluoro moiety, or a 2'-deoxy moiety.

B14. The synthetic guide RNA of any one of embodiments 6-13, wherein the stability-enhancing modification comprises a phosphorothioate internucleotide linkage, a phosphonoacetate internucleotide linkage, a thiophosphonoacetate internucleotide linkage, a methylphosphonate internucleotide linkage, a boranophosphate internucleotide linkage, or a phosphorodithioate internucleotide linkage.

B15. The synthetic guide RNA of any one of embodiments 6-14, wherein the stability-enhancing modification comprises a 3'-phosphonoacetate or a 3'-thiophosphonoacetate.

B16. The synthetic guide RNA any one of embodiments 6-15, wherein the stability-enhancing modification comprises a 2'-O-methyl-3'-phosphorothioate nucleotide, a 2'-O-methyl-3'-phosphonoacetate nucleotide, or a 2'-O-methyl-3'-thiophosphonoacetate nucleotide.

B17. The synthetic guide RNA of any one of embodiments 6-16, wherein the stability-enhancing modification comprises a 2'-fluoro-3'-phosphorothioate nucleotide, a 2'-fluoro-3'-phosphonoacetate nucleotide, or a 2'-fluoro-3'-thiophosphonoacetate nucleotide.

B18. The synthetic guide RNA of any one of the preceding embodiments, comprising a specificity-altering modification.

B19. The synthetic guide RNA of embodiment 18, wherein the specificity-altering modification is located in the guide sequence.

B20. The synthetic guide RNA of any one of embodiment 18 or 19, wherein the specificity-altering modification comprises a 2-thiouracil, a 4-thiouracil or a 2-aminoadenine.

B21. The synthetic guide RNA of any one of embodiments 18-20, wherein the specificity-altering modification comprises a phosphorothioate internucleotide linkage, a phosphonoacetate internucleotide linkage, a thiophosphonoacetate internucleotide linkage, a methylphosphonate internucleotide linkage, a boranophosphate internucleotide linkage, or a phosphorodithioate internucleotide linkage.

B22. The synthetic guide RNA of any one of embodiments 18-21, wherein the specificity-altering modification comprises a 3'-phosphonoacetate or a 3'-thiophosphonoacetate.

B23. The synthetic guide RNA of any one of the preceding embodiments, comprising a fluorescent dye or a label.

B24. The synthetic guide RNA of any one of the preceding embodiments, comprising one or more isotopic labels.

B25. The synthetic guide RNA of any one of the preceding embodiments, wherein the guide RNA is conjugated to an oligonucleotide, an aptamer, an amino acid, a peptide, a protein, a steroid, a lipid, a folic acid, a vitamin, a sugar, or an oligosaccharide.

B26. The synthetic guide RNA of any one of the preceding embodiments, wherein the synthetic guide RNA is a single guide RNA, wherein the crRNA segment and the tracrRNA segment are linked through a loop L.

B27. The synthetic guide RNA of embodiment 26, wherein the loop L comprises 1, 2, 3, 4, 5, 6, 7, 8, 9, or 10 nucleotides.

B28. The synthetic guide RNA of embodiment 26 or 27, wherein the loop L comprises a nucleotide sequence of GNRA, wherein N represents A, C, G, or U and R represents A or G.

B29. The synthetic guide RNA of embodiment 26, 27 or 28, wherein the loop L comprises a nucleotide sequence of GAAA.

B30. The synthetic guide RNA of any one of embodiments 26-29, wherein the loop L comprises one or more modified nucleotides.

B31. The synthetic guide RNA of embodiment 30, wherein the loop L comprises a fluorescent dye.

B32. The synthetic guide RNA of embodiment 31, wherein the dye is conjugated to a 2-(4-butylamido-dye)propane-1,3-diol bis(phosphodiester) linker.

B33. The synthetic guide RNA of any one of the preceding embodiments, wherein the crRNA segment is at the 5' end of the guide RNA.

B34. The synthetic guide RNA of any one of the preceding embodiments, wherein the tracrRNA segment is at the 3' end of the guide RNA.

B35. The synthetic guide RNA of any of the preceding embodiments, wherein the crRNA segment comprises from 25 to 70 nucleotides.

B36. The synthetic guide RNA of any of the preceding embodiments, wherein the guide sequence comprises from 15 to 30 nucleotides.

B37. The synthetic guide RNA of any of the preceding embodiments, wherein the stem sequence comprises from 10 to 50 nucleotides.

B38. The synthetic guide RNA of any of the preceding embodiments, comprising one or more triazolo linkage(s).

B39. The synthetic guide RNA of any of the preceding embodiments, comprising one or more squarate linkage(s).

B40. The synthetic guide RNA of any of the preceding embodiments, wherein the guide RNA comprises a nucleotide composition of:

$$M_m N_n$$

wherein each N independently represents an unmodified nucleotide and each M is selected from a 2'-O-methyl ribonucleotide, a 2'-O-methyl-3'-P(S) ribonucleotide, a 2'-O-methyl-3'-PACE ribonucleotide, a 2'-O-methyl-3'-thioPACE ribonucleotide, and a 2'-deoxynucleotide;

wherein each M is at any position in the sequence of the guide RNA; and wherein m is an integer between 1 and 220, and n is an integer between 0 and 219, and 50<m+n≤220.

B41. The synthetic guide RNA of embodiment 38, wherein m+n≤150, and each of m and n are independently selected from an integer between 0 and 150, provided that m is not 0.

B42. The synthetic guide RNA of any of the preceding embodiments, wherein the guide RNA comprises a nucleotide sequence of:

$$M_m N_n M'_{m'} N'_{n'} M''_{m''}$$

wherein each M, M' and M" independently represent a modified nucleotide and each N and N' independently represent an unmodified ribonucleotide;

wherein any given M is the same or different from any other M, any given N is the same or different from any other N, any given M' is the same or different from any other M', any given N' is the same or different from any other N', any given M" is the same or different from any other M"; and wherein m is an integer between 0 and 40, n is an integer between 20 and 130, m' is an integer between 0 and 10, n' is an integer between 0 and 50, m" is an integer between 0 and 10, provided that m+m'+m" is greater than or equal to 1.

B43. The synthetic guide RNA of any of the preceding embodiments, wherein the crRNA segment comprises a nucleotide sequence of:

$$M_m N_n M'_{m'} N'_{n'}$$

wherein M and M' each represent a modified nucleotide and N and N' each represent an unmodified ribonucleotide;

wherein any given M is the same or different from any other M, any given N is the same or different from any other N, any given M' is the same or different from any other M', any given N' is the same or different from any other N'; and wherein n and n' are each independently selected from an integer between 0 and 50, and wherein m and m' are each independently selected from an integer between 0 and 25, provided that m+m' is greater than or equal to 1.

B44. The synthetic guide RNA of any of the preceding embodiments, wherein the guide sequence comprises a nucleotide sequence of:

$$M_m N_n M'_{m'} N'_{n'}$$

wherein M and M' each represent a modified nucleotide and N and N' each represent an unmodified ribonucleotide;

wherein any given M is the same or different from any other M, any given N is the same or different from any other N, any given M' is the same or different from any other M', any given N' is the same or different from any other N'; and wherein m, n, m', and n' are each independently selected from an integer between 0 and 40, provided that m+m' is greater than or equal to 1.

B45. The synthetic guide RNA of any of the preceding embodiments, wherein the tracrRNA segment comprises a nucleotide sequence of:

$$N_n M_m N'_{n'} M'_{m'}$$

wherein M and M' each represent a modified nucleotide and N and N' each represent an unmodified ribonucleotide;

wherein any given M is the same or different from any other M, any given N is the same or different from any other N, any given M' is the same or different from any other M', any given N' is the same or different from any other N'; and wherein n is an integer between 0 and 130 m is an integer between 0 and 40, and n' is an integer between 0 and 130, and m' is an integer between 0 and 40, provided that m+m' is greater than or equal to 1.

B46. The synthetic guide RNA of any one of embodiments 40-43, wherein m, m', m+m', or m+m'+m" is 1, 2, 3, 4, 5, 6, 7, 8, 9, 10, 11, 12, 13, 14, 15, 16, 17, 18, 19, or 20.

B47. The synthetic guide RNA of any one of embodiments 40-43, wherein m, m', m+m', or m+m'+m" is 1, 2, 3, 4, 5, or 6.

B48. The synthetic guide RNA of any one of embodiments 40-45, wherein n is 16, 17, 18, or 19.

B49. The synthetic guide RNA of any one of embodiments 40-45, wherein n, n', or n+n' is an integer between 75 and 115.

B50. The synthetic guide RNA of any one of embodiments 40-47, wherein each M is independently selected from the group consisting of a 2'-modified nucleotide, a 3'-modified nucleotide, and combinations thereof.

B51. The synthetic guide RNA of embodiment 48, wherein the 2'-modified nucleotide is selected from the group consisting of a 2'-deoxy nucleotide, a 2'-O-methyl nucleotide, a 2'-fluoro nucleotide, and a 2'-O—$C_{1-3}$alkyl-O—$C_{1-3}$alkyl nucleotide.

B52. The synthetic guide RNA of embodiment 48, wherein the 3'-modified nucleotide is selected from the group consisting of a 3'-phosphonoacetate nucleotide and a 3'-thiophosphonoacetate nucleotide.

B53. The synthetic guide RNA of embodiment 48, wherein the combination of the 2'-modified nucleotide and the 3'-modified nucleotide comprises a 2'-O-methyl-3'-phosphorothioate nucleotide, a 2'-O-methyl-3'-phosphonoacetate nucleotide, or a 2'-O-methyl-3'-thiophosphonoacetate nucleotide.

B54. A method for cleaving a target polynucleotide comprising contacting the target polynucleotide with a CRISPR-associated protein and the synthetic guide RNA of any one of the preceding embodiments and cleaving the target polynucleotide.

B55. The method of embodiment 52, further comprising contacting the target polynucleotide with an exogenous CRISPR-associated protein.

B56. The method of embodiment 53, wherein the CRISPR-associated protein is Cas9.

B57. The method of any one of embodiments 52-54, wherein the cleavage results in a functional knockout of a target gene.

B58. The method of any one of embodiments 52-55, further comprising repairing the cleaved target polynucleotide by homology-directed repair with an exogenous or endogenous template polynucleotide.

B59. The method of embodiment 56, wherein the exogenous or endogenous template polynucleotide comprises at least one sequence having substantial sequence identity with a sequence on either side of the cleavage site.

B60. The method of any one of embodiments 52-57, further comprising repairing the cleaved target polynucleotide by non-homologous end joining.

B61. The method of any one of embodiments 56-58, wherein the repairing step produces an insertion, deletion, or substitution of one or more nucleotides of the target polynucleotide.

B62. The method of embodiment 59, wherein the insertion, deletion, or substitution results in one or more amino acid changes in a protein expressed from a gene comprising the target polynucleotide.

B63. The method of any one of embodiments 52-60, wherein the target polynucleotide is contacted with the CRISPR-associated protein and the synthetic guide RNA in vitro.

B64. The method of any one of embodiments 52-61, wherein the target polynucleotide contacted with the CRISPR-associated protein and the synthetic guide RNA is within the genome of a cell in vitro or in vivo.

B65. The method of embodiment 62, wherein the cell is isolated from a multicellular source prior to contacting the target polynucleotide with the CRISPR-associated protein and the synthetic guide RNA.

B66. The method of embodiment 63, wherein the source is a plant, an animal, a multicellular protist, or a fungus.

B67. The method of any one of embodiments 62-64, wherein the cell, or a cell derived therefrom, is returned to the source after contacting the target polynucleotide with the CRISPR-associated protein and the synthetic guide RNA.

B68. A method of modifying a target polynucleotide in a cell comprising introducing into the cell the synthetic guide RNA of any one of embodiments 1-51 and introducing into the cell a CRISPR-associated protein or a nucleic acid that expresses a CRISPR-associated protein in the cell.

B69. The method of embodiment 66, wherein the CRISPR-associated-protein is Cas9.

B70. A method of altering expression of at least one gene product in a cell comprising introducing into the cell the synthetic guide RNA of any one of embodiments 1-51 and further introducing into the cell a CRISPR-associated-protein or a nucleic acid that expresses a CRISPR-associated protein in the cell, wherein the cell contains and expresses a DNA molecule having a target sequence and encoding the gene product.

B71. The method of embodiment 68, wherein the CRISPR-associated-protein is Cas9.

B72. The method of embodiment 69, wherein the CRISPR-associated-protein cleaves the DNA molecule.

B73. A set or library of RNA molecules comprising two or more synthetic guide RNAs of any one of embodiments 1-51.

B74. A kit comprising the synthetic guide RNA of any one of embodiments 1-51 or the set or library of RNA molecules of embodiment 71.

B75. The kit of embodiment 72, further comprising a CRISPR-associated protein or a nucleic acid encoding the CRISPR-associated protein.

B76. The kit of embodiment 73, wherein the CRISPR-associated-protein is Cas9.

B77. The synthetic guide RNA, method or kit of any of the preceding embodiments, wherein the synthetic guide RNA comprises an end modification.

B78. The synthetic guide RNA of any of the preceding embodiments, having a single RNA strand or two separate complementary RNA strands, wherein the guide RNA comprises at least one stability-enhancing modification at both ends of each RNA strand.

C1. A synthetic guide RNA comprising:
(a) a crRNA segment comprising (i) a guide sequence capable of hybridizing to a target sequence in a polynucleotide, (ii) a stem sequence; and
(b) a tracrRNA segment comprising a nucleotide sequence that is partially or completely complementary to the stem sequence, wherein the synthetic guide RNA comprises one or more modifications, and wherein the synthetic guide RNA has gRNA functionality.

C2. The synthetic guide RNA of embodiment C1, wherein one or more of the modifications comprises a stability-enhancing modification.

C3. The synthetic guide RNA of embodiment C2, wherein one or more of the stability-enhancing modifications is located in the guide sequence.

C4. The synthetic guide RNA of embodiment C2, wherein the stability-enhancing modification comprises a 2'-O-methyl moiety, a Z base, a 2'-deoxy nucleotide, a phosphorothioate internucleotide linkage, a phosphonoacetate (PACE) internucleotide linkage, or a thiophosphonoacetate (thioPACE) internucleotide linkage, or combinations thereof.

C5. The synthetic guide RNA of any of the foregoing embodiments, comprising less than 26 consecutive 2'-O-methyl modified nucleotides at a 5' end of the guide RNA.

C6. The synthetic guide RNA of any of the foregoing embodiments, comprising a Z base replacing a cytosine in the synthetic guide RNA.

C7. The synthetic guide RNA of any of the foregoing embodiments, comprising at least one 2-thiouracil at a position corresponding to a uridine that can engage in U-G wobble pairing with a potential off-target sequence.

C8. The synthetic guide RNA of any of the foregoing embodiments, comprising one or more modifications selected from the group consisting of a 2'-O-methyl nucleotide with a 3'-phosphorothioate group, a 2'-O-methyl nucleotide with a 3'-phosphonoacetate group, a 2'-O-methyl nucleotide with a 3'-thiophosphonoacetate group, and a 2'-deoxy nucleotide with a 3'-phosphonoacetate group.

C9. The synthetic guide RNA of any of the foregoing embodiments, comprising at least two modifications.

C10. The synthetic guide RNA any of the foregoing embodiments, comprising up to 50 modifications.

C11. The synthetic guide RNA of any of the foregoing embodiments, comprising a single RNA strand or two separate RNA strands, and one or more modifications at a 5' end of each RNA strand, at a 3' end of each RNA strand, or at both a 5' end and a 3' end of each RNA strand.

C12. The synthetic guide RNA of any of the foregoing embodiments, comprising 7 or fewer consecutive modified nucleotides at a 5' end or at a 3' end or at each of 5' and 3' ends.

C13. The synthetic guide RNA of any of the foregoing embodiments, comprising one or more 5-methyluridine nucleotides at one or more of a 5' end, a 3' end, or a stem-loop.

C14. The synthetic guide RNA of any of the foregoing embodiments, wherein one or more of the modifications alters base-pairing thermostability.

C15. The synthetic guide RNA of embodiment C14, wherein said one or more modifications enhances the base-pairing thermostability.

C16. The synthetic guide RNA of embodiment C15, wherein said one or more modifications is independently selected from a 2-thiouracil (2-thioU), a 4-thiouracil (4-thioU), a 2-aminoadenine, a 2'-O-methyl, a 2'-fluoro, a 5-methyluridine, a 5-methylcytidine, and a locked nucleic acid modification (LNA).

C17. The synthetic guide RNA of embodiment C15, wherein said one or more modifications decreases the base-pairing thermostability.

C18. The synthetic guide RNA of embodiment C17, wherein said one or more modifications is independently selected from a 2-thiouracil, a 2'-deoxy, a phosphorothioate linkage, a phosphorodithioate linkage, a boranophosphonate linkage, a phosphonoacetate linkage, a thiophosphonoacetate linkage, and an unlocked nucleic acid modification (ULNA).

C19. The synthetic guide RNA of any of the foregoing embodiments, comprising one or more 2'-O-methylA-2'-O-methylU base pairs.

C20. The synthetic guide RNA of any of the foregoing embodiments, wherein one or more of the modifications is a specificity-altering modification.

C21. The synthetic guide RNA of embodiment C20, wherein the specificity-altering modification is located in the guide sequence.

C22. The synthetic guide RNA of any of the foregoing embodiments, wherein the specificity-altering modification comprises a 2-thiouracil, a 4-thiouracil, a 2-aminoadenine, a 2'-O-methyl, a 2'-fluoro, a LNA, a phosphorothioate linkage, a phosphorodithioate linkage, a boranophosphonate linkage, a phosphonoacetate linkage, a thiophosphonoacetate linkage, an ULNA, a 2'-deoxy, a 5-methyluridine, a 5-methylcytidine, or combinations thereof.

C23. The synthetic guide RNA of any of the foregoing embodiments, comprising a fluorescent dye or a label.

C24. The synthetic guide RNA of embodiment C23, wherein the fluorescent dye or a label is bound to a stem-loop of the synthetic guide RNA.

C25. A method for genomic editing to modify a DNA sequence, or regulating the expression of a gene of interest, or cleaving a target polynucleotide comprising: contacting the DNA sequence, the gene of interest, or the target polynucleotide with a CRISPR-associated protein and the synthetic guide RNA of any of the foregoing embodiments, and editing, regulating or cleaving the DNA sequence, the gene of interest or the target polynucleotide.

C26. The method of embodiment C25, wherein the method is performed in vitro, and the synthetic guide RNA comprises 15 or more 2'-O-methyl modifications throughout the guide sequence.

C27. A set or library of RNA molecules comprising two or more synthetic guide RNAs of any of the foregoing embodiments.

C28. A kit comprising the synthetic guide RNA of any of the foregoing embodiments.

C29. An array of RNA molecules comprising two or more synthetic guide RNAs of any of the foregoing embodiments.

The foregoing description of exemplary or preferred embodiments should be taken as illustrating, rather than as limiting, the present invention as defined by the claims. As will be readily appreciated, numerous variations and combinations of the features set forth above can be utilized without departing from the present invention as set forth in the claims. Such variations are not regarded as a departure from the scope of the invention, and all such variations are intended to be included within the scope of the following claims. All references cited herein are incorporated by reference in their entireties.

We claim:

1. A synthetic CRISPR guide RNA comprising:
   (a) a crRNA segment comprising (i) a guide sequence capable of hybridizing to a target sequence in a polynucleotide, (ii) a stem sequence; and
   (b) a tracrRNA segment comprising a nucleotide sequence that is partially or completely complementary to the stem sequence,
   wherein the synthetic guide RNA has gRNA functionality comprising associating with a Cas protein and targeting the gRNA:Cas protein complex to the target sequence, and comprises one or more modifications in the guide sequence, wherein the one or more modifications comprises a 2'-O-methyl.

2. A method for genome editing to modify a DNA sequence, or for regulating the expression of a gene of interest, or for cleaving a target polynucleotide, or for binding a target polynucleotide comprising: contacting the DNA sequence, the gene of interest, or the target polynucleotide with a CRISPR-associated (Cas) protein and the synthetic guide RNA of claim 1, and editing, regulating, cleaving, or binding the DNA sequence, the gene of interest, or the target polynucleotide.

3. A set or library of RNA molecules comprising two or more synthetic guide RNAs of claim 1.

4. The synthetic guide RNA of claim 1 wherein the guide RNA is a single-guide RNA (sgRNA).

5. The synthetic guide RNA of claim 1, wherein said one or more modifications comprises a 2'-O-methyl nucleotide with a 3'-phosphorothioate.

6. The synthetic guide RNA of claim 1, wherein said one or more modifications comprises a 2'-O-methyl nucleotide with a 3'-phosphonoacetate.

7. The synthetic guide RNA of claim 1, wherein said one or more modifications comprises a 2'-O-methyl nucleotide with a 3'-thiophosphonoacetate.

8. The synthetic guide RNA of claim 1 further comprising one or more phosphorothioate internucleotide linkage, phosphonoacetate (PACE) internucleotide linkage, and/or thiophosphonoacetate (thioPACE) internucleotide linkage.

9. The synthetic guide RNA of claim 1, further comprising up to three phosphorothioate, PACE, and/or thioPACE internucleotide linkages in the guide sequence.

10. The synthetic guide RNA of claim 1, further comprising up to seven phosphorothioate, PACE, and/or thioPACE internucleotide linkages in the guide sequence.

11. The synthetic guide RNA of claim 1, further comprising up to ten phosphorothioate, PACE, and/or thioPACE internucleotide linkages in the guide sequence.

12. The synthetic guide RNA of claim 1, comprising up to five consecutive phosphorothioate internucleotide linkages at a 5'-end of the guide RNA.

13. The synthetic guide RNA of claim 12, further comprising up to five consecutive phosphorothioate, PACE, and/or thioPACE internucleotide linkages at a 3'-end of the guide RNA.

14. The synthetic guide RNA of claim 1, further comprising a fluorophore at a 5'-end of the guide RNA.

15. The synthetic guide RNA of claim 1, comprising one or more end modification.

16. The synthetic guide RNA of claim 1, comprising at least 2 consecutive 2'-O-methyl modifications.

17. The synthetic guide RNA of claim 1, comprising at least six 2'-O-methyl modifications.

18. The synthetic guide RNA of claim 1, comprising at least twenty 2'-O-methyl modifications.

19. A synthetic CRISPR crRNA molecule comprising a guide sequence capable of hybridizing to a target sequence in a polynucleotide, wherein the synthetic crRNA molecule comprises one or more modifications in the guide sequence;
   wherein the synthetic crRNA molecule has gRNA functionality comprising associating with a Cas protein and targeting the gRNA:Cas protein complex to the target sequence; and
   wherein the one or more modifications comprises a 2'-O-methyl.

20. The synthetic CRISPR crRNA of claim 19, further comprising one or more phosphorothioate internucleotide linkage, phosphonoacetate (PACE) internucleotide linkage, and/or thiophosphonoacetate (thioPACE) internucleotide linkage.

21. The synthetic CRISPR crRNA of claim 19, wherein said one or more modifications comprises a 2'-O-methyl nucleotide with a 3'-phosphorothioate.

22. The synthetic CRISPR crRNA of claim 19, wherein said one or more modifications comprises a 2'-O-methyl nucleotide with a 3'-phosphonoacetate.

23. The synthetic CRISPR crRNA of claim 19, wherein said one or more modifications comprises a 2'-O-methyl nucleotide with a 3'-thiophosphonoacetate.

24. The synthetic CRISPR crRNA of claim 19, further comprising up to three phosphorothioate, PACE, and/or thioPACE internucleotide linkages in the guide sequence.

25. The synthetic CRISPR crRNA of claim 19, further comprising up to seven phosphorothioate, PACE, and/or thioPACE internucleotide linkages in the guide sequence.

26. The synthetic CRISPR crRNA of claim 19, further comprising up to ten phosphorothioate, PACE, and/or thioPACE internucleotide linkages in the guide sequence.

27. The synthetic CRISPR crRNA of claim 19, comprising up to five consecutive phosphorothioate internucleotide linkages at a 5'-end of the crRNA.

28. The synthetic CRISPR crRNA of claim 27, further comprising up to five consecutive phosphorothioate, PACE, and/or thioPACE internucleotide linkages at a 3'-end of the crRNA.

29. The synthetic CRISPR crRNA of claim 19, further comprising a fluorophore at a 5'-end of the crRNA.

30. The synthetic CRISPR crRNA of claim 19, comprising at least 2 consecutive 2'-O-methyl modifications.

31. The synthetic CRISPR crRNA of claim 19, comprising at least six 2'-O-methyl modifications.

32. The synthetic CRISPR crRNA of claim 19, comprising at least twenty 2'-O-methyl modifications.

33. A method for genome editing to modify a DNA sequence, or for regulating the expression of a gene of interest, or for cleaving a target polynucleotide, or for binding a target polynucleotide comprising: contacting the DNA sequence, the gene of interest, or the target polynucleotide with a CRISPR-associated (Cas) protein and the CRISPR crRNA of claim 19, and editing, regulating, cleaving, or binding the DNA sequence, the gene of interest, or the target polynucleotide.

* * * * *

SEQUENCE LISTING

<160> NUMBER OF SEQ ID NOS: 143

<210> SEQ ID NO 1
<211> LENGTH: 1368
<212> TYPE: PRT
<213> ORGANISM: Streptococcus pyogenes

<400> SEQUENCE: 1

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365
```

```
Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
        530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
        690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
```

```
           785                 790                 795                 800
Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
                835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
                930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
                995                 1000                1005

Val Tyr Gly Asp Tyr Lys Val Tyr Asp Val Arg Lys Met Ile Ala
                1010                1015                1020

Lys Ser Glu Gln Glu Ile Gly Lys Ala Thr Ala Lys Tyr Phe Phe
                1025                1030                1035

Tyr Ser Asn Ile Met Asn Phe Phe Lys Thr Glu Ile Thr Leu Ala
                1040                1045                1050

Asn Gly Glu Ile Arg Lys Arg Pro Leu Ile Glu Thr Asn Gly Glu
                1055                1060                1065

Thr Gly Glu Ile Val Trp Asp Lys Gly Arg Asp Phe Ala Thr Val
                1070                1075                1080

Arg Lys Val Leu Ser Met Pro Gln Val Asn Ile Val Lys Lys Thr
                1085                1090                1095

Glu Val Gln Thr Gly Gly Phe Ser Lys Glu Ser Ile Leu Pro Lys
                1100                1105                1110

Arg Asn Ser Asp Lys Leu Ile Ala Arg Lys Lys Asp Trp Asp Pro
                1115                1120                1125

Lys Lys Tyr Gly Gly Phe Asp Ser Pro Thr Val Ala Tyr Ser Val
                1130                1135                1140

Leu Val Val Ala Lys Val Glu Lys Gly Lys Ser Lys Lys Leu Lys
                1145                1150                1155

Ser Val Lys Glu Leu Leu Gly Ile Thr Ile Met Glu Arg Ser Ser
                1160                1165                1170

Phe Glu Lys Asn Pro Ile Asp Phe Leu Glu Ala Lys Gly Tyr Lys
                1175                1180                1185

Glu Val Lys Lys Asp Leu Ile Ile Lys Leu Pro Lys Tyr Ser Leu
                1190                1195                1200
```

```
Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Gly Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 2
<211> LENGTH: 7
<212> TYPE: PRT
<213> ORGANISM: Simian virus 40

<400> SEQUENCE: 2

Pro Lys Lys Lys Arg Lys Val
1               5

<210> SEQ ID NO 3
<211> LENGTH: 7
<212> TYPE: PRT
<213> ORGANISM: Simian virus 40

<400> SEQUENCE: 3

Pro Lys Lys Lys Arg Arg Val
1               5

<210> SEQ ID NO 4
<211> LENGTH: 16
<212> TYPE: PRT
<213> ORGANISM: Artificial Sequence
<220> FEATURE:
<223> OTHER INFORMATION: synthetic construct

<400> SEQUENCE: 4

Lys Arg Pro Ala Ala Thr Lys Lys Ala Gly Gln Ala Lys Lys Lys Lys
1               5                   10                  15

<210> SEQ ID NO 5
<211> LENGTH: 20
<212> TYPE: PRT
<213> ORGANISM: Human immunodeficiency virus
<220> FEATURE:
<221> NAME/KEY: misc_feature
<223> OTHER INFORMATION: tat protein

<400> SEQUENCE: 5
```

```
Gly Arg Lys Lys Arg Arg Gln Arg Arg Pro Pro Gln Pro Lys Lys
1               5                   10                  15

Lys Arg Lys Val
            20
```

<210> SEQ ID NO 6
<211> LENGTH: 19
<212> TYPE: PRT
<213> ORGANISM: Hepatitis B virus
<220> FEATURE:
<221> NAME/KEY: misc_feature
<223> OTHER INFORMATION: middle S protein, partial

<400> SEQUENCE: 6

```
Pro Leu Ser Ser Ile Phe Ser Arg Ile Gly Asp Pro Pro Lys Lys
1               5                   10                  15

Arg Lys Val
```

<210> SEQ ID NO 7
<211> LENGTH: 24
<212> TYPE: PRT
<213> ORGANISM: Artificial Sequence
<220> FEATURE:
<223> OTHER INFORMATION: synthetic construct

<400> SEQUENCE: 7

```
Gly Ala Leu Phe Leu Gly Trp Leu Gly Ala Ala Gly Ser Thr Met Gly
1               5                   10                  15

Ala Pro Lys Lys Lys Arg Lys Val
            20
```

<210> SEQ ID NO 8
<211> LENGTH: 27
<212> TYPE: PRT
<213> ORGANISM: Artificial Sequence
<220> FEATURE:
<223> OTHER INFORMATION: synthetic construct

<400> SEQUENCE: 8

```
Gly Ala Leu Phe Leu Gly Phe Leu Gly Ala Ala Gly Ser Thr Met Gly
1               5                   10                  15

Ala Trp Ser Gln Pro Lys Lys Lys Arg Lys Val
            20                  25
```

<210> SEQ ID NO 9
<211> LENGTH: 21
<212> TYPE: PRT
<213> ORGANISM: Artificial Sequence
<220> FEATURE:
<223> OTHER INFORMATION: synthetic construct

<400> SEQUENCE: 9

```
Lys Glu Thr Trp Trp Glu Thr Trp Trp Thr Glu Trp Ser Gln Pro Lys
1               5                   10                  15

Lys Lys Arg Lys Val
            20
```

<210> SEQ ID NO 10
<211> LENGTH: 390
<212> TYPE: DNA
<213> ORGANISM: Artificial Sequence
<220> FEATURE:
<223> OTHER INFORMATION: synthetic construct

```
<400> SEQUENCE: 10
agaatttaac tgtggtcaca tttgctttat cgactggctt catctcacag ctcatcttac    60
gcaagttcga tgagtatgcc agtcactttc aatttggttg aatgttcccg tgacatgcga   120
gttctgtcga ccatgtgccg cggattgaat cctcaaggg tggtgataga tgctacggtg   180
gtgatgcgca tgcgctcagt cctcatctcc ctcaagcagg ccccgctggt gggtcggagt   240
ccctagtgaa gccaccaata tagtggtcgt gtcaagcaac tgtccacgct ccaccctcga   300
ggtcgtaaca taaacgtact aaggcacgag taaacaagat cgatagcaag aacatggtat   360
agactgacgg agagctcgcc attagtctga                                    390

<210> SEQ ID NO 11
<211> LENGTH: 390
<212> TYPE: DNA
<213> ORGANISM: Artificial Sequence
<220> FEATURE:
<223> OTHER INFORMATION: synthetic construct

<400> SEQUENCE: 11
agaatttaac tgtggtcaca tttgctttat cgactggctt catctcacag ctcatcttac    60
gcaagttcga tgagtatgcc agtcactttc aatttggttg aatgttcccg tgacatgcga   120
gttctgtcga ccatgtgccg cggattgaat cctcaaggg tggtgataga tgctacggtg   180
gtgatgcgta tgcactcagt cctcaactcc ctcaagcagg cgaccctgg gggtcggagt   240 ccctagtgaa gccaccaata tagtggtcgt gtcaagcaac tgtccacgct ccaccctcga   300
ggtcgtaaca taaacgtact aaggcacgag taaacaagat cgatagcaag aacatggtat   360
agactgacgg agagctcgcc attagtctga                                    390

<210> SEQ ID NO 12
<211> LENGTH: 390
<212> TYPE: DNA
<213> ORGANISM: Artificial Sequence
<220> FEATURE:
<223> OTHER INFORMATION: synthetic construct

<400> SEQUENCE: 12
agaatttaac tgtggtcaca tttgctttat cgactggctt catctcacag ctcatcttac    60
gcaagttcga tgagtatgcc agtcactttc aatttggttg aatgttcccg tgacatgcga   120
gttctgtcga ccatgtgccg cggattgaat cctcaaggg tggtgataga tgctacggtg   180
gtgatgcaat aaatttcagc cctcatttcc ctcaagcagg ggttacttta gggtcggagt   240
ccctagtgaa gccaccaata tagtggtcgt gtcaagcaac tgtccacgct ccaccctcga   300
ggtcgtaaca taaacgtact aaggcacgag taaacaagat cgatagcaag aacatggtat   360
agactgacgg agagctcgcc attagtctga                                    390

<210> SEQ ID NO 13
<211> LENGTH: 390
<212> TYPE: DNA
<213> ORGANISM: Artificial Sequence
<220> FEATURE:
<223> OTHER INFORMATION: synthetic construct

<400> SEQUENCE: 13
agaatttaac tgtggtcaca tttgctttat cgactggctt catctcacag ctcatcttac    60
gcaagttcga tgagtatgcc agtcactttc aatttggttg aatgttcccg tgacatgcga   120
gttctgtcga ccatgtgccg cggattgaat cctcaaggg tggtgataga tgctacggtg   180
```

| | |
|---|---|
| gtgatgctct ccagcccact cctcatcccc ctcaagccgg tcccaggctg gggtcggagt | 240 |
| ccctagtgaa gccaccaata tagtggtcgt gtcaagcaac tgtccacgct ccaccctcga | 300 |
| ggtcgtaaca taaacgtact aaggcacgag taaacaagat cgatagcaag aacatggtat | 360 |
| agactgacgg agagctcgcc attagtctga | 390 |

```
<210> SEQ ID NO 14
<211> LENGTH: 2838
<212> TYPE: DNA
<213> ORGANISM: Artificial Sequence
<220> FEATURE:
<223> OTHER INFORMATION: synthetic construct

<400> SEQUENCE: 14
```

| | |
|---|---|
| gcgtttctgg gtgagcaaaa acaggaaggc aaaatgccgc aaaaaaggga ataagggcga | 60 |
| cacggaaatg ttgaatactc atactcttcc ttttcaata ttattgaagc atttatcagg | 120 |
| gttattgtct catgagcgga tacatatttg aatgtattta gaaaaataaa caatagggg | 180 |
| ttccgcgcac atttccccga aaagtgccac ctaaattgta agcgttaata ttttgttaaa | 240 |
| attcgcgtta aattttttgtt aaatcagctc atttttttaac caataggccg aaatcggcaa | 300 |
| aatcccttat aaatcaaaag aatagaccga datagggttg agtgttgttc cagtttggaa | 360 |
| caagagtcca ctattaaaga acgtggactc caacgtcaaa gggcgaaaaa ccgtctatca | 420 |
| gggcgatggc ccactacgtg aaccatcacc ctaatcaagt ttttgggt cgaggtgccg | 480 |
| taaagcacta atcggaacc ctaaagggag ccccccgattt agagcttgac ggggaaagcc | 540 |
| ggcgaacgtg gcgagaaagg aagggaagaa agcgaaagga gcgggcgcta gggcgctggc | 600 |
| aagtgtagcg gtcacgctgc gcgtaaccac cacacccgcc gcgcttaatg cgccgctaca | 660 |
| gggcgcgtcc cattcgccat tcaggctgcg caactgttgg gaagggcgat cggtgcgggc | 720 |
| ctcttcgcta ttacgccagc tggcgaaagg gggatgtgct gcaaggcgat taagttgggt | 780 |
| aacgccaggg ttttcccagt cacgacgttg taaaacgacg ccagtgagc gcgcgtaata | 840 |
| cgactcacta tagggcgaat tgggtacgat cgatgcggcc tcgcaggcca agatgtctc | 900 |
| ccgcatgcgc tcagtcctca tctccctcaa gcaggccctg ctggtgcact gaagagccac | 960 |
| cctgtgcgcg tgatatgcag ctccagcttt tgttcccttt agtgagggtt aattgcgcgc | 1020 |
| ttggcgtaat catggtcata gctgtttcct gtgtgaaatt gttatccgct cacaattcca | 1080 |
| cacaacatac gagccggaag cataaagtgt aaagcctggg gtgcctaatg agtgagctaa | 1140 |
| ctcacattaa ttgcgttgcg ctcactgccc gctttccagt cgggaaacct gtcgtgccag | 1200 |
| ctgcattaat gaatcggcca acgcgcgggg agaggcggtt tgcgtattgg gcgctcttcc | 1260 |
| gcttcctcgc tcactgactc gctgcgctcg gtcgttcggc tgcggcgagc ggtatcagct | 1320 |
| cactcaaagg cggtaatacg gttatccaca gaatcagggg ataacgcagg aaagaacatg | 1380 |
| tgagcaaaag gccagcaaaa ggccaggaac cgtaaaaagg ccgcgttgct ggcgtttttc | 1440 |
| cataggctcc gcccccctga cgagcatcac aaaaatcgac gctcaagtca gaggtggcga | 1500 |
| aacccgacag gactataaag ataccaggcg tttccccctg gaagctccct cgtgcgctct | 1560 |
| cctgttccga ccctgccgct taccggatac ctgtccgcct ttctcccttc gggaagcgtg | 1620 |
| gcgctttctc atagctcacg ctgtaggtat ctcagttcgg tgtaggtcgt tcgctccaag | 1680 |
| ctgggctgtg tgcacgaacc ccccgttcag cccgaccgct gcgccttatc cggtaactat | 1740 |
| cgtcttgagt ccaacccggt aagacacgac ttatcgccac tggcagcagc cactggtaac | 1800 |

| | |
|---|---|
| aggattagca gagcgaggta tgtaggcggt gctacagagt tcttgaagtg gtggcctaac | 1860 |
| tacggctaca ctagaaggac agtatttggt atctgcgctc tgctgaagcc agttaccttc | 1920 |
| ggaaaaagag ttggtagctc ttgatccggc aaacaaacca ccgctggtag cggtggtttt | 1980 |
| tttgtttgca agcagcagat tacgcgcaga aaaaaaggat ctcaagaaga tcctttgatc | 2040 |
| ttttctacgg ggtctgacgc tcagtggaac gaaaactcac gttaagggat tttggtcatg | 2100 |
| agattatcaa aaaggatctt cacctagatc cttttaaatt aaaaatgaag ttttaaatca | 2160 |
| atctaaagta tatatgagta aacttggtct gacagttacc aatgcttaat cagtgaggca | 2220 |
| cctatctcag cgatctgtct atttcgttca tccatagttg cctgactccc cgtcgtgtag | 2280 |
| ataactacga tacgggaggg cttaccatct ggccccagtg ctgcaatgat accgcgagac | 2340 |
| ccacgctcac cggctccaga tttatcagca ataaaccagc cagccggaag ggccgagcgc | 2400 |
| agaagtggtc ctgcaacttt atccgcctcc atccagtcta ttaattgttg ccgggaagct | 2460 |
| agagtaagta gttcgccagt taatagtttg cgcaacgttg ttgccattgc tacaggcatc | 2520 |
| gtggtgtcac gctcgtcgtt tggtatggct tcattcagct ccggttccca acgatcaagg | 2580 |
| cgagttacat gatcccccat gttgtgcaaa aaagcggtta gctccttcgg tcctccgatc | 2640 |
| gttgtcagaa gtaagttggc cgcagtgtta tcactcatgg ttatggcagc actgcataat | 2700 |
| tctcttactg tcatgccatc cgtaagatgc ttttctgtga ctggtgagta ctcaaccaag | 2760 |
| tcattctgag aatagtgtat gcggcgaccg agttgctctt gcccggcgtc aatacgggat | 2820 |
| aataccgcgc cacatagc | 2838 |

<210> SEQ ID NO 15
<211> LENGTH: 2838
<212> TYPE: DNA
<213> ORGANISM: Artificial Sequence
<220> FEATURE:
<223> OTHER INFORMATION: synthetic construct

<400> SEQUENCE: 15

| | |
|---|---|
| gcgtttctgg gtgagcaaaa acaggaaggc aaaatgccgc aaaaaaggga taagggcga | 60 |
| cacggaaatg ttgaatactc atactcttcc ttttcaata ttattgaagc atttatcagg | 120 |
| gttattgtct catgagcgga tacatatttg aatgtattta gaaaaataaa caaatagggg | 180 |
| ttccgcgcac atttccccga aaagtgccac ctaaattgta agcgttaata ttttgttaaa | 240 |
| attcgcgtta aattttttgtt aaatcagctc attttttaac caataggccg aaatcggcaa | 300 |
| aatcccttat aaatcaaaag aatagaccga tagggttg agtgttgttc cagtttggaa | 360 |
| caagagtcca ctattaaaga acgtggactc caacgtcaaa gggcgaaaaa ccgtctatca | 420 |
| gggcgatggc ccactacgtg aaccatcacc taatcaagt tttttggggt cgaggtgccg | 480 |
| taaagcacta atcggaacc ctaaagggag cccccgattt agagcttgac ggggaaagcc | 540 |
| ggcgaacgtg gcgagaaagg aagggaagaa agcgaaagga gcgggcgcta gggcgctggc | 600 |
| aagtgtagcg gtcacgctgc gcgtaaccac cacacccgcc gcgcttaatg cgccgctaca | 660 |
| gggcgcgtcc cattcgccat tcaggctgcg caactgttgg gaagggcgat cggtgcgggc | 720 |
| ctcttcgcta ttacgccagc tggcgaaagg gggatgtgct gcaaggcgat taagttgggt | 780 |
| aacgccaggg ttttcccagt cacgacgttg taaaacgacg gccagtgagc gcgcgtaata | 840 |
| cgactcacta tagggcgaat tgggtacgat cgatgcggcc tcgcagggca aagaggtctc | 900 |
| ctgtatgcac tcagtcctca actccctcaa gcaggcgacc cttggtgcac tgacaaaccg | 960 |
| ctcctgcgcg tgatatgcag ctccagcttt tgttcccttt agtgagggtt aattgcgcgc | 1020 |

```
ttggcgtaat catggtcata gctgtttcct gtgtgaaatt gttatccgct cacaattcca    1080
cacaacatac gagccggaag cataaagtgt aaagcctggg gtgcctaatg agtgagctaa    1140
ctcacattaa ttgcgttgcg ctcactgccc gctttccagt cgggaaacct gtcgtgccag    1200
ctgcattaat gaatcggcca acgcgcgggg agaggcggtt tgcgtattgg gcgctcttcc    1260
gcttcctcgc tcactgactc gctgcgctcg tcgttcggc tgcggcgagc ggtatcagct    1320
cactcaaagg cggtaatacg gttatccaca gaatcagggg ataacgcagg aaagaacatg    1380
tgagcaaaag gccagcaaaa ggccaggaac cgtaaaaagg ccgcgttgct ggcgtttttc    1440
cataggctcc gccccctga cgagcatcac aaaaatcgac gctcaagtca gaggtggcga    1500
aacccgacag gactataaag ataccaggcg tttccccctg gaagctccct cgtgcgctct    1560
cctgttccga ccctgccgct taccggatac ctgtccgcct ttctcccttc gggaagcgtg    1620
gcgctttctc atagctcacg ctgtaggtat ctcagttcgg tgtaggtcgt tcgctccaag    1680
ctgggctgtg tgcacgaacc ccccgttcag cccgaccgct gcgccttatc cggtaactat    1740
cgtcttgagt ccaacccggt aagacacgac ttatcgccac tggcagcagc cactggtaac    1800
aggattagca gagcgaggta tgtaggcggt gctacagagt tcttgaagtg gtggcctaac    1860
tacggctaca ctagaaggac agtatttggt atctgcgctc tgctgaagcc agttaccttc    1920
ggaaaaagag ttggtagctc ttgatccggc aaacaaacca ccgctggtag cggtggtttt    1980
tttgtttgca agcagcagat tacgcgcaga aaaaaggat ctcaagaaga tcctttgatc    2040
ttttctacgg ggtctgacgc tcagtggaac gaaaactcac gttaagggat tttggtcatg    2100
agattatcaa aaaggatctt cacctagatc cttttaaatt aaaaatgaag ttttaaatca    2160
atctaaagta tatatgagta aacttggtct gacagttacc aatgcttaat cagtgaggca    2220
cctatctcag cgatctgtct atttcgttca tccatagttg cctgactccc cgtcgtgtag    2280
ataactacga tacgggaggg cttaccatct ggccccagtg ctgcaatgat accgcgagac    2340
ccacgctcac cggctccaga tttatcagca ataaaccagc cagccggaag ggccgagcgc    2400
agaagtggtc ctgcaacttt atccgcctcc atccagtcta ttaattgttg ccgggaagct    2460
agagtaagta gttcgccagt taatagtttg cgcaacgttg ttgccattgc tacaggcatc    2520
gtggtgtcac gctcgtcgtt tggtatggct tcattcagct ccggttccca acgatcaagg    2580
cgagttacat gatcccccat gttgtgcaaa aaagcggtta gctccttcgg tcctccgatc    2640
gttgtcagaa gtaagttggc cgcagtgtta tcactcatgg ttatggcagc actgcataat    2700
tctcttactg tcatgccatc cgtaagatgc ttttctgtga ctggtgagta ctcaaccaag    2760
tcattctgag aatagtgtat gcggcgaccg agttgctctt gcccggcgtc aatacgggat    2820
aataccgcgc cacatagc                                                  2838
```

<210> SEQ ID NO 16
<211> LENGTH: 2838
<212> TYPE: DNA
<213> ORGANISM: Artificial Sequence
<220> FEATURE:
<223> OTHER INFORMATION: synthetic construct

<400> SEQUENCE: 16

```
gcgtttctgg gtgagcaaaa acaggaaggc aaaatgccgc aaaaaaggga ataagggcga      60
cacggaaatg ttgaatactc atactcttcc ttttcaata ttattgaagc atttatcagg     120
gttattgtct catgagcgga tacatatttg aatgtattta gaaaaataaa caaatagggg    180
```

```
ttccgcgcac atttccccga aaagtgccac ctaaattgta agcgttaata ttttgttaaa      240
attcgcgtta aattttttgtt aaatcagctc attttttaac caataggccg aaatcggcaa     300
aatcccttat aaatcaaaag aatagaccga gatagggttg agtgttgttc cagtttggaa      360
caagagtcca ctattaaaga acgtggactc caacgtcaaa gggcgaaaaa ccgtctatca      420 ggcgatggc ccactacgtg aaccatcacc ctaatcaagt ttttggggt cgaggtgccg        480 taaagcacta aatcggaacc ctaaagggag cccccgattt agagcttgac ggggaaagcc      540
ggcgaacgtg gcgagaaagg aagggaagaa agcgaaagga gcgggcgcta gggcgctggc     600
aagtgtagcg gtcacgctgc gcgtaaccac cacacccgcc gcgcttaatg cgccgctaca      660
gggcgcgtcc cattcgccat tcaggctgcg caactgttgg gaagggcgat cggtgcgggc     720
ctcttcgcta ttacgccagc tggcgaaagg gggatgtgct gcaaggcgat taagttgggt     780
aacgccaggg ttttcccagt cacgacgttg taaaacgacg gccagtgagc gcgcgtaata    840
cgactcacta tagggcgaat tgggtacgat cgatgcggcc tcaggagagg gagccatgct    900
catctccagc ccactcctca tcccctcaa gccggtccca ggctgagagg ctaaagcttg      960
tctttgcgcg tgatatgcag ctccagcttt tgttcccttt agtgagggtt aattgcgcgc    1020
ttggcgtaat catggtcata gctgtttcct gtgtgaaatt gttatccgct cacaattcca    1080
cacaacatac gagccggaag cataaagtgt aaagcctggg gtgcctaatg agtgagctaa    1140
ctcacattaa ttgcgttgcg ctcactgccc gctttccagt cgggaaacct gtcgtgccag    1200
ctgcattaat gaatcggcca acgcgcgggg agaggcggtt tgcgtattgg gcgctcttcc    1260
gcttcctcgc tcactgactc gctgcgctcg gtcgttcggc tgcggcgagc ggtatcagct    1320
cactcaaagg cggtaatacg gttatccaca gaatcagggg ataacgcagg aaagaacatg    1380
tgagcaaaag gccagcaaaa ggccaggaac cgtaaaaagg ccgcgttgct ggcgtttttc    1440
cataggctcc gcccccctga cgagcatcac aaaaatcgac gctcaagtca gaggtggcga    1500
aacccgacag gactataaag ataccaggcg tttccccctg gaagctccct cgtgcgctct    1560
cctgttccga ccctgccgct taccggatac ctgtccgcct ttctcccttc gggaagcgtg    1620
gcgctttctc atagctcacg ctgtaggtat ctcagttcgg tgtaggtcgt tcgctccaag    1680
ctgggctgtg tgcacgaacc ccccgttcag cccgaccgct gcgccttatc cggtaactat    1740
cgtcttgagt ccaacccggt aagacacgac ttatcgccac tggcagcagc cactggtaac    1800
aggattagca gagcgaggta tgtaggcggt gctacagagt tcttgaagtg gtggcctaac    1860
tacggctaca ctagaaggac agtatttggt atctgcgctc tgctgaagcc agttaccttc    1920
ggaaaaagag ttggtagctc ttgatccggc aaacaaacca ccgctggtag cggtggtttt    1980
tttgtttgca agcagcagat tacgcgcaga aaaaaggat ctcaagaaga tcctttgatc    2040
ttttctacgg ggtctgacgc tcagtggaac gaaaactcac gttaagggat tttggtcatg    2100
agattatcaa aaaggatctt cacctagatc cttttaaatt aaaaatgaag ttttaaatca    2160
atctaaagta tatatgagta aacttggtct gacagttacc aatgcttaat cagtgaggca    2220
cctatctcag cgatctgtct atttcgttca tccatagttg cctgactccc cgtcgtgtag    2280
ataactacga tacgggaggg cttaccatct ggccccagtg ctgcaatgat accgcgagac    2340
ccacgctcac cggctccaga tttatcagca ataaccagc cagccggaag ggccgagcgc    2400
agaagtggtc ctgcaacttt atccgcctcc atccagtcta ttaattgttg ccgggaagct    2460
agagtaagta gttcgccagt taatagtttg cgcaacgttg ttgccattgc tacaggcatc    2520
gtggtgtcac gctcgtcgtt tggtatggct tcattcagct ccggttccca acgatcaagg    2580
```

```
cgagttacat gatcccccat gttgtgcaaa aaagcggtta gctccttcgg tcctccgatc    2640
gttgtcagaa gtaagttggc cgcagtgtta tcactcatgg ttatggcagc actgcataat    2700
tctcttactg tcatgccatc cgtaagatgc ttttctgtga ctggtgagta ctcaaccaag    2760
tcattctgag aatagtgtat gcggcgaccg agttgctctt gcccggcgtc aatacgggat    2820
aataccgcgc cacatagc                                                  2838
```

<210> SEQ ID NO 17
<211> LENGTH: 2995
<212> TYPE: DNA
<213> ORGANISM: Artificial Sequence
<220> FEATURE:
<223> OTHER INFORMATION: synthetic construct

<400> SEQUENCE: 17

```
gccgggcaag agcaactcgg tcgccgcata cactattctc agaatgactt ggttgagtac      60
tcaccagtca cagaaaagca tcttacggat ggcatgacag taagagaatt atgcagtgct     120
gccataacca tgagtgataa cactgcggcc aacttacttc tgacaacgat cggaggaccg     180
aaggagctaa ccgcttttttt gcacaacatg ggggatcatg taactcgcct tgatcgttgg     240
gaaccggagc tgaatgaagc cataccaaac gacgagcgtg acaccacgat gcctgtagca     300
atggcaacaa cgttgcgcaa actattaact ggcgaactac ttactctagc ttcccggcaa     360
caattaatag actggatgga ggcggataaa gttgcaggac cacttctgcg ctcggccctt     420
ccggctggct ggtttattgc tgataaatct ggagccggtg agcgtgggtc tcgcggtatc     480
attgcagcac tggggccaga tggtaagccc tcccgtatcg tagttatcta cacgacgggg     540
agtcaggcaa ctatggatga acgaaataga cagatcgctg agataggtgc ctcactgatt     600
aagcattggt aactgtcaga ccaagtttac tcatatatac tttagattga tttaaaactt     660
catttttaat ttaaaaggat ctaggtgaag atcctttttg ataatctcat gaccaaaatc     720
ccttaacgtg agttttcgtt ccactgagcg tcagaccccg tagaaaagat caaaggatct     780
tcttgagatc ctttttttct gcgcgtaatc tgctgcttgc aaacaaaaaa accaccgcta     840
ccagcggtgg tttgtttgcc ggatcaagag ctaccaactc tttttccgaa ggtaactggc     900
ttcagcagag cgcagatacc aaatactgtt cttctagtgt agccgtagtt aggccaccac     960
ttcaagaact ctgtagcacc gccacatacc tcgctctgct aatcctgtta ccagtggctg    1020
cttgccagtg gcgataagtc gtgtcttacc gggttggact caagacgata gttaccggat    1080
aaggcgcagc ggtcgggctg aacggggggt tcgtgcacac agcccagctt ggagcgaacg    1140
acctacaccg aactgagata cctacagcgt gagctatgag aaagcgccac gcttcccgaa    1200
gggagaaagg cggacaggta tccggtaagc ggcagggtcg gaacaggaga gcgcacgagg    1260
gagcttccag ggggaaacgc ctggtatctt tatagtcctg tcgggtttcg ccacctctga    1320
cttgagcgtc gatttttgtg atgctcgtca gggggggcgga gcctatggaa aaacgccagc    1380
aacgcggcct ttttacggtt cctggccttt tgctggcctt ttgctcacat gttctttcct    1440
gcgttatccc ctgattctgt ggataaccgt attaccgcct ttgagtgagc tgataccgct    1500
cgccgcagcc gaacgaccga gcgcagcgag tcagtgagcg aggaagcgga agagcgccca    1560
atacgcaaac cgcctctccc cgcgcgttgg ccgattcatt aatgcagctg gcacgacagg    1620
tttcccgact ggaaagcggg cagtgagcgc aacgcaatta atgtgagtta gctcactcat    1680
taggcacccc aggctttaca ctttatgctt ccggctcgta tgttgtgtgg aattgtgagc    1740
```

```
ggataacaat ttcacacagg aaacagctat gaccatgatt acgccaagcg cgcaattaac    1800
cctcactaaa gggaacaaaa gctgggtacc gggcccccc tcgacaccag ttgcattcga    1860
ttcctgtttg taattgtcca attcctgcag cccgggggat cggcagatgt agtgtttcca    1920
caggggatcc actagttcta gagcggccgc caccgcggtg gagctccaat tcgccctata    1980
gtgagtcgta ttacgcgcgc tcactggccg tcgttttaca acgtcgtgac tgggaaaacc    2040
ctggcgttac ccaacttaat cgccttgcag cacatcccc tttcgccagc tggcgtaata    2100
gcgaagaggc ccgcaccgat cgcccttccc aacagttgcg cagcctgaat ggcgaatgga    2160
aattgtaagc gttaatattt tgttaaaatt cgcgttaaat ttttgttaaa tcagctcatt    2220
ttttaaccaa taggccgaaa tcggcaaaat cccttataaa tcaaaagaat agaccgagat    2280
agggttgagt gttgttccag tttggaacaa gagtccacta ttaaagaacg tggactccaa    2340
cgtcaaaggg cgaaaaaccg tctatcaggg cgatggccca ctacgtgaac catcacccta    2400 atcaagttt tgggggtcga ggtgccgtaa agcactaaat cggaaccta aagggagccc    2460 ccgatttaga gcttgacggg gaaagccggc gaacgtggcg agaaaggaag gaagaaagc    2520 gaaaggagcg gcgctaggg cgctggcaag tgtagcggtc acgctgcgcg taaccaccac    2580
acccgccgcg cttaatgcgc cgctacaggg cgcgtcaggt ggcacttttc ggggaaatgt    2640
gcgcggaacc cctatttgtt tatttttcta aatacattca aatatgtatc cgctcatgag    2700
acaataaccc tgataaatgc ttcaataata ttgaaaaagg aagagtatga gtattcaaca    2760
tttccgtgtc gcccttattc cctttttttgc ggcattttgc cttcctgttt ttgctcaccc    2820
agaaacgctg gtgaaagtaa aagatgctga agatcagttg ggtgcacgag tgggttacat    2880
cgaactggat ctcaacagcg gtaagatcct tgagagtttt cgccccgaag aacgttttcc    2940
aatgatgagc acttttaaag ttctgctatg tggcgcggta ttatcccgta ttgac         2995
```

<210> SEQ ID NO 18
<211> LENGTH: 2838
<212> TYPE: DNA
<213> ORGANISM: Artificial Sequence
<220> FEATURE:
<223> OTHER INFORMATION: synthetic construct

<400> SEQUENCE: 18

```
gcgtttctgg gtgagcaaaa acaggaaggc aaaatgccgc aaaaaaggga ataagggcga     60
cacggaaatg ttgaatactc atactcttcc tttttcaata ttattgaagc atttatcagg    120
gttattgtct catgagcgga tacatatttg aatgtattta gaaaaataaa caaataggg     180 ttccgcgcac atttccccga aaagtgccac ctaaattgta agcgttaata ttttgttaaa    240
attgcgttta aattttttgtt aaatcagctc attttttaac caataggccg aaatcggcaa    300 atcccttat aaatcaaaag aatagaccga gatagggttg agtgttgttc cagtttggaa    360
caagagtcca ctattaaaga acgtggactc caacgtcaaa gggcgaaaaa ccgtctatca    420
gggcgatggc ccactacgtg aaccatcacc ctaatcaagt ttttgggggt cgaggtgccg    480
taaagcacta atcggaacc ctaaagggag cccccgattt agagcttgac ggggaaagcc    540
ggcgaacgtg gcgagaaagg aagggaagaa agcgaaagga gcgggcgcta gggcgctggc    600
aagtgtagcg gtcacgctgc gcgtaaccac cacacccgcc gcgcttaatg cgccgctaca    660
gggcgcgtcc cattcgccat tcaggctgcg caactgttgg gaagggcgat cggtgcgggc    720
ctcttcgcta ttacgccagc tggcgaaagg gggatgtgct gcaaggcgat taagttgggt    780
aacgccaggg ttttcccagt cacgacgttg taaaacgacg gccagtgagc gcgcgtaata    840
```

```
cgactcacta tagggcgaat tgggtacgat cgatgcggcc tcaagagctt cactgagtag      900
gattaagata ttgcagatgt agtgtttcca cagggtggct cttcagtgca ccagcggaac      960
ctgctgcgcg tgatatgcag ctccagcttt tgttcccttt agtgagggtt aattgcgcgc     1020
ttggcgtaat catggtcata gctgtttcct gtgtgaaatt gttatccgct cacaattcca     1080
cacaacatac gagccggaag cataaagtgt aaagcctggg gtgcctaatg agtgagctaa     1140
ctcacattaa ttgcgttgcg ctcactgccc gctttccagt cgggaaacct gtcgtgccag     1200
ctgcattaat gaatcggcca acgcgcgggg agaggcggtt tgcgtattgg gcgctcttcc     1260
gcttcctcgc tcactgactc gctgcgctcg tcgttcggc tgcggcgagc ggtatcagct      1320
cactcaaagg cggtaatacg gttatccaca gaatcagggg ataacgcagg aaagaacatg     1380
tgagcaaaag gccagcaaaa ggccaggaac cgtaaaaagg ccgcgttgct ggcgtttttc     1440
cataggctcc gcccccctga cgagcatcac aaaaatcgac gctcaagtca gaggtggcga     1500
aacccgacag gactataaag ataccaggcg tttccccctg gaagctccct cgtgcgctct     1560
cctgttccga ccctgccgct taccggatac ctgtccgcct ttctcccttc gggaagcgtg     1620
gcgctttctc atagctcacg ctgtaggtat ctcagttcgg tgtaggtcgt tcgctccaag     1680
ctgggctgtg tgcacgaacc ccccgttcag cccgaccgct gcgccttatc cggtaactat     1740
cgtcttgagt ccaacccggt aagacacgac ttatcgccac tggcagcagc cactggtaac     1800
aggattagca gagcgaggta tgtaggcggt gctacagagt tcttgaagtg gtggcctaac     1860
tacggctaca ctagaaggac agtatttggt atctgcgctc tgctgaagcc agttaccttc     1920
ggaaaaagag ttggtagctc ttgatccggc aaacaaacca ccgctggtag cggtggtttt     1980
tttgtttgca agcagcagat tacgcgcaga aaaaaaggat ctcaagaaga tcctttgatc     2040
ttttctacgg ggtctgacgc tcagtggaac gaaaactcac gttaagggat tttggtcatg     2100
agattatcaa aaaggatctt cacctagatc cttttaaatt aaaaatgaag ttttaaatca     2160
atctaaagta tatatgagta aacttggtct gacagttacc aatgcttaat cagtgaggca     2220
cctatctcag cgatctgtct atttcgttca tccatagttg cctgactccc cgtcgtgtag     2280
ataactacga tacgggaggg cttaccatct ggccccagtg ctgcaatgat accgcgagac     2340
ccacgctcac cggctccaga tttatcagca ataaaccagc cagccggaag ggccgagcgc     2400
agaagtggtc ctgcaacttt atccgcctcc atccagtcta ttaattgttg ccgggaagct     2460
agagtaagta gttcgccagt taatagtttg cgcaacgttg ttgccattgc tacaggcatc     2520
gtggtgtcac gctcgtcgtt tggtatggct tcattcagct ccggttccca acgatcaagg     2580
cgagttacat gatcccccat gttgtgcaaa aaagcggtta gctccttcgg tcctccgatc     2640
gttgtcagaa gtaagttggc cgcagtgtta tcactcatgg ttatggcagc actgcataat     2700
tctcttactg tcatgccatc cgtaagatgc ttttctgtga ctggtgagta ctcaaccaag     2760
tcattctgag aatagtgtat gcggcgaccg agttgctctt gcccggcgtc aatacgggat     2820
aataccgcgc cacatagc                                                    2838
```

<210> SEQ ID NO 19
<211> LENGTH: 2838
<212> TYPE: DNA
<213> ORGANISM: Artificial Sequence
<220> FEATURE:
<223> OTHER INFORMATION: synthetic construct

<400> SEQUENCE: 19

```
gcgtttctgg gtgagcaaaa acaggaaggc aaaatgccgc aaaaaaggga ataagggcga    60
cacggaaatg ttgaatactc atactcttcc tttttcaata ttattgaagc atttatcagg   120
gttattgtct catgagcgga tacatatttg aatgtattta gaaaaataaa caaatagggg   180
ttccgcgcac atttccccga aaagtgccac ctaaattgta agcgttaata ttttgttaaa   240
attcgcgtta aattttttgtt aaatcagctc attttttaac caataggccg aaatcggcaa   300
aatcccttat aaatcaaaag aatagaccga gatagggttg agtgttgttc cagtttggaa   360
caagagtcca ctattaaaga acgtggactc caacgtcaaa gggcgaaaaa ccgtctatca   420
gggcgatggc ccactacgtg aaccatcacc ctaatcaagt tttttggggt cgaggtgccg   480
taaagcacta atcggaacc ctaaagggag cccccgattt agagcttgac ggggaaagcc    540
ggcgaacgtg gcgagaaagg aagggaagaa agcgaaagga gcgggcgcta gggcgctggc   600
aagtgtagcg gtcacgctgc gcgtaaccac cacacccgcc gcgcttaatg cgccgctaca   660
gggcgcgtcc cattcgccat tcaggctgcg caactgttgg gaagggcgat cggtgcgggc   720
ctcttcgcta ttacgccagc tggcgaaagg gggatgtgct gcaaggcgat taagttgggt   780
aacgccaggg ttttcccagt cacgacgttg taaaacgacg gccagtgagc gcgcgtaata   840
cgactcacta tagggcgaat tgggtacgat cgatgcggcc tctctgaata gagttgggaa   900
gagatgcata caacatatgt agtatttcca cagggaatac aatggacaaa tgacctcaag   960
agcaggcgcg tgatatgcag ctccagcttt tgttcccttt agtgagggtt aattgcgcgc  1020
ttggcgtaat catggtcata gctgtttcct gtgtgaaatt gttatccgct cacaattcca  1080
cacaacatac gagccggaag cataaagtgt aaagcctggg gtgcctaatg agtgagctaa  1140
ctcacattaa ttgcgttgcg ctcactgccc gctttccagt cgggaaacct gtcgtgccag  1200
ctgcattaat gaatcggcca acgcgcgggg agaggcggtt tgcgtattgg gcgctcttcc  1260
gcttcctcgc tcactgactc gctgcgctcg tcgttcggc tgcggcgagc ggtatcagct   1320
cactcaaagg cggtaatacg gttatccaca gaatcagggg ataacgcagg aaagaacatg  1380
tgagcaaaag gccagcaaaa ggccaggaac cgtaaaaagg ccgcgttgct ggcgtttttc  1440
cataggctcc gccccctga cgagcatcac aaaaatcgac gctcaagtca gaggtggcga   1500
aacccgacag gactataaag ataccaggcg tttccccctg gaagctccct cgtgcgctct  1560
cctgttccga ccctgccgct taccggatac ctgtccgcct ttctcccttc gggaagcgtg  1620
gcgctttctc atagctcacg ctgtaggtat ctcagttcgg tgtaggtcgt tcgctccaag  1680
ctgggctgtg tgcacgaacc ccccgttcag cccgaccgct gcgccttatc cggtaactat  1740
cgtcttgagt ccaacccggt aagacacgac ttatcgccac tggcagcagc cactggtaac  1800
aggattagca gagcgaggta tgtaggcggt gctacagagt tcttgaagtg gtggcctaac  1860
tacggctaca ctagaaggac agtatttggt atctgcgctc tgctgaagcc agttaccttc  1920
ggaaaaagag ttggtagctc ttgatccggc aaacaaacca ccgctggtag cggtggtttt  1980
tttgtttgca agcagcagat tacgcgcaga aaaaaaggat ctcaagaaga tcctttgatc  2040
ttttctacgg ggtctgacgc tcagtggaac gaaaactcac gttaagggat tttggtcatg  2100
agattatcaa aaaggatctt cacctagatc cttttaaatt aaaaatgaag ttttaaatca  2160
atctaaagta tatatgagta aacttggtct gacagttacc aatgcttaat cagtgaggca  2220
cctatctcag cgatctgtct atttcgttca tccatagttg cctgactccc cgtcgtgtag  2280
ataactacga tacgggaggg cttaccatct ggccccagtg ctgcaatgat accgcgagac  2340
ccacgctcac cggctccaga tttatcagca ataaaccagc cagccggaag ggccgagcgc  2400
```

| | |
|---|---:|
| agaagtggtc ctgcaacttt atccgcctcc atccagtcta ttaattgttg ccgggaagct | 2460 |
| agagtaagta gttcgccagt taatagtttg cgcaacgttg ttgccattgc tacaggcatc | 2520 |
| gtggtgtcac gctcgtcgtt tggtatggct tcattcagct ccggttccca acgatcaagg | 2580 |
| cgagttacat gatcccccat gttgtgcaaa aaagcggtta gctccttcgg tcctccgatc | 2640 |
| gttgtcagaa gtaagttggc cgcagtgtta tcactcatgg ttatggcagc actgcataat | 2700 |
| tctcttactg tcatgccatc cgtaagatgc ttttctgtga ctggtgagta ctcaaccaag | 2760 |
| tcattctgag aatagtgtat gcggcgaccg agttgctctt gcccggcgtc aatacgggat | 2820 |
| aataccgcgc cacatagc | 2838 |

<210> SEQ ID NO 20
<211> LENGTH: 2838
<212> TYPE: DNA
<213> ORGANISM: Artificial Sequence
<220> FEATURE:
<223> OTHER INFORMATION: synthetic construct

<400> SEQUENCE: 20

| | |
|---|---:|
| gcgtttctgg gtgagcaaaa acaggaaggc aaaatgccgc aaaaaaggga taagggcga | 60 |
| cacggaaatg ttgaatactc atactcttcc tttttcaata ttattgaagc atttatcagg | 120 |
| gttattgtct catgagcgga tacatatttg aatgtattta gaaaaataaa caaataggg | 180 |
| ttccgcgcac atttccccga aaagtgccac ctaaattgta agcgttaata ttttgttaaa | 240 |
| attgcgttta atttttgtt aaatcagctc attttttaac caataggccg aaatcggcaa | 300 |
| aatcccttat aaatcaaaag aatagaccga gatagggttg agtgttgttc cagtttggaa | 360 |
| caagagtcca ctattaaaga acgtggactc caacgtcaaa gggcgaaaaa ccgtctatca | 420 |
| gggcgatggc ccactacgtg aaccatcacc ctaatcaagt tttttggggt cgaggtgccg | 480 |
| taaagcacta aatcggaacc ctaaagggag cccccgattt agagcttgac ggggaaagcc | 540 |
| ggcgaacgtg gcgagaaagg aagggaagaa agcgaaagga gcgggcgcta gggcgctggc | 600 |
| aagtgtagcg gtcacgctgc gcgtaaccac cacacccgcc gcgcttaatg cgccgctaca | 660 |
| gggcgcgtcc cattcgccat tcaggctgcg caactgttgg gaagggcgat cggtgcgggc | 720 |
| ctcttcgcta ttacgccagc tggcgaaagg gggatgtgct gcaaggcgat taagttgggt | 780 |
| aacgccaggg ttttcccagt cacgacgttg taaaacgacg ccagtgagc gcgcgtaata | 840 |
| cgactcacta tagggcgaat tgggtacgat cgatgcggcc tcgggcagct gcaggaataa | 900 |
| gagggatgtg aatggtaatg atggcttcaa catggcgctt gctcttcatt ccctgggtgt | 960 |
| agtctgcgcg tgatatgcag ctccagcttt tgttcccttt agtgagggtt aattgcgcgc | 1020 |
| ttggcgtaat catggtcata gctgtttcct gtgtgaaatt gttatccgct cacaattcca | 1080 |
| cacaacatac gagccggaag cataaagtgt aaagcctggg gtgcctaatg agtgagctaa | 1140 |
| ctcacattaa ttgcgttgcg ctcactgccc gctttccagt cgggaaacct gtcgtgccag | 1200 |
| ctgcattaat gaatcggcca acgcgcgggg agaggcggtt tgcgtattgg gcgctcttcc | 1260 |
| gcttcctcgc tcactgactc gctgcgctcg gtcgttcggc tgcggcgagc ggtatcagct | 1320 |
| cactcaaagg cggtaatacg gttatccaca gaatcagggg ataacgcagg aaagaacatg | 1380 |
| tgagcaaaag gccagcaaaa ggccaggaac cgtaaaaagg ccgcgttgct ggcgtttttc | 1440 |
| cataggctcc gcccccctga cgagcatcac aaaaatcgac gctcaagtca gaggtggcga | 1500 |
| aacccgacag gactataaag ataccaggcg tttccccctg gaagctccct cgtgcgctct | 1560 |

| | |
|---|---|
| cctgttccga ccctgccgct taccggatac ctgtccgcct ttctcccttc gggaagcgtg | 1620 |
| gcgctttctc atagctcacg ctgtaggtat ctcagttcgg tgtaggtcgt tcgctccaag | 1680 |
| ctgggctgtg tgcacgaacc ccccgttcag cccgaccgct gcgccttatc cggtaactat | 1740 |
| cgtcttgagt ccaacccggt aagacacgac ttatcgccac tggcagcagc cactggtaac | 1800 |
| aggattagca gagcgaggta tgtaggcggt gctacagagt tcttgaagtg gtggcctaac | 1860 |
| tacggctaca ctagaaggac agtatttggt atctgcgctc tgctgaagcc agttaccttc | 1920 |
| ggaaaagag ttggtagctc ttgatccggc aaacaaacca ccgctggtag cggtggtttt | 1980 |
| tttgtttgca agcagcagat tacgcgcaga aaaaaggat ctcaagaaga tcctttgatc | 2040 |
| ttttctacgg ggtctgacgc tcagtggaac gaaaactcac gttaagggat tttggtcatg | 2100 |
| agattatcaa aaaggatctt cacctagatc ctttaaatt aaaaatgaag ttttaaatca | 2160 |
| atctaaagta tatatgagta acttggtct gacagttacc aatgcttaat cagtgaggca | 2220 |
| cctatctcag cgatctgtct atttcgttca tccatagttg cctgactccc cgtcgtgtag | 2280 |
| ataactacga tacgggaggg cttaccatct ggccccagtg ctgcaatgat accgcgagac | 2340 |
| ccacgctcac cggctccaga tttatcagca ataaaccagc cagccggaag ggccgagcgc | 2400 |
| agaagtggtc ctgcaacttt atccgcctcc atccagtcta ttaattgttg ccgggaagct | 2460 |
| agagtaagta gttcgccagt taatagtttg cgcaacgttg ttgccattgc tacaggcatc | 2520 |
| gtggtgtcac gctcgtcgtt tggtatggct tcattcagct ccggttccca acgatcaagg | 2580 |
| cgagttacat gatcccccat gttgtgcaaa aaagcggtta gctccttcgg tcctccgatc | 2640 |
| gttgtcagaa gtaagttggc cgcagtgtta tcactcatgg ttatggcagc actgcataat | 2700 |
| tctcttactg tcatgccatc cgtaagatgc ttttctgtga ctggtgagta ctcaaccaag | 2760 |
| tcattctgag aatagtgtat gcggcgaccg agttgctctt gcccggcgtc aatacgggat | 2820 |
| aataccgcgc cacatagc | 2838 |

<210> SEQ ID NO 21
<211> LENGTH: 2838
<212> TYPE: DNA
<213> ORGANISM: Artificial Sequence
<220> FEATURE:
<223> OTHER INFORMATION: synthetic construct

<400> SEQUENCE: 21

| | |
|---|---|
| gcgtttctgg gtgagcaaaa acaggaaggc aaaatgccgc aaaaaaggga taagggcga | 60 |
| cacggaaatg ttgaatactc atactcttcc tttttcaata ttattgaagc atttatcagg | 120 |
| gttattgtct catgagcgga tacatatttg aatgtattta gaaaaataaa caaataggggg | 180 |
| ttccgcgcac atttccccga aaagtgccac ctaaattgta agcgttaata ttttgttaaa | 240 |
| attcgcgtta attttttgtt aaatcagctc atttttaac caataggccg aaatcggcaa | 300 |
| aatcccttat aaatcaaaag aatagaccga gatagggttg agtgttgttc agtttggaa | 360 |
| caagagtcca ctattaaaga acgtggactc caacgtcaaa gggcgaaaaa ccgtctatca | 420 |
| gggcgatggc ccactacgtg aaccatcacc ctaatcaagt ttttttggggt cgaggtgccg | 480 |
| taaagcacta aatcggaacc ctaaagggag cccccgattt agagcttgac ggggaaagcc | 540 |
| ggcgaacgtg gcgagaaagg aagggaagaa agcgaaagga gcgggcgcta gggcgctggc | 600 |
| aagtgtagcg gtcacgctgc gcgtaaccac cacacccgcc gcgcttaatg cgccgctaca | 660 |
| gggcgcgtcc cattcgccat tcaggctgcg caactgttgg gaagggcgat cggtgcgggc | 720 |
| ctcttcgcta ttacgccagc tggcgaaagg gggatgtgct gcaaggcgat taagttgggt | 780 |

```
aacgccaggg ttttcccagt cacgacgttg taaaacgacg gccagtgagc gcgcgtaata      840
cgactcacta tagggcgaat tgggtacgat cgatgcggcc tcctccttac tgcagccgaa      900
gtccggcctc aggatgttgt cgatgaaaaa gttggtggtg cggtgcagct gggccgctgg      960
ctgcggcgcg tgatatgcag ctccagcttt tgttcccttt agtgagggtt aattgcgcgc     1020
ttggcgtaat catggtcata gctgtttcct gtgtgaaatt gttatccgct cacaattcca     1080
cacaacatac gagccggaag cataaagtgt aaagcctggg gtgcctaatg agtgagctaa     1140
ctcacattaa ttgcgttgcg ctcactgccc gctttccagt cgggaaacct gtcgtgccag     1200
ctgcattaat gaatcggcca acgcgcgggg agaggcggtt tgcgtattgg gcgctcttcc     1260
gcttcctcgc tcactgactc gctgcgctcg tcgttcggc tgcggcgagc ggtatcagct     1320
cactcaaagg cggtaatacg gttatccaca gaatcagggg ataacgcagg aaagaacatg     1380
tgagcaaaag gccagcaaaa ggccaggaac cgtaaaaagg ccgcgttgct ggcgtttttc     1440
cataggctcc gccccctga cgagcatcac aaaaatcgac gctcaagtca gaggtggcga     1500
aacccgacag gactataaag ataccaggcg tttccccctg gaagctccct cgtgcgctct     1560
cctgttccga ccctgccgct taccggatac ctgtccgcct ttctcccttc gggaagcgtg     1620
gcgctttctc atagctcacg ctgtaggtat ctcagttcgg tgtaggtcgt tcgctccaag     1680
ctgggctgtg tgcacgaacc ccccgttcag cccgaccgct gcgccttatc cggtaactat     1740
cgtcttgagt ccaacccggt aagacacgac ttatcgccac tggcagcagc cactggtaac     1800
aggattagca gagcgaggta tgtaggcggt gctacagagt tcttgaagtg gtggcctaac     1860
tacggctaca ctagaaggac agtatttggt atctgcgctc tgctgaagcc agttaccttc     1920
ggaaaaagag ttggtagctc ttgatccggc aaacaaacca ccgctggtag cggtggtttt     1980
tttgtttgca agcagcagat tacgcgcaga aaaaaaggat ctcaagaaga tcctttgatc     2040
ttttctacgg ggtctgacgc tcagtggaac gaaaactcac gttaagggat tttggtcatg     2100
agattatcaa aaaggatctt cacctagatc cttttaaatt aaaaatgaag ttttaaatca     2160
atctaaagta tatatgagta aacttggtct gacagttacc aatgcttaat cagtgaggca     2220
cctatctcag cgatctgtct atttcgttca tccatagttg cctgactccc cgtcgtgtag     2280
ataactacga tacggagggg cttaccatct ggccccagtg ctgcaatgat accgcgagac     2340
ccacgctcac cggctccaga tttatcagca ataaccagc cagccggaag ggccgagcgc     2400
agaagtggtc ctgcaacttt atccgcctcc atccagtcta ttaattgttg ccgggaagct     2460
agagtaagta gttcgccagt taatagtttg cgcaacgttg ttgccattgc tacaggcatc     2520
gtggtgtcac gctcgtcgtt tggtatggct tcattcagct ccggttccca acgatcaagg     2580
cgagttacat gatcccccat gttgtgcaaa aaagcggtta gctccttcgg tcctccgatc     2640
gttgtcagaa gtaagttggc cgcagtgtta tcactcatgg ttatggcagc actgcataat     2700
tctcttactg tcatgccatc cgtaagatgc ttttctgtga ctggtgagta ctcaaccaag     2760
tcattctgag aatagtgtat gcggcgaccg agttgctctt gcccggcgtc aatacgggat     2820
aataccgcgc cacatagc                                                   2838
```

<210> SEQ ID NO 22
<211> LENGTH: 2838
<212> TYPE: DNA
<213> ORGANISM: Artificial Sequence
<220> FEATURE:
<223> OTHER INFORMATION: synthetic construct

<400> SEQUENCE: 22

```
gcgtttctgg gtgagcaaaa acaggaaggc aaaatgccgc aaaaaaggga ataagggcga         60
cacggaaatg ttgaatactc atactcttcc tttttcaata ttattgaagc atttatcagg        120
gttattgtct catgagcgga tacatatttg aatgtattta gaaaaataaa caaataggggg       180 ttccgcgcac atttccccga aaagtgccac ctaaattgta agcgttaata ttttgttaaa        240
attcgcgtta aattttttgtt aaatcagctc attttttaac caataggccg aaatcggcaa      300
aatcccttat aaatcaaaag aatagaccga gatagggttg agtgttgttc cagtttggaa        360
caagagtcca ctattaaaga acgtggactc aacgtcaaa gggcgaaaaa ccgtctatca         420
gggcgatggc ccactacgtg aaccatcacc ctaatcaagt tttttggggt cgaggtgccg        480
taaagcacta aatcggaacc ctaaagggag cccccgattt agagcttgac ggggaaagcc       540
ggcgaacgtg gcgagaaagg aagggaagaa agcgaaagga gcgggcgcta gggcgctggc        600
aagtgtagcg gtcacgctgc gcgtaaccac cacacccgcc gcgcttaatg cgccgctaca       660
gggcgcgtcc cattcgccat tcaggctgcg caactgttgg gaagggcgat cggtgcgggc       720
ctcttcgcta ttacgccagc tggcgaaagg gggatgtgct gcaaggcgat taagttgggt       780
aacgccaggg ttttcccagt cacgacgttg taaaacgacg ccagtgagc gcgcgtaata       840 cgactcacta tagggcgaat tgggtacgat cgatgcggcc tcgtcctttc gccggccgaa       900
ctcgggccgc aggatgttgt cgatgaagaa gttggtgatg cggtgcgggt gctggtggtt      960
gccgggcgcg tgatatgcag ctccagcttt tgttcccttt agtgagggtt aattgcgcgc      1020
ttggcgtaat catggtcata gctgtttcct gtgtgaaatt gttatccgct cacaattcca      1080
cacaacatac gagccggaag cataaagtgt aaagcctggg gtgcctaatg agtgagctaa      1140
ctcacattaa ttgcgttgcg ctcactgccc gctttccagt cgggaaacct gtcgtgccag      1200
ctgcattaat gaatcggcca acgcgcgggg agaggcggtt tgcgtattgg gcgctcttcc      1260
gcttcctcgc tcactgactc gctgcgctcg gtcgttcggc tgcggcgagc ggtatcagct      1320
cactcaaagg cggtaatacg gttatccaca gaatcagggg ataacgcagg aaagaacatg      1380
tgagcaaaag gccagcaaaa ggccaggaac cgtaaaaagg ccgcgttgct ggcgtttttc      1440
cataggctcc gcccccctga cgagcatcac aaaaatcgac gctcaagtca gaggtggcga      1500
aacccgacag gactataaag ataccaggcg tttccccctg gaagctccct cgtgcgctct      1560
cctgttccga ccctgccgct taccggatac ctgtccgcct ttctcccttc gggaagcgtg      1620
gcgctttctc atagctcacg ctgtaggtat ctcagttcgg tgtaggtcgt tcgctccaag      1680
ctgggctgtg tgcacgaacc ccccgttcag cccgaccgct gcgccttatc cggtaactat      1740
cgtcttgagt ccaacccggt aagacacgac ttatcgccac tggcagcagc cactggtaac      1800
aggattagca gagcgaggta tgtaggcggt gctacagagt tcttgaagtg gtggcctaac      1860
tacggctaca ctagaaggac agtatttggt atctgcgctc tgctgaagcc agttaccttc      1920
ggaaaaagag ttggtagctc ttgatccggc aaacaaacca ccgctggtag cggtggtttt      1980
tttgtttgca agcagcagat tacgcgcaga aaaaaaggat ctcaagaaga tcctttgatc      2040
ttttctacgg ggtctgacgc tcagtggaac gaaaactcac gttaagggat tttggtcatg      2100
agattatcaa aaaggatctt cacctagatc cttttaaatt aaaaatgaag ttttaaatca      2160
atctaaagta tatatgagta aacttggtct gacagttacc aatgcttaat cagtgaggca      2220
cctatctcag cgatctgtct atttcgttca tccatagttg cctgactccc cgtcgtgtag      2280
ataactacga tacgggaggg cttaccatct ggccccagtg ctgcaatgat accgcgagac      2340
```

```
ccacgctcac cggctccaga tttatcagca ataaaccagc cagccggaag ggccgagcgc      2400
agaagtggtc ctgcaacttt atccgcctcc atccagtcta ttaattgttg ccgggaagct      2460
agagtaagta gttcgccagt taatagtttg cgcaacgttg ttgccattgc tacaggcatc      2520
gtggtgtcac gctcgtcgtt tggtatggct tcattcagct ccggttccca acgatcaagg      2580
cgagttacat gatcccccat gttgtgcaaa aaagcggtta gctccttcgg tcctccgatc      2640
gttgtcagaa gtaagttggc cgcagtgtta tcactcatgg ttatggcagc actgcataat      2700
tctcttactg tcatgccatc cgtaagatgc ttttctgtga ctggtgagta ctcaaccaag      2760
tcattctgag aatagtgtat gcggcgaccg agttgctctt gcccggcgtc aatacgggat      2820
aataccgcgc cacatagc                                                    2838

<210> SEQ ID NO 23
<211> LENGTH: 2838
<212> TYPE: DNA
<213> ORGANISM: Artificial Sequence
<220> FEATURE:
<223> OTHER INFORMATION: synthetic construct

<400> SEQUENCE: 23
gcgtttctgg gtgagcaaaa acaggaaggc aaaatgccgc aaaaaaggga ataagggcga        60
cacggaaatg ttgaatactc atactcttcc ttttcaata ttattgaagc atttatcagg       120
gttattgtct catgagcgga tacatatttg aatgtattta gaaaaataaa caaatagggg       180
ttccgcgcac atttccccga aaagtgccac ctaaattgta agcgttaata ttttgttaaa       240 attgcgtta aattttgtt aaatcagctc attttttaac caataggccg aaatcggcaa       300
aatcccttat aaatcaaaag aatagaccga gatagggttg agtgttgttc cagtttggaa       360
caagagtcca ctattaaaga acgtggactc caacgtcaaa gggcgaaaaa ccgtctatca       420
gggcgatggc ccactacgtg aaccatcacc ctaatcaagt tttttggggt cgaggtgccg       480
taaagcacta atcggaacc ctaaagggag cccccgattt agagcttgac ggggaaagcc       540
ggcgaacgtg gcgagaaagg aagggaagaa agcgaaagga gcgggcgcta gggcgctggc       600
aagtgtagcg gtcacgctgc gcgtaaccac cacacccgcc gcgcttaatg cgccgctaca       660
gggcgcgtcc cattcgccat tcaggctgcg caactgttgg gaagggcgat cggtgcgggc       720
ctcttcgcta ttacgccagc tggcgaaagg gggatgtgct gcaaggcgat taagttgggt       780
aacgccaggg ttttcccagt cacgacgttg taaaacgacg ccagtgagc gcgcgtaata       840 cgactcacta tagggcgaat tgggtacgat cgatgcggcc tcggaacatt ggtaattaaa       900
cttaacgcct cagatttaga cgaaggattg aatgggaaca ttgtttattc attctcgaat       960
gatacgcgcg tgatatgcag ctccagcttt tgttcccttt agtgagggtt aattgcgcgc      1020
ttggcgtaat catggtcata gctgtttcct gtgtgaaatt gttatccgct cacaattcca      1080
cacaacatac gagccggaag cataaagtgt aaagcctggg gtgcctaatg agtgagctaa      1140
ctcacattaa ttgcgttgcg ctcactgccc gctttccagt cgggaaacct gtcgtgccag      1200
ctgcattaat gaatcggcca acgcgcgggg agaggcggtt tgcgtattgg gcgctcttcc      1260
gcttcctcgc tcactgactc gctgcgctcg gtcgttcggc tgcggcgagc ggtatcagct      1320
cactcaaagg cggtaatacg gttatccaca gaatcagggg ataacgcagg aaagaacatg      1380
tgagcaaaag gccagcaaaa ggccaggaac cgtaaaaagg ccgcgttgct ggcgtttttc      1440
cataggctcc gccccctga cgagcatcac aaaaatcgac gctcaagtca gaggtggcga      1500
```

```
aacccgacag gactataaag ataccaggcg tttccccctg gaagctccct cgtgcgctct    1560
cctgttccga ccctgccgct taccggatac ctgtccgcct ttctcccttc gggaagcgtg    1620
gcgctttctc atagctcacg ctgtaggtat ctcagttcgg tgtaggtcgt tcgctccaag    1680
ctgggctgtg tgcacgaacc ccccgttcag cccgaccgct gcgccttatc cggtaactat    1740
cgtcttgagt ccaacccggt aagacacgac ttatcgccac tggcagcagc cactggtaac    1800
aggattagca gagcgaggta tgtaggcggt gctacagagt tcttgaagtg gtggcctaac    1860
tacggctaca ctagaaggac agtatttggt atctgcgctc tgctgaagcc agttaccttc    1920
ggaaaaagag ttggtagctc ttgatccggc aaacaaacca ccgctggtag cggtggtttt    1980
tttgtttgca agcagcagat tacgcgcaga aaaaaaggat ctcaagaaga tcctttgatc    2040
ttttctacgg ggtctgacgc tcagtggaac gaaaactcac gttaagggat tttggtcatg    2100
agattatcaa aaaggatctt cacctagatc cttttaaatt aaaaatgaag ttttaaatca    2160
atctaaagta tatatgagta aacttggtct gacagttacc aatgcttaat cagtgaggca    2220
cctatctcag cgatctgtct atttcgttca tccatagttg cctgactccc cgtcgtgtag    2280
ataactacga tacggagggg cttaccatct ggccccagtg ctgcaatgat accgcgagac    2340
ccacgctcac cggctccaga tttatcagca ataaccagcc agccggaag gccgagcgc    2400
agaagtggtc ctgcaacttt atccgcctcc atccagtcta ttaattgttg ccgggaagct    2460
agagtaagta gttcgccagt taatagtttg cgcaacgttg ttgccattgc tacaggcatc    2520
gtggtgtcac gctcgtcgtt tggtatggct tcattcagct ccggttccca acgatcaagg    2580
cgagttacat gatcccccat gttgtgcaaa aaagcggtta gctccttcgg tcctccgatc    2640
gttgtcagaa gtaagttggc cgcagtgtta tcactcatgg ttatggcagc actgcataat    2700
tctcttactg tcatgccatc cgtaagatgc ttttctgtga ctggtgagta ctcaaccaag    2760
tcattctgag aatagtgtat gcggcgaccg agttgctctt gcccggcgtc aatacgggat    2820
aataccgcgc cacatagc                                                2838

<210> SEQ ID NO 24
<211> LENGTH: 2838
<212> TYPE: DNA
<213> ORGANISM: Artificial Sequence
<220> FEATURE:
<223> OTHER INFORMATION: synthetic construct

<400> SEQUENCE: 24
gcgtttctgg gtgagcaaaa acaggaaggc aaaatgccgc aaaaaaggga ataagggcga      60
cacggaaatg ttgaatactc atactcttcc ttttcaata ttattgaagc atttatcagg     120
gttattgtct catgagcgga tacatatttg aatgtattta gaaaaataaa caaataggg     180
ttccgcgcac atttccccga aaagtgccac ctaaattgta agcgttaata ttttgttaaa    240
attgcgtta aattttgtt aaatcagctc attttttaac caataggccg aaatcggcaa    300
aatcccttat aaatcaaaag aatagaccga gatagggttg agtgttgttc cagtttggaa    360
caagagtcca ctattaaaga acgtggactc caacgtcaaa gggcgaaaaa ccgtctatca    420
gggcgatggc ccactacgtg aaccatcacc ctaatcaagt tttttggggt cgaggtgccg    480
taaagcacta aatcggaacc ctaaagggag cccccgattt agagcttgac ggggaaagcc    540
ggcgaacgtg gcgagaaagg aagggaagaa agcgaaagga gcgggcgcta gggcgctggc    600
aagtgtagcg gtcacgctgc gcgtaaccac cacacccgcc gcgcttaatg cgccgctaca    660
gggcgcgtcc cattcgccat tcaggctgcg caactgttgg gaagggcgat cggtgcgggc    720
```

```
ctcttcgcta ttacgccagc tggcgaaagg gggatgtgct gcaaggcgat taagttgggt    780
aacgccaggg ttttcccagt cacgacgttg taaaacgacg ccagtgagc gcgcgtaata    840 cgactcacta tagggcgaat tgggtacgat cgatgcggcc tcggaacgct ggtgattcat    900
cccaatgcct cagatttaga cgaaggcttg aatggggata ttatttactc cttctccagt    960
gatgtgcgcg tgatatgcag ctccagcttt tgttcccttt agtgagggtt aattgcgcgc   1020
ttggcgtaat catggtcata gctgtttcct gtgtgaaatt gttatccgct cacaattcca   1080
cacaacatac gagccggaag cataaagtgt aaagcctggg gtgcctaatg agtgagctaa   1140
ctcacattaa ttgcgttgcg ctcactgccc gctttccagt cgggaaacct gtcgtgccag   1200
ctgcattaat gaatcggcca acgcgcgggg agaggcggtt tgcgtattgg gcgctcttcc   1260
gcttcctcgc tcactgactc gctgcgctcg gtcgttcggc tgcggcgagc ggtatcagct   1320
cactcaaagg cggtaatacg gttatccaca gaatcagggg ataacgcagg aaagaacatg   1380
tgagcaaaag gccagcaaaa ggccaggaac cgtaaaaagg ccgcgttgct ggcgtttttc   1440
cataggctcc gcccccctga cgagcatcac aaaaatcgac gctcaagtca gaggtggcga   1500
aacccgacag gactataaag ataccaggcg tttccccctg gaagctccct cgtgcgctct   1560
cctgttccga ccctgccgct taccggatac ctgtccgcct ttctcccttc gggaagcgtg   1620
gcgctttctc atagctcacg ctgtaggtat ctcagttcgg tgtaggtcgt tcgctccaag   1680
ctgggctgtg tgcacgaacc ccccgttcag cccgaccgct gcgccttatc cggtaactat   1740
cgtcttgagt ccaacccggt aagacacgac ttatcgccac tggcagcagc cactggtaac   1800
aggattagca gagcgaggta tgtaggcggt gctacagagt tcttgaagtg gtggcctaac   1860
tacggctaca ctagaaggac agtatttggt atctgcgctc tgctgaagcc agttaccttc   1920
ggaaaaagag ttggtagctc ttgatccggc aaacaaacca ccgctggtag cggtggtttt   1980
tttgtttgca agcagcagat tacgcgcaga aaaaaaggat ctcaagaaga tcctttgatc   2040
ttttctacgg ggtctgacgc tcagtggaac gaaaactcac gttaagggat tttggtcatg   2100
agattatcaa aaaggatctt cacctagatc cttttaaatt aaaaatgaag ttttaaatca   2160
atctaaagta tatatgagta aacttggtct gacagttacc aatgcttaat cagtgaggca   2220
cctatctcag cgatctgtct atttcgttca tccatagttg cctgactccc cgtcgtgtag   2280
ataactacga tacgggaggg cttaccatct ggccccagtg ctgcaatgat accgcgagac   2340
ccacgctcac cggctccaga tttatcagca ataaaccagc cagccggaag ggccgagcgc   2400
agaagtggtc ctgcaacttt atccgcctcc atccagtcta ttaattgttg ccgggaagct   2460
agagtaagta gttcgccagt taatagtttg cgcaacgttg ttgccattgc tacaggcatc   2520
gtggtgtcac gctcgtcgtt tggtatggct tcattcagct ccggttccca acgatcaagg   2580
cgagttacat gatcccccat gttgtgcaaa aaagcggtta gctccttcgg tcctccgatc   2640
gttgtcagaa gtaagttggc cgcagtgtta tcactcatgg ttatggcagc actgcataat   2700
tctcttactg tcatgccatc cgtaagatgc ttttctgtga ctggtgagta ctcaaccaag   2760
tcattctgag aatagtgtat gcggcgaccg agttgctctt gcccggcgtc aatacgggat   2820
aataccgcgc cacatagc                                                 2838
```

<210> SEQ ID NO 25
<211> LENGTH: 56
<212> TYPE: RNA
<213> ORGANISM: Artificial Sequence
<220> FEATURE:

<223> OTHER INFORMATION: synthetic construct

<400> SEQUENCE: 25
aguccucauc ucccucaagc guuuaagagc uaugcuguuu ugaauggucc caaaac    56

<210> SEQ ID NO 26
<211> LENGTH: 86
<212> TYPE: RNA
<213> ORGANISM: Artificial Sequence
<220> FEATURE:
<223> OTHER INFORMATION: synthetic construct

<400> SEQUENCE: 26
ggaaccauuc aaaacagcau agcaaguuua aauaaggcua guccguuauc aacuuguaaa    60
aguggcaccg agucggugcu uuuuuu    86

<210> SEQ ID NO 27
<211> LENGTH: 56
<212> TYPE: RNA
<213> ORGANISM: Artificial Sequence
<220> FEATURE:
<223> OTHER INFORMATION: synthetic construct

<400> SEQUENCE: 27
ugguaaugau ggcuucaaca guuuuagagc uaugcuguuu ugaauggucc caaaac    56

<210> SEQ ID NO 28
<211> LENGTH: 86
<212> TYPE: RNA
<213> ORGANISM: Artificial Sequence
<220> FEATURE:
<223> OTHER INFORMATION: synthetic construct

<400> SEQUENCE: 28
ggaaccauuc aaaacagcau agcaaguuua aauaaggcua guccguuauc aacuuguaaa    60
aguggcaccg agucggugcu uuuuuu    86

<210> SEQ ID NO 29
<211> LENGTH: 56
<212> TYPE: RNA
<213> ORGANISM: Artificial Sequence
<220> FEATURE:
<223> OTHER INFORMATION: synthetic construct

<400> SEQUENCE: 29
aguccucauc ucccucaagc guuuaagagc uaugcuguuu ugaauggucc caaaac    56

<210> SEQ ID NO 30
<211> LENGTH: 86
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (57)..(57)
<223> OTHER INFORMATION: u is 5-(3-Aminoallyl)-uridine-5'-triphosphate,
      labeled with Cyanine5

<400> SEQUENCE: 30
ggaaccauuc aaaacagcau agcaaguuua aauaaggcua guccguuauc aacuuguaaa    60
aguggcaccg agucggugcu uuuuuu    86

<210> SEQ ID NO 31

```
<211> LENGTH: 56
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-methyl
<222> LOCATION: (1)..(3)
<220> FEATURE:
<221> NAME/KEY: 2'-O-methyl
<222> LOCATION: (53)..(55)

<400> SEQUENCE: 31
ugguaaugau ggcuucaaca guuuuagagc uaugcuguuu ugaauggucc caaaac      56

<210> SEQ ID NO 32
<211> LENGTH: 86
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl
<222> LOCATION: (1)..(3)
<220> FEATURE:
<221> NAME/KEY: 2'-O-Methyl
<222> LOCATION: (83)..(85)

<400> SEQUENCE: 32
ggaaccauuc aaaacagcau agcaaguuua aauaaggcua guccguuauc aacuuguaaa      60
aguggcaccg agucggugcu uuuuuu      86

<210> SEQ ID NO 33
<211> LENGTH: 56
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl
<222> LOCATION: (1)..(3)
<220> FEATURE:
<221> NAME/KEY: phosphorothioate internucleotide linkage
<222> LOCATION: (1)..(4)
<220> FEATURE:
<221> NAME/KEY: 2'-O-Methyl
<222> LOCATION: (53)..(55)
<220> FEATURE:
<221> NAME/KEY: phosphorothioate internucleotide linkage
<222> LOCATION: (53)..(56)

<400> SEQUENCE: 33
ugguaaugau ggcuucaaca guuuuagagc uaugcuguuu ugaauggucc caaaac      56

<210> SEQ ID NO 34
<211> LENGTH: 86
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(3)
<220> FEATURE:
<221> NAME/KEY: phosphorothioate internucleotide linkage
<222> LOCATION: (1)..(4)
<220> FEATURE:
<221> NAME/KEY: 2'-O-Methyl nucleotide
<222> LOCATION: (83)..(85)
<220> FEATURE:
<221> NAME/KEY: phosphorothioate internucleotide linkage
<222> LOCATION: (83)..(86)
```

<400> SEQUENCE: 34
ggaaccauuc aaaacagcau agcaaguuua aauaaggcua guccguuauc aacuuguaaa    60
aguggcaccg agucggugcu uuuuuu    86

<210> SEQ ID NO 35
<211> LENGTH: 56
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(3)
<220> FEATURE:
<221> NAME/KEY: thiophosphonoacetate internucleotide linkage
<222> LOCATION: (1)..(4)
<220> FEATURE:
<221> NAME/KEY: 2'-O-Methyl nucleotide
<222> LOCATION: (53)..(55)
<220> FEATURE:
<221> NAME/KEY: thiophosphonoacetate internucleotide linkage
<222> LOCATION: (53)..(56)

<400> SEQUENCE: 35
ugguaaugau ggcuucaaca guuuuagagc uaugcuguuu ugaauggucc caaaac    56

<210> SEQ ID NO 36
<211> LENGTH: 86
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(3)
<220> FEATURE:
<221> NAME/KEY: thiophosphonoacetate internucleotide linkage
<222> LOCATION: (1)..(4)
<220> FEATURE:
<221> NAME/KEY: 2'-O-Methyl nucleotide
<222> LOCATION: (83)..(85)
<220> FEATURE:
<221> NAME/KEY: thiophosphonoacetate internucleotide linkage
<222> LOCATION: (83)..(86)

<400> SEQUENCE: 36
ggaaccauuc aaaacagcau agcaaguuua aauaaggcua guccguuauc aacuuguaaa    60
aguggcaccg agucggugcu uuuuuu    86

<210> SEQ ID NO 37
<211> LENGTH: 56
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(1)
<220> FEATURE:
<221> NAME/KEY: thiophosphonoacetate internucleotide linkage
<222> LOCATION: (1)..(2)
<220> FEATURE:
<221> NAME/KEY: 2'-O-Methyl nucleotide
<222> LOCATION: (55)..(55)
<220> FEATURE:
<221> NAME/KEY: thiophosphonoacetate internucleotide linkage
<222> LOCATION: (55)..(56)

<400> SEQUENCE: 37

```
ugguaaugau ggcuucaaca guuuuagagc uaugcuguuu ugaauggucc caaaac          56
```

<210> SEQ ID NO 38
<211> LENGTH: 86
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(1)
<220> FEATURE:
<221> NAME/KEY: thiophosphonoacetate internucleotide linkage
<222> LOCATION: (1)..(2)
<220> FEATURE:
<221> NAME/KEY: 2'-O-Methyl nucleotide
<222> LOCATION: (85)..(85)
<220> FEATURE:
<221> NAME/KEY: thiophosphonoacetate internucleotide linkage
<222> LOCATION: (85)..(86)

<400> SEQUENCE: 38

```
ggaaccauuc aaaacagcau agcaaguuua aauaaggcua guccguuauc aacuuguaaa     60
aguggcaccg agucggugcu uuuuuu                                         86
```

<210> SEQ ID NO 39
<211> LENGTH: 56
<212> TYPE: RNA
<213> ORGANISM: Artificial Sequence
<220> FEATURE:
<223> OTHER INFORMATION: synthetic construct
<220> FEATURE:
<221> NAME/KEY: 2-thiouridine nucleotide
<222> LOCATION: (3)..(3)

<400> SEQUENCE: 39

```
aguccucauc ucccucaagc guuuaagagc uaugcuguuu ugaauggucc caaaac         56
```

<210> SEQ ID NO 40
<211> LENGTH: 56
<212> TYPE: RNA
<213> ORGANISM: Artificial Sequence
<220> FEATURE:
<223> OTHER INFORMATION: synthetic construct
<220> FEATURE:
<221> NAME/KEY: 2-thiouridine nucleotide
<222> LOCATION: (9)..(9)

<400> SEQUENCE: 40

```
aguccucauc ucccucaagc guuuaagagc uaugcuguuu ugaauggucc caaaac         56
```

<210> SEQ ID NO 41
<211> LENGTH: 56
<212> TYPE: RNA
<213> ORGANISM: Artificial Sequence
<220> FEATURE:
<223> OTHER INFORMATION: synthetic construct
<220> FEATURE:
<221> NAME/KEY: 2-thiouridine nucleotide
<222> LOCATION: (11)..(11)

<400> SEQUENCE: 41

```
aguccucauc ucccucaagc guuuaagagc uaugcuguuu ugaauggucc caaaac         56
```

<210> SEQ ID NO 42
<211> LENGTH: 113
<212> TYPE: RNA
<213> ORGANISM: Artificial Sequence
<220> FEATURE:

<223> OTHER INFORMATION: synthetic construct

<400> SEQUENCE: 42
aguccucauc ucccucaagc guuuagagc uaugcgggua acagcauagc aaguuuaaau    60
aaggcuaguc cguuaucaac uugaaaaagu ggcaccgagu cggugcuuuu uuu          113

<210> SEQ ID NO 43
<211> LENGTH: 100
<212> TYPE: RNA
<213> ORGANISM: Artificial Sequence
<220> FEATURE:
<223> OTHER INFORMATION: synthetic construct

<400> SEQUENCE: 43
aguccucauc ucccucaagc guuuagagc uaguaauagc aaguuaaaau aaggcuaguc    60
cguuaucaac uugaaaaagu ggcaccgagu cggugcuuuu                         100

<210> SEQ ID NO 44
<211> LENGTH: 113
<212> TYPE: RNA
<213> ORGANISM: Artificial Sequence
<220> FEATURE:
<223> OTHER INFORMATION: synthetic construct

<400> SEQUENCE: 44
gcagauguag uguuuccaca guuuagagc uaugcuggaa acagcauagc aaguuuaaau    60
aaggcuaguc cguuaucaac uugaaaaagu ggcaccgagu cggugcuuuu uuu          113

<210> SEQ ID NO 45
<211> LENGTH: 111
<212> TYPE: RNA
<213> ORGANISM: Artificial Sequence
<220> FEATURE:
<223> OTHER INFORMATION: synthetic construct

<400> SEQUENCE: 45
uccucaucuc ccucaagcgu uuagagcua ugcugguaac agcauagcaa guuuaaauaa    60 ggcuagccg uuaucaacuu gaaaagugg caccgagucg gugcuuuuuu u              111

<210> SEQ ID NO 46
<211> LENGTH: 110
<212> TYPE: RNA
<213> ORGANISM: Artificial Sequence
<220> FEATURE:
<223> OTHER INFORMATION: synthetic construct

<400> SEQUENCE: 46
ccucaucucc cucaagcguu uaagagcuau gcugguaaca gcauagcaag uuuaaauaag    60
gcuaguccgu uaucaacuug aaaaguggc accgagucgg ugcuuuuuu                110

<210> SEQ ID NO 47
<211> LENGTH: 114
<212> TYPE: RNA
<213> ORGANISM: Artificial Sequence
<220> FEATURE:
<223> OTHER INFORMATION: synthetic construct

<400> SEQUENCE: 47
gaguccucau ucccucaag cguuuagag cuaugcuggu aacagcauag caaguuuaaa    60
uaaggcuagu ccguuaucaa cuugaaaaag uggcaccgag ucggugcuuu uuuu         114

```
<210> SEQ ID NO 48
<211> LENGTH: 115
<212> TYPE: RNA
<213> ORGANISM: Artificial Sequence
<220> FEATURE:
<223> OTHER INFORMATION: synthetic construct

<400> SEQUENCE: 48
ggaguccuca ucucccucaa gcguuuaaga gcuaugcugg uaacagcaua gcaaguuuaa      60
auaaggcuag uccguuauca acuugaaaaa guggcaccga gucggugcuu uuuuu         115

<210> SEQ ID NO 49
<211> LENGTH: 113
<212> TYPE: RNA
<213> ORGANISM: Artificial Sequence
<220> FEATURE:
<223> OTHER INFORMATION: synthetic construct

<400> SEQUENCE: 49
aguccucauc ucccucaagc guuuaagagc uaugcuggua acagcauagc aaguuuaaau      60
aauucuaguc cguuaucaac uugaaaaagu ggcaccgagu cggugcuuuu uuu           113

<210> SEQ ID NO 50
<211> LENGTH: 113
<212> TYPE: RNA
<213> ORGANISM: Artificial Sequence
<220> FEATURE:
<223> OTHER INFORMATION: synthetic construct

<400> SEQUENCE: 50
aguccucauc ucccucaagc guuuaagagc uaugcuggua acagcauagc aaguuuaaau      60
aaaacuaguc cguuaucaac uugaaaaagu ggcaccgagu cggugcuuuu uuu           113

<210> SEQ ID NO 51
<211> LENGTH: 113
<212> TYPE: RNA
<213> ORGANISM: Artificial Sequence
<220> FEATURE:
<223> OTHER INFORMATION: synthetic construct

<400> SEQUENCE: 51
aguccucauc ucccucaagc guuuaagagc uaugcuggua acagcauagc aaguuuaaau      60
aaaacuaguu uguuaucaac uugaaaaagu ggcaccgagu cggugcuuuu uuu           113

<210> SEQ ID NO 52
<211> LENGTH: 111
<212> TYPE: RNA
<213> ORGANISM: Artificial Sequence
<220> FEATURE:
<223> OTHER INFORMATION: synthetic construct

<400> SEQUENCE: 52
ggacuuuuuu uaguccucau cucccucaag cguuuuagag cuagaaauag caaguuaaaa      60
uaaggcuagu ccguuaucaa cuugaaaaag uggcaccgag ucggugcuuu u             111

<210> SEQ ID NO 53
<211> LENGTH: 116
<212> TYPE: RNA
<213> ORGANISM: Artificial Sequence
<220> FEATURE:
<223> OTHER INFORMATION: synthetic construct

<400> SEQUENCE: 53
```

```
gaugaggacu uuuuuuaguc cucaucuccc ucaagcguuu uagagcuaga aauagcaagu    60
uaaaauaagg cuaguccguu aucaacuuga aaaagugguca ccgagucggu gcuuuu      116
```

<210> SEQ ID NO 54
<211> LENGTH: 111
<212> TYPE: RNA
<213> ORGANISM: Artificial Sequence
<220> FEATURE:
<223> OTHER INFORMATION: synthetic construct

<400> SEQUENCE: 54

```
gcuuguuuuu uaguccucau cucccucaag cguuuagag cuagaaauag caaguuaaaa    60
uaaggcuagu ccguuaucaa cuugaaaaag uggcaccgag ucggugcuuu u           111
```

<210> SEQ ID NO 55
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: a is 5'-dimethoxytrityl-adenosine
<222> LOCATION: (1)..(1)

<400> SEQUENCE: 55

```
aguccucauc ucccucaagc guuuaagagc uaugcuggua acagcauagc aaguuuaaau    60
aaggcuaguc cguuaucaac uugaaaaagu ggcaccgagu cggugcuuuu uuu          113
```

<210> SEQ ID NO 56
<211> LENGTH: 113
<212> TYPE: RNA
<213> ORGANISM: Artificial Sequence
<220> FEATURE:
<223> OTHER INFORMATION: synthetic construct

<400> SEQUENCE: 56

```
aguccucauc ucccucaagc guuuaagagc uaugcuggua acagcauagc aaguuuaaau    60
aaggcuaguc cguuaucaac uugaaaaagu ggcaccgagu cggugcuuuu uuu          113
```

<210> SEQ ID NO 57
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: fluorophore
<222> LOCATION: (39)..(39)
<220> FEATURE:
<221> NAME/KEY: misc_feature
<222> LOCATION: (39)..(39)
<223> OTHER INFORMATION: n is a, c, g, or u, unknown or other

<400> SEQUENCE: 57

```
aguccucauc ucccucaagc guuuaagagc uaugcuggna acagcauagc aaguuuaaau    60
aaggcuaguc cguuaucaac uugaaaaagu ggcaccgagu cggugcuuuu uuu          113
```

<210> SEQ ID NO 58
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl

```
<222> LOCATION: (1)..(3)
<220> FEATURE:
<221> NAME/KEY: fluorophore
<222> LOCATION: (39)..(39)
<220> FEATURE:
<221> NAME/KEY: misc_feature
<222> LOCATION: (39)..(39)
<223> OTHER INFORMATION: n is a, c, g, or u, unknown or other
<220> FEATURE:
<221> NAME/KEY: 2'-O-Methyl
<222> LOCATION: (110)..(112)

<400> SEQUENCE: 58
aguccucauc ucccucaagc guuuaagagc uaugcuggna acagcauagc aaguuuaaau      60
aaggcuaguc cguuaucaac uugaaaaagu ggcaccgagu cggugcuuuu uuu            113

<210> SEQ ID NO 59
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(3)
<220> FEATURE:
<221> NAME/KEY: phosphorothioate internucleotide linkage
<222> LOCATION: (1)..(4)
<220> FEATURE:
<221> NAME/KEY: fluorophore
<222> LOCATION: (39)..(39)
<220> FEATURE:
<221> NAME/KEY: misc_feature
<222> LOCATION: (39)..(39)
<223> OTHER INFORMATION: n is a, c, g, or u, unknown or other
<220> FEATURE:
<221> NAME/KEY: 2'-O-Methyl nucleotide
<222> LOCATION: (110)..(112)
<220> FEATURE:
<221> NAME/KEY: phosphorothioate internucleotide linkage
<222> LOCATION: (110)..(113)

<400> SEQUENCE: 59
aguccucauc ucccucaagc guuuaagagc uaugcuggna acagcauagc aaguuuaaau      60
aaggcuaguc cguuaucaac uugaaaaagu ggcaccgagu cggugcuuuu uuu            113

<210> SEQ ID NO 60
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(3)
<220> FEATURE:
<221> NAME/KEY: thiophosphonoacetate internucleotide linkage
<222> LOCATION: (1)..(4)
<220> FEATURE:
<221> NAME/KEY: fluorophore
<222> LOCATION: (39)..(39)
<220> FEATURE:
<221> NAME/KEY: misc_feature
<222> LOCATION: (39)..(39)
<223> OTHER INFORMATION: n is a, c, g, or u, unknown or other
<220> FEATURE:
<221> NAME/KEY: 2'-O-Methyl nucleotide
<222> LOCATION: (109)..(111)
<220> FEATURE:
<221> NAME/KEY: thiophosphonoacetate internucleotide linkage
<222> LOCATION: (109)..(112)
<220> FEATURE:
<221> NAME/KEY: 2'-O-Methyl nucleotide
```

<222> LOCATION: (110)..(112)

<400> SEQUENCE: 60
aguccucauc ucccucaagc guuuaagagc uaugcuggna acagcauagc aaguuuaaau    60
aaggcuaguc cguuaucaac uugaaaaagu ggcaccgagu cggugcuuuu uuu          113

<210> SEQ ID NO 61
<211> LENGTH: 102
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(1)
<220> FEATURE:
<221> NAME/KEY: thiophosphonoacetate internucleotide linkage
<222> LOCATION: (1)..(2)
<220> FEATURE:
<221> NAME/KEY: fluorophore
<222> LOCATION: (2)..(2)
<220> FEATURE:
<221> NAME/KEY: misc_feature
<222> LOCATION: (2)..(2)
<223> OTHER INFORMATION: n is a, c, g, or u, unknown or other
<220> FEATURE:
<221> NAME/KEY: fluorophore
<222> LOCATION: (68)..(68)
<220> FEATURE:
<221> NAME/KEY: misc_feature
<222> LOCATION: (68)..(68)
<223> OTHER INFORMATION: n is a, c, g, or u
<220> FEATURE:
<221> NAME/KEY: fluorophore
<222> LOCATION: (100)..(100)
<220> FEATURE:
<221> NAME/KEY: misc_feature
<222> LOCATION: (100)..(100)
<223> OTHER INFORMATION: n is a, c, g, or u
<220> FEATURE:
<221> NAME/KEY: 2'-O-Methyl nucleotide
<222> LOCATION: (101)..(101)
<220> FEATURE:
<221> NAME/KEY: thiophosphonoacetate internucleotide linkage
<222> LOCATION: (101)..(102)

<400> SEQUENCE: 61
ungcagaugu aguguuucca caguuuaaga gcuaguaaua gcaaguuuaa auaaggcuag    60
uccguuanca acuugaaaaa guggcaccga gucggugcun uu                      102

<210> SEQ ID NO 62
<211> LENGTH: 100
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(1)
<220> FEATURE:
<221> NAME/KEY: thiophosphonoacetate internucleotide linkage
<222> LOCATION: (1)..(2)
<220> FEATURE:
<221> NAME/KEY: fluorophore
<222> LOCATION: (34)..(34)
<220> FEATURE:
<221> NAME/KEY: misc_feature
<222> LOCATION: (34)..(34)
<223> OTHER INFORMATION: n is a, c, g, or u, unknown or other
<220> FEATURE:
<221> NAME/KEY: fluorophore
<222> LOCATION: (74)..(74)
<220> FEATURE:

```
<221> NAME/KEY: misc_feature
<222> LOCATION: (74)..(74)
<223> OTHER INFORMATION: n is a, c, g, or u, unknown or other
<220> FEATURE:
<221> NAME/KEY: fluorophore
<222> LOCATION: (90)..(90)
<220> FEATURE:
<221> NAME/KEY: misc_feature
<222> LOCATION: (90)..(90)
<223> OTHER INFORMATION: n is a, c, g, or u, unknown or other
<220> FEATURE:
<221> NAME/KEY: 2'-O-Methyl nucleotide
<222> LOCATION: (99)..(99)
<220> FEATURE:
<221> NAME/KEY: thiophosphonoacetate internucleotide linkage
<222> LOCATION: (99)..(100)

<400> SEQUENCE: 62
gcagauguag uguuuccaca guuuaagagc uagnaauagc aaguuuaaau aaggcuaguc      60
cguuaucaac uugnaaaagu ggcaccgagn cggugcuuuu                           100

<210> SEQ ID NO 63
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: phosphorothioate internucleotide linkage
<222> LOCATION: (1)..(3)

<400> SEQUENCE: 63
aguccucauc ucccucaagc guuuaagagc uaugcuggaa acagcauagc aaguuuaaau      60
aaggcuaguc cguuaucaac uugaaaaagu ggcaccgagu cggugcuuuu uuu            113

<210> SEQ ID NO 64
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: phosphorothioate internucleotide linkage
<222> LOCATION: (1)..(4)

<400> SEQUENCE: 64
aguccucauc ucccucaagc guuuaagagc uaugcuggaa acagcauagc aaguuuaaau      60
aaggcuaguc cguuaucaac uugaaaaagu ggcaccgagu cggugcuuuu uuu            113

<210> SEQ ID NO 65
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: phosphorothioate internucleotide linkage
<222> LOCATION: (1)..(5)

<400> SEQUENCE: 65
aguccucauc ucccucaagc guuuaagagc uaugcuggaa acagcauagc aaguuuaaau      60
aaggcuaguc cguuaucaac uugaaaaagu ggcaccgagu cggugcuuuu uuu            113

<210> SEQ ID NO 66
<211> LENGTH: 113
<212> TYPE: RNA
<213> ORGANISM: Artificial Sequence
```

<220> FEATURE:
<223> OTHER INFORMATION: synthetic construct
<220> FEATURE:
<221> NAME/KEY: phosphorothioate internucleotide linkage
<222> LOCATION: (109)..(113)

<400> SEQUENCE: 66
aguccucauc ucccucaagc guuuaagagc uaugcuggaa acagcauagc aaguuuaaau    60
aaggcuaguc cguuaucaac uugaaaaagu ggcaccgagu cggugcuuuu uuu          113

<210> SEQ ID NO 67
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (20)..(20)

<400> SEQUENCE: 67
aguccucauc ucccucaagc guuuaagagc uaugcuggua acagcauagc aaguuuaaau    60
aaggcuaguc cguuaucaac uugaaaaagu ggcaccgagu cggugcuuuu uuu          113

<210> SEQ ID NO 68
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (19)..(19)

<400> SEQUENCE: 68
aguccucauc ucccucaagc guuuaagagc uaugcuggua acagcauagc aaguuuaaau    60
aaggcuaguc cguuaucaac uugaaaaagu ggcaccgagu cggugcuuuu uuu          113

<210> SEQ ID NO 69
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (18)..(18)

<400> SEQUENCE: 69
aguccucauc ucccucaagc guuuaagagc uaugcuggua acagcauagc aaguuuaaau    60
aaggcuaguc cguuaucaac uugaaaaagu ggcaccgagu cggugcuuuu uuu          113

<210> SEQ ID NO 70
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (17)..(17)

<400> SEQUENCE: 70
aguccucauc ucccucaagc guuuaagagc uaugcuggua acagcauagc aaguuuaaau    60
aaggcuaguc cguuaucaac uugaaaaagu ggcaccgagu cggugcuuuu uuu          113

<210> SEQ ID NO 71
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (17)..(18)

<400> SEQUENCE: 71
aguccucauc ucccucaagc guuuaagagc uaugcuggua acagcauagc aaguuuaaau    60
aaggcuaguc cguuaucaac uugaaaaagu ggcaccgagu cggugcuuuu uuu           113

<210> SEQ ID NO 72
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(3)
<220> FEATURE:
<221> NAME/KEY: 2'-O-Methyl nucleotide
<222> LOCATION: (110)..(112)

<400> SEQUENCE: 72
aguccucauc ucccucaagc guuuaagagc uaugcuggua acagcauagc aaguuuaaau    60
aaggcuaguc cguuaucaac uugaaaaagu ggcaccgagu cggugcuuuu uuu           113

<210> SEQ ID NO 73
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(3)
<220> FEATURE:
<221> NAME/KEY: 2'-O-Methyl nucleotide
<222> LOCATION: (110)..(112)

<400> SEQUENCE: 73
gcagauguag uguuuccaca guuuaagagc uaugcuggaa acagcauagc aaguuuaaau    60
aaggcuaguc cguuaucaac uugaaaaagu ggcaccgagu cggugcuuuu uuu           113

<210> SEQ ID NO 74
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(20)

<400> SEQUENCE: 74
aguccucauc ucccucaagc guuuaagagc uaugcuggua acagcauagc aaguuuaaau    60
aaggcuaguc cguuaucaac uugaaaaagu ggcaccgagu cggugcuuuu uuu           113

<210> SEQ ID NO 75
<211> LENGTH: 113
<212> TYPE: RNA

```
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(26)

<400> SEQUENCE: 75
aguccucauc ucccucaagc guuuaagagc uaugcuggua acagcauagc aaguuuaaau     60
aaggcuaguc cguuaucaac uugaaaaagu ggcaccgagu cggugcuuuu uuu          113

<210> SEQ ID NO 76
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(37)

<400> SEQUENCE: 76
aguccucauc ucccucaagc guuuaagagc uaugcuggua acagcauagc aaguuuaaau     60
aaggcuaguc cguuaucaac uugaaaaagu ggcaccgagu cggugcuuuu uuu          113

<210> SEQ ID NO 77
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(7)
<220> FEATURE:
<221> NAME/KEY: 2'-O-Methyl nucleotide
<222> LOCATION: (9)..(11)
<220> FEATURE:
<221> NAME/KEY: 2'-O-Methyl nucleotide
<222> LOCATION: (13)..(14)
<220> FEATURE:
<221> NAME/KEY: 2'-O-Methyl nucleotide
<222> LOCATION: (20)..(20)
<220> FEATURE:
<221> NAME/KEY: 2'-O-Methyl nucleotide
<222> LOCATION: (30)..(31)
<220> FEATURE:
<221> NAME/KEY: 2'-O-Methyl nucleotide
<222> LOCATION: (33)..(33)
<220> FEATURE:
<221> NAME/KEY: 2'-O-Methyl nucleotide
<222> LOCATION: (35)..(36)
<220> FEATURE:
<221> NAME/KEY: 2'-O-Methyl nucleotide
<222> LOCATION: (42)..(42)
<220> FEATURE:
<221> NAME/KEY: 2'-O-Methyl nucleotide
<222> LOCATION: (45)..(45)
<220> FEATURE:
<221> NAME/KEY: 2'-O-Methyl nucleotide
<222> LOCATION: (76)..(77)
<220> FEATURE:
<221> NAME/KEY: 2'-O-Methyl nucleotide
<222> LOCATION: (80)..(82)
<220> FEATURE:
<221> NAME/KEY: 2'-O-Methyl nucleotide
<222> LOCATION: (90)..(90)
<220> FEATURE:
<221> NAME/KEY: 2'-O-Methyl nucleotide
<222> LOCATION: (95)..(96)
<220> FEATURE:
<221> NAME/KEY: 2'-O-Methyl nucleotide
<222> LOCATION: (100)..(101)
```

-continued

```
<220> FEATURE:
<221> NAME/KEY: 2'-O-Methyl nucleotide
<222> LOCATION: (104)..(104)
<220> FEATURE:
<221> NAME/KEY: 2'-O-Methyl nucleotide
<222> LOCATION: (106)..(112)

<400> SEQUENCE: 77
aguccucauc ucccucaagc guuuagagc uaugcuggua acagcauagc aaguuuaaau       60
aaggcuaguc cguuaucaac uugaaaaagu ggcaccgagu cggugcuuuu uuu           113

<210> SEQ ID NO 78
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(7)
<220> FEATURE:
<221> NAME/KEY: 2'-O-Methyl nucleotide
<222> LOCATION: (9)..(11)
<220> FEATURE:
<221> NAME/KEY: 2'-O-Methyl nucleotide
<222> LOCATION: (17)..(17)
<220> FEATURE:
<221> NAME/KEY: 2'-O-Methyl nucleotide
<222> LOCATION: (27)..(28)
<220> FEATURE:
<221> NAME/KEY: 2'-O-Methyl nucleotide
<222> LOCATION: (30)..(30)
<220> FEATURE:
<221> NAME/KEY: 2'-O-Methyl nucleotide
<222> LOCATION: (32)..(33)
<220> FEATURE:
<221> NAME/KEY: 2'-O-Methyl nucleotide
<222> LOCATION: (36)..(36)
<220> FEATURE:
<221> NAME/KEY: 2'-O-Methyl nucleotide
<222> LOCATION: (39)..(39)
<220> FEATURE:
<221> NAME/KEY: 2'-O-Methyl nucleotide
<222> LOCATION: (42)..(42)
<220> FEATURE:
<221> NAME/KEY: 2'-O-Methyl nucleotide
<222> LOCATION: (44)..(44)
<220> FEATURE:
<221> NAME/KEY: 2'-O-Methyl nucleotide
<222> LOCATION: (47)..(47)
<220> FEATURE:
<221> NAME/KEY: 2'-O-Methyl nucleotide
<222> LOCATION: (57)..(57)
<220> FEATURE:
<221> NAME/KEY: 2'-O-Methyl nucleotide
<222> LOCATION: (62)..(63)
<220> FEATURE:
<221> NAME/KEY: 2'-O-Methyl nucleotide
<222> LOCATION: (67)..(68)
<220> FEATURE:
<221> NAME/KEY: 2'-O-Methyl nucleotide
<222> LOCATION: (73)..(74)
<220> FEATURE:
<221> NAME/KEY: 2'-O-Methyl nucleotide
<222> LOCATION: (77)..(78)
<220> FEATURE:
<221> NAME/KEY: 2'-O-Methyl nucleotide
<222> LOCATION: (87)..(87)
<220> FEATURE:
<221> NAME/KEY: 2'-O-Methyl nucleotide
<222> LOCATION: (90)..(90)
<220> FEATURE:
<221> NAME/KEY: 2'-O-Methyl nucleotide
<222> LOCATION: (92)..(93)
<220> FEATURE:
<221> NAME/KEY: 2'-O-Methyl nucleotide
```

<222> LOCATION: (97)..(98)
<220> FEATURE:
<221> NAME/KEY: 2'-O-Methyl nucleotide
<222> LOCATION: (101)..(101)
<220> FEATURE:
<221> NAME/KEY: 2'-O-Methyl nucleotide
<222> LOCATION: (103)..(109)

<400> SEQUENCE: 78
aguccucauc ucccucaagc guuuaagagc uaugcuggua acagcauagc aaguuuaaau      60
aaggcuaguc cguuaucaac uugaaaaagu ggcaccgagu cggugcuuuu uuu            113

<210> SEQ ID NO 79
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(7)
<220> FEATURE:
<221> NAME/KEY: 2'-O-Methyl nucleotide
<222> LOCATION: (9)..(11)
<220> FEATURE:
<221> NAME/KEY: 2'-O-Methyl nucleotide
<222> LOCATION: (17)..(17)
<220> FEATURE:
<221> NAME/KEY: 2'-O-Methyl nucleotide
<222> LOCATION: (27)..(28)
<220> FEATURE:
<221> NAME/KEY: 2'-O-Methyl nucleotide
<222> LOCATION: (30)..(30)
<220> FEATURE:
<221> NAME/KEY: 2'-O-Methyl nucleotide
<222> LOCATION: (32)..(33)
<220> FEATURE:
<221> NAME/KEY: 2'-O-Methyl nucleotide
<222> LOCATION: (36)..(36)
<220> FEATURE:
<221> NAME/KEY: 2'-O-Methyl nucleotide
<222> LOCATION: (39)..(39)
<220> FEATURE:
<221> NAME/KEY: 2'-O-Methyl nucleotide
<222> LOCATION: (42)..(42)
<220> FEATURE:
<221> NAME/KEY: 2'-O-Methyl nucleotide
<222> LOCATION: (44)..(44)
<220> FEATURE:
<221> NAME/KEY: 2'-O-Methyl nucleotide
<222> LOCATION: (47)..(47)
<220> FEATURE:
<221> NAME/KEY: 2'-O-Methyl nucleotide
<222> LOCATION: (57)..(57)
<220> FEATURE:
<221> NAME/KEY: 2'-O-Methyl nucleotide
<222> LOCATION: (62)..(63)
<220> FEATURE:
<221> NAME/KEY: 2'-O-Methyl nucleotide
<222> LOCATION: (67)..(68)
<220> FEATURE:
<221> NAME/KEY: 2'-O-Methyl nucleotide
<222> LOCATION: (73)..(74)
<220> FEATURE:
<221> NAME/KEY: 2'-O-Methyl nucleotide
<222> LOCATION: (77)..(78)
<220> FEATURE:
<221> NAME/KEY: 2'-O-Methyl nucleotide
<222> LOCATION: (87)..(87)
<220> FEATURE:
<221> NAME/KEY: 2'-O-Methyl nucleotide
<222> LOCATION: (90)..(90)
<220> FEATURE:
<221> NAME/KEY: 2'-O-Methyl nucleotide
<222> LOCATION: (92)..(93)
<220> FEATURE:

<221> NAME/KEY: 2'-O-Methyl nucleotide
<222> LOCATION: (97)..(98)
<220> FEATURE:
<221> NAME/KEY: 2'-O-Methyl nucleotide
<222> LOCATION: (101)..(101)
<220> FEATURE:
<221> NAME/KEY: 2'-O-Methyl nucleotide
<222> LOCATION: (103)..(109)

<400> SEQUENCE: 79
aguccucauc ucccucaagc guuuaagagc uaugcuggua acagcauagc aaguuuaaau      60
aaggcuaguc cguuaucaac uugaaaaagu ggcaccgagu cggugcuuuu uuu            113

<210> SEQ ID NO 80
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(3)
<220> FEATURE:
<221> NAME/KEY: 2'-O-Methyl nucleotide
<222> LOCATION: (8)..(8)
<220> FEATURE:
<221> NAME/KEY: 2'-O-Methyl nucleotide
<222> LOCATION: (17)..(18)
<220> FEATURE:
<221> NAME/KEY: 2'-O-Methyl nucleotide
<222> LOCATION: (21)..(21)
<220> FEATURE:
<221> NAME/KEY: 2'-O-Methyl nucleotide
<222> LOCATION: (26)..(26)
<220> FEATURE:
<221> NAME/KEY: 2'-O-Methyl nucleotide
<222> LOCATION: (28)..(29)
<220> FEATURE:
<221> NAME/KEY: 2'-O-Methyl nucleotide
<222> LOCATION: (32)..(32)
<220> FEATURE:
<221> NAME/KEY: 2'-O-Methyl nucleotide
<222> LOCATION: (34)..(34)
<220> FEATURE:
<221> NAME/KEY: 2'-O-Methyl nucleotide
<222> LOCATION: (37)..(38)
<220> FEATURE:
<221> NAME/KEY: 2'-O-Methyl nucleotide
<222> LOCATION: (40)..(41)
<220> FEATURE:
<221> NAME/KEY: 2'-O-Methyl nucleotide
<222> LOCATION: (43)..(44)
<220> FEATURE:
<221> NAME/KEY: 2'-O-Methyl nucleotide
<222> LOCATION: (46)..(46)
<220> FEATURE:
<221> NAME/KEY: 2'-O-Methyl nucleotide
<222> LOCATION: (48)..(49)
<220> FEATURE:
<221> NAME/KEY: 2'-O-Methyl nucleotide
<222> LOCATION: (51)..(52)
<220> FEATURE:
<221> NAME/KEY: 2'-O-Methyl nucleotide
<222> LOCATION: (58)..(58)
<220> FEATURE:
<221> NAME/KEY: 2'-O-Methyl nucleotide
<222> LOCATION: (61)..(64)
<220> FEATURE:
<221> NAME/KEY: 2'-O-Methyl nucleotide
<222> LOCATION: (67)..(67)
<220> FEATURE:
<221> NAME/KEY: 2'-O-Methyl nucleotide
<222> LOCATION: (78)..(79)
<220> FEATURE:
<221> NAME/KEY: 2'-O-Methyl nucleotide
<222> LOCATION: (83)..(89)

```
<220> FEATURE:
<221> NAME/KEY: 2'-O-Methyl nucleotide
<222> LOCATION: (91)..(92)
<220> FEATURE:
<221> NAME/KEY: 2'-O-Methyl nucleotide
<222> LOCATION: (94)..(94)
<220> FEATURE:
<221> NAME/KEY: 2'-O-Methyl nucleotide
<222> LOCATION: (97)..(99)
<220> FEATURE:
<221> NAME/KEY: 2'-O-Methyl nucleotide
<222> LOCATION: (102)..(103)
<220> FEATURE:
<221> NAME/KEY: 2'-O-Methyl nucleotide
<222> LOCATION: (105)..(105)

<400> SEQUENCE: 80
aguccucauc ucccucaagc guuuaagagc uaugcuggua acagcauagc aaguuuaaau      60
aaggcuaguc cguuaucaac uugaaaaagu ggcaccgagu cggugcuuuu uuu            113

<210> SEQ ID NO 81
<211> LENGTH: 100
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(3)
<220> FEATURE:
<221> NAME/KEY: 2'-O-Methyl nucleotide
<222> LOCATION: (8)..(8)
<220> FEATURE:
<221> NAME/KEY: 2'-O-Methyl nucleotide
<222> LOCATION: (17)..(18)
<220> FEATURE:
<221> NAME/KEY: 2'-O-Methyl nucleotide
<222> LOCATION: (21)..(21)
<220> FEATURE:
<221> NAME/KEY: 2'-O-Methyl nucleotide
<222> LOCATION: (26)..(26)
<220> FEATURE:
<221> NAME/KEY: 2'-O-Methyl nucleotide
<222> LOCATION: (28)..(29)
<220> FEATURE:
<221> NAME/KEY: 2'-O-Methyl nucleotide
<222> LOCATION: (32)..(33)
<220> FEATURE:
<221> NAME/KEY: 2'-O-Methyl nucleotide
<222> LOCATION: (35)..(36)
<220> FEATURE:
<221> NAME/KEY: 2'-O-Methyl nucleotide
<222> LOCATION: (38)..(39)
<220> FEATURE:
<221> NAME/KEY: 2'-O-Methyl nucleotide
<222> LOCATION: (41)..(42)
<220> FEATURE:
<221> NAME/KEY: 2'-O-Methyl nucleotide
<222> LOCATION: (46)..(46)
<220> FEATURE:
<221> NAME/KEY: 2'-O-Methyl nucleotide
<222> LOCATION: (48)..(48)
<220> FEATURE:
<221> NAME/KEY: 2'-O-Methyl nucleotide
<222> LOCATION: (51)..(54)
<220> FEATURE:
<221> NAME/KEY: 2'-O-Methyl nucleotide
<222> LOCATION: (57)..(57)
<220> FEATURE:
<221> NAME/KEY: 2'-O-Methyl nucleotide
<222> LOCATION: (68)..(69)
<220> FEATURE:
<221> NAME/KEY: 2'-O-Methyl nucleotide
<222> LOCATION: (73)..(79)
<220> FEATURE:
<221> NAME/KEY: 2'-O-Methyl nucleotide
```

```
<222> LOCATION: (81)..(82)
<220> FEATURE:
<221> NAME/KEY: 2'-O-Methyl nucleotide
<222> LOCATION: (84)..(84)
<220> FEATURE:
<221> NAME/KEY: 2'-O-Methyl nucleotide
<222> LOCATION: (87)..(89)
<220> FEATURE:
<221> NAME/KEY: 2'-O-Methyl nucleotide
<222> LOCATION: (92)..(93)
<220> FEATURE:
<221> NAME/KEY: 2'-O-Methyl nucleotide
<222> LOCATION: (95)..(95)

<400> SEQUENCE: 81
aguccucauc ucccucaagc guuuuagagc uaguaauagc aaguuaaaau aaggcuaguc    60
cguuaucaac uugaaaaagu ggcaccgagu cggugcuuuu                        100

<210> SEQ ID NO 82
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(3)
<220> FEATURE:
<221> NAME/KEY: 2'-O-Methyl nucleotide
<222> LOCATION: (110)..(112)

<400> SEQUENCE: 82
gcagauguag uguuuccaca guuuaagagc uaugcuggaa acagcauagc aaguuuaaau    60
aaggcuaguc cguuaucaac uugaaaaagu ggcaccgagu cggugcuuuu uuu         113

<210> SEQ ID NO 83
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(3)
<220> FEATURE:
<221> NAME/KEY: 2'-O-Methyl nucleotide
<222> LOCATION: (6)..(6)
<220> FEATURE:
<221> NAME/KEY: 2'-O-Methyl nucleotide
<222> LOCATION: (8)..(8)
<220> FEATURE:
<221> NAME/KEY: 2'-O-Methyl nucleotide
<222> LOCATION: (11)..(11)
<220> FEATURE:
<221> NAME/KEY: 2'-O-Methyl nucleotide
<222> LOCATION: (13)..(17)
<220> FEATURE:
<221> NAME/KEY: 2'-O-Methyl nucleotide
<222> LOCATION: (30)..(31)
<220> FEATURE:
<221> NAME/KEY: 2'-O-Methyl nucleotide
<222> LOCATION: (33)..(33)
<220> FEATURE:
<221> NAME/KEY: 2'-O-Methyl nucleotide
<222> LOCATION: (35)..(36)
<220> FEATURE:
<221> NAME/KEY: 2'-O-Methyl nucleotide
<222> LOCATION: (39)..(39)
<220> FEATURE:
<221> NAME/KEY: 2'-O-Methyl nucleotide
<222> LOCATION: (42)..(42)
<220> FEATURE:
<221> NAME/KEY: 2'-O-Methyl nucleotide
```

```
<222> LOCATION: (45)..(45)
<220> FEATURE:
<221> NAME/KEY: 2'-O-Methyl nucleotide
<222> LOCATION: (47)..(47)
<220> FEATURE:
<221> NAME/KEY: 2'-O-Methyl nucleotide
<222> LOCATION: (50)..(50)
<220> FEATURE:
<221> NAME/KEY: 2'-O-Methyl nucleotide
<222> LOCATION: (56)..(56)
<220> FEATURE:
<221> NAME/KEY: 2'-O-Methyl nucleotide
<222> LOCATION: (60)..(60)
<220> FEATURE:
<221> NAME/KEY: 2'-O-Methyl nucleotide
<222> LOCATION: (65)..(66)
<220> FEATURE:
<221> NAME/KEY: 2'-O-Methyl nucleotide
<222> LOCATION: (69)..(71)
<220> FEATURE:
<221> NAME/KEY: 2'-O-Methyl nucleotide
<222> LOCATION: (76)..(77)
<220> FEATURE:
<221> NAME/KEY: 2'-O-Methyl nucleotide
<222> LOCATION: (80)..(82)
<220> FEATURE:
<221> NAME/KEY: 2'-O-Methyl nucleotide
<222> LOCATION: (90)..(90)
<220> FEATURE:
<221> NAME/KEY: 2'-O-Methyl nucleotide
<222> LOCATION: (93)..(93)
<220> FEATURE:
<221> NAME/KEY: 2'-O-Methyl nucleotide
<222> LOCATION: (95)..(96)
<220> FEATURE:
<221> NAME/KEY: 2'-O-Methyl nucleotide
<222> LOCATION: (100)..(101)
<220> FEATURE:
<221> NAME/KEY: 2'-O-Methyl nucleotide
<222> LOCATION: (104)..(104)
<220> FEATURE:
<221> NAME/KEY: 2'-O-Methyl nucleotide
<222> LOCATION: (106)..(112)

<400> SEQUENCE: 83
gcagauguag uguuuccaca guuuaagagc uaugcugguu acagcauagc aaguuuaaau    60
aaggcuaguc cguuaucaac uugaaaaagu ggcaccgagu cggugcuuuu uuu           113

<210> SEQ ID NO 84
<211> LENGTH: 100
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(5)
<220> FEATURE:
<221> NAME/KEY: 2'-O-Methyl nucleotide
<222> LOCATION: (26)..(29)
<220> FEATURE:
<221> NAME/KEY: 2'-O-Methyl nucleotide
<222> LOCATION: (32)..(33)
<220> FEATURE:
<221> NAME/KEY: 2'-O-Methyl nucleotide
<222> LOCATION: (35)..(36)
<220> FEATURE:
<221> NAME/KEY: 2'-O-Methyl nucleotide
<222> LOCATION: (38)..(39)
<220> FEATURE:
<221> NAME/KEY: 2'-O-Methyl nucleotide
<222> LOCATION: (41)..(42)
<220> FEATURE:
<221> NAME/KEY: 2'-O-Methyl nucleotide
<222> LOCATION: (46)..(46)
<220> FEATURE:
```

```
<221> NAME/KEY: 2'-O-Methyl nucleotide
<222> LOCATION: (48)..(49)
<220> FEATURE:
<221> NAME/KEY: 2'-O-Methyl nucleotide
<222> LOCATION: (52)..(54)
<220> FEATURE:
<221> NAME/KEY: 2'-O-Methyl nucleotide
<222> LOCATION: (57)..(57)
<220> FEATURE:
<221> NAME/KEY: 2'-O-Methyl nucleotide
<222> LOCATION: (68)..(69)
<220> FEATURE:
<221> NAME/KEY: 2'-O-Methyl nucleotide
<222> LOCATION: (73)..(79)
<220> FEATURE:
<221> NAME/KEY: 2'-O-Methyl nucleotide
<222> LOCATION: (81)..(82)
<220> FEATURE:
<221> NAME/KEY: 2'-O-Methyl nucleotide
<222> LOCATION: (84)..(84)
<220> FEATURE:
<221> NAME/KEY: 2'-O-Methyl nucleotide
<222> LOCATION: (87)..(89)
<220> FEATURE:
<221> NAME/KEY: 2'-O-Methyl nucleotide
<222> LOCATION: (92)..(93)
<220> FEATURE:
<221> NAME/KEY: 2'-O-Methyl nucleotide
<222> LOCATION: (95)..(95)

<400> SEQUENCE: 84
gcagauguag uguuuccaca guuuuagagc uaguaauagc aaguuaaaau aaggcuaguc    60
cguuaucaac uugaaaaagu ggcaccgagu cggugcuuuu                        100

<210> SEQ ID NO 85
<211> LENGTH: 100
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(3)
<220> FEATURE:
<221> NAME/KEY: 2'-O-Methyl nucleotide
<222> LOCATION: (6)..(6)
<220> FEATURE:
<221> NAME/KEY: 2'-O-Methyl nucleotide
<222> LOCATION: (8)..(8)
<220> FEATURE:
<221> NAME/KEY: 2'-O-Methyl nucleotide
<222> LOCATION: (11)..(11)
<220> FEATURE:
<221> NAME/KEY: 2'-O-Methyl nucleotide
<222> LOCATION: (13)..(17)
<220> FEATURE:
<221> NAME/KEY: 2'-O-Methyl nucleotide
<222> LOCATION: (25)..(25)
<220> FEATURE:
<221> NAME/KEY: 2'-O-Methyl nucleotide
<222> LOCATION: (30)..(31)
<220> FEATURE:
<221> NAME/KEY: 2'-O-Methyl nucleotide
<222> LOCATION: (34)..(34)
<220> FEATURE:
<221> NAME/KEY: 2'-O-Methyl nucleotide
<222> LOCATION: (37)..(37)
<220> FEATURE:
<221> NAME/KEY: 2'-O-Methyl nucleotide
<222> LOCATION: (40)..(40)
<220> FEATURE:
<221> NAME/KEY: 2'-O-Methyl nucleotide
<222> LOCATION: (50)..(50)
<220> FEATURE:
<221> NAME/KEY: 2'-O-Methyl nucleotide
<222> LOCATION: (55)..(56)
```

```
<220> FEATURE:
<221> NAME/KEY: 2'-O-Methyl nucleotide
<222> LOCATION: (59)..(61)
<220> FEATURE:
<221> NAME/KEY: 2'-O-Methyl nucleotide
<222> LOCATION: (66)..(67)
<220> FEATURE:
<221> NAME/KEY: 2'-O-Methyl nucleotide
<222> LOCATION: (70)..(72)
<220> FEATURE:
<221> NAME/KEY: 2'-O-Methyl nucleotide
<222> LOCATION: (80)..(80)
<220> FEATURE:
<221> NAME/KEY: 2'-O-Methyl nucleotide
<222> LOCATION: (83)..(83)
<220> FEATURE:
<221> NAME/KEY: 2'-O-Methyl nucleotide
<222> LOCATION: (85)..(86)
<220> FEATURE:
<221> NAME/KEY: 2'-O-Methyl nucleotide
<222> LOCATION: (90)..(91)
<220> FEATURE:
<221> NAME/KEY: 2'-O-Methyl nucleotide
<222> LOCATION: (94)..(94)
<220> FEATURE:
<221> NAME/KEY: 2'-O-Methyl nucleotide
<222> LOCATION: (96)..(99)

<400> SEQUENCE: 85
gcagauguag uguuuccaca guuuuagagc uaguaauagc aaguuaaaau aaggcuaguc    60
cguuaucaac uugaaaaagu ggcaccgagu cggugcuuuu                        100

<210> SEQ ID NO 86
<211> LENGTH: 113
<212> TYPE: DNA
<213> ORGANISM: Artificial Sequence
<220> FEATURE:
<223> OTHER INFORMATION: synthetic construct
<220> FEATURE:
<221> NAME/KEY: 2'-deoxy-nucleotide
<222> LOCATION: (1)..(20)

<400> SEQUENCE: 86
agtcctcatc tccctcaagc guuuagagc uaugcuggua acagcauagc aaguuuaaau    60
aaggcuaguc cguuaucaac uugaaaaagu ggcaccgagu cggugcuuuu uuu         113

<210> SEQ ID NO 87
<211> LENGTH: 113
<212> TYPE: DNA
<213> ORGANISM: Artificial Sequence
<220> FEATURE:
<223> OTHER INFORMATION: synthetic construct
<220> FEATURE:
<221> NAME/KEY: 2'-deoxy-nucleotide
<222> LOCATION: (1)..(26)

<400> SEQUENCE: 87
agtcctcatc tccctcaagc gtttaagagc uaugcuggua acagcauagc aaguuuaaau    60
aaggcuaguc cguuaucaac uugaaaaagu ggcaccgagu cggugcuuuu uuu         113

<210> SEQ ID NO 88
<211> LENGTH: 113
<212> TYPE: DNA
<213> ORGANISM: Artificial Sequence
<220> FEATURE:
<223> OTHER INFORMATION: synthetic construct
<220> FEATURE:
<221> NAME/KEY: 2'-deoxy-nucleotide
<222> LOCATION: (1)..(37)
```

<400> SEQUENCE: 88
agtcctcatc tccctcaagc gtttaagagc tatgctggua acagcauagc aaguuuaaau    60
aaggcuaguc cguuaucaac uugaaaaagu ggcaccgagu cggugcuuuu uuu    113

<210> SEQ ID NO 89
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-deoxy-nucleotide
<222> LOCATION: (15)..(15)
<220> FEATURE:
<221> NAME/KEY: phosphonoacetate internucleotide linkage
<222> LOCATION: (15)..(16)

<400> SEQUENCE: 89
gcagauguag uguuuccaca guuuaagagc uaugcuggua acagcauagc aaguuuaaau    60
aaggcuaguc cguuaucaac uugaaaaagu ggcaccgagu cggugcuuuu uuu    113

<210> SEQ ID NO 90
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(1)
<220> FEATURE:
<221> NAME/KEY: phosphonoacetate internucleotide linkage
<222> LOCATION: (1)..(2)

<400> SEQUENCE: 90
aguccucauc ucccucaagc guuuaagagc uaugcuggua acagcauagc aaguuuaaau    60
aaggcuaguc cguuaucaac uugaaaaagu ggcaccgagu cggugcuuuu uuu    113

<210> SEQ ID NO 91
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(2)
<220> FEATURE:
<221> NAME/KEY: phosphonoacetate internucleotide linkage
<222> LOCATION: (1)..(3)

<400> SEQUENCE: 91
aguccucauc ucccucaagc guuuaagagc uaugcuggua acagcauagc aaguuuaaau    60
aaggcuaguc cguuaucaac uugaaaaagu ggcaccgagu cggugcuuuu uuu    113

<210> SEQ ID NO 92
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(3)
<220> FEATURE:
<221> NAME/KEY: phosphonoacetate internucleotide linkage
<222> LOCATION: (1)..(4)

<400> SEQUENCE: 92
aguccucauc ucccucaagc guuuaagagc uaugcuggua acagcauagc aaguuuaaau      60
aaggcuaguc cguuaucaac uugaaaaagu ggcaccgagu cggugcuuuu uuu            113

<210> SEQ ID NO 93
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(4)
<220> FEATURE:
<221> NAME/KEY: phosphonoacetate internucleotide linkage
<222> LOCATION: (1)..(5)

<400> SEQUENCE: 93
aguccucauc ucccucaagc guuuaagagc uaugcuggua acagcauagc aaguuuaaau      60
aaggcuaguc cguuaucaac uugaaaaagu ggcaccgagu cggugcuuuu uuu            113

<210> SEQ ID NO 94
<211> LENGTH: 115
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(5)
<220> FEATURE:
<221> NAME/KEY: phosphonoacetate internucleotide linkage
<222> LOCATION: (1)..(6)

<400> SEQUENCE: 94
ggaguccuca ucucccucaa gcguuuaaga gcuaugcugg uaacagcaua gcaaguuuaa      60
auaaggcuag uccguuauca acuugaaaaa guggcaccga gucggugcuu uuuuu          115

<210> SEQ ID NO 95
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (109)..(112)
<220> FEATURE:
<221> NAME/KEY: phosphonoacetate internucleotide linkage
<222> LOCATION: (109)..(113)

<400> SEQUENCE: 95
aguccucauc ucccucaagc guuuaagagc uaugcuggua acagcauagc aaguuuaaau      60
aaggcuaguc cguuaucaac uugaaaaagu ggcaccgagu cggugcuuuu uuu            113

<210> SEQ ID NO 96
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (108)..(112)
<220> FEATURE:
<221> NAME/KEY: phosphonoacetate internucleotide linkage

<222> LOCATION: (108)..(113)

<400> SEQUENCE: 96
aguccucauc ucccucaagc guuuaagagc uaugcuggua acagcauagc aaguuuaaau    60
aaggcuaguc cguuaucaac uugaaaaagu ggcaccgagu cggugcuuuu uuu           113

<210> SEQ ID NO 97
<211> LENGTH: 114
<212> TYPE: RNA
<213> ORGANISM: Artificial Sequence
<220> FEATURE:
<223> OTHER INFORMATION: synthetic construct
<220> FEATURE:
<221> NAME/KEY: 5'-overhang (5' to the 20-nt guide sequence)
<222> LOCATION: (1)..(1)
<220> FEATURE:
<221> NAME/KEY: 2'-O-Methyl nucleotide
<222> LOCATION: (1)..(3)
<220> FEATURE:
<221> NAME/KEY: phosphonoacetate internucleotide linkage
<222> LOCATION: (1)..(4)

<400> SEQUENCE: 97
caguccucau ucccucaag cguuuaagag cuaugcuggu aacagcauag caaguuuaaa     60
uaaggcuagu ccguuaucaa cuugaaaaag uggcaccgag ucggugcuuu uuuu          114

<210> SEQ ID NO 98
<211> LENGTH: 114
<212> TYPE: RNA
<213> ORGANISM: Artificial Sequence
<220> FEATURE:
<223> OTHER INFORMATION: synthetic construct
<220> FEATURE:
<221> NAME/KEY: 5'-overhang (5' to the 20-nt guide sequence)
<222> LOCATION: (1)..(1)
<220> FEATURE:
<221> NAME/KEY: 2'-O-Methyl nucleotide
<222> LOCATION: (1)..(3)
<220> FEATURE:
<221> NAME/KEY: phosphonoacetate internucleotide linkage
<222> LOCATION: (1)..(4)

<400> SEQUENCE: 98
gaguccucau ucccucaag cguuuaagag cuaugcuggu aacagcauag caaguuuaaa     60
uaaggcuagu ccguuaucaa cuugaaaaag uggcaccgag ucggugcuuu uuuu          114

<210> SEQ ID NO 99
<211> LENGTH: 115
<212> TYPE: RNA
<213> ORGANISM: Artificial Sequence
<220> FEATURE:
<223> OTHER INFORMATION: synthetic construct
<220> FEATURE:
<221> NAME/KEY: 5'-overhang (5' to the 20-nt guide sequence)
<222> LOCATION: (1)..(2)
<220> FEATURE:
<221> NAME/KEY: 2'-O-Methyl nucleotide
<222> LOCATION: (1)..(5)
<220> FEATURE:
<221> NAME/KEY: phosphonoacetate internucleotide linkage
<222> LOCATION: (1)..(6)

<400> SEQUENCE: 99
ucaguccuca ucucccucaa gcguuuaaga gcuaugcugg uaacagcaua gcaaguuuaa    60
auaaggcuag uccguuauca acuugaaaaa guggcaccga gucggugcuu uuuuu         115

<210> SEQ ID NO 100

```
<211> LENGTH: 115
<212> TYPE: RNA
<213> ORGANISM: Artificial Sequence
<220> FEATURE:
<223> OTHER INFORMATION: synthetic construct
<220> FEATURE:
<221> NAME/KEY: 5'-overhang (5' to the 20-nt guide sequence)
<222> LOCATION: (1)..(2)
<220> FEATURE:
<221> NAME/KEY: 2'-O-Methyl nucleotide
<222> LOCATION: (1)..(5)
<220> FEATURE:
<221> NAME/KEY: phosphonoacetate internucleotide linkage
<222> LOCATION: (1)..(6)

<400> SEQUENCE: 100
agaguccuca ucucccucaa gcguuuaaga gcuaugcugg uaacagcaua gcaaguuuaa      60
auaaggcuag uccguuauca acuugaaaaa guggcaccga gucggugcuu uuuuu         115

<210> SEQ ID NO 101
<211> LENGTH: 116
<212> TYPE: RNA
<213> ORGANISM: Artificial Sequence
<220> FEATURE:
<223> OTHER INFORMATION: synthetic construct
<220> FEATURE:
<221> NAME/KEY: 5'-overhang (5' to the 20-nt guide sequence)
<222> LOCATION: (1)..(3)
<220> FEATURE:
<221> NAME/KEY: 2'-O-Methyl nucleotide
<222> LOCATION: (1)..(7)
<220> FEATURE:
<221> NAME/KEY: phosphonoacetate internucleotide linkage
<222> LOCATION: (1)..(8)
<220> FEATURE:
<221> NAME/KEY: 2'-O-Methyl nucleotide
<222> LOCATION: (112)..(115)
<220> FEATURE:
<221> NAME/KEY: phosphonoacetate internucleotide linkage
<222> LOCATION: (112)..(116)

<400> SEQUENCE: 101
cucaguccuc aucucccuca agcguuuaag agcuaugcug guaacagcau agcaaguuua      60
aauaaggcua guccguuauc aacuugaaaa aguggcaccg agucggugcu uuuuuu        116

<210> SEQ ID NO 102
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (20)..(20)
<220> FEATURE:
<221> NAME/KEY: phosphonoacetate internucleotide linkage
<222> LOCATION: (20)..(21)

<400> SEQUENCE: 102
aguccucauc ucccucaagc guuuagagc uaugcuggua acagcauagc aaguuuaaau      60
aaggcuaguc cguuaucaac uugaaaaagu ggcaccgagu cggugcuuuu uuu           113

<210> SEQ ID NO 103
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
```

```
<222> LOCATION: (19)..(20)
<220> FEATURE:
<221> NAME/KEY: phosphonoacetate internucleotide linkage
<222> LOCATION: (19)..(20)

<400> SEQUENCE: 103
aguccucauc ucccucaagc guuuaagagc uaugcuggua acagcauagc aaguuuaaau      60
aaggcuaguc cguuaucaac uugaaaaagu ggcaccgagu cggugcuuuu uuu            113

<210> SEQ ID NO 104
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (18)..(18)
<220> FEATURE:
<221> NAME/KEY: phosphonoacetate internucleotide linkage
<222> LOCATION: (18)..(19)

<400> SEQUENCE: 104
aguccucauc ucccucaagc guuuaagagc uaugcuggua acagcauagc aaguuuaaau      60
aaggcuaguc cguuaucaac uugaaaaagu ggcaccgagu cggugcuuuu uuu            113

<210> SEQ ID NO 105
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (17)..(17)
<220> FEATURE:
<221> NAME/KEY: phosphonoacetate internucleotide linkage
<222> LOCATION: (17)..(18)

<400> SEQUENCE: 105
aguccucauc ucccucaagc guuuaagagc uaugcuggua acagcauagc aaguuuaaau      60
aaggcuaguc cguuaucaac uugaaaaagu ggcaccgagu cggugcuuuu uuu            113

<210> SEQ ID NO 106
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (17)..(18)
<220> FEATURE:
<221> NAME/KEY: phosphonoacetate internucleotide linkage
<222> LOCATION: (17)..(19)

<400> SEQUENCE: 106
aguccucauc ucccucaagc guuuaagagc uaugcuggua acagcauagc aaguuuaaau      60
aaggcuaguc cguuaucaac uugaaaaagu ggcaccgagu cggugcuuuu uuu            113

<210> SEQ ID NO 107
<211> LENGTH: 113
<212> TYPE: RNA
<213> ORGANISM: Artificial Sequence
<220> FEATURE:
<223> OTHER INFORMATION: synthetic construct
<220> FEATURE:
```

```
<221> NAME/KEY: 2'-O-Methyl nucleotide
<222> LOCATION: (1)..(3)
<220> FEATURE:
<221> NAME/KEY: phosphorothioate internucleotide linkage
<222> LOCATION: (1)..(4)
<220> FEATURE:
<221> NAME/KEY: 2'-O-Methyl nucleotide
<222> LOCATION: (110)..(112)
<220> FEATURE:
<221> NAME/KEY: phosphorothioate internucleotide linkage
<222> LOCATION: (110)..(113)

<400> SEQUENCE: 107
aguccucauc ucccucaagc guuuaagagc uaugcuggua acagcauagc aaguuuaaau      60
aaggcuaguc cguuaucaac uugaaaaagu ggcaccgagu cggugcuuuu uuu           113

<210> SEQ ID NO 108
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(3)
<220> FEATURE:
<221> NAME/KEY: phosphorothioate internucleotide linkage
<222> LOCATION: (1)..(4)
<220> FEATURE:
<221> NAME/KEY: 2'-O-Methyl nucleotide
<222> LOCATION: (108)..(112)
<220> FEATURE:
<221> NAME/KEY: phosphorothioate internucleotide linkage
<222> LOCATION: (108)..(113)

<400> SEQUENCE: 108
gcagauguag uguuuccaca guuuaagagc uaugcuggaa acagcauagc aaguuuaaau      60
aaggcuaguc cguuaucaac uugaaaaagu ggcaccgagu cggugcuuuu uuu           113

<210> SEQ ID NO 109
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(5)
<220> FEATURE:
<221> NAME/KEY: phosphorothioate internucleotide linkage
<222> LOCATION: (1)..(6)
<220> FEATURE:
<221> NAME/KEY: 2'-O-Methyl nucleotide
<222> LOCATION: (108)..(112)
<220> FEATURE:
<221> NAME/KEY: phosphorothioate internucleotide linkage
<222> LOCATION: (108)..(113)

<400> SEQUENCE: 109
gcagauguag uguuuccaca guuuaagagc uaugcuggaa acagcauagc aaguuuaaau      60
aaggcuaguc cguuaucaac uugaaaaagu ggcaccgagu cggugcuuuu uuu           113

<210> SEQ ID NO 110
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
```

```
<222> LOCATION: (1)..(1)
<220> FEATURE:
<221> NAME/KEY: thiophosphonoacetate internucleotide linkage
<222> LOCATION: (1)..(2)
<220> FEATURE:
<221> NAME/KEY: 2'-O-Methyl nucleotide
<222> LOCATION: (110)..(112)
<220> FEATURE:
<221> NAME/KEY: thiophosphonoacetate internucleotide linkage
<222> LOCATION: (110)..(113)

<400> SEQUENCE: 110
aguccucauc ucccucaagc guuuaagagc uaugcuggua acagcauagc aaguuuaaau      60
aaggcuaguc cguuaucaac uugaaaaagu ggcaccgagu cggugcuuuu uuu            113

<210> SEQ ID NO 111
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(1)
<220> FEATURE:
<221> NAME/KEY: thiophosphonoacetate internucleotide linkage
<222> LOCATION: (1)..(2)
<220> FEATURE:
<221> NAME/KEY: 2'-O-Methyl nucleotide
<222> LOCATION: (112)..(112)
<220> FEATURE:
<221> NAME/KEY: thiophosphonoacetate internucleotide linkage
<222> LOCATION: (112)..(113)

<400> SEQUENCE: 111
aguccucauc ucccucaagc guuuaagagc uaugcuggua acagcauagc aaguuuaaau      60
aaggcuaguc cguuaucaac uugaaaaagu ggcaccgagu cggugcuuuu uuu            113

<210> SEQ ID NO 112
<211> LENGTH: 75
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(3)
<220> FEATURE:
<221> NAME/KEY: thiophosphonoacetate internucleotide linkage
<222> LOCATION: (1)..(4)
<220> FEATURE:
<221> NAME/KEY: 2'-O-Methyl nucleotide
<222> LOCATION: (72)..(74)
<220> FEATURE:
<221> NAME/KEY: thiophosphonoacetate internucleotide linkage
<222> LOCATION: (72)..(75)

<400> SEQUENCE: 112
aguccucauc ucccucaagc guuuaagagc uaugcuggua acagcauagc aaguuuaaau      60
aaggcuaguc cguuu                                                      75

<210> SEQ ID NO 113
<211> LENGTH: 77
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(1)
```

```
<220> FEATURE:
<221> NAME/KEY: thiophosphonoacetate internucleotide linkage
<222> LOCATION: (1)..(2)
<220> FEATURE:
<221> NAME/KEY: 2'-O-Methyl nucleotide
<222> LOCATION: (76)..(76)
<220> FEATURE:
<221> NAME/KEY: thiophosphonoacetate internucleotide linkage
<222> LOCATION: (76)..(77)

<400> SEQUENCE: 113
aguccucauc ucccucaagc guuuaagagc uaugcuggua acagcauagc aaguuuaaau    60
aaggcuaguc cguuauc                                                  77

<210> SEQ ID NO 114
<211> LENGTH: 78
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(1)
<220> FEATURE:
<221> NAME/KEY: thiophosphonoacetate internucleotide linkage
<222> LOCATION: (1)..(2)
<220> FEATURE:
<221> NAME/KEY: 2'-O-Methyl nucleotide
<222> LOCATION: (77)..(77)
<220> FEATURE:
<221> NAME/KEY: thiophosphonoacetate internucleotide linkage
<222> LOCATION: (77)..(78)

<400> SEQUENCE: 114
gaguccucau cucccucaag cguuuaagag cuaugcuggu aacagcauag caaguuuaaa    60
uaaggcuagu ccguuauc                                                 78

<210> SEQ ID NO 115
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(3)
<220> FEATURE:
<221> NAME/KEY: thiophosphonoacetate internucleotide linkage
<222> LOCATION: (1)..(4)
<220> FEATURE:
<221> NAME/KEY: 2'-O-Methyl nucleotide
<222> LOCATION: (110)..(112)
<220> FEATURE:
<221> NAME/KEY: thiophosphonoacetate internucleotide linkage
<222> LOCATION: (110)..(113)

<400> SEQUENCE: 115
gcagauguag uguuuccaca guuuaagagc uaugcuggaa acagcauagc aaguuuaaau    60
aaggcuaguc cguuaucaac uugaaaaagu ggcaccgagu cggugcuuuu uuu          113

<210> SEQ ID NO 116
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(1)
<220> FEATURE:
```

```
<221> NAME/KEY: thiophosphonoacetate internucleotide linkage
<222> LOCATION: (1)..(2)
<220> FEATURE:
<221> NAME/KEY: 2'-O-Methyl nucleotide
<222> LOCATION: (112)..(112)
<220> FEATURE:
<221> NAME/KEY: thiophosphonoacetate internucleotide linkage
<222> LOCATION: (112)..(113)

<400> SEQUENCE: 116
gcagauguag uguuuccaca guuuaagagc uaugcuggaa acagcauagc aaguuuaaau      60
aaggcuaguc cguuaucaac uugaaaaagu ggcaccgagu cggugcuuuu uuu           113

<210> SEQ ID NO 117
<211> LENGTH: 113
<212> TYPE: RNA
<213> ORGANISM: Artificial Sequence
<220> FEATURE:
<223> OTHER INFORMATION: synthetic construct

<400> SEQUENCE: 117
gauguugucg augaaaaagu guuuaagagc uaugcuggua acagcauagc aaguuuaaau      60
aaggcuaguc cguuaucaac uugaaaaagu ggcaccgagu cggugcuuuu uuu           113

<210> SEQ ID NO 118
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2-aminoadenosine
<222> LOCATION: (15)..(15)

<400> SEQUENCE: 118
gauguugucg augaaaaagu guuuaagagc uaugcuggua acagcauagc aaguuuaaau      60
aaggcuaguc cguuaucaac uugaaaaagu ggcaccgagu cggugcuuuu uuu           113

<210> SEQ ID NO 119
<211> LENGTH: 113
<212> TYPE: RNA
<213> ORGANISM: Artificial Sequence
<220> FEATURE:
<223> OTHER INFORMATION: synthetic construct

<400> SEQUENCE: 119
gauuuagacg aaggauugaa guuuaagagc uaugcuggua acagcauagc aaguuuaaau      60
aaggcuaguc cguuaucaac uugaaaaagu ggcaccgagu cggugcuuuu uuu           113

<210> SEQ ID NO 120
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2-aminoadenosine
<222> LOCATION: (15)..(15)

<400> SEQUENCE: 120
gauuuagacg aaggauugaa guuuaagagc uaugcuggua acagcauagc aaguuuaaau      60
aaggcuaguc cguuaucaac uugaaaaagu ggcaccgagu cggugcuuuu uuu           113

<210> SEQ ID NO 121
```

```
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 5-methylUridine
<222> LOCATION: (6)..(6)
<220> FEATURE:
<221> NAME/KEY: 5-methylUridine
<222> LOCATION: (8)..(8)
<220> FEATURE:
<221> NAME/KEY: 5-methylUridine
<222> LOCATION: (11)..(11)
<220> FEATURE:
<221> NAME/KEY: 5-methylUridine
<222> LOCATION: (13)..(15)
<220> FEATURE:
<221> NAME/KEY: 5-methylUridine
<222> LOCATION: (31)..(31)
<220> FEATURE:
<221> NAME/KEY: 5-methylUridine
<222> LOCATION: (33)..(33)
<220> FEATURE:
<221> NAME/KEY: 5-methylUridine
<222> LOCATION: (36)..(36)
<220> FEATURE:
<221> NAME/KEY: 5-methylUridine
<222> LOCATION: (39)..(39)
<220> FEATURE:
<221> NAME/KEY: 5-methylUridine
<222> LOCATION: (47)..(47)
<220> FEATURE:
<221> NAME/KEY: 5-methylUridine
<222> LOCATION: (81)..(82)
<220> FEATURE:
<221> NAME/KEY: 5-methylUridine
<222> LOCATION: (90)..(90)
<220> FEATURE:
<221> NAME/KEY: 5-methylUridine
<222> LOCATION: (104)..(104)
<220> FEATURE:
<221> NAME/KEY: 5-methylUridine
<222> LOCATION: (107)..(112)

<400> SEQUENCE: 121
gcagauguag uguuuccaca guuuaagagc uaugcuggua acagcauagc aaguuuaaau      60
aaggcuaguc cguuaucaac uugaaaaagu ggcaccgagu cggugcuuuu uuu           113

<210> SEQ ID NO 122
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: Z base
<222> LOCATION: (70)..(71)
<223> OTHER INFORMATION: Z base
<220> FEATURE:
<221> NAME/KEY: misc_feature
<222> LOCATION: (70)..(71)
<223> OTHER INFORMATION: n is a, c, g, or u, or unknown or other

<400> SEQUENCE: 122
aguccucauc ucccucaagc guuuaagagc uaugcuggua acagcauagc aaguuuaaau      60
aaggcuagun nguuaucaac uugaaaaagu ggcaccgagu cggugcuuuu uuu           113

<210> SEQ ID NO 123
<211> LENGTH: 100
<212> TYPE: RNA
<213> ORGANISM: Artificial Sequence
<220> FEATURE:
```

```
<223> OTHER INFORMATION: synthetic construct
<220> FEATURE:
<221> NAME/KEY: 2'-O-Methyl nucleotide
<222> LOCATION: (1)..(1)
<220> FEATURE:
<221> NAME/KEY: thiophosphonoacetate internucleotide linkage
<222> LOCATION: (1)..(2)
<220> FEATURE:
<221> NAME/KEY: 2'-O-Methyl-nucleotide
<222> LOCATION: (54)..(54)
<220> FEATURE:
<221> NAME/KEY: 2'-O-Methyl-nucleotide
<222> LOCATION: (57)..(57)
<220> FEATURE:
<221> NAME/KEY: 2'-O-Methyl nucleotide
<222> LOCATION: (99)..(99)
<220> FEATURE:
<221> NAME/KEY: thiophosphonoacetate internucleotide linkage
<222> LOCATION: (99)..(100)

<400> SEQUENCE: 123
aguccucauc ucccucaagc guuuagagc uaguaauagc aaguuuaaau aagguuaauc     60
cguuaucaac aagaaauugu ggcaccgagu cggugcuuuu                        100

<210> SEQ ID NO 124
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(1)
<220> FEATURE:
<221> NAME/KEY: thiophosphonoacetate internucleotide linkage
<222> LOCATION: (1)..(2)
<220> FEATURE:
<221> NAME/KEY: 2'-O-Methyl-nucleotide
<222> LOCATION: (64)..(64)
<220> FEATURE:
<221> NAME/KEY: 2'-O-Methyl-nucleotide
<222> LOCATION: (67)..(67)
<220> FEATURE:
<221> NAME/KEY: 2'-O-Methyl nucleotide
<222> LOCATION: (112)..(112)
<220> FEATURE:
<221> NAME/KEY: thiophosphonoacetate internucleotide linkage
<222> LOCATION: (112)..(113)

<400> SEQUENCE: 124
aguccucauc ucccucaagc guuuagagc uaugcuggua acagcauagc aaguuuaaau     60
aagguuaauc cguuaucaac aagaaauugu ggcaccgagu cggugcuuuu uuu         113

<210> SEQ ID NO 125
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: Z base
<222> LOCATION: (95)..(96)
<223> OTHER INFORMATION: Z base
<220> FEATURE:
<221> NAME/KEY: misc_feature
<222> LOCATION: (95)..(96)
<223> OTHER INFORMATION: n is a, c, g, or u, or unknown or other

<400> SEQUENCE: 125
aguccucauc ucccucaagc guuuagagc uaugcuggua acagcauagc aaguuuaaau     60
aaggcuaguc cguuaucaac uugaaaaagu ggcanngagu cggugcuuuu uuu         113
```

<210> SEQ ID NO 126
<211> LENGTH: 74
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(1)
<220> FEATURE:
<221> NAME/KEY: thiophosphonoacetate internucleotide linkage
<222> LOCATION: (1)..(2)
<220> FEATURE:
<221> NAME/KEY: 2'-O-Methyl nucleotide
<222> LOCATION: (73)..(73)
<220> FEATURE:
<221> NAME/KEY: thiophosphonoacetate internucleotide linkage
<222> LOCATION: (73)..(74)

<400> SEQUENCE: 126
aguccucauc ucccucaagc guuuaagagc uaugcuggua acagcauagc aaguuuaaau    60
aaggcuaguc cguu                                                     74

<210> SEQ ID NO 127
<211> LENGTH: 75
<212> TYPE: RNA
<213> ORGANISM: Artificial Sequence
<220> FEATURE:
<223> OTHER INFORMATION: synthetic construct
<220> FEATURE:
<221> NAME/KEY: 2'-O-Methyl nucleotide
<222> LOCATION: (1)..(1)
<220> FEATURE:
<221> NAME/KEY: thiophosphonoacetate internucleotide linkage
<222> LOCATION: (1)..(2)
<220> FEATURE:
<221> NAME/KEY: 2'-O-Methyl nucleotide
<222> LOCATION: (74)..(74)
<220> FEATURE:
<221> NAME/KEY: thiophosphonoacetate internucleotide linkage
<222> LOCATION: (74)..(75)

<400> SEQUENCE: 127
aguccucauc ucccucaagc guuuaagagc uaugcuggua acagcauagc aaguuuaaau    60
aaggcuaguc cguua                                                    75

<210> SEQ ID NO 128
<211> LENGTH: 50
<212> TYPE: DNA
<213> ORGANISM: Artificial Sequence
<220> FEATURE:
<223> OTHER INFORMATION: synthetic construct

<400> SEQUENCE: 128
ttatatgaac ataactcaat ttgtaaaaaa gggtattggg gaattcatta              50

<210> SEQ ID NO 129
<211> LENGTH: 50
<212> TYPE: DNA
<213> ORGANISM: Artificial Sequence
<220> FEATURE:
<223> OTHER INFORMATION: synthetic construct

<400> SEQUENCE: 129
aatatacttg tattgagtta aacatttttt cccataaccc cttaagtaat              50

<210> SEQ ID NO 130

```
<211> LENGTH: 98
<212> TYPE: RNA
<213> ORGANISM: Artificial Sequence
<220> FEATURE:
<223> OTHER INFORMATION: synthetic construct

<400> SEQUENCE: 130
auaacucaau uguaaaaaa guuuuagagc uauagcaagu uaaaauaagg uaguccguua      60
ucaacuugaa aaaguggcac cgagucggug cuuuuuuu                            98

<210> SEQ ID NO 131
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-deoxy-nucleotide
<222> LOCATION: (1)..(20)

<400> SEQUENCE: 131
aguccucauc ucccucaagc guuuaagagc uaugcuggua acagcauagc aaguuuaaau    60
aaggcuaguc cguuaucaac uugaaaaagu ggcaccgagu cggugcuuuu uuu          113

<210> SEQ ID NO 132
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (95)..(96)
<223> OTHER INFORMATION: Z base
<220> FEATURE:
<221> NAME/KEY: misc_feature
<222> LOCATION: (95)..(96)
<223> OTHER INFORMATION: n is a, c, g, or u, or unknown or other

<400> SEQUENCE: 132
aguccucauc ucccucaagc guuuaagagc uaugcuggua acagcauagc aaguuuaaau    60
aaggcuaguc cguuaucaac uugaaaaagu ggcanngagu cggugcuuuu uuu          113

<210> SEQ ID NO 133
<211> LENGTH: 113
<212> TYPE: RNA
<213> ORGANISM: Artificial Sequence
<220> FEATURE:
<223> OTHER INFORMATION: synthetic construct
<220> FEATURE:
<221> NAME/KEY: 2'-deoxy-nucleotide
<222> LOCATION: (1)..(37)

<400> SEQUENCE: 133
aguccucauc ucccucaagc guuuaagagc uaugcuggua acagcauagc aaguuuaaau    60
aaggcuaguc cguuaucaac uugaaaaagu ggcaccgagu cggugcuuuu uuu          113

<210> SEQ ID NO 134
<211> LENGTH: 23
<212> TYPE: DNA
<213> ORGANISM: Artificial Sequence
<220> FEATURE:
<223> OTHER INFORMATION: synthetic construct

<400> SEQUENCE: 134
ccagccaagc gcacctaatt tcc                                            23
```

<210> SEQ ID NO 135
<211> LENGTH: 88
<212> TYPE: RNA
<213> ORGANISM: Artificial Sequence
<220> FEATURE:
<223> OTHER INFORMATION: synthetic construct
<220> FEATURE:
<221> NAME/KEY: misc_feature
<222> LOCATION: (34)..(34)
<223> OTHER INFORMATION: site for fluorescent dye or label attachment

<400> SEQUENCE: 135
ggaaauuagg ugcgcuuggc guuuuagagc uagaaauagc aaguuaaaau aaggcuaguc    60
cgccaucaac uugaaaaagc ggaccga                                       88

<210> SEQ ID NO 136
<211> LENGTH: 23
<212> TYPE: DNA
<213> ORGANISM: Artificial Sequence
<220> FEATURE:
<223> OTHER INFORMATION: synthetic construct

<400> SEQUENCE: 136
agtcctcatc tccctcaagc agg                                           23

<210> SEQ ID NO 137
<211> LENGTH: 23
<212> TYPE: DNA
<213> ORGANISM: Artificial Sequence
<220> FEATURE:
<223> OTHER INFORMATION: synthetic construct

<400> SEQUENCE: 137
cctgcttgag ggagatgagg act                                           23

<210> SEQ ID NO 138
<211> LENGTH: 23
<212> TYPE: DNA
<213> ORGANISM: Artificial Sequence
<220> FEATURE:
<223> OTHER INFORMATION: synthetic construct

<400> SEQUENCE: 138
agtcctcaac tccctcaagc agg                                           23

<210> SEQ ID NO 139
<211> LENGTH: 23
<212> TYPE: DNA
<213> ORGANISM: Artificial Sequence
<220> FEATURE:
<223> OTHER INFORMATION: synthetic construct

<400> SEQUENCE: 139
cctgcttgag ggagttgagg act                                           23

<210> SEQ ID NO 140
<211> LENGTH: 23
<212> TYPE: DNA
<213> ORGANISM: Artificial Sequence
<220> FEATURE:
<223> OTHER INFORMATION: synthetic construct

<400> SEQUENCE: 140
agccctcatt tccctcaagc agg                                           23

```
<210> SEQ ID NO 141
<211> LENGTH: 23
<212> TYPE: DNA
<213> ORGANISM: Artificial Sequence
<220> FEATURE:
<223> OTHER INFORMATION: synthetic construct

<400> SEQUENCE: 141
cctgcttgag ggaaatgagg gct                                              23

<210> SEQ ID NO 142
<211> LENGTH: 23
<212> TYPE: DNA
<213> ORGANISM: Artificial Sequence
<220> FEATURE:
<223> OTHER INFORMATION: synthetic construct

<400> SEQUENCE: 142
actcctcatc cccctcaagc cgg                                              23

<210> SEQ ID NO 143
<211> LENGTH: 23
<212> TYPE: DNA
<213> ORGANISM: Artificial Sequence
<220> FEATURE:
<223> OTHER INFORMATION: synthetic construct

<400> SEQUENCE: 143
cctgcttgag ggggatgagg agt                                              23
```